US008642537B2

(12) United States Patent
Zimmerman et al.

(10) Patent No.: US 8,642,537 B2
(45) Date of Patent: Feb. 4, 2014

(54) HEPATITIS B VIRUS-BINDING POLYPEPTIDES AND METHODS OF USE THEREOF

(75) Inventors: Kimberley Zimmerman, Edmonton (CA); Michael A. Joyce, Edmonton (CA); Karl Fischer, Edmonton (CA); D. Lorne Tyrrell, Edmonton (CA)

(73) Assignee: The Governors of the University of Alberta, Edmonton, Alberta (CA)

( * ) Notice: Subject to any disclaimer, the term of this patent is extended or adjusted under 35 U.S.C. 154(b) by 544 days.

(21) Appl. No.: 12/677,639

(22) PCT Filed: Sep. 10, 2008

(86) PCT No.: PCT/IB2008/003791
§ 371 (c)(1),
(2), (4) Date: Jun. 2, 2010

(87) PCT Pub. No.: WO2009/060316
PCT Pub. Date: May 14, 2009

(65) Prior Publication Data

US 2011/0015122 A1 Jan. 20, 2011

Related U.S. Application Data

(60) Provisional application No. 60/972,644, filed on Sep. 14, 2007.

(51) Int. Cl.

| | |
|---|---|
| *A61K 38/16* | (2006.01) |
| *C07K 14/00* | (2006.01) |
| *C07H 21/00* | (2006.01) |
| *C12N 15/63* | (2006.01) |
| *C12N 5/10* | (2006.01) |
| *A61P 31/20* | (2006.01) |

(52) U.S. Cl.
USPC ........... 514/4.3; 530/350; 530/324; 536/23.1; 435/320.1; 435/325

(58) Field of Classification Search
None
See application file for complete search history.

(56) References Cited

U.S. PATENT DOCUMENTS 7,151,201 B2 * 12/2006 Barbas et al. ................ 800/278

OTHER PUBLICATIONS

Mino et al. Inhibition of DNA replication of human papillomavirus by artificial zinc finger proteins. J Virol. Jun. 2006;80(11):5405-12.
Reynolds, et al. Repression of the HIV-1 5' LTR promoter and inhibition of HIV-1 replication by using engineered zinc-finger transcription factors. Proc Natl Acad Sci U S A. Feb. 18, 2003;100(4):1615-20.
Beerli, et al. Toward controlling gene expression at will: specific regulation of the erbB-2/HER-2 promoter by using polydactyl zinc finger proteins constructed from modular building blocks. Proc Natl Acad Sci U S A. Dec. 8, 1998;95(25):14628-33.

(Continued)

*Primary Examiner* — Robert A Wax
*Assistant Examiner* — Danah Al-Awadi
(74) *Attorney, Agent, or Firm* — Paula A. Borden; Bozicevic, Field & Francis, LLP

(57) ABSTRACT

The present invention provides non-naturally occurring polypeptides that specifically bind hepatitis B virus (HBV) DNA; and polynucleotides encoding the polypeptides. The present invention further provides methods of detecting HBV DNA; methods of detecting a covalently closed circular DNA (cccDNA) form of HBV; and methods for treating HBV infection.

14 Claims, 57 Drawing Sheets

(56) References Cited

OTHER PUBLICATIONS

Lilienbaum, et al. Binding of nuclear factors to functional domains of the duck hepatitis B virus enhancer. J Virol. Oct. 1993;67(10):6192-200.

Liu, et al. Identification of factor-binding sites in the duck hepatitis B virus enhancer and in vivo effects of enhancer mutations. J Virol. Apr. 1994;68(4):2286-96.

Zimmerman, et al. Zinc finger proteins designed to specifically target duck hepatitis B virus covalently closed circular DNA inhibit viral transcription in tissue culture. J Virol. Aug. 2008;82(16):8013-21.

Mandell, Barbas. Zinc Finger Tools: custom DNA-binding domains for transcription factors and nucleases. Nucleic Acids Res. Jul. 1, 2006;34(Web Server issue):W516-23.

Dreier, et al. Insights into the molecular recognition of the 5'-GNN-3' family of DNA sequences by zinc finger domains. J Mol Biol. Nov. 3, 2000;303(4):489-502.

Segal, et al. Attenuation of HIV-1 replication in primary human cells with a designed zinc finger transcription factor. J Biol Chem. Apr. 9, 2004;279(15):14509-19.

* cited by examiner

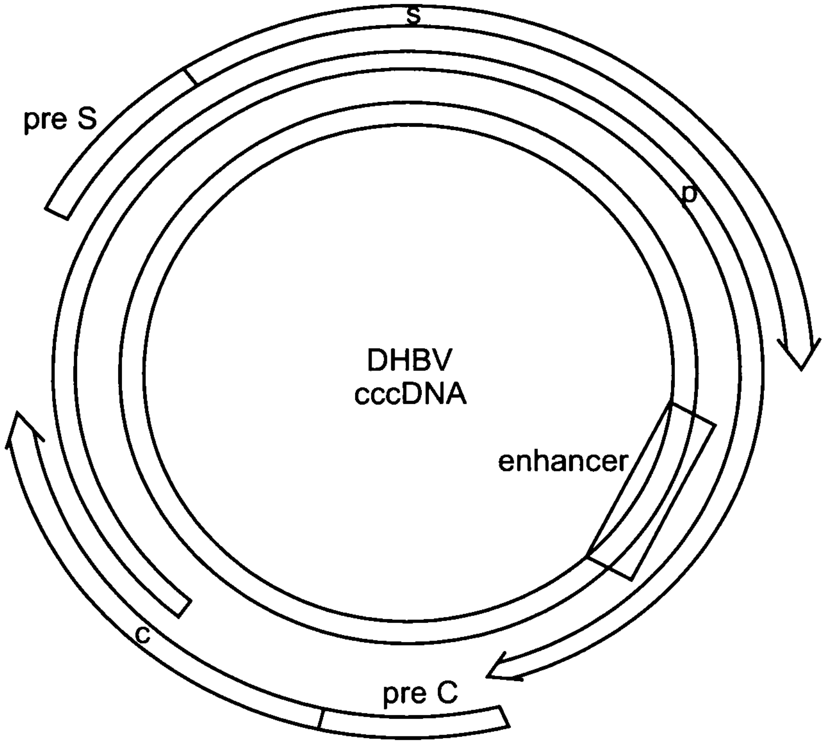

FIG. 1

```
              enhancer        C/EBPβ
2151 CACGTGTAGC TACAGATGCT ACCCCAACAC ATGGCGCAAT ATCCCATATC
     GTGCACATCG ATGTCTACGA TGGGGTTGTG TACCGCGTTA TAGGGTATAG

               HNF1/3                       ZFPc
2201 ACCGGCGGGA GCGCAGTGTT TGCTTTTTCA AAGGTCAGAG ATATACATGT
     TGGCCGGCCT CGCGTCACAA ACGAAAAAGT TTCCAGTCTC TATATGTACA
              ZFPd
                           ZFPa      ZFPe
2251 TCAGGAACTA TTGATGTCTT GTTTAGCCAA GATAATGATT AAACCGCGCT
     AGTCCTTGAT AACTACAGAA CAAATCGGTT CTATTACTAA TTTGGCGCGA
              ZFPf                   HNF1

2301 GTCTCTTATC TGATTCAACT TTTGTTTGCC ATAAGCGTTA TCAGACGTTA
     CAGAGAATAG ACTAAGTTGA AAACAAACGG TATTCGCAAT AGTCTGCAAT
                                            ZFPb
     P_core
2351 CCATGGCATT TTGCTATGTT GGCCAAACAA TTGCTCAAAC CTATACAATT
     GGTACCGTAA AACGATACAA CCGGTTTGTT AACGAGTTTG GATATGTTAA
```

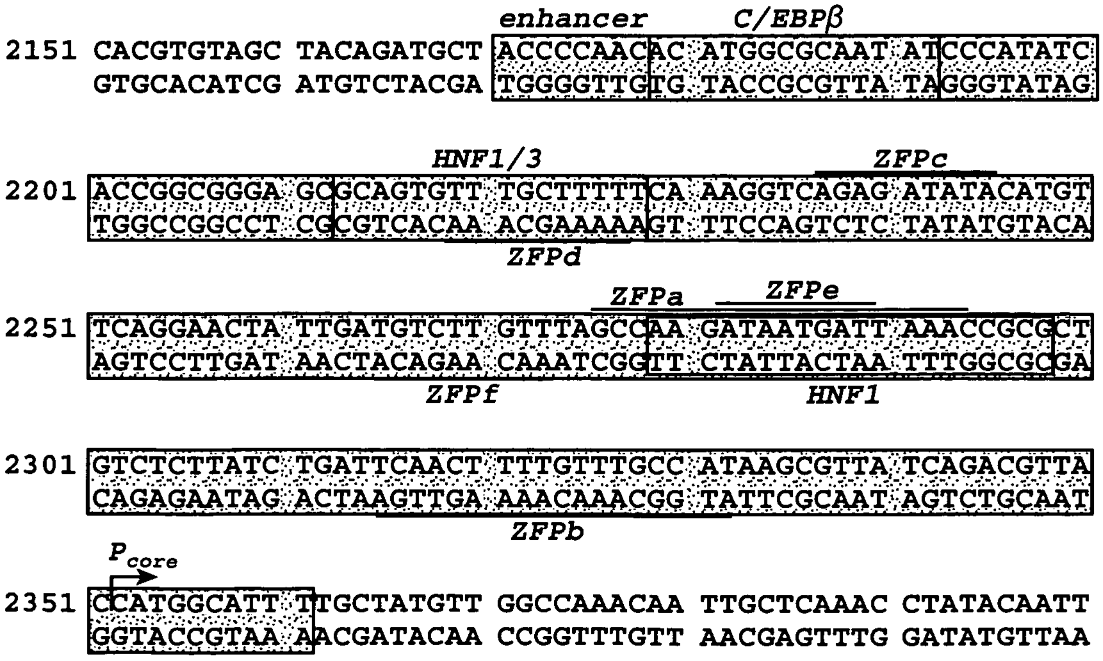

FIG. 2

ZFPd

ZFPe

```
      pre-S2/S promoter                                        ZFPr
3001 CATTCGGGCT GGGTTTCACC CCACCGCACG GAGGCCTTTT GGGGTGGAGC
     GTAAGCCCGA CCCAAAGTGG GGTGGCGTGC CTCCGGAAAA CCCCACCTCG
                                          ZFPq

       ZFPr         ZFPm                      ZFPu
3051 CCTCAGGCTC AGGGCATACT ACAAACTTTG CCAGCAAATC CGCCTCCTGC
     GGAGTCCGAG TCCCGTATGA TGTTTGAAAC GGTCGTTTAG GCGGAGGACG
                    ZFPt                                ZFPn

                   ZFPk                 ZFPw
3101 CTCCACCAAT CGCCAGACAG GAAGGCAGCC TACCCCGCTG TCTCCACCTT
     GAGGTGGTTA GCGGTCTGTC CTTCCGTCGG ATGGGGCGAC AGAGGTGGAA
       ZFPn       ZFPv                  ZFPp

                                 pre-S2
3151 TGAGAAACAC TCATCCTCAG GCCATGCAGT
     ACTCTTTGTG AGTAGGAGTC CGGTACGTCA
```

FIG. 16A

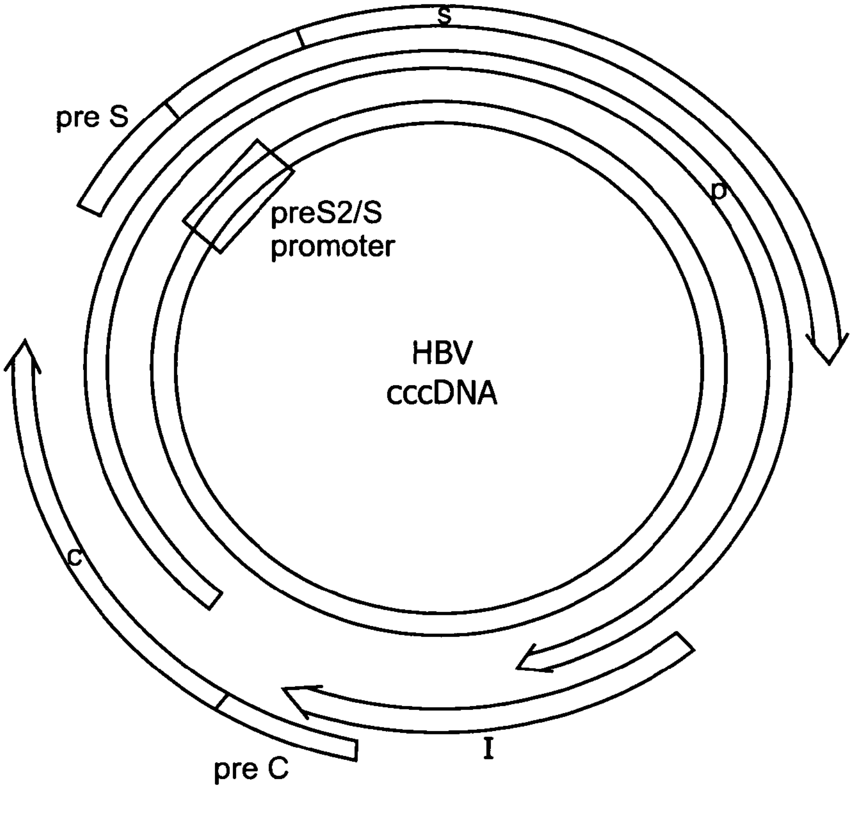

FIG. 16B

*ZFPa*
Nucleotide sequence:
5'CTGGAGCTCGAACCCGGCGAAAAGCCTTATAAGTGCCCAGAATGCGGCAA
ATCATTCAGCCAACGGGCCAACCTGAGGGCTCATCAGCGCACACACACAGGT
GAGAAGCCATACAAATGTCCAGAATGTGGTAAGTCTTTCTCTCACAAGAACG
CCCTGCAAAACCACCAGCGGACCCACACAGGCGAGAAGCCCTACAAGTGCC
CCGAGTGTGGCAAGTCTTTCAGCAGAAGGGACGAGCTGAATGTTCATCAAAG
GACTCATACTGGAGAGAAGCCATACAAATGTCCTGAATGCGGCAAGAGCTTC
AGCCAGAAATCCAGTCTGATCGCACACCAGCGAACGCACACTGGGGAGAAA
CCTTACAAATGCCCAGAATGTGGTAAATCTTTCAGCCGTAAAGATAACCTTA
AGAACCACCAACGCACCCACACAGGGGAAAAACCTTATAAGTGTCCCGAAT
GCGGCAAATCCTTCAGTGACTGCAGGGACCTCGCCCGCCATCAGCGGACACA
CACAGGTAAGAAGACAAGTACTAGT-3' (SEQ ID NO:161)

FIG. 23A

*ZFPa*
Amino Acid Sequence:
$NH_2$-
LELEPGEKPYKCPECGKSFSQRANLRAHQRTHTGEKPYKCPECGKSFSHKNA
LQNHQRTHTGEKPYKCPECGKSFSRRDELNVHQRTHTGEKPYKCPECGKSFSQK
SSLIAHQRTHTGEKPYKCPECGKSFSRKDNLKNHQRTHTGEKPYKCPECGKSFSD
CRDLARHQRTHTGKKTSTS-COOH (SSEQ ID NO:162)

FIG. 23B

*ZFPa*
DNA binding site:
5'-GCCAAGATAATGATTAAA-3' (SEQ ID NO:69)

FIG. 23C

*ZFPb*
Nucleotide sequence:
5'CTCGAGCCAGGTGAAAAACCCTACAAGTGCCCTGAGTGTGGCAAAAGCTTT
TCTCAAGCAGGACATCTCGCTAGTCATCAAAGGACTCACACCGGTGAAAAGC
CCTATAAGTGCCCCGAATGCGGAAAATCTTTTAGCCATAGGACCACACTGAC
AAACCACCAGCGAACACATACAGGGGAGAAGCCTTATAAGTGTCCCGAATG
CGGGAAGTCTTTTTCTCAGCGGGCAAACCTAAGAGCTCATCAGAGAACACAC
ACAGGCGAAAAACCTTACAAGTGTCCAGAGTGCGGAAAAAGCTTTTCAGATT
CTGGAAATCTTCGAGTGCACCAAAGAACTCACACGGGAGAGAAGCCTTATAA
GTGCCCCGAATGCGGCAAATCCTTCTCTCAGAGTGGCGACCTACGGAGACAC
CAGCGCACTCATACTGGCGAGAAGCCCTATAAGTGCCCTGAGTGTGGTAAAT
CCTTTTCTAGAAGAGACGAGCTGAATGTGCACCAACGGACTCACACAGGAAA
GAAGACTTCAACTAGT-3' (SEQ ID NO:163)

FIG. 24A

*ZFPb*
Amino acid sequence:
$NH_2$-
LELEPGEKPYKCPECGKSFSQAGHLASHQRTHTGEKPYKCPECGKSFSHRTTL
TNHQRTHTGEKPYKCPECGKSFSQRANLRAHQRTHTGEKPYKCPECGKSFSDSG
NLRVHQRTHTGEKPYKCPECGKSFSQSGDLRRHQRTHTGEKPYKCPECGKSFSR
RDELNVHQRTHTGKKTSTS-COOH (SEQ ID NO:164)

FIG. 24B

*ZFPb*
DNA binding site:
5'-ATGGCAAACAAAAGTTGA-3' (SEQ ID NO:62)

FIG. 24C

*ZFPc*

Nucleotide sequence:

5'CTGGAGCTGGAGCCCGGTGAGAAGCCCTACAAGTGCCCTGAGTGCGGTAA
AAGCTTTTCTCAGAAGTCATCCCTAATTGCACATCAGAGAACACACACAGGA
GAAAAACCCTATAAATGTCCAGAGTGCGGAAAGAGCTTCAGTACGTCTGGAA
ATCTGGTTAGGCACCAACGTACACACACAGGGGAGAAACCATACAAGTGTCC
TGAATGCGGTAAAAGTTTCTCTCAGCTGGCTCATTTGAGAGCTCATCAGCGCA
CACACACAGGTAAAAAGACGAGCACTAGT-3' (SEQ ID NO:165)

FIG. 25A

*ZFPc*

Amino acid sequence:

$NH_2$-
LELEPGEKPYKCPECGKSFSQKSSLIAHQRTHTGEKPYKCPECGKSFSTSGNLV
RHQRTHTGEKPYKCPECGKSFSQLAHLRAHQRTHTGKKTSTS-COOH (SEQ ID NO:166)

FIG. 25B

*ZFPc*

DNA binding site:

5'-AGAGATATA-3'

FIG. 25C

*ZFPd*
Nucleotide sequence:
5'CTGGAGTTGGAGCCCGGGGAGAAGCCCTACAAATGCCCTGAATGTGGAAA
ATCCTTTAGTCAGCGGGCAAACCTGCGTGCCCATCAGCGAACCCATACCGGC
GAGAAACCTTACAAATGCCCTGAGTGTGGAAAGTCTTTCTCTGAGAGGAGCC
ACCTCAGGGAGCACCAGAGGACACATACTGGAGAGAAACCCTACAAATGCC
CAGAATGTGGTAAGAGCTTCAGCCAGAGAGCAAATCTCCGTGCACACCAACG
GACACACACAGGCAAAAAGACCAGCACTAGT-3' (SEQ ID NO:167)

FIG. 26A

*ZFPd*
Amino acid sequence:
$NH_2$-
LELEPGEKPYKCPECGKSFSQRANLRAHQRTHTGEKPYKCPECGKSFSERSHL
REHQRTHTGEKPYKCPECGKSFSQRANLRAHQRTHTGKKTSTS-COOH (SEQ ID NO:168)

FIG. 26B

*ZFPd*
DNA binding site:
5'-AAAAGCAAA-3'

FIG. 26C

*ZFPe*
Nucleotide sequence:
5'CTGGAGCTCGAACCAGGAGAGAAGCCCTATAAGTGCCCAGAGTGCGGAAA
GTCCTTTTCACATAAAAACGCTCTCCAGAATCATCAACGCACACACACAGGA
GAAAAGCCATACAAATGCCCAGAATGCGGGAAGTCCTTCTCAAGACGTGACG
AGCTGAACGTTCACCAACGCACTCACACCGGTGAAAAGCCATACAAGTGTCC
AGAGTGCGGTAAGAGCTTCAGCCAAAAAAGTAGTCTCATAGCACACCAGAG
AACTCATACAGGTAAAAAGACTTCTACTAGT-3' (SEQ ID NO:169)

FIG. 27A

*ZFPe*
Amino acid sequence:
$NH_2$-
LELEPGEKPYKCPECGKSFSHKNALQNHQRTHTGEKPYKCPECGKSFSRRDE
LNVHQRTHTGEKPYKCPECGKSFSQKSSLIAHQRTHTGKKTSTS-COOH (SEQ ID NO:170)

FIG. 27B

*ZFPe*
DNA binding site:
5'-ATAATGATT-3'

FIG. 27C

*ZFPf*

Nucleotide sequence:

5'CTGGAGCTGGAGCCAGGTGAAAAGCCATACAAATGTCCTGAGTGCGGTAA
GTCTTTTTCCAGTCCCGCCGACCTTACTCGTCACCAGCGCACACACACAGGAG
AGAAACCCTATAAATGCCCAGAATGCGGAAAGAGTTTTAGCCGCAAGGATAA
TCTTAAGAATCATCAGAGAACACATACCGGCGAAAAACCATACAAATGCCCT
GAGTGTGGGAAGTCTTTCTCTGACTCCGGAAATCTCAGGGTCCACCAACGGA
CACATACTGGAAAGAAGACCTCAACTAGT-3' (SEQ ID NO:171)

FIG. 28A

*ZFPf*

Amino acid sequence:

$NH_2$-
LELEPGEKPYKCPECGKSFSSPADLTRHQRTHTGEKPYKCPECGKSFSRKDNL
KNHQRTHTGEKPYKCPECGKSFSDSGNLRVHQRTHTGKKTSTS-COOH (SEQ ID NO:172)

FIG. 28B

*ZFPf*

DNA binding site:

5'-AACAAGACA-3'

FIG. 28C

ZFPg
Nucleotide sequence:
5'ACTAGTGCCTTGGAGTTGGAACCCGGCGAAAAACCCTACAAGTGCCCAGA
ATGCGGCAAGTCTTTTAGCACCAGCGGGAGTCTCGTTAGACACCAGCGGACG
CACACAGGCGAGAAGCCATACAAATGTCCAGAGTGTGGTAAGTCATTTTCAA
GATCCGACGACCTGGTGAGGCACCAGAGAACCCATACTGGAGAGAAGCCCT
ACAAATGTCCAGAATGTGGGAAAAGTTTCTCTGAGCGTTCTCACTTGAGGGA
ACATCAGAGAACTCATACAGGAGAGAAGCCCTATAAATGCCCCGAGTGCGG
AAAAAGCTTTTCAGATCCAGGTAATCTTGTGAGGCATCAGAGAACACATACA
GGAGAAAAGCCATACAAGTGCCCTGAGTGTGGAAAGAGCTTCAGCCAACTG
GCCCATCTTCGTGCACATCAGAGAACGCATACTGGGGAAAAACCATATAAGT
GCCCTGAATGTGGGAAATCTTTCTCACAAAAATCCAGCCTTATAGCTCACCAG
CGTACACATACAGGAAAAAAGACATCTACTAGT-3' (SEQ ID NO:173)

FIG. 29A

ZFPg
Amino acid sequence:
NH₂-
LEPGEKPYKCPECGKSFSTSGSLVRHQRTHTGEKPYKCPECGKSFSRSDDLVR
HQRTHTGEKPYKCPECGKSFSERSHLREHQRTHTGEKPYKCPECGKSFSDPGNLV
RHQRTHTGEKPYKCPECGKSFSQLAHLRAHQRTHTGEKPYKCPECGKSFSQKSS
LIAHQRTHTGKKTS-COOH (SEQ ID NO:174)

FIG. 29B

ZFPg
DNA binding site:
5'-ATAAGAGACAGCGCGGTT-3' (SEQ ID NO:63)

FIG. 29C

ZFPk
Nucleotide sequence:
5'CTCGAGGGTGATATCCTGGAGCCCGGCGAGAAACCGTATAAATGCCCCGA
GTGCGGCAAGTCCTTTAGCCAGAGGGCGCACCTGGAACGGCACCAAAGAAC
ACATACTGGGGAAAAGCCATACAAGTGCCCTGAGTGCGGCAAGTCATTCTCT
TCACCCGCCGACCTGACAAGGCACCAGAGAACTCACACTGGCGAAAAGCCAT
ACAAGTGCCCTGAATGCGGGAAATCCTTTTCCCGGGCTGACAATCTGACCGA
GCATCAGCGCACCCACACAGGCGAGAAGCCTTACAAGTGCCCGGAGTGTGGC
AAGAGCTTTTCACACACGGGGCACCTGTTGGAACATCAAAGGACTCACACTG
GCGAAAAGCCCTATAAATGTCCGGAGTGTGGGAAGAGTTTTAGCACCACCGG
GAATCTGACCGTACACCAACGGACACACACAGGCGAGAAACCCTACAAGTG
CCCCGAATGTGGCAAATCTTTCAGCGATAAGAAAGATTTGACAAGGCATCAG
AGAACACACACTGGTAAGAAGACGTCTGATATCGGTACTAGT-3' (SEQ ID NO:175)

FIG. 30A

ZFPk
Amino acid sequence:
$NH_2$-
LEPGEKPYKCPECGKSFSQRAHLERHQRTHTGEKPYKCPECGKSFSSPADLTR
HQRTHTGEKPYKCPECGKSFSRADNLTEHQRTHTGEKPYKCPECGKSFSHTGHL
LEHQRTHTGEKPYKCPECGKSFSTTGNLTVHQRTHTGEKPYKCPECGKSFSDKK
DLTRHQRTHTGKKTS-COOH (SEQ ID NO:176)

FIG. 30B

ZFPk
DNA binding site:
5'-ACCAATCGCCAGACAGGA-3' (SEQ ID NO:65)

FIG. 30C

ZFPm
Nucleotide sequence:
5'CTCGAGGGTGATATCCTGGAGCCAGGAGAAAAACCTTACAAATGCCCGGA
ATGTGGAAAGTCCTTCTCACAGAGCGGCAATCTGACGGAGCACCAGCGCACG
CACACTGGGGAAAAGCCCTACAAGTGTCCAGAATGCGGGAAGTCCTTTTCCC
AGAACAGCACGCTGACCGAACACCAGCGCACCCATACTGGTGAGAAGCCCT
ATAAGTGCCCAGAGTGCGGCAAGTCTTTTAGTCAGAAATCTAGTCTGATTGCT
CATCAGCGGACTCATACCGGGGAAAAGCCCTACAAGTGTCCGGAGTGTGGCA
AGAGCTTCTCCGATCCAGGCCATCTCGTCCGGCACCAGCGAACCCATACAGG
GGAGAAACCATATAAATGCCCTGAGTGTGGAAAGTCTTTCAGTCGAGCCGAC
AATCTGACCGAACACCAACGCACCCACACCGGTGAGAAACCATACAAATGCC
CAGAATGCGGCAAGTCTTTTTCCACAAGTGGAGAACTCGTTCGGCACCAGAG
GACGCACACTGGTAAAAAGACATCAGATATCGGTACTAGT-3' (SEQ ID
NO:177)

FIG. 31A

ZFPm
Amino acid sequence:
$NH_2$-
LEPGEKPYKCPECGKSFSQSGNLTEHQRTHTGEKPYKCPECGKSFSQNSTLTE
HQRTHTGEKPYKCPECGKSFSQKSSLIAHQRTHTGEKPYKCPECGKSFSDPGHLV
RHQRTHTGEKPYKCPECGKSFSRADNLTEHQRTHTGEKPYKCPECGKSFSTSGEL
VRHQRTHTGKKTS-COOH (SEQ ID NO:178)

FIG. 31B

ZFPm
DNA binding site:
5'-GCTCAGGGCATACTACAA-3' (SEQ ID NO:66)

FIG. 31C

ZFPn

Nucleotide sequence:

5'CTCGAGGGTGATATCCTCGAACCCGGTGAGAAACCTTATAAGTGTCCCGAA
TGTGGGAAGAGTTTCTCCCGCAGCGACGATCTTGTGCGCCACCAAAGGACAC
ACACAGGGGAGAAACCTTATAAGTGCCCCGAGTGTGGGAAGAGCTTCAGTCG
GTCTGATAACCTGGTGAGGCACCAGAGGACACACACCGGCGAAAAACCTTAT
AAATGTCCCGAGTGCGGCAAAAGTTTTTCACGAGCCGATAACCTCACTGAGC
ATCAACGAACCCATACAGGGGAAAAACCATACAAGTGCCCTGAGTGCGGTA
AGAGTTTTTCAAGAAGCGACCACCTGACTAATCACCAGCGCACCCACACTGG
CGAGAAGCCCTACAAGTGCCCAGAATGCGGTAAATCTTTTTCTCGGTCTGATC
ACCTTACTACACACCAGAGAACGCATACTGGAGAGAAGCCGTACAAATGTCC
CGAGTGCGGAAAGAGCTTTAGCCGCAGTGATCATCTGACCACTCACCAGCGA
ACCCATACCGGAAAGAAGACGTCCGATATCGGTACTAGT-3' (SEQ ID NO:179)

FIG. 32A

ZFPn

Amino acid sequence:

$NH_2$-
LEPGEKPYKCPECGKSFSRSDDLVRHQRTHTGEKPYKCPECGKSFSRSDNLVR
HQRTHTGEKPYKCPECGKSFSRADNLTEHQRTHTGEKPYKCPECGKSFSRSDHL
TNHQRTHTGEKPYKCPECGKSFSRSDHLTTHQRTHTGEKPYKCPECGKSFSRSDH
LTTHQRTHTGKKTS-COOH (SEQ ID NO:180)

FIG. 32B

ZFPn

DNA binding site:

5'-TGGTGGAGGCAGGAGGCG-3' (SEQ ID NO:67)

FIG. 32C

ZFPp
Nucleotide sequence:
5'CTCGAGGGTGATATCTTGGAACCAGGCGAAAAGCCATATAAATGTCCTGAG
TGCGGGAAGTCTTTCAGTACCAAGAACTCTCTTACCGAGCACCAGCGCACAC
ACACAGGAGAGAAACCCTACAAGTGCCCCGAATGCGGAAAGAGTTTCAGCA
GGAATGATGCTCTTACCGAGCACCAGAGGACTCACACGGGCGAAAAACCAT
ACAAGTGTCCCGAGTGTGGGAAGAGTTTCAGCAGGTCCGACCATCTTACTAA
TCATCAGCGCACACACACTGGAGAGAAGCCCTATAAATGTCCAGAGTGCGGC
AAAAGTTTCAGTACTTCCGGACATCTCGTGCGGCACCAAAGGACACATACTG
GCGAAAAGCCTTACAAGTGTCCCGAGTGTGGCAAGTCCTTTAGTCGCTCTGA
CAAGCTCACTGAGCATCAGAGAACACACACTGGAGAGAAACCATACAAGTG
CCCCGAGTGTGGGAAATCCTTCAGCAGGGCAGACAATCTGACCGAACACCAA
CGGACCCATACAGGAAAAAAAACCAGCGATATCGGTACTAGT-3' (SEQ ID NO:181)

FIG. 33A

ZFPp
Amino acid sequence:
$NH_2$-
LEPGEKPYKCPECGKSFSTKNSLTEHQRTHTGEKPYKCPECGKSFSRNDALTE
HQRTHTGEKPYKCPECGKSFSRSDHLTNHQRTHTGEKPYKCPECGKSFSTSGHL
VRHQRTHTGEKPYKCPECGKSFSRSDKLTEHQRTHTGEKPYKCPECGKSFSRAD
NLTEHQRTHTGKKTS-COOH (SEQ ID NO:182)

FIG. 33B

ZFPp
DNA binding site:
5'-CAGCGGGGTAGGCTGCCT-3' (SEQ ID NO:68)

FIG. 33C

ZFPq
Nucleotide sequence:
5'CTCGAGGGTGATATCTTGGAACCCGGTGAAAAACCATACAAATGTCCGGAA
TGCGGAAAATCCTTCAGTAGGAACGACACCCTGACTGAACATCAGAGAACAC
ACACCGGCGAAAAGCCATACAAGTGTCCCGAGTGTGGAAAATCCTTTTCCAC
AAAAAATTCCCTGACTGAGCACCAGCGGACGCATACAGGGGAGAAACCATA
CAAATGCCCAGAGTGTGGGAAGTCATTTTCCAGGTCTGACCATCTGACCAAC
CATCAAAGGACCCACACCGGCAAAAAGACAAGCGATATCGGTACTAGT-3'
(SEQ ID NO:183)

FIG. 34A

ZFPq
Amino acid sequence:
$NH_2$-
LEPGEKPYKCPECGKSFSRNDTLTEHQRTHTGEKPYKCPECGKSFSTKNSLTE
HQRTHTGEKPYKCPECGKSFSRSDHLTNHQRTHTGKKTS-COOH (SEQ ID NO:184)

FIG. 34B

ZFPq
DNA binding site:
5'-AGGCCTCCG-3'

FIG. 34C

ZFPr
Nucleotide sequence:
5'CTCGAGGGTGATATCCTGGAGCCTGGCGAAAAGCCTTACAAATGCCCTGAA
TGTGGAAAGAGTTTTTCCAGAGCAGACAATTTGACAGAGCATCAGCGGACCC
ATACAGGAGAAAAGCCTTATAAATGCCCCGAGTGTGGTAAGAGTTTTTCTAC
TAAGAATAGTCTGACTGAACATCAACGAACTCACACTGGAGAGAAGCCTTAT
AAATGTCCCGAGTGTGGGAAATCTTTTTCCGAAAGATCCCACCTTAGAGAAC
ACCAGCGGACACATACAGGGAAGAAAACCTCTGATATCGGTACTAGT-3'
(SEQ ID NO:185)

FIG. 35A

ZFPr
Amino acid sequence:
$NH_2$-
LEPGEKPYKCPECGKSFSRADNLTEHQRTHTGEKPYKCPECGKSFSTKNSLTE
HQRTHTGEKPYKCPECGKSFSERSHLREHQRTHTGKKTS-COOH (SEQ ID NO:186)

FIG. 35B

ZFPr
DNA binding site:
5'-AGCCCTCAG-3'

FIG. 35C

ZFPt

Nucleotide sequence:

5'CTCGAGGGTGATATCCTTGAGCCCGGAGAGAAGCCATACAAATGCCCTGAG
TGTGGAAAGAGCTTCTCCTCTAAGAAGCACCTGGCCGAGCATCAACGAACCC
ACACGGGGGAGAAACCTTATAAATGCCCGGAGTGTGGCAAATCATTTTCCAG
AAGAGATGAACTTAATGTTCACCAGAGGACCCACACAGGTGAGAAGCCTTAC
AAGTGTCCCGAATGTGGAAAATCCTTTAGCCACCGCACTACGCTCACTAATC
ACCAGCGAACCCACACTGGCAAAAAGACATCTGATATCGGTACTAGT-3' (SEQ ID NO:187)

FIG. 36A

ZFPt

Amino acid sequence:

$NH_2$-
LEPGEKPYKCPECGKSFSSKKHLAEHQRTHTGEKPYKCPECGKSFSRRDELN
VHQRTHTGEKPYKCPECGKSFSHRTTLTNHQRTHTGKKTS-COOH (SEQ ID NO:188)

FIG. 36B

ZFPt

DNA binding site:

5'-AGTATGCCC -3'

FIG. 36C

ZFPu
Nucleotide sequence:
5'CTCGAGGGTGATATCCTGGAGCCCGGAGAGAAGCCATACAAATGTCCAGA
GTGTGGCAAATCCTTCAGCACAACAGGCAATCTGACTGTGCATCAGCGCACG
CATACTGGAGAGAAACCATACAAATGTCCAGAGTGCGGCAAGAGCTTCTCAC
AGAGCGGTGACCTGCGCAGACACCAGAGGACACACACCGGTGAAAAACCCT
ATAAATGTCCCGAATGCGGAAAATCCTTCTCAACTAGCCATAGTCTGACTGA
GCACCAGCGCACGCATACCGGCAAGAAGACCTCTGATATCGGTACTAGT-3'
(SEQ ID NO:189)

FIG. 37A

ZFPu
Amino acid sequence:
$NH_2$-
LEPGEKPYKCPECGKSFSTTGNLTVHQRTHTGEKPYKCPECGKSFSQSGDLRR
HQRTHTGEKPYKCPECGKSFSTSHSLTEHQRTHTGKKTS-COOH (SEQ ID
NO:190)

FIG. 37B

ZFPu
DNA binding site:
5'-CCAGCAAAT -3'

FIG. 37C

ZFPv
Nucleotide sequence:
5'CTCGAGGGTGATATCCTGGAGCCAGGCGAAAAGCCATACAAGTGCCCAGA
GTGCGGCAAGAGCTTCTCACGCTCAGACCACCTCACTACACACCAGCGGACC
CACACCGGCGAGAAGCCGTACAAATGTCCCGAATGTGGCAAGAGTTTCTCAA
CTTCAGGAAATCTTGTACGGCATCAGAGAACTCACACAGGAGAGAAACCATA
TAAGTGTCCTGAATGTGGTAAAAGTTTCTCCGACCCCGGACATCTCGTGCGCC
ACCAGAGGACCCATACAGGCAAGAAGACATCAGATATCGGTACTAGT-3'
(SEQ ID NO:191)

FIG. 38A

ZFPv
Amino acid sequence:
$NH_2$-
LEPGEKPYKCPECGKSFSRSDHLTTHQRTHTGEKPYKCPECGKSFSTSGNLVR
HQRTHTGEKPYKCPECGKSFSDPGHLVRHQRTHTGKKTS-COOH (SEQ ID
NO:192)

FIG. 38B

ZFPv
DNA binding site:
5'-GGCGATTGG -3'

FIG. 38C

ZFPw
Nucleotide sequence:
5'CTCGAGGGTGATATCCTCGAACCAGGCGAAAAACCGTACAAATGTCCTGAG
TGTGGCAAGTCATTCAGCGATAAGAAGGACCTTACTAGACATCAACGGACAC
ATACCGGGGAAAAACCCTACAAGTGTCCAGAATGCGGCAAGAGTTTTTCCAC
TAAAAATAGTCTGACAGAACATCAAAGAACCCACACCGGGGAGAAACCTTAT
AAATGCCCTGAATGTGGGAAATCCTTCTCCCGGGCTGATAACTTGACAGAGC
ATCAGAGGACTCACACCGGTAAAAAGACGTCCGATATCGGTACTAGT-3' (SEQ
ID NO:193)

FIG. 39A

ZFPw
Amino acid sequence:
$NH_2$-
LEPGEKPYKCPECGKSFSDKKDLTRHQRTHTGEKPYKCPECGKSFSTKNSLTE
HQRTHTGEKPYKCPECGKSFSRADNLTEHQRTHTGKKTS-COOH (SEQ ID
NO:194)

FIG. 39B

ZFPw
DNA binding site:
5'-CAGCCTACC -3'

FIG. 39C

```
   1 aattccacaa cctttcacca aactctgcaa gatcccagag tgagaggcct gtatttccct
  61 gctggtggct ccagttcagg agcagtaaac cctgttccga ctactgcctc tcccttatcg
 121 tcaatcttct cgaggattgg ggaccctgcg ctgaacatgg agaacatcac atcaggattc
 181 ctaggacccc ttctcgtgtt acaggcgggg tttttcttgt tgacaagaat cctcacaata
 241 ccgcagagtc tagactcgtg gtggacttct ctcaattttc taggggggaac taccgtgtgt
 301 cttggccaaa attcgcagtc cccaacctcc aatcactcac caacctcctg tcctccaact
 361 tgtcctggtt atcgctggat gtgtctgcgg cgttttatca tcttcctctt catcctgctg
 421 ctatgcctca tcttcttgtt ggttcttctg gactatcaag gtatgttgcc cgtttgtcct
 481 ctaattccag gatcctcaac caccagcacg ggaccatgcc gaacctgcat gactactgct
 541 caaggaacct ctatgtatcc ctcctgttgc tgtaccaaac cttcggacgg aaattgcacc
 601 tgtattccca tcccatcatc ctgggctttc ggaaaattcc tatgggagtg ggcctcagcc
 661 cgtttctcct ggctcagttt actagtgcca tttgttcagt ggttcgtagg gctttccccc
 721 actgtttggc tttcagttat atggatgatg tggtattggg ggccaagtct gtacagcatc
 781 ttgagtccct ttttaccgct gttaccaatt ttcttttgtc tttgggtata catttaaacc
 841 ctaacaaaac aaagagatgg ggttactctc tgaattttat gggttatgtc attggaagtt
 901 atgggtcctt gccacaagaa cacatcatac aaaaaatcaa agaatgtttt agaaaacttc
 961 ctattaacag gcctattgat tggaaagtat gtcaacgaat tgtgggtctt ttgggttttg
1021 ctgccccatt tacacaatgt ggttatcctg cgttaatgcc cttgtatgca tgtattcaat
1081 ctaagcaggc tttcactttc tcgccaactt acaaggcctt tctgtgtaaa caatacctga
1141 acctttaccc cgttgcccgg caacggccag gtctgtgcca agtgtttgct gacgcaaccc
1201 ccactggctg gggcttggtc atgggccatc agcgcgtgcg tggaaccttt tcggctcctc
1261 tgccgatcca tactgcggaa ctcctagccg cttgttttgc tcgcagcagg tctggagcaa
1321 acattatcgg gactgataac tctgttgtcc tctcccgcaa atatacatcg tatccatggc
1381 tgctaggctg tgctgccaac tggatcctgc gcgggacgtc ctttgtttac gtcccgtcgg
1441 cgctgaatcc tgcggacgac ccttctcggg gtcgcttggg actctctcgt ccccttctcc
1501 gtctgccgtt ccgaccgacc acggggcgca cctctcttta cgcggactcc ccgtctgtgc
1561 cttctcatct gccggaccgt gtgcacttcg cttcacctct gcacgtcgca tggagaccac
1621 cgtgaacgcc caccgaatgt tgcccaaggt cttacataag aggactcttg gactctctgc
1681 aatgtcaacg accgaccttg aggcatactt caaagactgt ttgtttaaag actgggagga
1741 gttgggggag gagattagat taaaggtctt tgtactagga ggctgtaggc ataaattggt
1801 ctgcgcacca gcaccatgca actttttcac ctctgcctaa tcatctcttg ttcatgtcct
1861 actgttcaag cctccaagct gtgccttggg tggctttggg gcatggacat cgacccttat
1921 aaagaatttg gagctactgt ggagttactc tcgtttttgc cttctgactt ctttccttca
1981 gtacgagatc ttctagatac cgcctcagct ctgtatcggg aagccttaga gtctcctgag
2041 cattgttcac ctcaccatac tgcactcagg caagcaattc tttgctgggg ggaactaatg
2101 actctagcta cctgggtggg tgttaatttg gaagatccag catctagaga cctagtagtc
2161 agttatgtca acactaatat gggcctaaag ttcaggcaac tcttgtggtt tcacatttct
2221 tgtctcactt ttggaagaga aaccgttata gagtatttgg tgtctttcgg agtgtggatt
2281 cgcactcctc cagcttatag accaccaaat gcccctatcc tatcaacact tccggaaact
2341 actgttgtta gacgacgagg caggtcccct agaagaagaa ctccctcgcc tcgcagacga
2401 aggtctcaat cgccgcgtcg cagaagatct caatctcggg aacctcaatg ttagtattcc
2461 ttggactcat aaggtgggga actttactgg tctttattct tctactgtac ctgtctttaa
2521 tcctcattgg aaaacaccat cttttcctaa tatacattta caccaagaca ttatcaaaaa
2581 atgtgaacag tttgtaggcc cacttacagt taatgagaaa agaagattgc aattgattat
2641 gcctgctagg ttttatccaa aggttaccaa atatttacca ttggataagg gtattaaacc
2701 ttattatcca gaacatctag ttaatcatta cttccaaact agacactatt tacacactct
2761 atggaaggcg ggtatattat ataagagaga aacaacacat agcgcctcat tttgtgggtc
2821 accatattct tgggaacaag atctacagca tggggcagaa tctttccacc agcaatcctc
2881 tgggattctt tcccgaccac cagttggatc cagccttcag agcaaacaca gcaaatccag
2941 attgggactt caatcccaac aaggacacct ggccagacgc caacaaggta ggagctggag
3001 cattcgggct gggtttcacc ccaccgcacg gaggcctttt ggggtggagc cctcaggctc
3061 agggcatact acaaactttg ccagcaaatc cgcctcctgc ctccaccaat cgccagacag
3121 gaaggcagcc taccccgctg tctccacctt tgagaaacac tcatcctcag gccatgcagt
3181 gg
```

(SEQ ID NO:195)

FIG. 40

1 catgctcatt tgaaagctta tgcaaaaatt aacgaggaat cactggatag ggctaggaga
61 ttgctttggt ggcattacaa ctgtttactg tggggagaag ctcaagttac taactatatt
121 tctcgcttgc gtacttggtt gtcaactcct gagaaatata gaggtagaga tgccccgacc
181 attgaagcaa tcactagacc aatccaggtg gctcagggag gcagaaaaac aactacgggt
241 actagaaaac ctcgtggact cgaacctaga agaagaaaag ttaaaaccac agttgtctat
301 gggagaagac gttcaaagtc ccgggaaagg agagccccta catcccaacg tgcgggctcc
361 cctctcccac gtagttcgag cagccaccat agatctccct cgcctaggaa ataaattacc
421 tgctaggcat cacttaggta aattgtcagg actatatcaa atgaagggct gtacttttaa
481 cccagaatgg aaagtaccag atatttcgga tactcatttt aatttagatg tagtgaatga
541 gtgcccttcc cgaaattgga aatatttgac tccagccaaa ttctggccca agagcatttc
601 ctactttcct gtccaggtag gggttaaacc aaagtatcct gacaatgtga tgcaacatga
661 atcaatagta ggtaaatatt taaccaggct ctatgaagca ggaatccttt ataagcggat
721 atctaaacat ttggtaacat ttaaaggtca gccttataat tgggaacagc aacaccttgt
781 caatcaacat cacatttatg atggggcaac atccagcaaa atcaatggac gtcagacgga
841 tagaaggagg agaaatactg ttaaaccaac ttgccggaag gatgatccca aaagggactt
901 tgacatggtc aggcaagttt ccaacgctag atcacgtgtt agaccatgtg caaacaatgg
961 aggagataaa caccctccag aatcagggag cttggcctgc tggggcggga aggagagtag
1021 gattatcaaa tccgactcct caagagattc ctcagcccca gtggactccc gaggaagacc
1081 aaaaagcacg cgaagctttt cgccgttatc aagaagaaag accaccggaa accaccacca
1141 ttcctccgtc ttcccctcct cagtggaagc tacaacccgg ggacgatcca ctcctgggaa
1201 atcagtctct cctcgagact catccgctat accagtcaga accagcggtg ccagtgataa
1261 aaactccccc cttgaagaag aaaatgtctg gtaccttcgg gggaatacta gctggcctaa
1321 tcggattact ggtaagcttt ttcttgttga taaaaattct agaaatactg aggaggctag
1381 attggtggtg gatttctctc agttctccaa agggaaaaat gcaatgcgct ttccaagata
1441 ctggagccca aatctctcca cattacgtag gatcctgccc gtggggatgc ccaggatttc
1501 tttggaccta tctcaggctt tttatcatct tcctcttaat cctgctagta gcagcaggct
1561 tgctgtatct gacggacaac gggtctacta ttttaggaaa gctccaatgg gcgtcggtct
1621 cagccctttt ctcctccatc tcttcactac tgccctcgga tccgaaatct ctcgtcgctt
1681 taacgtttgg actttcactt atatggatga cttcctcctc tgccacccaa acgctcgtca
1741 ccttaacgca attagccacg ctgtctgctc ttttttacaa gagttaggaa taagaataaa
1801 ctttgacaaa accacgcctt ctccggtgaa tgaaataaga ttcctcggtt accagattga
1861 tgaaaatttc atgaagattg aagaaagcag atggaaagaa ttaaggactg taatcaagaa
1921 aataaaagta ggagaatggt atgactggaa atgtattcaa agatttgtgg ggcatttgaa
1981 ttttgtcttg ccttttacta aaggtaatat tgaaatgtta aaaccaatgt atgctgctat
2041 tactaaccaa gtaaacttta gcttctcttc atcctatagg actttgttat ataaactaac
2101 aatgggtgtg tgtaaattaa gaataaagcc aaagtcctct gtacctttgc cacgtgtagc
2161 tacagatgct accccaacac atggcgcaat atcccatatc accggcggga gcgcagtgtt
2221 tgctttttca aaggtcagag atatacatgt tcaggaacta ttgatgtctt gtttagccaa
2281 gataatgatt aaaccgcgct gtctcttatc tgattcaact tttgtttgcc ataagcgtta
2341 tcagacgtta ccatggcatt ttgctatgtt ggccaaacaa ttgctcaaac ctatacaatt
2401 gtactttgtc ccgagcaaat acaatcctgc tgacggccca tccaggcaca aacctcctga
2461 ttggacggct tttccataca cccctctctc gaaagcaata tatattccac ataggctatg
2521 tggaacttaa gaattacacc cctctccttc ggagctgctt gccaaggtat ctttacgtct
2581 acattgctgt tgtcgtgtgt gactgtacct ttggtatgta ccattgttta tgattcttgc
2641 ttatatatgg atatcaatgc ttctagagcc ttagccaatg tgtatgatct gccagatgat
2701 ttctttccaa aaatagatga tcttgttaga gatgctaaag acgctttaga gccttattgg
2761 aaatcagatt caataaagaa acatgttttg attgcaactc actttgtgga tcttattgaa
2821 gacttttggc agactacaca gggtatgcat gaaatagccg aatcattaag agctgttata
2881 cctcccacta ctactcctgt tccaccgggt tatcttattc agcacgaaga agctgaagag
2941 ataccttttgg gagatttatt taaacaccaa gaagaaagga tagtgagctt tcaacctgac
3001 tatccgatta cggctagaat t (SEQ ID NO:196)

FIG. 41

5'
caactagtcaaaagtgaactggaggagaagaaatctgaacttcgtcataaattgaaatatgtgcctcatgaatatattgaattaattg
aaattgccagaaattccactcaggatagaattcttgaaatgaaggtaatggaatttttatgaaagtttatggatatagaggtaaacat
ttgggtggatcaaggaaaccggacggagcaatttatactgtcggatctcctattgattacggtgtgatcgtggatactaaagcttat
agcggaggttataatctgccaattggccaagcagatgaaatgcaacgatatgtcgaagaaaatcaaacacgaaacaaacatatc
aaccctaatgaatggtggaaagtctatccatcttctgtaacggaatttaagtttttatttgtgagtggtcactttaaaggaaactacaaa
gctcagcttacacgattaaatcatatcactaattgtaatggagctgttcttagtgtagaagagcttttaattggtggagaaatgattaa
agccggcacattaaccttagaggaagtgagacggaaatttaataacggcgagataaacttt 3' (SEQ ID NO:197)

FIG. 42A

QLVKSELEEKKSELRHKLKYVPHEYIELIEIARNSTQDRILEMKVMEFFMKVYGYRGKHL
GGSRKPDGAIYTVGSPIDYGVIVDTKAYSGGYNLPIGQADEMQRYVEENQTRNKHINPNE
WWKVYPSSVTEFKFLFVSGHFKGNYKAQLTRLNHITNCNGAVLSVEELLIGGEMIKAGTL
TLEEVRRKFNNGEINF (SEQ ID NO:198)

FIG. 42B

5'
caactagtcaaaagtgaactggaggagaagaaatctgaacttcgtcataaattgaaatatgtgcctcatgaatatattgaattaattg
aaattgccagaaattccactcaggatagaattcttgaaatgaaggtaatggaatttttatgaaagtttatggatatagaggtaaacat
ttgggtggatcaaggaaaccggacggagcaatttatactgtcggatctcctattgattacggtgtgatcgtggatactaaagcttat
agcggaggttataatctgccaattggccaagcagatgaaatgcaacgatatgtcgaagaaaatcaaacacgaaacaaacatatc
aaccctaatgaatggtggaaagtctatccatcttctgtaacggaatttaagtttttatttgtgagtggtcactttaaaggaaactacaaa
gctcagcttacacgattaaatcatatcactaattgtaatggagctgttcttagtgtagaagagcttttaattggtggagaaatgattaa
agccggcacattaaccttagaggaagtgagacggaaatttaataacggcgagataaacttttaa 3' (SEQ ID NO:199)

FIG. 42C

QLVKSELEEKKSELRHKLKYVPHEYIELIEIARNSTQDRILEMKVMEFFMKVYGYRGKHLGGSRKPDGAIYTVGSPIDY
GVIVDTKAYSGGYNLPIGQADEMQRYVEENQTRNKHINPNEWWKVYPSSVTEFKFLFVSGHFKGNYKAQLTRLNHITNC
NGAVLSVEELLIGGEMIKAGTLTLEEVRRKFNNGEINF (SEQ ID NO:200)

FIG. 42D

5'
CTCGAGGGTGATATCTTGGAACCCGGTGAAAAACCATACAAATGTCCGGAATGCGGAAAATCCTTCAGTAGGAACGACA
CCCTGACTGAACATCAGAGAACACACACCGGCGAAAAGCCATACAAGTGTCCCGAGTGTGGAAAATCCTTTTCCACAAA
AAATTCCCTGACTGAGCACCAGCGGACGCATACAGGGGAGAAACCATACAAATGCCCAGAGTGTGGGAAGTCATTTTCC
AGGTCTGACCATCTGACCAACCATCAAAGGACCCACACCGGCAAAAAGACAAGCGATATCGGTACTAGTcaactagtcaa
aagtgaactggaggagaagaaatctgaacttcgtcataaattgaaatatgtgcctcatgaatatattgaattaattgaaattgccaga
aattccactcaggatagaattcttgaaatgaaggtaatggaatttttttatgaaagtttatggatatagaggtaaacatttgggtggatc
aaggaaaccggacggagcaatttatactgtcggatctcctattgattacggtgtgatcgtggatactaaagcttatagcggaggtta
taatctgccaattggccaagcagatgaaatgcaacgatatgtcgaagaaaatcaaacacgaaacaaacatatcaaccctaatgaa
tggtggaaagtctatccatcttctgtaacggaatttaagtttttatttgtgagtggtcactttaaaggaaactacaaagctcagcttaca
cgattaaatcatatcactaattgtaatggagctgttcttagtgtagaagagcttttaattggtggagaaatgattaaagccggcacatt
aaccttagaggaagtgagacggaaatttaataacggcgagataaacttttaa 3' (SEQ ID NO:201)

FIG. 42E

LEPGEKPYKCPECGKSFSRNDTLTEHQRTHTGEKPYKCPECGKSFSTKNSLTE
HQRTHTGEKPYKCPECGKSFSRSDHLTNHQRTHTGKKTSQLVKSELEEKKSELRHKLKYVPHEYIELIEIARNSTQDRI
LEMKVMEFFMKVYGYRGKHLGGSRKPDGAIYTVGSPIDYGVIVDTKAYSGGYNLPIGQADEMQRYVEENQTRNKHINPN
EWWKVYPSSVTEFKFLFVSGHFKGNYKAQLTRLNHITNCNGAVLSVEELLIGGEMIKAGTLTLEEVRRKFNNGEINF
(SEQ ID NO:202)

FIG. 42F

```
atgctttctg aaaacacgac tattctgatg gctaacggtg aaattaaaga catcgcaaac gtcacggcta
actcttacgt tatgtgcgca gatggctccg ctgcccgcgt cataaatgtc acacagggct atcagaaaat
ctataatata cagcaaaaaa ccaaacacag agcttttgaa ggtgaacctg gtaggttaga tcccaggcgt
agaacagttt atcagcgtct tgcattacaa tgtactgcag gtcataaatt gtcagtcagg gtccctacca
aaccactgtt ggaaaaaagt ggtagaaatg ccaccaaata taaagtgaga tggagaaatc tgcagcaatg
tcagacgctt gatggtagga taataataat tccaaaaaac catcataaga cattcccaat gacagttgaa
ggtgagtttg ccgcaaaacg cttcatagaa gaaatggagc gctctaaagg agaatatttc aactttgaca
ttgaagttag agatttggat tatcttgatg ctcaattgag aatttctagc tgcataagat ttggtccagt
actcgcagga aatggtgttt tatctaaatt tctcactgga cgtagtgacc ttgtaactcc tgctgtaaaa
agtatggctt ggatgcttgg tctgtggtta ggtgacagta caacaaaaga gccagaaatc tcagtagata
gcttggatcc taagctaatg gagagtttaa gagaaaatgc gaaaatctgg ggtctctacc ttacggtttg
tgacgatcac gttccgctac gtgccaaaca tgtaaggctt cattatggag atggtccaga tgaaaacagg
aagacaagga atttgaggaa aaataatcca ttctggaaag ctgtcacaat tttaaagttt aaaagggatc
ttgatggaga gaagcaaatc cctgaattta tgtacggcga gcatatagaa gttcgtgaag cattcttagc
cggcttgatc gactcagatg ggtacgttgt gaaaaagggc gaaggccctg aatcttataa aatagcaatt
caaactgttt attcatccat tatggacgga attgtccata tttca (SEQ ID NO:203)
```

FIG. 43A

```
MLSENTTILM ANGEIKDIAN VTANSYVMCA DGSAARVINV TQGYQKIYNI QQKTKHRAFE GEPGRLDPRR
RTVYQRLALQ CTAGHKLSVR VPTKPLLEKS GRNATKYKVR WRNLQQCQTL DGRIIIIPKN HHKTFPMTVE
GEFAAKRFIE EMERSKGEYF NFDIEVRDLD YLDAQLRISS CIRFGPVLAG NGVLSKFLTG RSDLVTPAVK
SMAWMLGLWL GDSTTKEPEI SVDSLDPKLM ESLRENAKIW GLYLTVCDDH VPLRAKHVRL HYGDGPDENR
KTRNLRKNNP FWKAVTILKF KRDLDGEKQI PEFMYGEHIE VREAFLAGLI DSDGYVVKKG EGPESYKIAI
QTVYSSIMDG IVHIS (SEQ ID NO:204)
```

FIG. 43B

```
atgctttctg aaaacacgac tattctgatg gctaacggtg aaattaaaga catcgcaaac gtcacggcta
actcttacgt tatgtgcgca gatggctccg ctgcccgcgt cataaatgtc acacagggct atcagaaaat
ctataatata cagcaaaaaa ccaaacacag agcttttgaa ggtgaacctg gtaggttaga tcccaggcgt
agaacagttt atcagcgtct tgcattacaa tgtactgcag gtcataaatt gtcagtcagg gtccctacca
aaccactgtt ggaaaaaagt ggtagaaatg ccaccaaata taaagtgaga tggagaaatc tgcagcaatg
tcagacgctt gatggtagga taataataat tccaaaaaac catcataaga cattcccaat gacagttgaa
ggtgagtttg ccgcaaaacg cttcatagaa gaaatggagc gctctaaagg agaatatttc aactttgaca
ttgaagttag agatttggat tatcttgatg ctcaattgag aatttctagc tgcataagat ttggtccagt
actcgcagga aatggtgttt tatctaaatt tctcactgga cgtagtgacc ttgtaactcc tgctgtaaaa
agtatggctt ggatgcttgg tctgtggtta ggtgacagta caacaaaaga gccagaaatc tcagtagata
gcttggatcc taagctaatg gagagtttaa gagaaaatgc gaaaatctgg ggtctctacc ttacggtttg
tgacgatcac gttccgctac gtgccaaaca tgtaaggctt cattatggag atggtccaga tgaaaacagg
aagacaagga atttgaggaa aaataatcca ttctggaaag ctgtcacaat tttaaagttt aaaagggatc
ttgatggaga gaagcaaatc cctgaattta tgtacggcga gcatatagaa gttcgtgaag cattcttagc
cggcttgatc gactcagatg ggtacgttgt gaaaaagggc gaaggccctg aatcttataa aatagcaatt
caaactgttt attcatccat tatggacgga attgtccata tttca-3' (SEQ ID NO:205)
```

FIG. 43C

MLSENTTILM ANGEIKDIAN VTANSYVMCA DGSAARVINV TQGYQKIYNI QQKTKHRAFE GEPGRLDPRR
RTVYQRLALQ CTAGHKLSVR VPTKPLLEKS GRNATKYKVR WRNLQQCQTL DGRIIIIPKN HHKTFPMTVE
GEFAAKRFIE EMERSKGEYF NFDIEVRDLD YLDAQLRISS CIRFGPVLAG NGVLSKFLTG RSDLVTPAVK
SMAWMLGLWL GDSTTKEPEI SVDSLDPKLM ESLRENAKIW GLYLTVCDDH VPLRAKHVRL HYGDGPDENR
KTRNLRKNNP FWKAVTILKF KRDLDGEKQI PEFMYGEHIE VREAFLAGLI DSDGYVVKKG EGPESYKIAI
QTVYSSIMDG IVHIS- (SEQ ID NO:206)

FIG. 43D atgctttctg aaaacacgac tattctgatg gctaacggtg aaattaaaga catcgcaaac gtcacggcta
actcttacgt tatgtgcgca gatggctccg ctgcccgcgt cataaatgtc acacagggct atcagaaaat
ctataatata cagcaaaaaa ccaaacacag agcttttgaa ggtgaacctg gtaggttaga tcccaggcgt
agaacagttt atcagcgtct tgcattacaa tgtactgcag gtcataaatt gtcagtcagg gtccctacca
aaccactgtt ggaaaaaagt ggtagaaatg ccaccaaata taaagtgaga tggagaaatc tgcagcaatg
tcagacgctt gatggtagga taataataat tccaaaaaac catcataaga cattcccaat gacagttgaa
ggtgagtttg ccgcaaaacg cttcatagaa gaaatggagc gctctaaagg agaatatttc aactttgaca
ttgaagttag agatttggat tatcttgatg ctcaattgag aatttctagc tgcataagat ttggtccagt
actcgcagga aatggtgttt tatctaaatt tctcactgga cgtagtgacc ttgtaactcc tgctgtaaaa
agtatggctt ggatgcttgg tctgtggtta ggtgacagta caacaaaaga gccagaaatc tcagtagata
gcttggatcc taagctaatg gagagtttaa gagaaaatgc gaaaatctgg ggtctctacc ttacggtttg
tgacgatcac gttccgctac gtgccaaaca tgtaaggctt cattatggag atggtccaga tgaaaacagg
aagacaagga atttgaggaa aaataatcca ttctggaaag ctgtcacaat tttaaagttt aaaagggatc
ttgatggaga gaagcaaatc cctgaattta tgtacggcga gcatatagaa gttcgtgaag cattcttagc
cggcttgatc gactcagatg ggtacgttgt gaaaaagggc gaaggccctg aatcttataa aatagcaatt
caaactgttt attcatccat tatggacgga attgtccata tttcaCTCGA GGGTGATATC CTGGAGCCCG
GCGAGAAACC GTATAAATGC CCCGAGTGCG GCAAGTCCTT TAGCCAGAGG GCGCACCTGG AACGGCACCA
AAGAACACAT ACTGGGGAAA AGCCATACAA GTGCCCTGAG TGCGGCAAGT CATTCTCTTC ACCCGCCGAC
CTGACAAGGC ACCAGAGAAC TCACACTGGC GAAAAGCCAT ACAAGTGCCC TGAATGCGGG AAATCCTTTT
CCCGGGCTGA CAATCTGACC GAGCATCAGC GCACCCACAC AGGCGAGAAG CCTTACAAGT GCCCGGAGTG
TGGCAAGAGC TTTTCACACA CGGGGCACCT GTTGGAACAT CAAAGGACTC ACACTGGCGA AAAGCCCTAT
AAATGTCCGG AGTGTGGGAA GAGTTTTAGC ACCACCGGGA ATCTGACCGT ACACCAACGG ACACACACAG
GCGAGAAACC CTACAAGTGC CCCGAATGTG GCAAATCTTT CAGCGATAAG AAAGATTTGA CAAGGCATCA
GAGAACACAC ACTGGTAAGA AGACGTCTGA TATCGGTACT AGT (SEQ ID NO:207)

FIG. 43E

MLSENTTILM ANGEIKDIAN VTANSYVMCA DGSAARVINV TQGYQKIYNI QQKTKHRAFE
GEPGRLDPRR RTVYQRLALQ CTAGHKLSVR VPTKPLLEKS GRNATKYKVR WRNLQQCQTL
DGRIIIIPKN HHKTFPMTVE GEFAAKRFIE EMERSKGEYF NFDIEVRDLD YLDAQLRISS
CIRFGPVLAG NGVLSKFLTG RSDLVTPAVK SMAWMLGLWL GDSTTKEPEI SVDSLDPKLM
ESLRENAKIW GLYLTVCDDH VPLRAKHVRL HYGDGPDENR KTRNLRKNNP FWKAVTILKF
KRDLDGEKQI PEFMYGEHIE VREAFLAGLI DSDGYVVKKG EGPESYKIAI QTVYSSIMDG
IVHISLEPGE KPYKCPECGK SFSQRAHLER HQRTHTGEKP YKCPECGKSF SSPADLTRHQ
RTHTGEKPYK CPECGKSFSR ADNLTEHQRT HTGEKPYKCP ECGKSFSHTG HLLEHQRTHT
GEKPYKCPEC GKSFSTTGNL TVHQRTHTGE KPYKCPECGK SFSDKKDLTR HQRTHTGKKT S
(SEQ ID NO:208)

FIG. 43F 1 ttccacaacc tttcaccaaa ctctgcaaga tcccagagtg agaggcctgt atttccctgc
61 tggtggctcc agttcaggaa cagtaaaccc tgttccgact actgcctctc ccttatcgtc
121 aatcttctcg aggattgggg accctgcgct gaacatggag aacatcacat caggattcct
181 aggacccctt ctcgtgttac aggcggggtt tttcttgttg acaagaatcc tcacaatacc
241 gcagagtcta gactcgtggt ggacttctct caattttcta gggggaacta ccgtgtgtct
301 tggccaaaat tcgcagtccc caacctccaa tcactcacca acctcctgtc ctccaacttg
361 tcctggttat cgctggatgt gtctgcggcg ttttatcatc ttcctcttca tcctgctgct
421 atgcctcatc ttcttgttgg ttcttctgga ctatcaaggt atgttgcccg tttgtcctct
481 aattccagga tcctcaacca ccagcacggg accatgccga acctgcatga ctactgctca
541 aggaacctct atgtatccct cctgttgctg taccaaacct tcggacggaa attgcacctg
601 tattcccatc ccatcatcct gggctttcgg aaaattccta tgggagtggg cctcagcccg
661 tttctcctgg ctcagtttac tagtgccatt tgttcagtgg ttcgtagggc tttcccccac
721 tgtttggctt tcagttatat ggatgatgtg gtattggggg ccaagtctgt acagcatctt
781 gagtcccttt ttaccgctgt taccaatttt cttttgtctt tgggtataca tttaaaccct
841 aacaaaacaa agagatgggg ttactctctg aattttatgg gttatgtcat tggaagttat
901 gggtccttgc cacaagaaca catcatacaa aaaatcaaag aatgttttag aaaacttcct
961 attaacaggc ctattgattg gaaagtatgt caaagaattg tgggtctttt gggttttgct
1021 gcccccttta cacaatgtgg ttatcctgcg ttaatgccct tgtatgcatg tattcaatct
1081 aagcaggctt tcactttctc gccaacttac aaggcctttc tgtgtaaaca atacctgaac
1141 ctttaccccg ttgcccggca acggccaggt ctgtgccaag tgtttgctga cgcaaccccc
1201 actggctggg gcttggtcat gggccatcag cgcatgcgtg gaacctttc ggctcctctg
1261 ccgatccata ctgcggaact cctagccgct tgttttgctc gcagcaggtc tggagcaaac
1321 attatcggga ctgataactc tgttgtcctc tcccgcaaat atacatcgta tccatggctg
1381 ctaggctgtg ctgccaactg gatcctgcgc gggacgtcct ttgtttacgt cccgtcggcg
1441 ctgaatcctg cggacgaccc ttctcggggt cgcttgggac tctctcgtcc tcttctccgt
1501 ctgccgttcc gaccgaccac ggggcgcacc tctctttacg cggactcccc gtctgtgcct
1561 tctcatctgc cggaccgtgt gcacttcgct tcacctctgc acgtcgcatg gagaccaccg
1621 tgaacgccca ccggatgttg cccaaggtct tacataagag gactcttgga ctctctgcaa
1681 tgtcaacgac cgaccttgag gcatacttca aagactgttt gtttaaagac tgggaggagt
1741 tgggggagga gatgaggtta aaggtctttg tactaagagg ctgtatgcat aaattggtct
1801 gcgcaccagc accatgcaac tttttcacct ctgcctaatc atctcttgtt catgtcctac
1861 tgttcaagcc tccaagctgt gccttgggtg gctttggggc atggacatcg acccttataa
1921 agaatttgga gctactgtgg agttactctc gtttttgcct tctgacttct ttccttcagt
1981 acgagatctt ctagataccg cctcagctct gtatcgggaa gccttagagt ctcctgagca
2041 ttgttcacct caccatactg cactcaggca agcaattctt tgctgggggg aactaatgac
2101 tctagctacc tgggtgggtg ttaatttgga agatccagca tctagagacc tagtagtcag
2161 ttatgtcaac actaatatgg gcctaaagtt caggcaactc ttgtggtttc acatttcttg
2221 tctcactttt ggaagagaaa ccgttataga gtatttggtg tctttcggag tgtggattcg
2281 cactcctcca gcttatagac caccaaatgc ccctatccta tcaacacttc cggaaactac
2341 tgttgttaga cgacgaggca ggtcccctag aagaagaact ccctcgcctc gcagacgaag
2401 gtctcaatcg ccgcgtcgca gaagatctca atctcgggaa tctcaatgtt agtattcctt
2461 ggactcataa ggtggggaac tttactggtc tttattcttc tactgtacct gtctttaatc
2521 ctcattggaa aacaccatct ttcctaata tacatttaca tcaagacatc atcaaaaaat
2581 gtgaacagtt tgtaggccca cttacagtta atgagaaaag aagattgcaa ttgattatgc
2641 ctgctaggtt ttatccaaag gttaccaaat atttaccatt ggataagggt attaaacctt
2701 attatccaca acatctagtt aatcattact tcaaaactag acactattta cacactctat
2761 ggaaggcggg tatattatat aagagagaaa caacacatag cgcctcattt tgtgggtcac
2821 catattcttg ggaacaagat ctacagcatg gggcagaatc tttccaccag caatcctctg
2881 ggattctttc ccgaccacca gttggatcca gccttcagag caaacaccgc aaatccagat
2941 tgggacttca atcccaacaa ggacacctgg ccagacgcca acaaggtagg agctggagca
3001 ttcgggctgg gtttcacccc accgcacgga ggccttttgg ggtggagccc tcaggctcag
3061 ggcatactac aaactttgcc agcaaatccg cctcctgcct ccaccaatcg ccagacagga
3121 aggcagccta ccccgctgtc tccacctttg agaaacactc atcctcaggc catgcagtgg
3181 aa (SEQ ID NO:209)

FIG. 44

```
   1 ctccaccaca ttccaccaag ctctgctaga tcccagagtg aggggcctat attttcctgc
  61 tggtggctcc agttccggaa cagtaaaccc tgttccgact actgcctcac ccatatcgtc
 121 aatcttctcg aggactgggg accctgcaca gaacatggag aacacaacat caggattcct
 181 aggacccctg ctcgtgttac aggcggggtt tttcttgttg acaaaaatcc tcacaatacc
 241 acagagtcta gactcgtggt ggacttctct caattttcta gggggagcac ccacgtgtcc
 301 tggccaaaat tcgcagtccc caacctccaa tcactcacca acctcttgtc ctccaatttg
 361 tcctggctat cgctggatgt gtctgcggcg ttttatcata ttcctcttca tcctgctgct
 421 atgcctcatc ttcttgttgg ttcttctgga ctaccaaggt atgttgcccg tttgtcctct
 481 acttccagga acaacaacta ccagcacggg accatgcaag acctgcacga ttcctgctca
 541 aggaacctct atgtttccct cttgttgctg tacaaaacct tcggacggaa actgcacttg
 601 tattcccatc ccatcatcct gggctttcgc aagattccta tgggagtggg cctcagtccg
 661 tttctcctgg ctcagtttac tagtgccatt tgttcagtgg ttcgtagggc tttcccccac
 721 tgtttggctt tcagttatat ggatgatgtg gtattggggg ccaagtctgt acaacatctt
 781 gagtcccttt ttacctctat taccaatttt cttttgtctt tgggtataca tttgaatcct
 841 aataaaacca aacgttgggg ctactccctt aacttcatgg gatatgtaat tggaagttgg
 901 ggtactttac cacaggaaca tattgtacgg aaactcaagc aatgttttcg aaaactgcct
 961 gtaaatagac ctattgattg gaaagtatgt caaagaattg tgggtctttt gggctttgct
1021 gcccctttta cacaatgtgg ctatcctgcc ttgatgcctt tatatgcatg tatacactct
1081 aagcaggctt tcactttctc gccaacttac aaggcctttc tgtgtaaaca atatctgcac
1141 ctttaccccg ttgcccggca acggtcaggt ctctgccaag tgtttgctga cgcaaccccc
1201 actggatggg gcttggccat aggccatcgg cgcatgcgcg gaacctttgt ggctcctctg
1261 ccgatccata ctgcggaact cctagcagct tgttttgctc gcagccggtc tggagcaaaa
1321 cttatcggga ctgacaactc tgttgtcctc tctcggaaat acacctcctt cccatggctg
1381 ctcgggtgtg ctgccaactg gatccttcgc gggacgtcct ttgtctacgt cccgtcggcg
1441 ctgaatcccg cggacgaccc gtctcggggc cgtttggggc tctatcgtcc ccttcttcat
1501 ctgccgttcc ggccgaccac ggggcgcacc tctctttacg cggtctcccc gtctgtgcct
1561 tctcatctgc cggaccgtgt gcacttcgct tcacctctgc acgtcgcatg gagaccaccg
1621 tgaacgccca ccaggtcttg cccaaggtct tacataagag gactcttgga ctctcatcaa
1681 tgtcaacgac cgaccttgag gcatacttca aagactgttt gtttaaggac tgggaggagt
1741 tgggggagga gattaggtta aaggtctttg tactaggagg ctgtaggcat aaattggtct
1801 gttcaccagc accatgcaac tttttcacct ctgcctaatc atctcatgtt catgtcctac
1861 tgttcaagcc tccaagctgt gccttgggtg gctttggggc atggacattg acccgtataa
1921 agaatttgga gcttctgtgg agttactctc tttttgcct tctgacttct ttccttctat
1981 tcgagatctc ctcgacaccg cctctgctct gtatcgggag gccttagagt ctccggaaca
2041 ttgttcacct caccatacag cactcaggca agctattctg tgttggggtg agttgatgaa
2101 tctggccacc tgggtgggaa gtaatttgga agacccagca tccagggaat tagtagtcag
2161 ctatgtcaat gttaatatgg gcctaaaaat cagacaacta ttgtggtttc acatttcctg
2221 tcttactttt ggaagagaaa ctgttcttga gtatttggta tcttttggag tgtggattcg
2281 cactcctcca gcttacagac caccaaatgc ccctatctta tcaacacttc cggaaactac
2341 tgttgttaga cgacgaggca ggtcccctag aagaagaact ccctcgcctc gcagacgaag
2401 gtctcaatcg ccgcgtcgca gaagatctca atctcgggaa tctcaatgtt agtatccctt
2461 ggactcataa ggtgggaaac tttactgggc tttattcttc tactgtacct gtctttaatc
2521 ctgagtggca aactccctcc tttcctaaca ttcatttaca ggaggacatt attaatagat
2581 gtgaacaata tgtgggccct cttacaacta atgaaaaaag gagattaaaa ttaattatgc
2641 ctgctaggtt ttatcctaac cttaccaaat acttgccctt ggataaaggc attaaacctt
2701 attatcctga acatgcagtt aatcattact tcaaaactag gcattattta catactctgt
2761 ggaaggccgg cattctatat aagagagaaa ctacacgcag cgcttcattt tgtgggtcac
2821 catattcttg ggaacaagag ctacagcatg ggaggttggt cttccaaacc tcgacaaggc
2881 atggggacga atctttctgt tcccaatcct ctgggatttt ttcccgatca ccagttggac
2941 cctgcgttcg gagccaactc aaacaatcca gattgggact tcaaccccaa caaggatcac
3001 tggccagagg caaatcaggt aggagcggga gcattcgggc cagggttcac ccccaccacac
3061 ggcggtcttt tggggtggag ccctcaggct cagggcatat tgaccacagt gccagcagcg
3121 cctcctcctg cctccaccaa tcggcagtca ggaagacagc ctactcccat ctctccacct
3181 ctaagagaca gtcatcctca ggccatgcag tggaa (SEQ ID NO:210)
```

FIG. 45

```
   1 ctccaccacg ttccaccaaa ctcttcaaga tcccagagtc agggctctgt actttcctgc
  61 tggtggctcc agttcaggaa cagtaaaccc tgttcagaac actgcctctt ccatatcgtc
 121 aatcttatcg acgactgggg accctgtgcc gaacatggag aacatcgcat caggactcct
 181 aggacccctg ctcgtgttac aggcggggtt tttctcgttg acaaaaatcc tcacaatacc
 241 acagagtcta gactcgtggt ggacttctct caattttcta gggggaacac ccgtgtgtct
 301 tggccaaaat tcgcagtccc aaatctccag tcactcacca acttgttgtc ctccgatttg
 361 tcctggttat cgctggatgt gtctgcggcg ttttatcatc ttcctctgca tcctgctgct
 421 atgcctcatc ttcttgttgg ttcttctgga ctatcaaggt atgttgcccg tttgtcctct
 481 aattccagga tcatcaacca ccagcacagg accatgcaaa acctgcacga ctcctgctca
 541 aggaacctct atgtttccct catgttgctg tataaaacct acggacggaa actgcacctg
 601 tattcccatc ccatcatctt gggctttcgc aaaataccta tgggagtggg cctcagtccg
 661 tttctcttgg ctcagtttac tagtgccatt tgttcagtgg ttcgtagggc tttcccccac
 721 tgtctggctt tcagttatat ggatgatgtg gttttggggg ccaagtctgt acaacatctt
 781 gagtcccttt atgccgctgt taccaatttt cttttgtctt tgggcataca tttaaaccct
 841 cagaaaacaa aaagatgggg ctactccctt aacttcatgg ggtatgtaat tggaagttgg
 901 gggaccttac cccaagaaca tattgtgttg aaaatcaaac aatgttttag gaaacttcct
 961 gtaaacaggc ctattgattg gaaagtatgt caacgaattg tgggtctttt gggatttgct
1021 gctcctttca cacaatgtgg atatcctgct ttaatgcctt tatatgcatg tatacaagct
1081 aaacaggctt ttactttttc gccaacgtat aaggcctttc tccacaaaca atatctgaac
1141 ctttaccccg ttgctcggca acggccaggt ctgtgccaag tgtttgctga cgcaaccccc
1201 actggctggg gcttggccat aggccatcag cgcatgcgtg ggacctttgt gtctcctctg
1261 ccgatccata ctgcggaact cctagccgct tgttttgctc gcagcaggtc tggagcaaaa
1321 cttatcggga ctgacaattc tgtcgtcctt tcccgcaaat atacatcgtt tccatggctg
1381 ctaggctgtg ctgccaactg gatcctgcgc gggacgtcct ttgtctacgt cccgtcggcg
1441 ctgaatcccg cggacgaccc ctcccggggc cgcttggggc tctaccgccc gcttctccgc
1501 ctgccgtacc gtccgaccac ggggcgcacc tctctttacg cggactcccc gtctgtgcct
1561 tctcatctgc cggaccgtgt gcacttcgct tcacctctgc acgtcgcatg gagaccaccg
1621 tgaacgccca tcggaacctg cccaaggtct tgcataagag gactcttgga ctttcagcaa
1681 tgtcaacgac cgaccttgag gcatacttca aagactgtgt gtttactgag tgggaggagt
1741 tgggggagga gatcaggtta aaggtctttg tactaggagg ctgtaggcat aaattggtct
1801 gttcaccagc accatgcaac tttttcacct ctgcctaatc atctcatgtt catgtcctac
1861 tgttcaagcc tccaagctgt gccttgggtg gctttggggc atggacattg acacctataa
1921 agaatttgga gcttctgtgg agttactctc ttttttgcct tctgacttct ttccttctat
1981 tcgagatctt ctcgacaccg cctctgctct gtatcgggag gccttagagt ctccggaaca
2041 ttgttcacct caccatacgg cactcaggca agctattgtg tgttggggtg agttgatgaa
2101 tctagccacc tgggtgggaa gtaatttgga agacccagcc tcccgggaat tagtagtcag
2161 ttatgtcaat gttaatatgg gcctaaaaat cagacaacta ttgtggtttc acatttcctg
2221 tcttactttt ggaagagaaa ctgttcttga atatttggtg tcttttggag tgtggattcg
2281 cacacctcca gcatatagac caccaaatgc ccctatctta tcaacacttc cggaaactac
2341 tgttgttaga cgacgaggca ggtcccctag aagaagaact ccctcgcctc gcagacgaag
2401 gtctcaatcg ccgcgtcgca gaagatctca atctcgggaa tctaaatgtt agtattcctt
2461 ggactcataa ggtgggaaac tttacggggc tttattcttc tacggtacct agctttaatc
2521 ctcaatggca aactccttca tttcctgaca ttcatttgca ggaggacatc attgataagt
2581 gtaaacaatt tgtgggaccc cttacagtga atgaaaacag gagactaaaa ttgattatgc
2641 ctgctaggtt ctatcccaat gttactaaat atttgccctt agataaagga attaaacctt
2701 attatccaga gcatgtagtt aatcattact tccagacgag acattattta catactcttt
2761 ggaaggcggg tatcttatat aaaagagaga caacacgtag cgcctcattt tgcgggtcac
2821 catattcttg ggaacaagag ctacagcatg ggaggttggt cctccaaacc tcgaaaaggc
2881 atggggacaa atctttccgt ccccaatcct ctgggattct ttcccgatca ccagttggac
2941 cctgcattca aagccaactc cgacaatccc gattgggacc tcaacccaca caaggacaac
3001 tggccggact ccaacaaggt gggagtggga gcattcgggc cgggattcac tccaccccat
3061 gggggactgt tggggtggag ccctcaagct cagggcatac tcacaactgt gccaacagct
3121 cctcctcctg cctccaccaa tcggcagtta ggaaggaagc ctactcccct gtctccacct
3181 ctaagagaca ctcatcctca ggcaatgcag tggaa (SEQ ID NO:211)
```

FIG. 46

```
   1 ttccacaaca tttcaccaag ctctgcagga tcccagagta agaggcctgt attttcctgc
  61 tggtggctcc agttccggaa cagtgaaccc tgttccgact actgcctcac tcatctcgtc
 121 aatcttctcg aggattgggg accctgcacc gaacatggaa agcatcacat caggattcct
 181 aggacccctg ctcgtattac aggcggggtt tttcttgttg acaaaaatcc tcacaatacc
 241 gcagagtcta gactcgtggt ggacttctct caattttcta gggggagctc ccgtgtgtct
 301 tggccaaaat tcgcagtccc caacctccaa tcactcacca acctcttgtc ctccaatttg
 361 tcctggctat cgctggatgt gtctgcggcg ttttatcatc ttcctcttca tcctgctgct
 421 atgcctcatc ttcttgttgg ttcttctgga ctatcaaggt atgttgcccg tttgtcctct
 481 aattccagga tcatcaacca ccagtacggg accctgccga acctgcacga ctcttgctca
 541 aggaacctct atgtttccct catgttgctg ttcaaaacct tcggacggaa attgcacttg
 601 tattcccatc ccatcatcat gggctttcgg aaaattccta tgggagtggg cctcagcccg
 661 tttctcctgg ctcagtttac tagtgccatt tgttcagtgg ttcgccgggc tttcccccac
 721 tgtctggctt tcagttatat ggatgatgtg gtattggggg ccaagtctgt acaacatctt
 781 gagtcccttt atacctctgt taccaatttt cttttgtctt tgggtataca tttaaatccc
 841 aacaaaacaa aaagatgggg atattccctg aatttcatgg gttatgtaat tggaagttgg
 901 ggatcattac cacaggaaca catcataatg aaaatcaaag actgttttag aaaactcccc
 961 gttaaccggc ctattgattg gaaagtatgt caacgaattg tgggtctttt gggctttgct
1021 gcccctttta cacaatgtgg gtatcctgct ttaatgcctc tgtatgcgtg tattcaatct
1081 aagcaggctt tcactttctc gccaacttac aaggcctttc tgtgtaaaca atacctgaac
1141 ctttaccccg ttgcccggca acggccaggt ctgtgccaag tgtttgctga tgcaaccccc
1201 actggctggg gcttggccat aggccatcag cgcatgcgcg gaacctttat ggctcctctg
1261 ccgatccata ctgcggaact cctagccgct tgttttgctc gcagcaggtc tggagcgaaa
1321 cttatcggga cagataattc tgtcgttctc tcccggaaat atacatcctt tccatggctg
1381 ctaggctgtg ctgccaactg gatcctgcga gggacgtcct ttgtctacgt cccgtcagcg
1441 ctgaatcctg cggacgaccc gtctcggggt cgcttgggga tctatcgtcc ccttctccgt
1501 ctgccgttcc agccgtccac ggggcgcacc tctctttacg cggtctcccc gtctgtgcct
1561 tctcatctgc cggaccgtgt gcacttcgct tcacctctgc acgtcgcatg gagaccaccg
1621 tgaacgccca ccaaatcttg cccaaggtct tacataagag gactcttgga ctctctgcaa
1681 tgtcaacgac cgaccttgag gcatacttca aagactgttt gtttaaagac tgggaggagt
1741 tgggggagga gattagatta aaggtctttg tactaggagg ctgtaggcat aaattggtct
1801 gcgcaccagc accatgcaac tttttcacct ctgcctaatc atctcttgtt catgtcctac
1861 tgttcaagcc tccaagctgt gccttgggtg gctttggggc atggacattg acccttataa
1921 agaatttgga gctactgtgg agttactctc gtttttgcct tctgacttct ttccttcagt
1981 aagagatctt ctagataccg cctcagcttt gtatcgggat gccttagaat ctcctgagca
2041 ttgttcaccg catcacactg cactcaggca agccattctt tgctgggggg aactaatgac
2101 tctagctacc tgggtgggtg taaatttgga agatccagca tccagggacc tagtagtcag
2161 ttatgtcaat actaatatgg gcctaaagtt caggcaatta ttgtggtttc acatttcttg
2221 tctcactttt ggaagagaaa ccgtcataga gtatttggtg tcttttggag tgtggattcg
2281 cactcctcca gcttatagac caccaaatgc ccctatctta tcaacacttc cggagaatac
2341 tgttgttaga cgaagaggca ggtcccctag aagaagaact ccctcgcctc gcagacgaag
2401 atctcaatcg ccgcgtcgca gaagatctca atctccagct tcccaatgtt agtattcctt
2461 ggactcacaa ggtgggaaat tttacggggc tttactcttc tactatacct gtctttaatc
2521 ctaactggaa aactccatct tttcctgata ttcatttgca ccaggacatt attaacaaat
2581 gtgaacaatt tgtaggtcct ctaacagtaa atgaaaaacg aagattaaac ttagtcatgc
2641 ctgctagatt ttttcccatc tctacgaaat atttgcccct agagaaaggt ataaaacctt
2701 attatccaga taatgtagtt aatcattact tccaaaccag acactattta cacaccctat
2761 ggaaggcggg catcttatat aaaagagaaa ctacacgtag cgcctcattt tgtgggtcac
2821 cttattcttg ggaacaagag ctacatcatg ggctttcttt ggacggtccc tctcgaatgg
2881 gggaagaatc attccaccac caatcctctg ggattttttc ccgaccacca gttggatcca
2941 gcattcagag caaacaccag aaatccagat tgggaccaca atcccaacaa agaccactgg
3001 acggaagcca acaaggtagg agtgggagca ttcgggccgg ggttcactcc cccacacgga
3061 ggccttttgg ggtggagccc tcaggctcaa ggcatgctaa aaacattgcc agcagatccg
3121 cctcctgcct ccaccaatcg gcagtcagga aggcagccta ccccaatcac tccacctttg
3181 agagacactc atcctcaggc catgcagtgg aa (SEQ ID NO:212)
```

FIG. 47

```
   1 ctcaacccag ttccaccagg ctctgttaga tccgagggta agggctctgt attttcctgc
  61 tggtggctcc agttcaggga cacagaaccc tgttccgact attgcctctc tcacatcatc
 121 aatcttctcg aagactgggg gccctgctat gaacatggag aacatcacat caggactcct
 181 aggacccctg ctcgtgttac aggcggtgtg tttcttgttg acaaaaatcc tcacaatacc
 241 acagagtcta gactcgtggt ggacttctct caattttcta gggggactac ccgggtgtcc
 301 tggccaaaat tcgcagtccc caacctccaa tcacttacca acctcctgtc ctccaacttg
 361 tcctggctat cgttggatgt gtctgcggcg ttttatcatc ttcctcttca tcctgctgct
 421 atgcctcatc ttcttgttgg ttcttctgga ctatcaaggt atgttgcccg tttgtcctct
 481 acttccagga tccacaacca ccagcacggg accatgcaaa acctgcacaa ctcttgctca
 541 aggaacctct atgtttccct cctgttgctg ttccaaaccc tcggacggaa actgcacctg
 601 tattcccatc ccatcatctt gggctttagg aaaataccta tgggagtggg cctcagcccg
 661 tttctcctgg ctcagtttac tagtgcaatt tgttcagtgg tgcgtagggc tttcccccac
 721 tgtctggctt ttagttatat ggatgatctg gtattggggg ccaaatctgt gcagcatctt
 781 gagtcccttt ataccgctgt taccaatttt ttgttatctg tgggtatcca tttaaatact
 841 tctaaaacaa aaagatgggg ttacaaccta catttcatgg gttatgttat tggtagttgg
 901 ggaacgttac cccaagatca tattgtacac aaaatcaaag attgttttcg gaaacttcct
 961 gtaaatcgtc caattgattg gaaagtttgt cagcgcattg tgggtctttt gggctttgcg
1021 gcccctttca cccaatgtgg ttatcctgct ctcatgcctt tatatacctg tattactgct
1081 aaacaggctt ttgtcttttc gccaacttac aaggcctttc tctgtaaaca atacatgaac
1141 ctttaccccg ttgctcggca acggccaggc ctgtgccaag tgtttgctga cgcaaccccc
1201 actggttggg gcttggccat tggccatcag cgcatgcgtg gaacctttgt ggctcctctg
1261 ccgatccata ctgcggaact ccttgcagcc tgtttcgctc gcagccggtc tggagcgaac
1321 attatcggca cagacaactc tgttgtcctc tctaggaagt acacctcctt tccatggctg
1381 ctcggttgtg ctgccaactg gatcctgcgc gggacgtcct ttgtttacgt cccgtcggcg
1441 ctgaatcccg cggacgaccc ttcccggggt cgcttggggc tgtaccgccc ccttcttcgt
1501 ctgccgttcc agccgacgac gggtcgcacc tctctttacg cggactcccc gtctgttcct
1561 tctcatctgc cggaccgtgt gcacttcgct tcacctctgc acgtcgcatg gagaccaccg
1621 tgaacgcccc ctggaatctg ccaacagtct tacataagag gactcttgga ctttcaggac
1681 ggtcaatgac ctggatcgaa gaatacatca aagactgtgt atttaaggac tgggaggagc
1741 tgggggagga gatcaggtta aaggtctttg tactaggagg ctgtaggcat aaattggtct
1801 gttcaccagc accatgcaac tttttcacct ctgcctaatc atcttttgtt catgtcccac
1861 tgttcaagcc tccaagctgt gccttgggtg gctttggggc atggacattg acccttataa
1921 agaatttgga gcttctgtgg aattgctctc tttttgcct tctgatttct tcccgtctgt
1981 tcgggaccta ctcgacaccg cttcagccct ttaccgggat gctctagagt caccggaaca
2041 ttgcaccccc aatcataccg ctctcaggca agctattttg tgctggggtg agttaatgac
2101 tttggcttcc tgggtgggta ataatttgga agaccctgca gctagggatt tagtagttaa
2161 ttatgtcaac actaatatgg gcctgaaaat tagacaactg ttgtggtttc acatttcctg
2221 tcttactttt ggaagagaaa cagttcttga gtatttggtg tcctttggag tgtggattcg
2281 cactccacct gcttataggc caccaaatgc ccctatccta tccacacttc cggaaactac
2341 tgttgttaga cgaagaggca ggtcccctag aagaagaact ccctcgcctc gccgacgaag
2401 atctcaatcg ccgcgtcgca gaagatctca atctccagct tcccaatgtt agtattcctt
2461 ggactcataa ggtgggaaat tttacggggc tctactcttc tactgtacct gctttcaatc
2521 ctaactggtt aactccttct tttcctgata ttcatttaca tcaagatctg atatctaaat
2581 gtgaacaatt tgtaggcccg ctcactaaaa atgaattgag aagattaaaa ttggtcatgc
2641 cagctagatt ttatcctaag gttaccaaat actttcctat ggagaaaggg attaaaccct
2701 attatcctga gcattcagtt aatcattatt ttaaaacaag acattatttg catactcttt
2761 ggaaggcggg aatcttatat aagagagaat ccacacgtag cgcctcattt tgtgggtcac
2821 catattcctg ggaacaagag ctacagcatg ggagcacctc tctcaacgac aagaaggggc
2881 atgggactga atctttctgt gcccaatcct ctgggcttcc tgccagacca tcagctggat
2941 ccgctattca gggcaaattc cagcagtccc gactgggact tcaacacaaa caaggacagt
3001 tggccaatgg caaacaaggt aggagtggga ggctacggcc cagggtttac acccccacac
3061 ggtggcctgc tggggtggag ccctcaggca cagggtgttt tracaacctt gccagcagat
3121 ccgcctcctg cttccaccaa tcggcggtcc gggagaaagc caaccccagt ctctccacct
3181 ctaagagaca cacatccaca ggccatgcag tggaa (SEQ ID NO:213)
```

FIG. 48

```
   1 ttccactgcc ttccaccaag cactgcagga tcccagagtc aggggtccgt attttcctgc
  61 tggtggctcc agttcaggaa cagtaaaccc tgctccgaat attgcctctc acatctcgtc
 121 aatctccgcg aggactgggg accctgtgac gaacatggag aacatcacat caggactcct
 181 aggacccctg ctcgtgttac aggcggggtt tttcttgttg acaagaatcc tcacaatacc
 241 gcagagtcta ggctcgtggt ggacttctct caattttcta gggggatcac ccgtgtgtct
 301 tggccaaaat tcgcagtccc caacctccaa tcactcacca acctcctgtc ctccaatttg
 361 tcctggttat cgttggatgt gtctgcggcg ttttatcata ttcctcttca tcctgctgct
 421 atgcctcatc ttcttattgg ttcttctgga ttatcaaggt atgttgcccg tttgtcctct
 481 aattccagga tcaacaacaa ccggtacggg accatgcaaa acctgcacga ctcctgctca
 541 aggcaactct atgtttccct catgttgctg tacaaaacct acggacggaa attgcacctg
 601 tattcccatc ccatcgtcct gggctttcgc aaaataccta tgggagtggg cctcagtccg
 661 tttctcttgg ctcagtttac tagtgccatt tgttcagtgg ttcgtagggc tttcccccac
 721 tgtttggctt tcagctatat ggatgatgtg gtattggggg ccaagactgt acagcatcgt
 781 gagtcccttt ataccgctgt taccaatttt cttttgtctc tgggtataca tttaaaccct
 841 aacaaaacaa aaagatgggg ttattcccta aacttcatgg gttacataat tggaagttgg
 901 ggaactttgc cacaggatca tattgtacaa aagatcaaac actgttttag aaaacttcct
 961 gttaacaggc ctattgattg gaaagtatgt caaagaattg tgggtctttt gggctttgct
1021 gctccattta cacaatgtgg atatcctgcc ttaatgcctt tgtatgcatg tatacaagct
1081 aaacaggctt tcactttctc gccaacttac aaggcctttc taagtaaaca gtacatgaac
1141 ctttaccccg ttgctcggca acggcctggt ctgtgccaag tgtttgctga cgcaaccccc
1201 actggctggg gcttggccat aggccatcag cgcatgcgtg gaacctttgt ggctcctctg
1261 ccgatccata ctgcggaact cctagccgct tgttttgctc gcagccggtc tggagcaaag
1321 ctcatcggaa ctgacaattc tgtcgtcctc tcgcggaaat atacatcgtt tccatggctg
1381 ctaggctgta ctgccaactg gatccttcgc gggacgtcct ttgtttacgt cccgtcggcg
1441 ctgaatcccg cggacgaccc ctctcggggc cgcttgggac tctatcgtcc ccttctccgt
1501 ctgccgttcc agccgaccac ggggcgcacc tctctttacg cggtctcccc gtctgtgcct
1561 tctcatctgc cggtccgtgt gcacttcgct tcacctctgc acgttgcatg gagaccaccg
1621 tgaacgccca tcagatcctg cccaaggtct tacataagag gactcttgga ctcccagcaa
1681 tgtcaacgac cgaccttgag gcctacttca aagactgtgt gtttaaggac tgggaggagc
1741 tgggggagga gagtaggtta atgatctttg tattaggagg ctgtaggcat aaattggtct
1801 gcgcaccagc accatgcaac tttttcacct ctgccaaatc atctcttgta catgtcccac
1861 tgttcaagcc tccaagctgt gccttgggtg gctttggggc atggacattg acccttataa
1921 agaatttgga gctactgttg agttactctc gtttttgcct tctgacttct ttccttccgt
1981 cagagatctt ctagacaccg cctcagctct gtatcgagaa gccttagagt ctcctgagca
2041 ctgctcacct caccatactg cactcaggca agccattctc tgctgggggg aattgatgac
2101 tctagctacc tgggtgggta ataatttgga tgatccagca tccagggatc tagtagtcaa
2161 ttatgttaat actaacatgg gtttaaagat caggcaacta ttgtggtttc atatatcttg
2221 ccttactttt ggaagagaga ctgtacttga atatttggtc tctttcggag tgtggattcg
2281 cactcctcca ccctatagac caccaaatgc ccctatctta tcaacacttc cggaaactac
2341 tgttattaga cgacgggacc gaggcaggtc ccctagaaga agaactccct cgcctcgcag
2401 acgcagatct caatcgccgc gtcgcagaag atctcaatct cgggaatctc aatgttagta
2461 ttccttggac tcataaggtg ggaaacttta cggggcttta ttcctctaca gtacctatct
2521 ttaatcctga atggcaaact ccttcctttc ctaagattca tttacaagag gacattatta
2581 ataggtgtca acaatttgtg ggccctctca ctgtaaatga aaagagaaga ttgaaattaa
2641 ttatgcctgc tagattctat cctacccaca ctaaatattt gcccttagac aaaggaatta
2701 aaccttatta tccagatcag gtagttaatc attacttcca aaccagacat tatttacata
2761 ctctttggaa ggcgggtatt ctatataaga gggaaaccac acgtagcgca tcattttgcg
2821 ggtcaccata ttcttgggaa caagagctac agcatgggag gttggtcatc aaaacctcgc
2881 aaaggcatgg ggacgaatct ttctgttccc aaccctctgg gattctttcc cgatcatcag
2941 ttggaccctg cattcggagc caactcaaac aatccagatt gggacttcaa ccccatcaag
3001 gaccactggc cagcagccaa ccaggtggga gtgggggcat tcgggccagg gctcacccct
3061 ccacacggcg gtatcttggg gtggagccct caggctcagg gcatattgac cacagtgtca
3121 acaattcctc ctcctgcctc caccaatcgg cagtcaggaa ggcagcctac tcccatctct
3181 ccacctctcc gagacagtca tcctcaggcc acgcagtgga a (SEQ ID NO:214)
```

FIG. 49

SEQUENCE LISTING

```
<160> NUMBER OF SEQ ID NOS: 218

<210> SEQ ID NO 1
<211> LENGTH: 35
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Variable amino acid; Region may encompass 0-2
      residues
<220> FEATURE:
<221> NAME/KEY: MOD_RES
<222> LOCATION: (4)..(7)
<223> OTHER INFORMATION: Variable amino acid; Region may encompass 2-4
      residues
<220> FEATURE:
<221> NAME/KEY: MOD_RES
<222> LOCATION: (9)..(11)
```

```
<223> OTHER INFORMATION: Variable amino acid
<220> FEATURE:
<221> NAME/KEY: MOD_RES
<222> LOCATION: (14)..(20)
<223> OTHER INFORMATION: Variable amino acid
<220> FEATURE:
<221> NAME/KEY: MOD_RES
<222> LOCATION: (22)..(24)
<223> OTHER INFORMATION: Variable amino acid
<220> FEATURE:
<221> NAME/KEY: MOD_RES
<222> LOCATION: (26)..(35)
<223> OTHER INFORMATION: Variable amino acid; Region may encompass 2-10
      residues

<400> SEQUENCE: 1

Xaa Xaa Cys Xaa Xaa Xaa Xaa Cys Xaa Xaa Xaa Phe Ser Xaa Xaa Xaa
1               5                   10                  15

Xaa Xaa Xaa Xaa His Xaa Xaa Xaa His Xaa Xaa Xaa Xaa Xaa Xaa Xaa
            20                  25                  30

Xaa Xaa Xaa
        35


<210> SEQ ID NO 2
<211> LENGTH: 400
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(102)
<223> OTHER INFORMATION: Variable amino acid; Region may encompass 1-102
      residues
<220> FEATURE:
<221> NAME/KEY: MOD_RES
<222> LOCATION: (104)..(107)
<223> OTHER INFORMATION: Variable amino acid; Region may encompass 2-4
      residues
<220> FEATURE:
<221> NAME/KEY: MOD_RES
<222> LOCATION: (109)..(111)
<223> OTHER INFORMATION: Variable amino acid
<220> FEATURE:
<221> NAME/KEY: MOD_RES
<222> LOCATION: (114)..(120)
<223> OTHER INFORMATION: Variable amino acid
<220> FEATURE:
<221> NAME/KEY: MOD_RES
<222> LOCATION: (122)..(124)
<223> OTHER INFORMATION: Variable amino acid
<220> FEATURE:
<221> NAME/KEY: MOD_RES
<222> LOCATION: (126)..(135)
<223> OTHER INFORMATION: Variable amino acid; Region may encompass 2-10
      residues
<220> FEATURE:
<221> NAME/KEY: MOD_RES
<222> LOCATION: (136)..(137)
<223> OTHER INFORMATION: Variable amino acid; Region may encompass 0-2
      residues
<220> FEATURE:
<221> NAME/KEY: MOD_RES
<222> LOCATION: (139)..(142)
<223> OTHER INFORMATION: Variable amino acid; Region may encompass 2-4
      residues
<220> FEATURE:
<221> NAME/KEY: MOD_RES
<222> LOCATION: (144)..(146)
<223> OTHER INFORMATION: Variable amino acid
<220> FEATURE:
<221> NAME/KEY: MOD_RES
<222> LOCATION: (149)..(155)
<223> OTHER INFORMATION: Variable amino acid
<220> FEATURE:
```

<221> NAME/KEY: MOD_RES
<222> LOCATION: (157)..(159)
<223> OTHER INFORMATION: Variable amino acid
<220> FEATURE:
<221> NAME/KEY: MOD_RES
<222> LOCATION: (161)..(170)
<223> OTHER INFORMATION: Variable amino acid; Region may encompass 2-10 residues
<220> FEATURE:
<221> NAME/KEY: MOD_RES
<222> LOCATION: (171)..(172)
<223> OTHER INFORMATION: Variable amino acid; Region may encompass 0-2 residues; May or may not be present
<220> FEATURE:
<221> NAME/KEY: MOD_RES
<222> LOCATION: (174)..(177)
<223> OTHER INFORMATION: Variable amino acid; Region may encompass 2-4 residues; May or may not be present
<220> FEATURE:
<221> NAME/KEY: MOD_RES
<222> LOCATION: (179)..(181)
<223> OTHER INFORMATION: Variable amino acid; May or may not be present
<220> FEATURE:
<221> NAME/KEY: MOD_RES
<222> LOCATION: (184)..(190)
<223> OTHER INFORMATION: Variable amino acid; May or may not be present
<220> FEATURE:
<221> NAME/KEY: MOD_RES
<222> LOCATION: (192)..(194)
<223> OTHER INFORMATION: Variable amino acid; May or may not be present
<220> FEATURE:
<221> NAME/KEY: MOD_RES
<222> LOCATION: (196)..(205)
<223> OTHER INFORMATION: Variable amino acid; Region may encompass 2-10 residues; May or may not be present
<220> FEATURE:
<221> NAME/KEY: MOD_RES
<222> LOCATION: (206)..(207)
<223> OTHER INFORMATION: Variable amino acid; Region may encompass 0-2 residues; May or may not be present
<220> FEATURE:
<221> NAME/KEY: MOD_RES
<222> LOCATION: (209)..(212)
<223> OTHER INFORMATION: Variable amino acid; Region may encompass 2-4 residues; May or may not be present
<220> FEATURE:
<221> NAME/KEY: MOD_RES
<222> LOCATION: (214)..(216)
<223> OTHER INFORMATION: Variable amino acid; May or may not be present
<220> FEATURE:
<221> NAME/KEY: MOD_RES
<222> LOCATION: (219)..(225)
<223> OTHER INFORMATION: Variable amino acid; May or may not be present
<220> FEATURE:
<221> NAME/KEY: MOD_RES
<222> LOCATION: (227)..(229)
<223> OTHER INFORMATION: Variable amino acid; May or may not be present
<220> FEATURE:
<221> NAME/KEY: MOD_RES
<222> LOCATION: (231)..(240)
<223> OTHER INFORMATION: Variable amino acid; Region may encompass 2-10 residues; May or may not be present
<220> FEATURE:
<221> NAME/KEY: MOD_RES
<222> LOCATION: (241)..(242)
<223> OTHER INFORMATION: Variable amino acid; Region may encompass 0-2 residues; May or may not be present
<220> FEATURE:
<221> NAME/KEY: MOD_RES
<222> LOCATION: (244)..(247)
<223> OTHER INFORMATION: Variable amino acid; Region may encompass 2-4 residues; May or may not be present
<220> FEATURE:
<221> NAME/KEY: MOD_RES
<222> LOCATION: (249)..(251)
<223> OTHER INFORMATION: Variable amino acid; May or may not be present
<220> FEATURE:
<221> NAME/KEY: MOD_RES
<222> LOCATION: (254)..(260)
<223> OTHER INFORMATION: Variable amino acid; May or may not be present

```
<220> FEATURE:
<221> NAME/KEY: MOD_RES
<222> LOCATION: (262)..(264)
<223> OTHER INFORMATION: Variable amino acid; May or may not be present
<220> FEATURE:
<221> NAME/KEY: MOD_RES
<222> LOCATION: (266)..(275)
<223> OTHER INFORMATION: Variable amino acid; Region may encompass 2-10
      residues; May or may not be present
<220> FEATURE:
<221> NAME/KEY: MOD_RES
<222> LOCATION: (276)..(277)
<223> OTHER INFORMATION: Variable amino acid; Region may encompass 0-2
      residues
<220> FEATURE:
<221> NAME/KEY: MOD_RES
<222> LOCATION: (279)..(282)
<223> OTHER INFORMATION: Variable amino acid; Region may encompass 2-4
      residues
<220> FEATURE:
<221> NAME/KEY: MOD_RES
<222> LOCATION: (284)..(286)
<223> OTHER INFORMATION: Variable amino acid
<220> FEATURE:
<221> NAME/KEY: MOD_RES
<222> LOCATION: (289)..(295)
<223> OTHER INFORMATION: Variable amino acid
<220> FEATURE:
<221> NAME/KEY: MOD_RES
<222> LOCATION: (297)..(299)
<223> OTHER INFORMATION: Variable amino acid
<220> FEATURE:
<221> NAME/KEY: MOD_RES
<222> LOCATION: (301)..(400)
<223> OTHER INFORMATION: Variable amino acid; Region may encompass 1-100
      residues

<400> SEQUENCE: 2

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Cys Xaa Xaa Xaa Xaa Cys Xaa Xaa Xaa Phe
            100                 105                 110

Ser Xaa Xaa Xaa Xaa Xaa Xaa Xaa His Xaa Xaa Xaa His Xaa Xaa Xaa
        115                 120                 125

Xaa Xaa Xaa Xaa Xaa Xaa Xaa Xaa Xaa Cys Xaa Xaa Xaa Xaa Cys Xaa
    130                 135                 140

Xaa Xaa Phe Ser Xaa Xaa Xaa Xaa Xaa Xaa His Xaa Xaa Xaa His
145                 150                 155                 160

Xaa Xaa Xaa Xaa Xaa Xaa Xaa Xaa Xaa Xaa Xaa Xaa Cys Xaa Xaa Xaa
                165                 170                 175

Xaa Cys Xaa Xaa Xaa Phe Ser Xaa Xaa Xaa Xaa Xaa Xaa His Xaa
            180                 185                 190

Xaa Xaa His Xaa Xaa Xaa Xaa Xaa Xaa Xaa Xaa Xaa Xaa Xaa Xaa Cys
        195                 200                 205

Xaa Xaa Xaa Xaa Cys Xaa Xaa Xaa Phe Ser Xaa Xaa Xaa Xaa Xaa Xaa
    210                 215                 220
```

```
Xaa His Xaa Xaa Xaa His Xaa Xaa Xaa Xaa Xaa Xaa Xaa Xaa Xaa Xaa
225                 230                 235                 240

Xaa Xaa Cys Xaa Xaa Xaa Xaa Cys Xaa Xaa Xaa Phe Ser Xaa Xaa Xaa
                245                 250                 255

Xaa Xaa Xaa Xaa His Xaa Xaa Xaa His Xaa Xaa Xaa Xaa Xaa Xaa Xaa
            260                 265                 270

Xaa Xaa Xaa Xaa Xaa Cys Xaa Xaa Xaa Xaa Cys Xaa Xaa Xaa Phe Ser
        275                 280                 285

Xaa Xaa Xaa Xaa Xaa Xaa Xaa His Xaa Xaa Xaa His Xaa Xaa Xaa Xaa
    290                 295                 300

Xaa Xaa Xaa Xaa Xaa Xaa Xaa Xaa Xaa Xaa Xaa Xaa Xaa Xaa Xaa Xaa
305                 310                 315                 320

Xaa Xaa Xaa Xaa Xaa Xaa Xaa Xaa Xaa Xaa Xaa Xaa Xaa Xaa Xaa Xaa
                325                 330                 335

Xaa Xaa Xaa Xaa Xaa Xaa Xaa Xaa Xaa Xaa Xaa Xaa Xaa Xaa Xaa Xaa
            340                 345                 350

Xaa Xaa Xaa Xaa Xaa Xaa Xaa Xaa Xaa Xaa Xaa Xaa Xaa Xaa Xaa Xaa
        355                 360                 365

Xaa Xaa Xaa Xaa Xaa Xaa Xaa Xaa Xaa Xaa Xaa Xaa Xaa Xaa Xaa Xaa
    370                 375                 380

Xaa Xaa Xaa Xaa Xaa Xaa Xaa Xaa Xaa Xaa Xaa Xaa Xaa Xaa Xaa Xaa
385                 390                 395                 400
```

<210> SEQ ID NO 3
<211> LENGTH: 295
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(102)
<223> OTHER INFORMATION: Variable amino acid; Region may encompass 1-102
      residues
<220> FEATURE:
<221> NAME/KEY: MOD_RES
<222> LOCATION: (104)..(107)
<223> OTHER INFORMATION: Variable amino acid; Region may encompass 2-4
      residues
<220> FEATURE:
<221> NAME/KEY: MOD_RES
<222> LOCATION: (109)..(111)
<223> OTHER INFORMATION: Variable amino acid
<220> FEATURE:
<221> NAME/KEY: MOD_RES
<222> LOCATION: (114)..(120)
<223> OTHER INFORMATION: Variable amino acid
<220> FEATURE:
<221> NAME/KEY: MOD_RES
<222> LOCATION: (122)..(124)
<223> OTHER INFORMATION: Variable amino acid
<220> FEATURE:
<221> NAME/KEY: MOD_RES
<222> LOCATION: (126)..(135)
<223> OTHER INFORMATION: Variable amino acid; Region may encompass 2-10
      residues
<220> FEATURE:
<221> NAME/KEY: MOD_RES
<222> LOCATION: (136)..(137)
<223> OTHER INFORMATION: Variable amino acid; Region may encompass 0-2
      residues
<220> FEATURE:
<221> NAME/KEY: MOD_RES
<222> LOCATION: (139)..(142)
<223> OTHER INFORMATION: Variable amino acid; Region may encompass 2-4
      residues
<220> FEATURE:

-continued

```
<221> NAME/KEY: MOD_RES
<222> LOCATION: (144)..(146)
<223> OTHER INFORMATION: Variable amino acid
<220> FEATURE:
<221> NAME/KEY: MOD_RES
<222> LOCATION: (149)..(155)
<223> OTHER INFORMATION: Variable amino acid
<220> FEATURE:
<221> NAME/KEY: MOD_RES
<222> LOCATION: (157)..(159)
<223> OTHER INFORMATION: Variable amino acid
<220> FEATURE:
<221> NAME/KEY: MOD_RES
<222> LOCATION: (161)..(170)
<223> OTHER INFORMATION: Variable amino acid; Region may encompass 2-10
      residues
<220> FEATURE:
<221> NAME/KEY: MOD_RES
<222> LOCATION: (171)..(172)
<223> OTHER INFORMATION: Variable amino acid; Region may encompass 0-2
      residues
<220> FEATURE:
<221> NAME/KEY: MOD_RES
<222> LOCATION: (174)..(177)
<223> OTHER INFORMATION: Variable amino acid; Region may encompass 2-4
      residues
<220> FEATURE:
<221> NAME/KEY: MOD_RES
<222> LOCATION: (179)..(181)
<223> OTHER INFORMATION: Variable amino acid
<220> FEATURE:
<221> NAME/KEY: MOD_RES
<222> LOCATION: (184)..(190)
<223> OTHER INFORMATION: Variable amino acid
<220> FEATURE:
<221> NAME/KEY: MOD_RES
<222> LOCATION: (192)..(194)
<223> OTHER INFORMATION: Variable amino acid
<220> FEATURE:
<221> NAME/KEY: MOD_RES
<222> LOCATION: (196)..(295)
<223> OTHER INFORMATION: Variable amino acid; Region may encompass 1-100
      residues

<400> SEQUENCE: 3

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Cys Xaa Xaa Xaa Xaa Cys Xaa Xaa Xaa Phe
            100                 105                 110

Ser Xaa Xaa Xaa Xaa Xaa Xaa Xaa His Xaa Xaa Xaa His Xaa Xaa Xaa
        115                 120                 125

Xaa Xaa Xaa Xaa Xaa Xaa Xaa Xaa Xaa Cys Xaa Xaa Xaa Xaa Cys Xaa
    130                 135                 140

Xaa Xaa Phe Ser Xaa Xaa Xaa Xaa Xaa Xaa Xaa His Xaa Xaa Xaa His
145                 150                 155                 160

Xaa Xaa Xaa Xaa Xaa Xaa Xaa Xaa Xaa Xaa Xaa Xaa Cys Xaa Xaa Xaa
                165                 170                 175

Xaa Cys Xaa Xaa Xaa Phe Ser Xaa Xaa Xaa Xaa Xaa Xaa Xaa His Xaa
```

-continued

```
            180                 185                 190

Xaa Xaa His Xaa Xaa Xaa Xaa Xaa Xaa Xaa Xaa Xaa Xaa Xaa Xaa Xaa
        195                 200                 205

Xaa Xaa Xaa Xaa Xaa Xaa Xaa Xaa Xaa Xaa Xaa Xaa Xaa Xaa Xaa Xaa
    210                 215                 220

Xaa Xaa Xaa Xaa Xaa Xaa Xaa Xaa Xaa Xaa Xaa Xaa Xaa Xaa Xaa Xaa
225                 230                 235                 240

Xaa Xaa Xaa Xaa Xaa Xaa Xaa Xaa Xaa Xaa Xaa Xaa Xaa Xaa Xaa Xaa
                245                 250                 255

Xaa Xaa Xaa Xaa Xaa Xaa Xaa Xaa Xaa Xaa Xaa Xaa Xaa Xaa Xaa Xaa
            260                 265                 270

Xaa Xaa Xaa Xaa Xaa Xaa Xaa Xaa Xaa Xaa Xaa Xaa Xaa Xaa Xaa Xaa
        275                 280                 285

Xaa Xaa Xaa Xaa Xaa Xaa Xaa
    290                 295


<210> SEQ ID NO 4
<211> LENGTH: 400
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(102)
<223> OTHER INFORMATION: Variable amino acid; Region may encompass 1-102
      residues
<220> FEATURE:
<221> NAME/KEY: MOD_RES
<222> LOCATION: (104)..(107)
<223> OTHER INFORMATION: Variable amino acid; Region may encompass 2-4
      residues
<220> FEATURE:
<221> NAME/KEY: MOD_RES
<222> LOCATION: (109)..(111)
<223> OTHER INFORMATION: Variable amino acid
<220> FEATURE:
<221> NAME/KEY: MOD_RES
<222> LOCATION: (114)..(120)
<223> OTHER INFORMATION: Variable amino acid
<220> FEATURE:
<221> NAME/KEY: MOD_RES
<222> LOCATION: (122)..(124)
<223> OTHER INFORMATION: Variable amino acid
<220> FEATURE:
<221> NAME/KEY: MOD_RES
<222> LOCATION: (126)..(135)
<223> OTHER INFORMATION: Variable amino acid; Region may encompass 2-10
      residues
<220> FEATURE:
<221> NAME/KEY: MOD_RES
<222> LOCATION: (136)..(137)
<223> OTHER INFORMATION: Variable amino acid; Region may encompass 0-2
      residues
<220> FEATURE:
<221> NAME/KEY: MOD_RES
<222> LOCATION: (139)..(142)
<223> OTHER INFORMATION: Variable amino acid; Region may encompass 2-4
      residues
<220> FEATURE:
<221> NAME/KEY: MOD_RES
<222> LOCATION: (144)..(146)
<223> OTHER INFORMATION: Variable amino acid
<220> FEATURE:
<221> NAME/KEY: MOD_RES
<222> LOCATION: (149)..(155)
<223> OTHER INFORMATION: Variable amino acid
<220> FEATURE:
<221> NAME/KEY: MOD_RES
<222> LOCATION: (157)..(159)
<223> OTHER INFORMATION: Variable amino acid
```

<220> FEATURE:
<221> NAME/KEY: MOD_RES
<222> LOCATION: (161)..(170)
<223> OTHER INFORMATION: Variable amino acid; Region may encompass 2-10 residues
<220> FEATURE:
<221> NAME/KEY: MOD_RES
<222> LOCATION: (171)..(172)
<223> OTHER INFORMATION: Variable amino acid; Region may encompass 0-1 residues
<220> FEATURE:
<221> NAME/KEY: MOD_RES
<222> LOCATION: (174)..(177)
<223> OTHER INFORMATION: Variable amino acid; Region may encompass 2-4 residues
<220> FEATURE:
<221> NAME/KEY: MOD_RES
<222> LOCATION: (179)..(181)
<223> OTHER INFORMATION: Variable amino acid
<220> FEATURE:
<221> NAME/KEY: MOD_RES
<222> LOCATION: (184)..(190)
<223> OTHER INFORMATION: Variable amino acid
<220> FEATURE:
<221> NAME/KEY: MOD_RES
<222> LOCATION: (192)..(194)
<223> OTHER INFORMATION: Variable amino acid
<220> FEATURE:
<221> NAME/KEY: MOD_RES
<222> LOCATION: (196)..(205)
<223> OTHER INFORMATION: Variable amino acid; Region may encompass 2-10 residues
<220> FEATURE:
<221> NAME/KEY: MOD_RES
<222> LOCATION: (206)..(207)
<223> OTHER INFORMATION: Variable amino acid; Region may encompass 0-2 residues
<220> FEATURE:
<221> NAME/KEY: MOD_RES
<222> LOCATION: (209)..(212)
<223> OTHER INFORMATION: Variable amino acid; Region may encompass 2-4 residues
<220> FEATURE:
<221> NAME/KEY: MOD_RES
<222> LOCATION: (214)..(216)
<223> OTHER INFORMATION: Variable amino acid
<220> FEATURE:
<221> NAME/KEY: MOD_RES
<222> LOCATION: (219)..(225)
<223> OTHER INFORMATION: Variable amino acid
<220> FEATURE:
<221> NAME/KEY: MOD_RES
<222> LOCATION: (227)..(229)
<223> OTHER INFORMATION: Variable amino acid
<220> FEATURE:
<221> NAME/KEY: MOD_RES
<222> LOCATION: (231)..(240)
<223> OTHER INFORMATION: Variable amino acid; Region may encompass 2-10 residues
<220> FEATURE:
<221> NAME/KEY: MOD_RES
<222> LOCATION: (241)..(242)
<223> OTHER INFORMATION: Variable amino acid; Region may encompass 0-2 residues
<220> FEATURE:
<221> NAME/KEY: MOD_RES
<222> LOCATION: (244)..(247)
<223> OTHER INFORMATION: Variable amino acid; Region may encompass 2-4 residues
<220> FEATURE:
<221> NAME/KEY: MOD_RES
<222> LOCATION: (249)..(251)
<223> OTHER INFORMATION: Variable amino acid
<220> FEATURE:
<221> NAME/KEY: MOD_RES
<222> LOCATION: (254)..(260)
<223> OTHER INFORMATION: Variable amino acid
<220> FEATURE:
<221> NAME/KEY: MOD_RES
<222> LOCATION: (262)..(264)

```
<223> OTHER INFORMATION: Variable amino acid
<220> FEATURE:
<221> NAME/KEY: MOD_RES
<222> LOCATION: (266)..(275)
<223> OTHER INFORMATION: Variable amino acid; Region may encompass 2-10
      residues
<220> FEATURE:
<221> NAME/KEY: MOD_RES
<222> LOCATION: (276)..(277)
<223> OTHER INFORMATION: Variable amino acid; Region may encompass 0-2
      residues
<220> FEATURE:
<221> NAME/KEY: MOD_RES
<222> LOCATION: (279)..(282)
<223> OTHER INFORMATION: Variable amino acid; Region may encompass 2-4
      residues
<220> FEATURE:
<221> NAME/KEY: MOD_RES
<222> LOCATION: (284)..(286)
<223> OTHER INFORMATION: Variable amino acid
<220> FEATURE:
<221> NAME/KEY: MOD_RES
<222> LOCATION: (289)..(295)
<223> OTHER INFORMATION: Variable amino acid
<220> FEATURE:
<221> NAME/KEY: MOD_RES
<222> LOCATION: (297)..(299)
<223> OTHER INFORMATION: Variable amino acid
<220> FEATURE:
<221> NAME/KEY: MOD_RES
<222> LOCATION: (301)..(400)
<223> OTHER INFORMATION: Variable amino acid; Region may encompass 1-100
      residues

<400> SEQUENCE: 4

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Cys Xaa Xaa Xaa Xaa Cys Xaa Xaa Xaa Phe
            100                 105                 110

Ser Xaa Xaa Xaa Xaa Xaa Xaa Xaa His Xaa Xaa Xaa His Xaa Xaa Xaa
        115                 120                 125

Xaa Xaa Xaa Xaa Xaa Xaa Xaa Xaa Xaa Cys Xaa Xaa Xaa Xaa Cys Xaa
    130                 135                 140

Xaa Xaa Phe Ser Xaa Xaa Xaa Xaa Xaa Xaa Xaa His Xaa Xaa Xaa His
145                 150                 155                 160

Xaa Xaa Xaa Xaa Xaa Xaa Xaa Xaa Xaa Xaa Xaa Xaa Cys Xaa Xaa Xaa
                165                 170                 175

Xaa Cys Xaa Xaa Xaa Phe Ser Xaa Xaa Xaa Xaa Xaa Xaa Xaa His Xaa
            180                 185                 190

Xaa Xaa His Xaa Xaa Xaa Xaa Xaa Xaa Xaa Xaa Xaa Xaa Xaa Xaa Cys
        195                 200                 205

Xaa Xaa Xaa Xaa Cys Xaa Xaa Xaa Phe Ser Xaa Xaa Xaa Xaa Xaa Xaa
    210                 215                 220

Xaa His Xaa Xaa Xaa His Xaa Xaa Xaa Xaa Xaa Xaa Xaa Xaa Xaa Xaa
225                 230                 235                 240
```

```
Xaa Xaa Cys Xaa Xaa Xaa Xaa Cys Xaa Xaa Xaa Phe Ser Xaa Xaa Xaa
                245                 250                 255

Xaa Xaa Xaa Xaa His Xaa Xaa Xaa His Xaa Xaa Xaa Xaa Xaa Xaa Xaa
            260                 265                 270

Xaa Xaa Xaa Xaa Xaa Cys Xaa Xaa Xaa Xaa Cys Xaa Xaa Xaa Phe Ser
        275                 280                 285

Xaa Xaa Xaa Xaa Xaa Xaa Xaa His Xaa Xaa Xaa His Xaa Xaa Xaa Xaa
    290                 295                 300

Xaa Xaa Xaa Xaa Xaa Xaa Xaa Xaa Xaa Xaa Xaa Xaa Xaa Xaa Xaa Xaa
305                 310                 315                 320

Xaa Xaa Xaa Xaa Xaa Xaa Xaa Xaa Xaa Xaa Xaa Xaa Xaa Xaa Xaa Xaa
                325                 330                 335

Xaa Xaa Xaa Xaa Xaa Xaa Xaa Xaa Xaa Xaa Xaa Xaa Xaa Xaa Xaa Xaa
            340                 345                 350

Xaa Xaa Xaa Xaa Xaa Xaa Xaa Xaa Xaa Xaa Xaa Xaa Xaa Xaa Xaa Xaa
        355                 360                 365

Xaa Xaa Xaa Xaa Xaa Xaa Xaa Xaa Xaa Xaa Xaa Xaa Xaa Xaa Xaa Xaa
    370                 375                 380

Xaa Xaa Xaa Xaa Xaa Xaa Xaa Xaa Xaa Xaa Xaa Xaa Xaa Xaa Xaa Xaa
385                 390                 395                 400
```

<210> SEQ ID NO 5
<211> LENGTH: 400
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (1)..(100)
<223> OTHER INFORMATION: Variable amino acid; Region may encompass 1-100 residues
<220> FEATURE:
<221> NAME/KEY: MOD_RES
<222> LOCATION: (104)..(107)
<223> OTHER INFORMATION: Variable amino acid; Region may encompass 2-4 residues
<220> FEATURE:
<221> NAME/KEY: MOD_RES
<222> LOCATION: (109)..(111)
<223> OTHER INFORMATION: Variable amino acid
<220> FEATURE:
<221> NAME/KEY: MOD_RES
<222> LOCATION: (114)..(120)
<223> OTHER INFORMATION: Variable amino acid
<220> FEATURE:
<221> NAME/KEY: MOD_RES
<222> LOCATION: (122)..(124)
<223> OTHER INFORMATION: Variable amino acid
<220> FEATURE:
<221> NAME/KEY: MOD_RES
<222> LOCATION: (126)..(135)
<223> OTHER INFORMATION: Variable amino acid; Region may encompass 2-10 residues
<220> FEATURE:
<221> NAME/KEY: MOD_RES
<222> LOCATION: (139)..(142)
<223> OTHER INFORMATION: Variable amino acid; Region may encompass 2-4 residues
<220> FEATURE:
<221> NAME/KEY: MOD_RES
<222> LOCATION: (144)..(146)
<223> OTHER INFORMATION: Variable amino acid
<220> FEATURE:
<221> NAME/KEY: MOD_RES
<222> LOCATION: (149)..(155)
<223> OTHER INFORMATION: Variable amino acid
<220> FEATURE:

<221> NAME/KEY: MOD_RES
<222> LOCATION: (157)..(159)
<223> OTHER INFORMATION: Variable amino acid
<220> FEATURE:
<221> NAME/KEY: MOD_RES
<222> LOCATION: (161)..(170)
<223> OTHER INFORMATION: Variable amino acid; Region may encompass 2-10 residues
<220> FEATURE:
<221> NAME/KEY: MOD_RES
<222> LOCATION: (174)..(177)
<223> OTHER INFORMATION: Variable amino acid; Region may encompass 2-4 residues; May or may not be present
<220> FEATURE:
<221> NAME/KEY: MOD_RES
<222> LOCATION: (179)..(181)
<223> OTHER INFORMATION: Variable amino acid; May or may not be present
<220> FEATURE:
<221> NAME/KEY: MOD_RES
<222> LOCATION: (184)..(190)
<223> OTHER INFORMATION: Variable amino acid; May or may not be present
<220> FEATURE:
<221> NAME/KEY: MOD_RES
<222> LOCATION: (192)..(194)
<223> OTHER INFORMATION: Variable amino acid; May or may not be present
<220> FEATURE:
<221> NAME/KEY: MOD_RES
<222> LOCATION: (196)..(205)
<223> OTHER INFORMATION: Variable amino acid; Region may encompass 2-10 residues; May or may not be present
<220> FEATURE:
<221> NAME/KEY: MOD_RES
<222> LOCATION: (209)..(212)
<223> OTHER INFORMATION: Variable amino acid; Region may encompass 2-4 residues; May or may not be present
<220> FEATURE:
<221> NAME/KEY: MOD_RES
<222> LOCATION: (214)..(216)
<223> OTHER INFORMATION: Variable amino acid; May or may not be present
<220> FEATURE:
<221> NAME/KEY: MOD_RES
<222> LOCATION: (219)..(225)
<223> OTHER INFORMATION: Variable amino acid; May or may not be present
<220> FEATURE:
<221> NAME/KEY: MOD_RES
<222> LOCATION: (227)..(229)
<223> OTHER INFORMATION: Variable amino acid; May or may not be present
<220> FEATURE:
<221> NAME/KEY: MOD_RES
<222> LOCATION: (231)..(240)
<223> OTHER INFORMATION: Variable amino acid; Region may encompass 2-10 residues; May or may not be present
<220> FEATURE:
<221> NAME/KEY: MOD_RES
<222> LOCATION: (244)..(247)
<223> OTHER INFORMATION: Variable amino acid; Region may encompass 2-4 residues; May or may not be present
<220> FEATURE:
<221> NAME/KEY: MOD_RES
<222> LOCATION: (249)..(251)
<223> OTHER INFORMATION: Variable amino acid; May or may not be present
<220> FEATURE:
<221> NAME/KEY: MOD_RES
<222> LOCATION: (254)..(260)
<223> OTHER INFORMATION: Variable amino acid; May or may not be present
<220> FEATURE:
<221> NAME/KEY: MOD_RES
<222> LOCATION: (262)..(264)
<223> OTHER INFORMATION: Variable amino acid; May or may not be present
<220> FEATURE:
<221> NAME/KEY: MOD_RES
<222> LOCATION: (266)..(275)
<223> OTHER INFORMATION: Variable amino acid; Region may encompass 2-4 residues; May or may not be present
<220> FEATURE:
<221> NAME/KEY: MOD_RES
<222> LOCATION: (279)..(282)
<223> OTHER INFORMATION: Variable amino acid; Region may encompass 2-4 residues
<220> FEATURE:

```
<221> NAME/KEY: MOD_RES
<222> LOCATION: (284)..(286)
<223> OTHER INFORMATION: Variable amino acid
<220> FEATURE:
<221> NAME/KEY: MOD_RES
<222> LOCATION: (289)..(295)
<223> OTHER INFORMATION: Variable amino acid
<220> FEATURE:
<221> NAME/KEY: MOD_RES
<222> LOCATION: (297)..(299)
<223> OTHER INFORMATION: Variable amino acid
<220> FEATURE:
<221> NAME/KEY: MOD_RES
<222> LOCATION: (301)..(400)
<223> OTHER INFORMATION: Variable amino acid; Region may encompass 1-100
      residues

<400> SEQUENCE: 5

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
                85                  90                  95

Xaa Xaa Xaa Xaa Tyr Lys Cys Xaa Xaa Xaa Xaa Cys Xaa Xaa Xaa Phe
            100                 105                 110

Ser Xaa Xaa Xaa Xaa Xaa Xaa Xaa His Xaa Xaa Xaa His Xaa Xaa Xaa
        115                 120                 125

Xaa Xaa Xaa Xaa Xaa Xaa Xaa Tyr Lys Cys Xaa Xaa Xaa Xaa Cys Xaa
    130                 135                 140

Xaa Xaa Phe Ser Xaa Xaa Xaa Xaa Xaa Xaa Xaa His Xaa Xaa Xaa His
145                 150                 155                 160

Xaa Xaa Xaa Xaa Xaa Xaa Xaa Xaa Xaa Xaa Tyr Lys Cys Xaa Xaa Xaa
                165                 170                 175

Xaa Cys Xaa Xaa Xaa Phe Ser Xaa Xaa Xaa Xaa Xaa Xaa Xaa His Xaa
            180                 185                 190

Xaa Xaa His Xaa Xaa Xaa Xaa Xaa Xaa Xaa Xaa Xaa Xaa Tyr Lys Cys
        195                 200                 205

Xaa Xaa Xaa Xaa Cys Xaa Xaa Xaa Phe Ser Xaa Xaa Xaa Xaa Xaa Xaa
    210                 215                 220

Xaa His Xaa Xaa Xaa His Xaa Xaa Xaa Xaa Xaa Xaa Xaa Xaa Xaa Xaa
225                 230                 235                 240

Tyr Lys Cys Xaa Xaa Xaa Xaa Cys Xaa Xaa Xaa Phe Ser Xaa Xaa Xaa
                245                 250                 255

Xaa Xaa Xaa Xaa His Xaa Xaa Xaa His Xaa Xaa Xaa Xaa Xaa Xaa Xaa
            260                 265                 270

Xaa Xaa Xaa Tyr Lys Cys Xaa Xaa Xaa Xaa Cys Xaa Xaa Xaa Phe Ser
        275                 280                 285

Xaa Xaa Xaa Xaa Xaa Xaa Xaa His Xaa Xaa Xaa His Xaa Xaa Xaa Xaa
    290                 295                 300

Xaa Xaa Xaa Xaa Xaa Xaa Xaa Xaa Xaa Xaa Xaa Xaa Xaa Xaa Xaa Xaa
305                 310                 315                 320

Xaa Xaa Xaa Xaa Xaa Xaa Xaa Xaa Xaa Xaa Xaa Xaa Xaa Xaa Xaa Xaa
```

```
            325                 330                 335

Xaa Xaa Xaa Xaa Xaa Xaa Xaa Xaa Xaa Xaa Xaa Xaa Xaa Xaa Xaa Xaa
            340                 345                 350

Xaa Xaa Xaa Xaa Xaa Xaa Xaa Xaa Xaa Xaa Xaa Xaa Xaa Xaa Xaa Xaa
        355                 360                 365

Xaa Xaa Xaa Xaa Xaa Xaa Xaa Xaa Xaa Xaa Xaa Xaa Xaa Xaa Xaa Xaa
    370                 375                 380

Xaa Xaa Xaa Xaa Xaa Xaa Xaa Xaa Xaa Xaa Xaa Xaa Xaa Xaa Xaa Xaa
385                 390                 395                 400


<210> SEQ ID NO 6
<211> LENGTH: 295
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(100)
<223> OTHER INFORMATION: Variable amino acid; Region may encompass 1-100
      residues
<220> FEATURE:
<221> NAME/KEY: MOD_RES
<222> LOCATION: (104)..(107)
<223> OTHER INFORMATION: Variable amino acid; Region may encompass 2-4
      residues
<220> FEATURE:
<221> NAME/KEY: MOD_RES
<222> LOCATION: (109)..(111)
<223> OTHER INFORMATION: Variable amino acid
<220> FEATURE:
<221> NAME/KEY: MOD_RES
<222> LOCATION: (114)..(120)
<223> OTHER INFORMATION: Variable amino acid
<220> FEATURE:
<221> NAME/KEY: MOD_RES
<222> LOCATION: (122)..(124)
<223> OTHER INFORMATION: Variable amino acid
<220> FEATURE:
<221> NAME/KEY: MOD_RES
<222> LOCATION: (126)..(135)
<223> OTHER INFORMATION: Variable amino acid; Region may encompass 2-10
      residues
<220> FEATURE:
<221> NAME/KEY: MOD_RES
<222> LOCATION: (139)..(142)
<223> OTHER INFORMATION: Variable amino acid; Region may encompass 2-4
      residues
<220> FEATURE:
<221> NAME/KEY: MOD_RES
<222> LOCATION: (144)..(146)
<223> OTHER INFORMATION: Variable amino acid
<220> FEATURE:
<221> NAME/KEY: MOD_RES
<222> LOCATION: (149)..(155)
<223> OTHER INFORMATION: Variable amino acid
<220> FEATURE:
<221> NAME/KEY: MOD_RES
<222> LOCATION: (157)..(159)
<223> OTHER INFORMATION: Variable amino acid
<220> FEATURE:
<221> NAME/KEY: MOD_RES
<222> LOCATION: (161)..(170)
<223> OTHER INFORMATION: Variable amino acid; Region may encompass 2-10
      residues
<220> FEATURE:
<221> NAME/KEY: MOD_RES
<222> LOCATION: (174)..(177)
<223> OTHER INFORMATION: Variable amino acid; Region may encompass 2-4
      residues
<220> FEATURE:
<221> NAME/KEY: MOD_RES
<222> LOCATION: (179)..(181)
<223> OTHER INFORMATION: Variable amino acid
```

```
<220> FEATURE:
<221> NAME/KEY: MOD_RES
<222> LOCATION: (184)..(190)
<223> OTHER INFORMATION: Variable amino acid
<220> FEATURE:
<221> NAME/KEY: MOD_RES
<222> LOCATION: (192)..(194)
<223> OTHER INFORMATION: Variable amino acid
<220> FEATURE:
<221> NAME/KEY: MOD_RES
<222> LOCATION: (196)..(295)
<223> OTHER INFORMATION: Variable amino acid; Region may encompass 1-100
      residues

<400> SEQUENCE: 6

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
                85                  90                  95

Xaa Xaa Xaa Xaa Tyr Lys Cys Xaa Xaa Xaa Xaa Cys Xaa Xaa Xaa Phe
            100                 105                 110

Ser Xaa Xaa Xaa Xaa Xaa Xaa Xaa His Xaa Xaa Xaa His Xaa Xaa Xaa
        115                 120                 125

Xaa Xaa Xaa Xaa Xaa Xaa Xaa Tyr Lys Cys Xaa Xaa Xaa Xaa Cys Xaa
    130                 135                 140

Xaa Xaa Phe Ser Xaa Xaa Xaa Xaa Xaa Xaa His Xaa Xaa Xaa His
145                 150                 155                 160

Xaa Xaa Xaa Xaa Xaa Xaa Xaa Xaa Xaa Xaa Tyr Lys Cys Xaa Xaa Xaa
                165                 170                 175

Xaa Cys Xaa Xaa Xaa Phe Ser Xaa Xaa Xaa Xaa Xaa Xaa Xaa His Xaa
            180                 185                 190

Xaa Xaa His Xaa Xaa Xaa Xaa Xaa Xaa Xaa Xaa Xaa Xaa Xaa Xaa Xaa
        195                 200                 205

Xaa Xaa Xaa Xaa Xaa Xaa Xaa Xaa Xaa Xaa Xaa Xaa Xaa Xaa Xaa Xaa
    210                 215                 220

Xaa Xaa Xaa Xaa Xaa Xaa Xaa Xaa Xaa Xaa Xaa Xaa Xaa Xaa Xaa Xaa
225                 230                 235                 240

Xaa Xaa Xaa Xaa Xaa Xaa Xaa Xaa Xaa Xaa Xaa Xaa Xaa Xaa Xaa Xaa
                245                 250                 255

Xaa Xaa Xaa Xaa Xaa Xaa Xaa Xaa Xaa Xaa Xaa Xaa Xaa Xaa Xaa Xaa
            260                 265                 270

Xaa Xaa Xaa Xaa Xaa Xaa Xaa Xaa Xaa Xaa Xaa Xaa Xaa Xaa Xaa Xaa
        275                 280                 285

Xaa Xaa Xaa Xaa Xaa Xaa Xaa
    290                 295


<210> SEQ ID NO 7
<211> LENGTH: 401
<212> TYPE: PRT
<213> ORGANISM: Artificial Sequence
<220> FEATURE:
<223> OTHER INFORMATION: Description of Artificial Sequence: Synthetic
```

polypeptide
<220> FEATURE:
<221> NAME/KEY: MOD_RES
<222> LOCATION: (1)..(100)
<223> OTHER INFORMATION: Variable amino acid; Region may encompass 1-100 residues
<220> FEATURE:
<221> NAME/KEY: MOD_RES
<222> LOCATION: (104)..(107)
<223> OTHER INFORMATION: Variable amino acid; Region may encompass 2-4 residues
<220> FEATURE:
<221> NAME/KEY: MOD_RES
<222> LOCATION: (109)..(111)
<223> OTHER INFORMATION: Variable amino acid
<220> FEATURE:
<221> NAME/KEY: MOD_RES
<222> LOCATION: (114)..(120)
<223> OTHER INFORMATION: Variable amino acid
<220> FEATURE:
<221> NAME/KEY: MOD_RES
<222> LOCATION: (122)..(124)
<223> OTHER INFORMATION: Variable amino acid
<220> FEATURE:
<221> NAME/KEY: MOD_RES
<222> LOCATION: (126)..(135)
<223> OTHER INFORMATION: Variable amino acid; Region may encompass 2-10 residues
<220> FEATURE:
<221> NAME/KEY: MOD_RES
<222> LOCATION: (139)..(142)
<223> OTHER INFORMATION: Variable amino acid; Region may encompass 2-4 residues
<220> FEATURE:
<221> NAME/KEY: MOD_RES
<222> LOCATION: (144)..(146)
<223> OTHER INFORMATION: Variable amino acid
<220> FEATURE:
<221> NAME/KEY: MOD_RES
<222> LOCATION: (149)..(155)
<223> OTHER INFORMATION: Variable amino acid
<220> FEATURE:
<221> NAME/KEY: MOD_RES
<222> LOCATION: (157)..(159)
<223> OTHER INFORMATION: Variable amino acid
<220> FEATURE:
<221> NAME/KEY: MOD_RES
<222> LOCATION: (161)..(170)
<223> OTHER INFORMATION: Variable amino acid; Region may encompass 2-10 residues
<220> FEATURE:
<221> NAME/KEY: MOD_RES
<222> LOCATION: (174)..(177)
<223> OTHER INFORMATION: Variable amino acid; Region may encompass 2-4 residues
<220> FEATURE:
<221> NAME/KEY: MOD_RES
<222> LOCATION: (179)..(181)
<223> OTHER INFORMATION: Variable amino acid
<220> FEATURE:
<221> NAME/KEY: MOD_RES
<222> LOCATION: (184)..(190)
<223> OTHER INFORMATION: Variable amino acid
<220> FEATURE:
<221> NAME/KEY: MOD_RES
<222> LOCATION: (192)..(194)
<223> OTHER INFORMATION: Variable amino acid
<220> FEATURE:
<221> NAME/KEY: MOD_RES
<222> LOCATION: (196)..(205)
<223> OTHER INFORMATION: Variable amino acid; Region may encompass 2-10 residues
<220> FEATURE:
<221> NAME/KEY: MOD_RES
<222> LOCATION: (209)..(212)
<223> OTHER INFORMATION: Variable amino acid; Region may encompass 2-4 residues
<220> FEATURE:
<221> NAME/KEY: MOD_RES
<222> LOCATION: (214)..(216)

```
<223> OTHER INFORMATION: Variable amino acid
<220> FEATURE:
<221> NAME/KEY: MOD_RES
<222> LOCATION: (219)..(225)
<223> OTHER INFORMATION: Variable amino acid
<220> FEATURE:
<221> NAME/KEY: MOD_RES
<222> LOCATION: (227)..(229)
<223> OTHER INFORMATION: Variable amino acid
<220> FEATURE:
<221> NAME/KEY: MOD_RES
<222> LOCATION: (231)..(240)
<223> OTHER INFORMATION: Variable amino acid; Region may encompass 2-10
      residues
<220> FEATURE:
<221> NAME/KEY: MOD_RES
<222> LOCATION: (245)..(248)
<223> OTHER INFORMATION: Variable amino acid; Region may encompass 2-4
      residues
<220> FEATURE:
<221> NAME/KEY: MOD_RES
<222> LOCATION: (250)..(252)
<223> OTHER INFORMATION: Variable amino acid
<220> FEATURE:
<221> NAME/KEY: MOD_RES
<222> LOCATION: (255)..(261)
<223> OTHER INFORMATION: Variable amino acid
<220> FEATURE:
<221> NAME/KEY: MOD_RES
<222> LOCATION: (263)..(265)
<223> OTHER INFORMATION: Variable amino acid
<220> FEATURE:
<221> NAME/KEY: MOD_RES
<222> LOCATION: (267)..(276)
<223> OTHER INFORMATION: Variable amino acid; Region may encompass 2-10
      residues
<220> FEATURE:
<221> NAME/KEY: MOD_RES
<222> LOCATION: (280)..(283)
<223> OTHER INFORMATION: Variable amino acid; Region may encompass 2-4
      residues
<220> FEATURE:
<221> NAME/KEY: MOD_RES
<222> LOCATION: (285)..(287)
<223> OTHER INFORMATION: Variable amino acid
<220> FEATURE:
<221> NAME/KEY: MOD_RES
<222> LOCATION: (290)..(296)
<223> OTHER INFORMATION: Variable amino acid
<220> FEATURE:
<221> NAME/KEY: MOD_RES
<222> LOCATION: (298)..(300)
<223> OTHER INFORMATION: Variable amino acid
<220> FEATURE:
<221> NAME/KEY: MOD_RES
<222> LOCATION: (302)..(401)
<223> OTHER INFORMATION: Variable amino acid; Region may encompass 1-100
      residues

<400> SEQUENCE: 7

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
                85                  90                  95

Xaa Xaa Xaa Xaa Tyr Lys Cys Xaa Xaa Xaa Xaa Cys Xaa Xaa Xaa Phe
```

-continued

```
            100                 105                 110

Ser Xaa Xaa Xaa Xaa Xaa Xaa Xaa His Xaa Xaa Xaa His Xaa Xaa Xaa
        115                 120                 125

Xaa Xaa Xaa Xaa Xaa Xaa Xaa Tyr Lys Cys Xaa Xaa Xaa Xaa Cys Xaa
    130                 135                 140

Xaa Xaa Phe Ser Xaa Xaa Xaa Xaa Xaa Xaa Xaa His Xaa Xaa Xaa His
145                 150                 155                 160

Xaa Xaa Xaa Xaa Xaa Xaa Xaa Xaa Xaa Xaa Tyr Lys Cys Xaa Xaa Xaa
                165                 170                 175

Xaa Cys Xaa Xaa Xaa Phe Ser Xaa Xaa Xaa Xaa Xaa Xaa Xaa His Xaa
            180                 185                 190

Xaa Xaa His Xaa Xaa Xaa Xaa Xaa Xaa Xaa Xaa Xaa Xaa Tyr Lys Cys
        195                 200                 205

Xaa Xaa Xaa Xaa Cys Xaa Xaa Xaa Phe Ser Xaa Xaa Xaa Xaa Xaa Xaa
    210                 215                 220

Xaa His Xaa Xaa Xaa His Xaa Xaa Xaa Xaa Xaa Xaa Xaa Xaa Xaa Xaa
225                 230                 235                 240

Tyr Lys Lys Cys Xaa Xaa Xaa Xaa Cys Xaa Xaa Xaa Phe Ser Xaa Xaa
                245                 250                 255

Xaa Xaa Xaa Xaa Xaa His Xaa Xaa Xaa His Xaa Xaa Xaa Xaa Xaa Xaa
            260                 265                 270

Xaa Xaa Xaa Xaa Tyr Lys Cys Xaa Xaa Xaa Xaa Cys Xaa Xaa Xaa Phe
        275                 280                 285

Ser Xaa Xaa Xaa Xaa Xaa Xaa Xaa His Xaa Xaa Xaa His Xaa Xaa Xaa
    290                 295                 300

Xaa Xaa Xaa Xaa Xaa Xaa Xaa Xaa Xaa Xaa Xaa Xaa Xaa Xaa Xaa Xaa
305                 310                 315                 320

Xaa Xaa Xaa Xaa Xaa Xaa Xaa Xaa Xaa Xaa Xaa Xaa Xaa Xaa Xaa Xaa
                325                 330                 335

Xaa Xaa Xaa Xaa Xaa Xaa Xaa Xaa Xaa Xaa Xaa Xaa Xaa Xaa Xaa Xaa
            340                 345                 350

Xaa Xaa Xaa Xaa Xaa Xaa Xaa Xaa Xaa Xaa Xaa Xaa Xaa Xaa Xaa Xaa
        355                 360                 365

Xaa Xaa Xaa Xaa Xaa Xaa Xaa Xaa Xaa Xaa Xaa Xaa Xaa Xaa Xaa Xaa
    370                 375                 380

Xaa Xaa Xaa Xaa Xaa Xaa Xaa Xaa Xaa Xaa Xaa Xaa Xaa Xaa Xaa Xaa
385                 390                 395                 400

Xaa
```

<210> SEQ ID NO 8
<211> LENGTH: 351
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (1)..(100)
<223> OTHER INFORMATION: Variable amino acid; Region may encompass 1-100 residues
<220> FEATURE:
<221> NAME/KEY: MOD_RES
<222> LOCATION: (112)..(116)
<223> OTHER INFORMATION: Variable amino acid
<220> FEATURE:
<221> NAME/KEY: MOD_RES
<222> LOCATION: (138)..(142)
<223> OTHER INFORMATION: Variable amino acid
<220> FEATURE:

```
<221> NAME/KEY: MOD_RES
<222> LOCATION: (164)..(168)
<223> OTHER INFORMATION: Variable amino acid; May or may not be present
<220> FEATURE:
<221> NAME/KEY: MOD_RES
<222> LOCATION: (190)..(194)
<223> OTHER INFORMATION: Variable amino acid; May or may not be present
<220> FEATURE:
<221> NAME/KEY: MOD_RES
<222> LOCATION: (216)..(220)
<223> OTHER INFORMATION: Variable amino acid; May or may not be present
<220> FEATURE:
<221> NAME/KEY: MOD_RES
<222> LOCATION: (242)..(246)
<223> OTHER INFORMATION: Variable amino acid
<220> FEATURE:
<221> NAME/KEY: MOD_RES
<222> LOCATION: (252)..(351)
<223> OTHER INFORMATION: Variable amino acid; Region may encompass 1-100
      residues

<400> SEQUENCE: 8

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
                85                  90                  95

Xaa Xaa Xaa Xaa Tyr Lys Cys Pro Glu Cys Gly Lys Ser Phe Ser Xaa
            100                 105                 110

Xaa Xaa Xaa Xaa His Gln Arg Thr His Thr Gly Glu Lys Pro Tyr Lys
        115                 120                 125

Cys Pro Glu Cys Gly Lys Ser Phe Ser Xaa Xaa Xaa Xaa Xaa His Gln
    130                 135                 140

Arg Thr His Thr Gly Glu Lys Pro Tyr Lys Cys Pro Glu Cys Gly Lys
145                 150                 155                 160

Ser Phe Ser Xaa Xaa Xaa Xaa Xaa His Gln Arg Thr His Thr Gly Glu
                165                 170                 175

Lys Pro Tyr Lys Cys Pro Glu Cys Gly Lys Ser Phe Ser Xaa Xaa Xaa
            180                 185                 190

Xaa Xaa His Gln Arg Thr His Thr Gly Glu Lys Pro Tyr Lys Cys Pro
        195                 200                 205

Glu Cys Gly Lys Ser Phe Ser Xaa Xaa Xaa Xaa Xaa His Gln Arg Thr
    210                 215                 220

His Thr Gly Glu Lys Pro Tyr Lys Cys Pro Glu Cys Gly Lys Ser Phe
225                 230                 235                 240

Ser Xaa Xaa Xaa Xaa Xaa His Gln Arg Thr His Xaa Xaa Xaa Xaa Xaa
                245                 250                 255

Xaa Xaa Xaa Xaa Xaa Xaa Xaa Xaa Xaa Xaa Xaa Xaa Xaa Xaa Xaa Xaa
            260                 265                 270

Xaa Xaa Xaa Xaa Xaa Xaa Xaa Xaa Xaa Xaa Xaa Xaa Xaa Xaa Xaa Xaa
        275                 280                 285

Xaa Xaa Xaa Xaa Xaa Xaa Xaa Xaa Xaa Xaa Xaa Xaa Xaa Xaa Xaa Xaa
    290                 295                 300
```

```
Xaa Xaa Xaa Xaa Xaa Xaa Xaa Xaa Xaa Xaa Xaa Xaa Xaa Xaa Xaa Xaa
305                 310                 315                 320

Xaa Xaa Xaa Xaa Xaa Xaa Xaa Xaa Xaa Xaa Xaa Xaa Xaa Xaa Xaa Xaa
                325                 330                 335

Xaa Xaa Xaa Xaa Xaa Xaa Xaa Xaa Xaa Xaa Xaa Xaa Xaa Xaa Xaa
            340                 345                 350


<210> SEQ ID NO 9
<211> LENGTH: 279
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(100)
<223> OTHER INFORMATION: Variable amino acid; Region may encompass 1-100
      residues
<220> FEATURE:
<221> NAME/KEY: MOD_RES
<222> LOCATION: (112)..(118)
<223> OTHER INFORMATION: Variable amino acid
<220> FEATURE:
<221> NAME/KEY: MOD_RES
<222> LOCATION: (140)..(146)
<223> OTHER INFORMATION: Variable amino acid
<220> FEATURE:
<221> NAME/KEY: MOD_RES
<222> LOCATION: (168)..(174)
<223> OTHER INFORMATION: Variable amino acid
<220> FEATURE:
<221> NAME/KEY: MOD_RES
<222> LOCATION: (180)..(279)
<223> OTHER INFORMATION: Variable amino acid; Region may encompass 1-100
      residues

<400> SEQUENCE: 9

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
                85                  90                  95

Xaa Xaa Xaa Xaa Tyr Lys Cys Pro Glu Cys Gly Lys Ser Phe Ser Xaa
            100                 105                 110

Xaa Xaa Xaa Xaa Xaa Xaa His Gln Arg Thr His Thr Gly Glu Lys Pro
        115                 120                 125

Tyr Lys Cys Pro Glu Cys Gly Lys Ser Phe Ser Xaa Xaa Xaa Xaa Xaa
    130                 135                 140

Xaa Xaa His Gln Arg Thr His Thr Gly Glu Lys Pro Tyr Lys Cys Pro
145                 150                 155                 160

Glu Cys Gly Lys Ser Phe Ser Xaa Xaa Xaa Xaa Xaa Xaa Xaa His Gln
                165                 170                 175

Arg Thr His Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Xaa Xaa Xaa Xaa Xaa Xaa Xaa Xaa
        195                 200                 205
```

```
Xaa Xaa Xaa Xaa Xaa Xaa Xaa Xaa Xaa Xaa Xaa Xaa Xaa Xaa Xaa Xaa
    210                 215                 220

Xaa Xaa Xaa Xaa Xaa Xaa Xaa Xaa Xaa Xaa Xaa Xaa Xaa Xaa Xaa Xaa
225                 230                 235                 240

Xaa Xaa Xaa Xaa Xaa Xaa Xaa Xaa Xaa Xaa Xaa Xaa Xaa Xaa Xaa Xaa
                245                 250                 255

Xaa Xaa Xaa Xaa Xaa Xaa Xaa Xaa Xaa Xaa Xaa Xaa Xaa Xaa Xaa Xaa
            260                 265                 270

Xaa Xaa Xaa Xaa Xaa Xaa Xaa
        275


<210> SEQ ID NO 10
<211> LENGTH: 363
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(100)
<223> OTHER INFORMATION: Variable amino acid; Region may encompass 1-100
      residues
<220> FEATURE:
<221> NAME/KEY: MOD_RES
<222> LOCATION: (112)..(118)
<223> OTHER INFORMATION: Variable amino acid
<220> FEATURE:
<221> NAME/KEY: MOD_RES
<222> LOCATION: (140)..(146)
<223> OTHER INFORMATION: Variable amino acid
<220> FEATURE:
<221> NAME/KEY: MOD_RES
<222> LOCATION: (168)..(174)
<223> OTHER INFORMATION: Variable amino acid
<220> FEATURE:
<221> NAME/KEY: MOD_RES
<222> LOCATION: (196)..(202)
<223> OTHER INFORMATION: Variable amino acid
<220> FEATURE:
<221> NAME/KEY: MOD_RES
<222> LOCATION: (224)..(230)
<223> OTHER INFORMATION: Variable amino acid
<220> FEATURE:
<221> NAME/KEY: MOD_RES
<222> LOCATION: (252)..(258)
<223> OTHER INFORMATION: Variable amino acid
<220> FEATURE:
<221> NAME/KEY: MOD_RES
<222> LOCATION: (264)..(363)
<223> OTHER INFORMATION: Variable amino acid; Region may encompass 1-100
      residues

<400> SEQUENCE: 10

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
                85                  90                  95

Xaa Xaa Xaa Xaa Tyr Lys Cys Pro Glu Cys Gly Lys Ser Phe Ser Xaa
```

-continued

```
            100                 105                 110

Xaa Xaa Xaa Xaa Xaa Xaa His Gln Arg Thr His Thr Gly Glu Lys Pro
        115                 120                 125

Tyr Lys Cys Pro Glu Cys Gly Lys Ser Phe Ser Xaa Xaa Xaa Xaa Xaa
    130                 135                 140

Xaa Xaa His Gln Arg Thr His Thr Gly Glu Lys Pro Tyr Lys Cys Pro
145                 150                 155                 160

Glu Cys Gly Lys Ser Phe Ser Xaa Xaa Xaa Xaa Xaa Xaa Xaa His Gln
                165                 170                 175

Arg Thr His Thr Gly Glu Lys Pro Tyr Lys Cys Pro Glu Cys Gly Lys
            180                 185                 190

Ser Phe Ser Xaa Xaa Xaa Xaa Xaa Xaa Xaa His Gln Arg Thr His Thr
        195                 200                 205

Gly Glu Lys Pro Tyr Lys Cys Pro Glu Cys Gly Lys Ser Phe Ser Xaa
    210                 215                 220

Xaa Xaa Xaa Xaa Xaa Xaa His Gln Arg Thr His Thr Gly Glu Lys Pro
225                 230                 235                 240

Tyr Lys Cys Pro Glu Cys Gly Lys Ser Phe Ser Xaa Xaa Xaa Xaa Xaa
                245                 250                 255

Xaa Xaa His Gln Arg Thr His Xaa Xaa Xaa Xaa Xaa Xaa Xaa Xaa Xaa
            260                 265                 270

Xaa Xaa Xaa Xaa Xaa Xaa Xaa Xaa Xaa Xaa Xaa Xaa Xaa Xaa Xaa Xaa
        275                 280                 285

Xaa Xaa Xaa Xaa Xaa Xaa Xaa Xaa Xaa Xaa Xaa Xaa Xaa Xaa Xaa Xaa
    290                 295                 300

Xaa Xaa Xaa Xaa Xaa Xaa Xaa Xaa Xaa Xaa Xaa Xaa Xaa Xaa Xaa Xaa
305                 310                 315                 320

Xaa Xaa Xaa Xaa Xaa Xaa Xaa Xaa Xaa Xaa Xaa Xaa Xaa Xaa Xaa Xaa
                325                 330                 335

Xaa Xaa Xaa Xaa Xaa Xaa Xaa Xaa Xaa Xaa Xaa Xaa Xaa Xaa Xaa Xaa
            340                 345                 350

Xaa Xaa Xaa Xaa Xaa Xaa Xaa Xaa Xaa Xaa Xaa
        355                 360
```

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 11

```
Gln Arg Ala Asn Leu Arg Ala
1               5
```

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 12

```
Gln Lys Ser Ser Leu Ile Ala
1               5
```

<210> SEQ ID NO 13

<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 13

Gln Leu Ala His Leu Arg Ala
1 5

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 14

Glu Arg Ser His Leu Arg Glu
1 5

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 15

Arg Arg Asp Glu Leu Asn Val
1 5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 16

Asp Lys Lys Asp Leu Thr Arg
1 5

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 17

Arg Ser Asp His Leu Thr Asn
1 5

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 18

Thr Thr Gly Asn Leu Thr Val 1 5

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 19

Asp Ser Gly Asn Leu Arg Val
1 5

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 20

Arg Lys Asp Asn Leu Lys Asn
1 5

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 21

His Lys Asn Ala Leu Gln Asn
1 5

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 22

Ser Pro Ala Asp Leu Thr Arg
1 5

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 23

Thr His Leu Asp Leu Ile Arg
1 5

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 24

Arg Thr Asp Thr Leu Arg Asp
1 5

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 25

His Arg Thr Thr Leu Thr Asn
1 5

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 26

Arg Ala Asp Asn Leu Thr Glu
1 5

<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 27

Gln Asn Ser Thr Leu Thr Glu
1 5

<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 28

Gln Ser Gly Asn Leu Thr Glu
1 5

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 29

Thr Lys Asn Ser Leu Thr Glu
1 5

<210> SEQ ID NO 30
<211> LENGTH: 7
<212> TYPE: PRT

<213> ORGANISM: Artificial Sequence
<220> FEATURE:
<223> OTHER INFORMATION: Description of Artificial Sequence: Synthetic
peptide

<400> SEQUENCE: 30

Thr Ser Gly Asn Leu Thr Glu
1 5

<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 31

Ser Lys Lys Ala Leu Thr Glu
1 5

<210> SEQ ID NO 32
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 32

Thr Thr Gly Ala Leu Thr Glu
1 5

<210> SEQ ID NO 33
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 33

Arg Asn Asp Ala Leu Thr Glu
1 5

<210> SEQ ID NO 34
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 34

Thr Ser His Ser Leu Thr Glu
1 5

<210> SEQ ID NO 35
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 35

Ser Lys Lys His Leu Ala Glu
1 5

<210> SEQ ID NO 36
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 36

Arg Asn Asp Thr Leu Thr Glu
1 5

<210> SEQ ID NO 37
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 37

Gln Ser Gly His Leu Thr Glu
1 5

<210> SEQ ID NO 38
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 38

Ser Arg Arg Thr Leu Arg Ala
1 5

<210> SEQ ID NO 39
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 39

His Thr Gly His Leu Leu Glu
1 5

<210> SEQ ID NO 40
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 40

Arg Ser Asp Lys Leu Thr Glu
1 5

<210> SEQ ID NO 41
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 41

```
Gln Ser Gly Asp Leu Arg Arg
1               5


<210> SEQ ID NO 42
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Gln Arg Ala His Leu Glu Arg
1               5


<210> SEQ ID NO 43
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Thr Ser Gly Glu Leu Val Arg
1               5


<210> SEQ ID NO 44
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Thr Ser Gly His Leu Val Arg
1               5


<210> SEQ ID NO 45
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Thr Ser Gly Asn Leu Val Arg
1               5


<210> SEQ ID NO 46
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Asp Pro Gly His Leu Val Arg
1               5


<210> SEQ ID NO 47
<211> LENGTH: 7
<212> TYPE: PRT
<213> ORGANISM: Artificial Sequence
<220> FEATURE:
```

<223> OTHER INFORMATION: Description of Artificial Sequence: Synthetic peptide

<400> SEQUENCE: 47

Arg Ser Asp Asn Leu Val Arg
1 5

<210> SEQ ID NO 48
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 48

Asp Cys Arg Asp Leu Ala Arg
1 5

<210> SEQ ID NO 49
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 49

Gln Ser Ser Asn Leu Val Arg
1 5

<210> SEQ ID NO 50
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 50

Asp Pro Gly Asn Leu Val Arg
1 5

<210> SEQ ID NO 51
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 51

Gln Ser Ser Ser Leu Val Arg
1 5

<210> SEQ ID NO 52
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 52

Thr Ser Gly Ser Leu Val Arg
1 5

<210> SEQ ID NO 53

<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 53

Asp Pro Gly Ala Leu Val Arg
1 5

<210> SEQ ID NO 54
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 54

Arg Ser Asp Glu Leu Val Arg
1 5

<210> SEQ ID NO 55
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 55

Arg Ser Asp Asp Leu Val Arg
1 5

<210> SEQ ID NO 56
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 56

Arg Ser Asp Lys Leu Val Arg
1 5

<210> SEQ ID NO 57
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 57

Arg Ser Asp His Leu Thr Thr
1 5

<210> SEQ ID NO 58
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 58

Arg Glu Asp Asn Leu His Thr 1 5

<210> SEQ ID NO 59
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 59

Gln Ala Gly His Leu Ala Ser
1 5

<210> SEQ ID NO 60
<211> LENGTH: 191
<212> TYPE: DNA
<213> ORGANISM: Hepatitus B virus

<400> SEQUENCE: 60
accccaacac atggcgcaat atcccatatc accggcggga gcgcagtgtt tgctttttca 60
aaggtcagag atatacatgt tcaggaacta ttgatgtctt gtttagccaa gataatgatt 120
aaaccgcgct gtctcttatc tgattcaact tttgtttgcc ataagcgtta tcagacgtta 180
ccatggcatt t 191

<210> SEQ ID NO 61
<211> LENGTH: 17
<212> TYPE: DNA
<213> ORGANISM: Hepatitus B virus

<400> SEQUENCE: 61
gccaagataa tgattaa 17

<210> SEQ ID NO 62
<211> LENGTH: 18
<212> TYPE: DNA
<213> ORGANISM: Hepatitus B virus

<400> SEQUENCE: 62
atggcaaaca aaagttga 18

<210> SEQ ID NO 63
<211> LENGTH: 18
<212> TYPE: DNA
<213> ORGANISM: Hepatitus B virus

<400> SEQUENCE: 63
ataagagaca gcgcggtt 18

<210> SEQ ID NO 64
<211> LENGTH: 144
<212> TYPE: DNA
<213> ORGANISM: Hepatitus B virus

<400> SEQUENCE: 64
ggctgggttt caccccaccg cacggaggcc ttttggggtg gagccctcag gctcagggca 60
tactacaaac tttgccagca aatccgcctc ctgcctccac caatcgccag acaggaaggc 120
agcctacccc gctgtctcca cctt 144

<210> SEQ ID NO 65
<211> LENGTH: 18
<212> TYPE: DNA

<213> ORGANISM: Hepatitus B virus

<400> SEQUENCE: 65
accaatcgcc agacagga 18

<210> SEQ ID NO 66
<211> LENGTH: 18
<212> TYPE: DNA
<213> ORGANISM: Hepatitus B virus

<400> SEQUENCE: 66
gctcagggca tactacaa 18

<210> SEQ ID NO 67
<211> LENGTH: 18
<212> TYPE: DNA
<213> ORGANISM: Hepatitus B virus

<400> SEQUENCE: 67
tggtggaggc aggaggcg 18

<210> SEQ ID NO 68
<211> LENGTH: 18
<212> TYPE: DNA
<213> ORGANISM: Hepatitus B virus

<400> SEQUENCE: 68
cagcggggta ggctgcct 18

<210> SEQ ID NO 69
<211> LENGTH: 18
<212> TYPE: DNA
<213> ORGANISM: Hepatitus B virus

<400> SEQUENCE: 69
gccaagataa tgattaaa 18

<210> SEQ ID NO 70
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 70

Cys Tyr Pro Tyr Asp Val Pro Asp Tyr Ala
1 5 10

<210> SEQ ID NO 71
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 71

Asp Tyr Lys Asp Asp Asp Asp Lys
1 5

<210> SEQ ID NO 72
<211> LENGTH: 11
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 72

Cys Glu Gln Lys Leu Ile Ser Glu Glu Asp Leu
1               5                   10

<210> SEQ ID NO 73
<211> LENGTH: 200
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(2)
<223> OTHER INFORMATION: Variable amino acid; Region may encompass 0-2
      residues
<220> FEATURE:
<221> NAME/KEY: MOD_RES
<222> LOCATION: (4)..(7)
<223> OTHER INFORMATION: Variable amino acid; Region may encompass 2-4
      residues
<220> FEATURE:
<221> NAME/KEY: MOD_RES
<222> LOCATION: (9)..(11)
<223> OTHER INFORMATION: Variable amino acid
<220> FEATURE:
<221> NAME/KEY: MOD_RES
<222> LOCATION: (14)..(20)
<223> OTHER INFORMATION: Variable amino acid
<220> FEATURE:
<221> NAME/KEY: MOD_RES
<222> LOCATION: (22)..(24)
<223> OTHER INFORMATION: Variable amino acid
<220> FEATURE:
<221> NAME/KEY: MOD_RES
<222> LOCATION: (26)..(35)
<223> OTHER INFORMATION: Variable amino acid; Region may encompass 2-10
      residues
<220> FEATURE:
<221> NAME/KEY: MOD_RES
<222> LOCATION: (36)..(37)
<223> OTHER INFORMATION: Variable amino acid; Region may encompass 0-2
      residues
<220> FEATURE:
<221> NAME/KEY: MOD_RES
<222> LOCATION: (39)..(42)
<223> OTHER INFORMATION: Variable amino acid; Region may encompass 2-4
      residues
<220> FEATURE:
<221> NAME/KEY: MOD_RES
<222> LOCATION: (44)..(46)
<223> OTHER INFORMATION: Variable amino acid
<220> FEATURE:
<221> NAME/KEY: MOD_RES
<222> LOCATION: (49)..(55)
<223> OTHER INFORMATION: Variable amino acid
<220> FEATURE:
<221> NAME/KEY: MOD_RES
<222> LOCATION: (57)..(59)
<223> OTHER INFORMATION: Variable amino acid
<220> FEATURE:
<221> NAME/KEY: MOD_RES
<222> LOCATION: (61)..(70)
<223> OTHER INFORMATION: Variable amino acid; Region may encompass 2-10
      residues
<220> FEATURE:
<221> NAME/KEY: MOD_RES
<222> LOCATION: (71)..(72)
<223> OTHER INFORMATION: Variable amino acid; Region may encompass 0-2
      residues; May or may not be present
<220> FEATURE:
<221> NAME/KEY: MOD_RES
<222> LOCATION: (74)..(77)
<223> OTHER INFORMATION: Variable amino acid; Region may encompass 2-4
      residues; May or may not be present <220> FEATURE:
<221> NAME/KEY: MOD_RES
<222> LOCATION: (79)..(81)
<223> OTHER INFORMATION: Variable amino acid; May or may not be present
<220> FEATURE:
<221> NAME/KEY: MOD_RES
<222> LOCATION: (84)..(90)
<223> OTHER INFORMATION: Variable amino acid; May or may not be present
<220> FEATURE:
<221> NAME/KEY: MOD_RES
<222> LOCATION: (92)..(94)
<223> OTHER INFORMATION: Variable amino acid; May or may not be present
<220> FEATURE:
<221> NAME/KEY: MOD_RES
<222> LOCATION: (96)..(105)
<223> OTHER INFORMATION: Variable amino acid; Region may encompass 2-10 residues; May or may not be present
<220> FEATURE:
<221> NAME/KEY: MOD_RES
<222> LOCATION: (106)..(107)
<223> OTHER INFORMATION: Variable amino acid; Region may encompass 0-2 residues; May or may not be present
<220> FEATURE:
<221> NAME/KEY: MOD_RES
<222> LOCATION: (109)..(112)
<223> OTHER INFORMATION: Variable amino acid; Region may encompass 2-4 residues; May or may not be present
<220> FEATURE:
<221> NAME/KEY: MOD_RES
<222> LOCATION: (114)..(116)
<223> OTHER INFORMATION: Variable amino acid; May or may not be present
<220> FEATURE:
<221> NAME/KEY: MOD_RES
<222> LOCATION: (119)..(125)
<223> OTHER INFORMATION: Variable amino acid; May or may not be present
<220> FEATURE:
<221> NAME/KEY: MOD_RES
<222> LOCATION: (127)..(129)
<223> OTHER INFORMATION: Variable amino acid; May or may not be present
<220> FEATURE:
<221> NAME/KEY: MOD_RES
<222> LOCATION: (131)..(140)
<223> OTHER INFORMATION: Variable amino acid; Region may encompass 2-10 residues; May or may not be present
<220> FEATURE:
<221> NAME/KEY: MOD_RES
<222> LOCATION: (141)..(142)
<223> OTHER INFORMATION: Variable amino acid; Region may encompass 0-2 residues; May or may not be present
<220> FEATURE:
<221> NAME/KEY: MOD_RES
<222> LOCATION: (144)..(147)
<223> OTHER INFORMATION: Variable amino acid; Region may encompass 2-4 residues; May or may not be present
<220> FEATURE:
<221> NAME/KEY: MOD_RES
<222> LOCATION: (149)..(151)
<223> OTHER INFORMATION: Variable amino acid; May or may not be present
<220> FEATURE:
<221> NAME/KEY: MOD_RES
<222> LOCATION: (154)..(160)
<223> OTHER INFORMATION: Variable amino acid; May or may not be present
<220> FEATURE:
<221> NAME/KEY: MOD_RES
<222> LOCATION: (162)..(164)
<223> OTHER INFORMATION: Variable amino acid; May or may not be present
<220> FEATURE:
<221> NAME/KEY: MOD_RES
<222> LOCATION: (166)..(175)
<223> OTHER INFORMATION: Variable amino acid; Region may encompass 2-10 residues; May or may not be present
<220> FEATURE:
<221> NAME/KEY: MOD_RES
<222> LOCATION: (176)..(177)
<223> OTHER INFORMATION: Variable amino acid; Region may encompass 0-2 residues
<220> FEATURE:
<221> NAME/KEY: MOD_RES
<222> LOCATION: (179)..(182)
<223> OTHER INFORMATION: Variable amino acid; Region may encompass 2-4 residues
<220> FEATURE:
<221> NAME/KEY: MOD_RES
<222> LOCATION: (184)..(186)
<223> OTHER INFORMATION: Variable amino acid
<220> FEATURE:
<221> NAME/KEY: MOD_RES
<222> LOCATION: (189)..(195)
<223> OTHER INFORMATION: Variable amino acid
<220> FEATURE:
<221> NAME/KEY: MOD_RES
<222> LOCATION: (197)..(199)
<223> OTHER INFORMATION: Variable amino acid

<400> SEQUENCE: 73

```
Xaa Xaa Cys Xaa Xaa Xaa Xaa Cys Xaa Xaa Xaa Phe Ser Xaa Xaa Xaa
1               5                   10                  15

Xaa Xaa Xaa Xaa His Xaa Xaa Xaa His Xaa Xaa Xaa Xaa Xaa Xaa Xaa
            20                  25                  30

Xaa Xaa Xaa Xaa Xaa Cys Xaa Xaa Xaa Xaa Cys Xaa Xaa Xaa Phe Ser
        35                  40                  45

Xaa Xaa Xaa Xaa Xaa Xaa Xaa His Xaa Xaa Xaa His Xaa Xaa Xaa Xaa
    50                  55                  60

Xaa Xaa Xaa Xaa Xaa Xaa Xaa Xaa Cys Xaa Xaa Xaa Xaa Cys Xaa Xaa
65                  70                  75                  80

Xaa Phe Ser Xaa Xaa Xaa Xaa Xaa Xaa Xaa His Xaa Xaa Xaa His Xaa
                85                  90                  95

Xaa Xaa Xaa Xaa Xaa Xaa Xaa Xaa Xaa Xaa Xaa Cys Xaa Xaa Xaa Xaa
            100                 105                 110

Cys Xaa Xaa Xaa Phe Ser Xaa Xaa Xaa Xaa Xaa Xaa Xaa His Xaa Xaa
        115                 120                 125

Xaa His Xaa Xaa Xaa Xaa Xaa Xaa Xaa Xaa Xaa Xaa Xaa Xaa Cys Xaa
    130                 135                 140

Xaa Xaa Xaa Cys Xaa Xaa Xaa Phe Ser Xaa Xaa Xaa Xaa Xaa Xaa Xaa
145                 150                 155                 160

His Xaa Xaa Xaa His Xaa Xaa Xaa Xaa Xaa Xaa Xaa Xaa Xaa Xaa Xaa
                165                 170                 175

Xaa Cys Xaa Xaa Xaa Xaa Cys Xaa Xaa Xaa Phe Ser Xaa Xaa Xaa Xaa
            180                 185                 190

Xaa Xaa Xaa His Xaa Xaa Xaa His
        195                 200
```

<210> SEQ ID NO 74
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 74

```
Ile Glu Gly Arg
1
```

<210> SEQ ID NO 75
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 75

```
Leu Val Pro Arg Gly Ser
1               5


<210> SEQ ID NO 76
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

His Pro Phe His Leu Val Ile His
1               5


<210> SEQ ID NO 77
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Lys Ile Pro Ile Lys
1               5


<210> SEQ ID NO 78
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Val Arg Ile Leu Glu Ser Trp Phe Ala Lys Asn Ile
1               5                   10


<210> SEQ ID NO 79
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Pro Lys Lys Lys Arg Lys Val
1               5


<210> SEQ ID NO 80
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Ala Ala Phe Glu Asp Leu Arg Val Arg Ser
1               5                   10


<210> SEQ ID NO 81
<211> LENGTH: 4
<212> TYPE: PRT
<213> ORGANISM: Artificial Sequence
<220> FEATURE:
<223> OTHER INFORMATION: Description of Artificial Sequence: Synthetic
```

peptide

<400> SEQUENCE: 81

Pro Arg Lys Arg
1

<210> SEQ ID NO 82
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 82

Val Ser Arg Lys Arg Pro Arg Pro Ala
1 5

<210> SEQ ID NO 83
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 83

Ala Pro Thr Lys Arg Lys
1 5

<210> SEQ ID NO 84
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 84

Lys Arg Pro Arg Pro
1 5

<210> SEQ ID NO 85
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 85

Pro Asn Lys Lys Lys Arg Lys
1 5

<210> SEQ ID NO 86
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 86

Arg Pro Ala Ala Thr Lys Lys Ala Gly Gln Ala Lys Lys Lys Lys Leu
1 5 10 15

Asp

<210> SEQ ID NO 87
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 87

Lys Lys Lys Ile Lys
1 5

<210> SEQ ID NO 88
<211> LENGTH: 19
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 88

Arg Val Thr Ile Arg Thr Val Arg Val Arg Arg Pro Pro Lys Gly Lys
1 5 10 15

His Arg Lys

<210> SEQ ID NO 89
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 89

Asp Gly Lys Lys Trp Ser
1 5

<210> SEQ ID NO 90
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 90

Lys Ala Lys Arg Gln Arg
1 5

<210> SEQ ID NO 91
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 91

Asp Arg Leu Arg Arg
1 5

<210> SEQ ID NO 92
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 92

Pro Lys Gln Lys Arg Lys
1 5

<210> SEQ ID NO 93
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 93

Val Arg Lys Lys Arg Lys Thr
1 5

<210> SEQ ID NO 94
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 94

Ala Lys Lys Ser Lys Gln Glu
1 5

<210> SEQ ID NO 95
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 95

Pro Ala Ala Lys Arg Val Lys Leu Asp
1 5

<210> SEQ ID NO 96
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 96

Arg Gln Arg Arg Asn Glu Leu Lys Arg Ser Phe
1 5 10

<210> SEQ ID NO 97
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 97

Thr Lys Lys Arg Lys Leu Glu
1 5

<210> SEQ ID NO 98
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 98

Pro Lys Thr Arg Arg Arg Pro
1 5

<210> SEQ ID NO 99
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 99

Ser Gln Arg Lys Arg Pro Pro
1 5

<210> SEQ ID NO 100
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 100

Arg Leu Pro Val Arg Arg Arg Arg Arg Val Pro
1 5 10

<210> SEQ ID NO 101
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 101

Gly Arg Lys Lys Arg
1 5

<210> SEQ ID NO 102
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 102

Val Trp Thr Thr Lys Gly Lys Arg Lys Arg Ile Asp Val
1 5 10

<210> SEQ ID NO 103
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 103

Arg Lys Phe Lys Lys
1 5

<210> SEQ ID NO 104
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Arg Arg Asn Arg Arg Arg Arg Trp
1               5

<210> SEQ ID NO 105
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Pro Arg Glu Ser Gly Lys Lys Arg Lys Arg Lys Arg Leu Lys Pro Thr
1               5                   10                  15

<210> SEQ ID NO 106
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Ser Ala Leu Ile Lys Lys Lys Lys Met Ala Pro
1               5                   10

<210> SEQ ID NO 107
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Pro Pro Lys Lys Arg
1               5

<210> SEQ ID NO 108
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Pro Lys Lys Lys Lys Lys
1               5

<210> SEQ ID NO 109
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Ser Lys Arg Val Ala Lys Arg Lys Leu
1 5

<210> SEQ ID NO 110
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 110

Pro Leu Leu Lys Lys Ile Lys Gln
1 5

<210> SEQ ID NO 111
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 111

Pro Pro Gln Lys Lys Ile Lys Ser
1 5

<210> SEQ ID NO 112
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 112

Pro Gln Pro Lys Lys Lys Pro
1 5

<210> SEQ ID NO 113
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 113

Phe Lys Arg Lys His Lys Lys Asp Ile Ser Gln Asn Lys Arg Ala Val
1 5 10 15

Arg Arg

<210> SEQ ID NO 114
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 114

Ser Lys Cys Leu Gly Trp Leu Trp Gly
1 5

<210> SEQ ID NO 115
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 115

Gly Lys Arg Lys Asn Lys Pro Lys
1 5

<210> SEQ ID NO 116
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 116

Lys Thr Arg Lys His Arg Gly
1 5

<210> SEQ ID NO 117
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 117

Lys His Arg Lys His Pro Gly
1 5

<210> SEQ ID NO 118
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 118

Met Cys Pro Lys Lys Arg Lys Val
1 5

<210> SEQ ID NO 119
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 119

Thr Gly Glu Lys Pro
1 5

<210> SEQ ID NO 120
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 120
agtactgcca agataatgat taaaagtact 30

<210> SEQ ID NO 121

<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 121
agtactatgg caaacaaaag ttgaagtact 30

<210> SEQ ID NO 122
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 122
agtactagag atataagtac t 21

<210> SEQ ID NO 123
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 123
agtactaaaa gcaaaagtac t 21

<210> SEQ ID NO 124
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 124
agtactataa tgattagtac t 21

<210> SEQ ID NO 125
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 125
agtactaaca agacaagtac t 21

<210> SEQ ID NO 126
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 126
agtactacca atcgccagac aggaagtact 30

<210> SEQ ID NO 127
<211> LENGTH: 30
<212> TYPE: DNA

<213> ORGANISM: Artificial Sequence
<220> FEATURE:
<223> OTHER INFORMATION: Description of Artificial Sequence: Synthetic
oligonucleotide

<400> SEQUENCE: 127
agtactgctc agggcatact acaaagtact 30

<210> SEQ ID NO 128
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 128
agtacttggt ggaggcagga ggcgagtact 30

<210> SEQ ID NO 129
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 129
agtactaggc ctccgagtac t 21

<210> SEQ ID NO 130
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 130
agtactagcc ctcagagtac t 21

<210> SEQ ID NO 131
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 131
agtactagta tgcccagtac t 21

<210> SEQ ID NO 132
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 132
agtactccag caaatagtac t 21

<210> SEQ ID NO 133
<211> LENGTH: 21
<212> TYPE: DNA
<213> ORGANISM: Artificial Sequence
<220> FEATURE:

<223> OTHER INFORMATION: Description of Artificial Sequence: Synthetic
oligonucleotide

<400> SEQUENCE: 133
agtactggcg attggagtac t 21

<210> SEQ ID NO 134
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 134
agtactcagc ctaccagtac t 21

<210> SEQ ID NO 135
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 135
tgaagggctg tacttttaac ccag 24

<210> SEQ ID NO 136
<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 136
caggatactt tggtttaacc cc 22

<210> SEQ ID NO 137
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 137
cgtggggatg cccaggattt cttt 24

<210> SEQ ID NO 138
<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 138
agatttcgga tccgagggca gt 22

<210> SEQ ID NO 139
<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 139
agctgcttgc caaggtatct tt 22

<210> SEQ ID NO 140
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 140
gctctaaagc gtctttagca tctc 24

<210> SEQ ID NO 141
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 141
gtttgccata agcgttatca gacg 24

<210> SEQ ID NO 142
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 142
aggggtgtat ggaaaagccg tc 22

<210> SEQ ID NO 143
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 143
gccaagataa tgattaaac 19

<210> SEQ ID NO 144
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 144
atggcaaaca aaagttgat 19

<210> SEQ ID NO 145
<211> LENGTH: 10
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 145
agagatatac 10

<210> SEQ ID NO 146
<211> LENGTH: 10
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 146
aaaagcaaag 10

<210> SEQ ID NO 147
<211> LENGTH: 10
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 147
ataatgatta 10

<210> SEQ ID NO 148
<211> LENGTH: 10
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 148
aacaagacaa 10

<210> SEQ ID NO 149
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 149
accaatcgcc agacaggaa 19

<210> SEQ ID NO 150
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 150
gctcagggca tactacaaa 19

<210> SEQ ID NO 151
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 151
tggtggaggc aggaggcgg 19

<210> SEQ ID NO 152
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 152
cagcggggta ggctgcctt 19

<210> SEQ ID NO 153
<211> LENGTH: 10
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 153
aggcctccgt 10

<210> SEQ ID NO 154
<211> LENGTH: 10
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 154
agccctcagt 10

<210> SEQ ID NO 155
<211> LENGTH: 10
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 155
agtatgccct 10

<210> SEQ ID NO 156
<211> LENGTH: 10
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 156
ccagcaaatc 10

<210> SEQ ID NO 157
<211> LENGTH: 10
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 157
ggcgattggt 10

<210> SEQ ID NO 158
<211> LENGTH: 10
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 158
cagcctaccc 10

<210> SEQ ID NO 159
<211> LENGTH: 250
<212> TYPE: DNA
<213> ORGANISM: Hepatitus B virus

<400> SEQUENCE: 159
cacgtgtagc tacagatgct accccaacac atggcgcaat atcccatatc accggcggga 60
gcgcagtgtt tgctttttca aaggtcagag atatacatgt tcaggaacta ttgatgtctt 120
gtttagccaa gataatgatt aaaccgcgct gtctcttatc tgattcaact tttgtttgcc 180
ataagcgtta tcagacgtta ccatggcatt ttgctatgtt ggccaaacaa ttgctcaaac 240
ctatacaatt 250

<210> SEQ ID NO 160
<211> LENGTH: 250
<212> TYPE: DNA
<213> ORGANISM: Hepatitus B virus

<400> SEQUENCE: 160
aattgtatag gtttgagcaa ttgtttggcc aacatagcaa aatgccatgg taacgtctga 60
taacgcttat ggcaaacaaa agttgaatca gataagagac agcgcggttt aatcattatc 120
ttggctaaac aagacatcaa tagttcctga acatgtatat ctctgacctt tgaaaaagca 180
aacactgcgc tccggccggt gatatgggat attgcgccat gtgttggggt agcatctgta 240
gctacacgtg 250

<210> SEQ ID NO 161
<211> LENGTH: 540
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 161
ctggagctcg aacccggcga aaagccttat aagtgcccag aatgcggcaa atcattcagc 60
caacgggcca acctgagggc tcatcagcgc acacacacag gtgagaagcc atacaaatgt 120
ccagaatgtg gtaagtcttt ctctcacaag aacgccctgc aaaaccacca gcggacccac 180
acaggcgaga agccctacaa gtgccccgag tgtggcaagt ctttcagcag aagggacgag 240
ctgaatgttc atcaaaggac tcatactgga gagaagccat acaaatgtcc tgaatgcggc 300
aagagcttca gccagaaatc cagtctgatc gcacaccagc gaacgcacac tggggagaaa 360
ccttacaaat gcccagaatg tggtaaatct ttcagccgta aagataacct taagaaccac 420
caacgcaccc acacagggga aaaaccttat aagtgtcccg aatgcggcaa atccttcagt 480
gactgcaggg acctcgcccg ccatcagcgg acacacacag gtaagaagac aagtactagt 540

<210> SEQ ID NO 162
<211> LENGTH: 180

<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 162

Leu Glu Leu Glu Pro Gly Glu Lys Pro Tyr Lys Cys Pro Glu Cys Gly
1               5                   10                  15

Lys Ser Phe Ser Gln Arg Ala Asn Leu Arg Ala His Gln Arg Thr His
            20                  25                  30

Thr Gly Glu Lys Pro Tyr Lys Cys Pro Glu Cys Gly Lys Ser Phe Ser
        35                  40                  45

His Lys Asn Ala Leu Gln Asn His Gln Arg Thr His Thr Gly Glu Lys
    50                  55                  60

Pro Tyr Lys Cys Pro Glu Cys Gly Lys Ser Phe Ser Arg Arg Asp Glu
65                  70                  75                  80

Leu Asn Val His Gln Arg Thr His Thr Gly Glu Lys Pro Tyr Lys Cys
                85                  90                  95

Pro Glu Cys Gly Lys Ser Phe Ser Gln Lys Ser Ser Leu Ile Ala His
            100                 105                 110

Gln Arg Thr His Thr Gly Glu Lys Pro Tyr Lys Cys Pro Glu Cys Gly
        115                 120                 125

Lys Ser Phe Ser Arg Lys Asp Asn Leu Lys Asn His Gln Arg Thr His
    130                 135                 140

Thr Gly Glu Lys Pro Tyr Lys Cys Pro Glu Cys Gly Lys Ser Phe Ser
145                 150                 155                 160

Asp Cys Arg Asp Leu Ala Arg His Gln Arg Thr His Thr Gly Lys Lys
                165                 170                 175

Thr Ser Thr Ser
        180

<210> SEQ ID NO 163
<211> LENGTH: 534
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 163
ctcgagccag gtgaaaaacc ctacaagtgc cctgagtgtg gcaaaagctt ttctcaagca 60
ggacatctcg ctagtcatca aaggactcac accggtgaaa agccctataa gtgccccgaa 120
tgcggaaaat cttttagcca taggaccaca ctgacaaacc accagcgaac acatacaggg 180
gagaagcctt ataagtgtcc cgaatgcggg aagtcttttt ctcagcgggc aaacctaaga 240
gctcatcaga gaacacacac aggcgaaaaa ccttacaagt gtccagagtg cggaaaaagc 300
ttttcagatt ctggaaatct tcgagtgcac caaagaactc acacgggaga gaagccttat 360
aagtgccccg aatgcggcaa atccttctct cagagtggcg acctacggag acaccagcgc 420
actcatactg gcgagaagcc ctataagtgc cctgagtgtg gtaaatcctt ttctagaaga 480
gacgagctga atgtgcacca acggactcac acaggaaaga agacttcaac tagt 534

<210> SEQ ID NO 164
<211> LENGTH: 180
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 164

Leu Glu Leu Glu Pro Gly Glu Lys Pro Tyr Lys Cys Pro Glu Cys Gly
1 5 10 15

Lys Ser Phe Ser Gln Ala Gly His Leu Ala Ser His Gln Arg Thr His
20 25 30

Thr Gly Glu Lys Pro Tyr Lys Cys Pro Glu Cys Gly Lys Ser Phe Ser
35 40 45

His Arg Thr Thr Leu Thr Asn His Gln Arg Thr His Thr Gly Glu Lys
50 55 60

Pro Tyr Lys Cys Pro Glu Cys Gly Lys Ser Phe Ser Gln Arg Ala Asn
65 70 75 80

Leu Arg Ala His Gln Arg Thr His Thr Gly Glu Lys Pro Tyr Lys Cys
85 90 95

Pro Glu Cys Gly Lys Ser Phe Ser Asp Ser Gly Asn Leu Arg Val His
100 105 110

Gln Arg Thr His Thr Gly Glu Lys Pro Tyr Lys Cys Pro Glu Cys Gly
115 120 125

Lys Ser Phe Ser Gln Ser Gly Asp Leu Arg Arg His Gln Arg Thr His
130 135 140

Thr Gly Glu Lys Pro Tyr Lys Cys Pro Glu Cys Gly Lys Ser Phe Ser
145 150 155 160

Arg Arg Asp Glu Leu Asn Val His Gln Arg Thr His Thr Gly Lys Lys
165 170 175

Thr Ser Thr Ser
180

<210> SEQ ID NO 165
<211> LENGTH: 288
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 165
ctggagctgg agcccggtga gaagccctac aagtgccctg agtgcggtaa aagcttttct 60
cagaagtcat ccctaattgc acatcagaga acacacacag gagaaaaacc ctataaatgt 120
ccagagtgcg gaaagagctt cagtacgtct ggaaatctgg ttaggcacca acgtacacac 180
acaggggaga aaccatacaa gtgtcctgaa tgcggtaaaa gtttctctca gctggctcat 240
ttgagagctc atcagcgcac acacacaggt aaaaagacga gcactagt 288

<210> SEQ ID NO 166
<211> LENGTH: 96
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 166

Leu Glu Leu Glu Pro Gly Glu Lys Pro Tyr Lys Cys Pro Glu Cys Gly
1 5 10 15

Lys Ser Phe Ser Gln Lys Ser Ser Leu Ile Ala His Gln Arg Thr His
20 25 30

Thr Gly Glu Lys Pro Tyr Lys Cys Pro Glu Cys Gly Lys Ser Phe Ser
35 40 45

Thr Ser Gly Asn Leu Val Arg His Gln Arg Thr His Thr Gly Glu Lys
    50                  55                  60

Pro Tyr Lys Cys Pro Glu Cys Gly Lys Ser Phe Ser Gln Leu Ala His
65                  70                  75                  80

Leu Arg Ala His Gln Arg Thr His Thr Gly Lys Lys Thr Ser Thr Ser
                85                  90                  95

<210> SEQ ID NO 167
<211> LENGTH: 288
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 167
ctggagttgg agcccgggga gaagccctac aaatgccctg aatgtggaaa atcctttagt     60
cagcgggcaa acctgcgtgc ccatcagcga acccataccg gcgagaaacc ttacaaatgc    120
cctgagtgtg gaaagtcttt ctctgagagg agccacctca gggagcacca gaggacacat    180
actggagaga aaccctacaa atgcccagaa tgtggtaaga gcttcagcca gagagcaaat    240
ctccgtgcac accaacggac acacacaggc aaaaagacca gcactagt                 288

<210> SEQ ID NO 168
<211> LENGTH: 96
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Leu Glu Leu Glu Pro Gly Glu Lys Pro Tyr Lys Cys Pro Glu Cys Gly
1               5                   10                  15

Lys Ser Phe Ser Gln Arg Ala Asn Leu Arg Ala His Gln Arg Thr His
            20                  25                  30

Thr Gly Glu Lys Pro Tyr Lys Cys Pro Glu Cys Gly Lys Ser Phe Ser
        35                  40                  45

Glu Arg Ser His Leu Arg Glu His Gln Arg Thr His Thr Gly Glu Lys
    50                  55                  60

Pro Tyr Lys Cys Pro Glu Cys Gly Lys Ser Phe Ser Gln Arg Ala Asn
65                  70                  75                  80

Leu Arg Ala His Gln Arg Thr His Thr Gly Lys Lys Thr Ser Thr Ser
                85                  90                  95

<210> SEQ ID NO 169
<211> LENGTH: 288
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 169
ctggagctcg aaccaggaga gaagccctat aagtgcccag agtgcggaaa gtccttttca     60
cataaaaacg ctctccagaa tcatcaacgc acacacacag gagaaaagcc atacaaatgc    120
ccagaatgcg ggaagtcctt ctcaagacgt gacgagctga acgttcacca acgcactcac    180
accggtgaaa agccatacaa gtgtccagag tgcggtaaga gcttcagcca aaaaagtagt    240
ctcatagcac accagagaac tcatacaggt aaaaagactt ctactagt                 288

<210> SEQ ID NO 170
<211> LENGTH: 96
<212> TYPE: PRT
<213> ORGANISM: Artificial Sequence
<220> FEATURE:
<223> OTHER INFORMATION: Description of Artificial Sequence: Synthetic peptide

<400> SEQUENCE: 170

```
Leu Glu Leu Glu Pro Gly Glu Lys Pro Tyr Lys Cys Pro Glu Cys Gly
1               5                   10                  15

Lys Ser Phe Ser His Lys Asn Ala Leu Gln Asn His Gln Arg Thr His
            20                  25                  30

Thr Gly Glu Lys Pro Tyr Lys Cys Pro Glu Cys Gly Lys Ser Phe Ser
        35                  40                  45

Arg Arg Asp Glu Leu Asn Val His Gln Arg Thr His Thr Gly Glu Lys
    50                  55                  60

Pro Tyr Lys Cys Pro Glu Cys Gly Lys Ser Phe Ser Gln Lys Ser Ser
65                  70                  75                  80

Leu Ile Ala His Gln Arg Thr His Thr Gly Lys Lys Thr Ser Thr Ser
                85                  90                  95
```

<210> SEQ ID NO 171
<211> LENGTH: 288
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 171

```
ctggagctgg agccaggtga aaagccatac aaatgtcctg agtgcggtaa gtctttttcc      60

agtcccgccg accttactcg tcaccagcgc acacacacag gagagaaacc ctataaatgc     120

ccagaatgcg gaaagagttt tagccgcaag gataatctta agaatcatca gagaacacat     180

accggcgaaa aaccatacaa atgccctgag tgtgggaagt ctttctctga ctccggaaat     240

ctcagggtcc accaacggac acatactgga aagaagacct caactagt                  288
```

<210> SEQ ID NO 172
<211> LENGTH: 96
<212> TYPE: PRT
<213> ORGANISM: Artificial Sequence
<220> FEATURE:
<223> OTHER INFORMATION: Description of Artificial Sequence: Synthetic peptide

<400> SEQUENCE: 172

```
Leu Glu Leu Glu Pro Gly Glu Lys Pro Tyr Lys Cys Pro Glu Cys Gly
1               5                   10                  15

Lys Ser Phe Ser Ser Pro Ala Asp Leu Thr Arg His Gln Arg Thr His
            20                  25                  30

Thr Gly Glu Lys Pro Tyr Lys Cys Pro Glu Cys Gly Lys Ser Phe Ser
        35                  40                  45

Arg Lys Asp Asn Leu Lys Asn His Gln Arg Thr His Thr Gly Glu Lys
    50                  55                  60

Pro Tyr Lys Cys Pro Glu Cys Gly Lys Ser Phe Ser Asp Ser Gly Asn
65                  70                  75                  80

Leu Arg Val His Gln Arg Thr His Thr Gly Lys Lys Thr Ser Thr Ser
                85                  90                  95
```

<210> SEQ ID NO 173
<211> LENGTH: 549
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 173
actagtgcct tggagttgga acccggcgaa aaaccctaca agtgcccaga atgcggcaag 60
tcttttagca ccagcgggag tctcgttaga caccagcgga cgcacacagg cgagaagcca 120
tacaaatgtc cagagtgtgg taagtcattt tcaagatccg acgacctggt gaggcaccag 180
agaacccata ctggagagaa gccctacaaa tgtccagaat gtgggaaaag tttctctgag 240
cgttctcact tgagggaaca tcagagaact catacaggag agaagcccta taaatgcccc 300
gagtgcggaa aaagcttttc agatccaggt aatcttgtga ggcatcagag aacacataca 360
ggagaaaagc catacaagtg ccctgagtgt ggaaagagct tcagccaact ggcccatctt 420
cgtgcacatc agagaacgca tactggggaa aaaccatata agtgccctga atgtgggaaa 480
tctttctcac aaaaatccag ccttatagct caccagcgta cacatacagg aaaaaagaca 540
tctactagt 549

<210> SEQ ID NO 174
<211> LENGTH: 176
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 174

Leu Glu Pro Gly Glu Lys Pro Tyr Lys Cys Pro Glu Cys Gly Lys Ser
1 5 10 15

Phe Ser Thr Ser Gly Ser Leu Val Arg His Gln Arg Thr His Thr Gly
20 25 30

Glu Lys Pro Tyr Lys Cys Pro Glu Cys Gly Lys Ser Phe Ser Arg Ser
35 40 45

Asp Asp Leu Val Arg His Gln Arg Thr His Thr Gly Glu Lys Pro Tyr
50 55 60

Lys Cys Pro Glu Cys Gly Lys Ser Phe Ser Glu Arg Ser His Leu Arg
65 70 75 80

Glu His Gln Arg Thr His Thr Gly Glu Lys Pro Tyr Lys Cys Pro Glu
85 90 95

Cys Gly Lys Ser Phe Ser Asp Pro Gly Asn Leu Val Arg His Gln Arg
100 105 110

Thr His Thr Gly Glu Lys Pro Tyr Lys Cys Pro Glu Cys Gly Lys Ser
115 120 125

Phe Ser Gln Leu Ala His Leu Arg Ala His Gln Arg Thr His Thr Gly
130 135 140

Glu Lys Pro Tyr Lys Cys Pro Glu Cys Gly Lys Ser Phe Ser Gln Lys
145 150 155 160

Ser Ser Leu Ile Ala His Gln Arg Thr His Thr Gly Lys Lys Thr Ser
165 170 175

<210> SEQ ID NO 175
<211> LENGTH: 558
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 175

```
ctcgagggtg atatcctgga gcccggcgag aaaccgtata aatgccccga gtgcggcaag     60

tcctttagcc agagggcgca cctggaacgg caccaaagaa cacatactgg ggaaaagcca    120

tacaagtgcc ctgagtgcgg caagtcattc tcttcacccg ccgacctgac aaggcaccag    180

agaactcaca ctggcgaaaa gccatacaag tgccctgaat gcgggaaatc cttttcccgg    240

gctgacaatc tgaccgagca tcagcgcacc cacacaggcg agaagcctta caagtgcccg    300

gagtgtggca agagcttttc acacacgggg cacctgttgg aacatcaaag gactcacact    360

ggcgaaaagc cctataaatg tccggagtgt gggaagagtt ttagcaccac cgggaatctg    420

accgtacacc aacggacaca cacaggcgag aaaccctaca agtgccccga atgtggcaaa    480

tctttcagcg ataagaaaga tttgacaagg catcagagaa cacacactgg taagaagacg    540

tctgatatcg gtactagt                                                  558
```

<210> SEQ ID NO 176
<211> LENGTH: 176
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 176

```
Leu Glu Pro Gly Glu Lys Pro Tyr Lys Cys Pro Glu Cys Gly Lys Ser
1               5                   10                  15

Phe Ser Gln Arg Ala His Leu Glu Arg His Gln Arg Thr His Thr Gly
            20                  25                  30

Glu Lys Pro Tyr Lys Cys Pro Glu Cys Gly Lys Ser Phe Ser Ser Pro
        35                  40                  45

Ala Asp Leu Thr Arg His Gln Arg Thr His Thr Gly Glu Lys Pro Tyr
    50                  55                  60

Lys Cys Pro Glu Cys Gly Lys Ser Phe Ser Arg Ala Asp Asn Leu Thr
65                  70                  75                  80

Glu His Gln Arg Thr His Thr Gly Glu Lys Pro Tyr Lys Cys Pro Glu
                85                  90                  95

Cys Gly Lys Ser Phe Ser His Thr Gly His Leu Leu Glu His Gln Arg
            100                 105                 110

Thr His Thr Gly Glu Lys Pro Tyr Lys Cys Pro Glu Cys Gly Lys Ser
        115                 120                 125

Phe Ser Thr Thr Gly Asn Leu Thr Val His Gln Arg Thr His Thr Gly
    130                 135                 140

Glu Lys Pro Tyr Lys Cys Pro Glu Cys Gly Lys Ser Phe Ser Asp Lys
145                 150                 155                 160

Lys Asp Leu Thr Arg His Gln Arg Thr His Thr Gly Lys Lys Thr Ser
                165                 170                 175
```

<210> SEQ ID NO 177
<211> LENGTH: 558
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 177
ctcgagggtg atatcctgga gccaggagaa aaaccttaca aatgcccgga atgtggaaag 60
tccttctcac agagcggcaa tctgacggag caccagcgca cgcacactgg ggaaaagccc 120
tacaagtgtc cagaatgcgg gaagtccttt tcccagaaca gcacgctgac cgaacaccag 180
cgcacccata ctggtgagaa gccctataag tgcccagagt gcggcaagtc ttttagtcag 240
aaatctagtc tgattgctca tcagcggact cataccgggg aaaagcccta caagtgtccg 300
gagtgtggca agagcttctc cgatccaggc catctcgtcc ggcaccagcg aacccataca 360
ggggagaaac catataaatg ccctgagtgt ggaaagtctt tcagtcgagc cgacaatctg 420
accgaacacc aacgcaccca caccggtgag aaaccataca aatgcccaga atgcggcaag 480
tctttttcca caagtggaga actcgttcgg caccagagga cgcacactgg taaaaagaca 540
tcagatatcg gtactagt 558

<210> SEQ ID NO 178
<211> LENGTH: 176
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 178

Leu Glu Pro Gly Glu Lys Pro Tyr Lys Cys Pro Glu Cys Gly Lys Ser
1 5 10 15

Phe Ser Gln Ser Gly Asn Leu Thr Glu His Gln Arg Thr His Thr Gly
20 25 30

Glu Lys Pro Tyr Lys Cys Pro Glu Cys Gly Lys Ser Phe Ser Gln Asn
35 40 45

Ser Thr Leu Thr Glu His Gln Arg Thr His Thr Gly Glu Lys Pro Tyr
50 55 60

Lys Cys Pro Glu Cys Gly Lys Ser Phe Ser Gln Lys Ser Ser Leu Ile
65 70 75 80

Ala His Gln Arg Thr His Thr Gly Glu Lys Pro Tyr Lys Cys Pro Glu
85 90 95

Cys Gly Lys Ser Phe Ser Asp Pro Gly His Leu Val Arg His Gln Arg
100 105 110

Thr His Thr Gly Glu Lys Pro Tyr Lys Cys Pro Glu Cys Gly Lys Ser
115 120 125

Phe Ser Arg Ala Asp Asn Leu Thr Glu His Gln Arg Thr His Thr Gly
130 135 140

Glu Lys Pro Tyr Lys Cys Pro Glu Cys Gly Lys Ser Phe Ser Thr Ser
145 150 155 160

Gly Glu Leu Val Arg His Gln Arg Thr His Thr Gly Lys Lys Thr Ser
165 170 175

<210> SEQ ID NO 179
<211> LENGTH: 558
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 179
ctcgagggtg atatcctcga acccggtgag aaaccttata agtgtcccga atgtgggaag 60
agtttctccc gcagcgacga tcttgtgcgc caccaaagga cacacacagg ggagaaacct 120
tataagtgcc ccgagtgtgg gaagagcttc agtcggtctg ataacctggt gaggcaccag 180
aggacacaca ccggcgaaaa accttataaa tgtcccgagt gcggcaaaag tttttcacga 240
gccgataacc tcactgagca tcaacgaacc catacagggg aaaaaccata caagtgccct 300
gagtgcggta agagtttttc aagaagcgac cacctgacta atcaccagcg cacccacact 360
ggcgagaagc cctacaagtg cccagaatgc ggtaaatctt tttctcggtc tgatcacctt 420
actacacacc agagaacgca tactggagag aagccgtaca aatgtcccga gtgcggaaag 480
agctttagcc gcagtgatca tctgaccact caccagcgaa cccataccgg aaagaagacg 540
tccgatatcg gtactagt 558

<210> SEQ ID NO 180
<211> LENGTH: 176
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 180

Leu Glu Pro Gly Glu Lys Pro Tyr Lys Cys Pro Glu Cys Gly Lys Ser
1 5 10 15

Phe Ser Arg Ser Asp Asp Leu Val Arg His Gln Arg Thr His Thr Gly
20 25 30

Glu Lys Pro Tyr Lys Cys Pro Glu Cys Gly Lys Ser Phe Ser Arg Ser
35 40 45

Asp Asn Leu Val Arg His Gln Arg Thr His Thr Gly Glu Lys Pro Tyr
50 55 60

Lys Cys Pro Glu Cys Gly Lys Ser Phe Ser Arg Ala Asp Asn Leu Thr
65 70 75 80

Glu His Gln Arg Thr His Thr Gly Glu Lys Pro Tyr Lys Cys Pro Glu
85 90 95

Cys Gly Lys Ser Phe Ser Arg Ser Asp His Leu Thr Asn His Gln Arg
100 105 110

Thr His Thr Gly Glu Lys Pro Tyr Lys Cys Pro Glu Cys Gly Lys Ser
115 120 125

Phe Ser Arg Ser Asp His Leu Thr Thr His Gln Arg Thr His Thr Gly
130 135 140

Glu Lys Pro Tyr Lys Cys Pro Glu Cys Gly Lys Ser Phe Ser Arg Ser
145 150 155 160

Asp His Leu Thr Thr His Gln Arg Thr His Thr Gly Lys Lys Thr Ser
165 170 175

<210> SEQ ID NO 181
<211> LENGTH: 558
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 181
ctcgagggtg atatcttgga accaggcgaa aagccatata aatgtcctga gtgcgggaag 60
tctttcagta ccaagaactc tcttaccgag caccagcgca cacacacagg agagaaaccc 120
tacaagtgcc ccgaatgcgg aaagagtttc agcaggaatg atgctcttac cgagcaccag 180
aggactcaca cgggcgaaaa accatacaag tgtcccgagt gtgggaagag tttcagcagg 240
tccgaccatc ttactaatca tcagcgcaca cacactggag agaagcccta taaatgtcca 300

-continued

```
gagtgcggca aaagtttcag tacttccgga catctcgtgc ggcaccaaag gacacatact    360

ggcgaaaagc cttacaagtg tcccgagtgt ggcaagtcct ttagtcgctc tgacaagctc    420

actgagcatc agagaacaca cactggagag aaaccataca agtgccccga gtgtgggaaa    480

tccttcagca gggcagacaa tctgaccgaa caccaacgga cccatacagg aaaaaaaacc    540

agcgatatcg gtactagt                                                  558


<210> SEQ ID NO 182
<211> LENGTH: 176
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 182

Leu Glu Pro Gly Glu Lys Pro Tyr Lys Cys Pro Glu Cys Gly Lys Ser
1               5                   10                  15

Phe Ser Thr Lys Asn Ser Leu Thr Glu His Gln Arg Thr His Thr Gly
            20                  25                  30

Glu Lys Pro Tyr Lys Cys Pro Glu Cys Gly Lys Ser Phe Ser Arg Asn
        35                  40                  45

Asp Ala Leu Thr Glu His Gln Arg Thr His Thr Gly Glu Lys Pro Tyr
    50                  55                  60

Lys Cys Pro Glu Cys Gly Lys Ser Phe Ser Arg Ser Asp His Leu Thr
65                  70                  75                  80

Asn His Gln Arg Thr His Thr Gly Glu Lys Pro Tyr Lys Cys Pro Glu
                85                  90                  95

Cys Gly Lys Ser Phe Ser Thr Ser Gly His Leu Val Arg His Gln Arg
            100                 105                 110

Thr His Thr Gly Glu Lys Pro Tyr Lys Cys Pro Glu Cys Gly Lys Ser
        115                 120                 125

Phe Ser Arg Ser Asp Lys Leu Thr Glu His Gln Arg Thr His Thr Gly
    130                 135                 140

Glu Lys Pro Tyr Lys Cys Pro Glu Cys Gly Lys Ser Phe Ser Arg Ala
145                 150                 155                 160

Asp Asn Leu Thr Glu His Gln Arg Thr His Thr Gly Lys Lys Thr Ser
                165                 170                 175


<210> SEQ ID NO 183
<211> LENGTH: 306
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 183

ctcgagggtg atatcttgga acccggtgaa aaaccataca aatgtccgga atgcggaaaa     60

tccttcagta ggaacgacac cctgactgaa catcagagaa cacacaccgg cgaaaagcca    120

tacaagtgtc ccgagtgtgg aaaatccttt tccacaaaaa attccctgac tgagcaccag    180

cggacgcata caggggagaa accatacaaa tgcccagagt gtgggaagtc attttccagg    240

tctgaccatc tgaccaacca tcaaaggacc cacaccggca aaaagacaag cgatatcggt    300

actagt                                                               306


<210> SEQ ID NO 184
```

<211> LENGTH: 92
<212> TYPE: PRT
<213> ORGANISM: Artificial Sequence
<220> FEATURE:
<223> OTHER INFORMATION: Description of Artificial Sequence: Synthetic peptide

<400> SEQUENCE: 184

```
Leu Glu Pro Gly Glu Lys Pro Tyr Lys Cys Pro Glu Cys Gly Lys Ser
1               5                   10                  15

Phe Ser Arg Asn Asp Thr Leu Thr Glu His Gln Arg Thr His Thr Gly
            20                  25                  30

Glu Lys Pro Tyr Lys Cys Pro Glu Cys Gly Lys Ser Phe Ser Thr Lys
        35                  40                  45

Asn Ser Leu Thr Glu His Gln Arg Thr His Thr Gly Glu Lys Pro Tyr
    50                  55                  60

Lys Cys Pro Glu Cys Gly Lys Ser Phe Ser Arg Ser Asp His Leu Thr
65                  70                  75                  80

Asn His Gln Arg Thr His Thr Gly Lys Lys Thr Ser
                85                  90
```

<210> SEQ ID NO 185
<211> LENGTH: 306
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 185

```
ctcgagggtg atatcctgga gcctggcgaa aagccttaca aatgccctga atgtggaaag     60

agtttttcca gagcagacaa tttgacagag catcagcgga cccatacagg agaaaagcct    120

tataaatgcc ccgagtgtgg taagagtttt tctactaaga atagtctgac tgaacatcaa    180

cgaactcaca ctggagagaa gccttataaa tgtcccgagt gtgggaaatc tttttccgaa    240

agatcccacc ttagagaaca ccagcggaca catacaggga agaaaacctc tgatatcggt    300

actagt                                                               306
```

<210> SEQ ID NO 186
<211> LENGTH: 92
<212> TYPE: PRT
<213> ORGANISM: Artificial Sequence
<220> FEATURE:
<223> OTHER INFORMATION: Description of Artificial Sequence: Synthetic peptide

<400> SEQUENCE: 186

```
Leu Glu Pro Gly Glu Lys Pro Tyr Lys Cys Pro Glu Cys Gly Lys Ser
1               5                   10                  15

Phe Ser Arg Ala Asp Asn Leu Thr Glu His Gln Arg Thr His Thr Gly
            20                  25                  30

Glu Lys Pro Tyr Lys Cys Pro Glu Cys Gly Lys Ser Phe Ser Thr Lys
        35                  40                  45

Asn Ser Leu Thr Glu His Gln Arg Thr His Thr Gly Glu Lys Pro Tyr
    50                  55                  60

Lys Cys Pro Glu Cys Gly Lys Ser Phe Ser Glu Arg Ser His Leu Arg
65                  70                  75                  80

Glu His Gln Arg Thr His Thr Gly Lys Lys Thr Ser
                85                  90
```

<210> SEQ ID NO 187
<211> LENGTH: 306
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 187
ctcgagggtg atatccttga gcccggagag aagccataca aatgccctga gtgtggaaag 60
agcttctcct ctaagaagca cctggccgag catcaacgaa cccacacggg ggagaaacct 120
tataaatgcc cggagtgtgg caaatcattt tccagaagag atgaacttaa tgttcaccag 180
aggacccaca caggtgagaa gccttacaag tgtcccgaat gtggaaaatc ctttagccac 240
cgcactacgc tcactaatca ccagcgaacc cacactggca aaaagacatc tgatatcggt 300
actagt 306

<210> SEQ ID NO 188
<211> LENGTH: 92
<212> TYPE: PRT
<213> ORGANISM: Artificial Sequence
<220> FEATURE:
<223> OTHER INFORMATION: Description of Artificial Sequence: Synthetic peptide

<400> SEQUENCE: 188

Leu Glu Pro Gly Glu Lys Pro Tyr Lys Cys Pro Glu Cys Gly Lys Ser
1 5 10 15

Phe Ser Ser Lys Lys His Leu Ala Glu His Gln Arg Thr His Thr Gly
20 25 30

Glu Lys Pro Tyr Lys Cys Pro Glu Cys Gly Lys Ser Phe Ser Arg Arg
35 40 45

Asp Glu Leu Asn Val His Gln Arg Thr His Thr Gly Glu Lys Pro Tyr
50 55 60

Lys Cys Pro Glu Cys Gly Lys Ser Phe Ser His Arg Thr Thr Leu Thr
65 70 75 80

Asn His Gln Arg Thr His Thr Gly Lys Lys Thr Ser
85 90

<210> SEQ ID NO 189
<211> LENGTH: 306
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 189
ctcgagggtg atatcctgga gcccggagag aagccataca aatgtccaga gtgtggcaaa 60
tccttcagca caacaggcaa tctgactgtg catcagcgca cgcatactgg agagaaacca 120
tacaaatgtc cagagtgcgg caagagcttc tcacagagcg gtgacctgcg cagacaccag 180
aggacacaca ccggtgaaaa accctataaa tgtcccgaat gcggaaaatc cttctcaact 240
agccatagtc tgactgagca ccagcgcacg cataccggca agaagacctc tgatatcggt 300
actagt 306

<210> SEQ ID NO 190
<211> LENGTH: 92
<212> TYPE: PRT
<213> ORGANISM: Artificial Sequence
<220> FEATURE:

<223> OTHER INFORMATION: Description of Artificial Sequence: Synthetic peptide

<400> SEQUENCE: 190

```
Leu Glu Pro Gly Glu Lys Pro Tyr Lys Cys Pro Glu Cys Gly Lys Ser
1               5                   10                  15

Phe Ser Thr Thr Gly Asn Leu Thr Val His Gln Arg Thr His Thr Gly
            20                  25                  30

Glu Lys Pro Tyr Lys Cys Pro Glu Cys Gly Lys Ser Phe Ser Gln Ser
        35                  40                  45

Gly Asp Leu Arg Arg His Gln Arg Thr His Thr Gly Glu Lys Pro Tyr
    50                  55                  60

Lys Cys Pro Glu Cys Gly Lys Ser Phe Ser Thr Ser His Ser Leu Thr
65                  70                  75                  80

Glu His Gln Arg Thr His Thr Gly Lys Lys Thr Ser
                85                  90
```

<210> SEQ ID NO 191
<211> LENGTH: 306
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 191

```
ctcgagggtg atatcctgga gccaggcgaa aagccataca agtgcccaga gtgcggcaag      60

agcttctcac gctcagacca cctcactaca caccagcgga cccacaccgg cgagaagccg     120

tacaaatgtc ccgaatgtgg caagagtttc tcaacttcag gaaatcttgt acggcatcag     180

agaactcaca caggagagaa accatataag tgtcctgaat gtggtaaaag tttctccgac     240

cccggacatc tcgtgcgcca ccagaggacc catacaggca agaagacatc agatatcggt     300

actagt                                                                306
```

<210> SEQ ID NO 192
<211> LENGTH: 92
<212> TYPE: PRT
<213> ORGANISM: Artificial Sequence
<220> FEATURE:
<223> OTHER INFORMATION: Description of Artificial Sequence: Synthetic peptide

<400> SEQUENCE: 192

```
Leu Glu Pro Gly Glu Lys Pro Tyr Lys Cys Pro Glu Cys Gly Lys Ser
1               5                   10                  15

Phe Ser Arg Ser Asp His Leu Thr Thr His Gln Arg Thr His Thr Gly
            20                  25                  30

Glu Lys Pro Tyr Lys Cys Pro Glu Cys Gly Lys Ser Phe Ser Thr Ser
        35                  40                  45

Gly Asn Leu Val Arg His Gln Arg Thr His Thr Gly Glu Lys Pro Tyr
    50                  55                  60

Lys Cys Pro Glu Cys Gly Lys Ser Phe Ser Asp Pro Gly His Leu Val
65                  70                  75                  80

Arg His Gln Arg Thr His Thr Gly Lys Lys Thr Ser
                85                  90
```

<210> SEQ ID NO 193
<211> LENGTH: 306
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 193

```
ctcgagggtg atatcctcga accaggcgaa aaaccgtaca aatgtcctga gtgtggcaag     60

tcattcagcg ataagaagga ccttactaga catcaacgga cacataccgg ggaaaaaccc    120

tacaagtgtc cagaatgcgg caagagtttt tccactaaaa atagtctgac agaacatcaa    180

agaacccaca ccggggagaa accttataaa tgccctgaat gtgggaaatc cttctcccgg    240

gctgataact tgacagagca tcagaggact cacaccggta aaaagacgtc cgatatcggt    300

actagt                                                               306
```

<210> SEQ ID NO 194
<211> LENGTH: 92
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 194

```
Leu Glu Pro Gly Glu Lys Pro Tyr Lys Cys Pro Glu Cys Gly Lys Ser
1               5                   10                  15

Phe Ser Asp Lys Lys Asp Leu Thr Arg His Gln Arg Thr His Thr Gly
            20                  25                  30

Glu Lys Pro Tyr Lys Cys Pro Glu Cys Gly Lys Ser Phe Ser Thr Lys
        35                  40                  45

Asn Ser Leu Thr Glu His Gln Arg Thr His Thr Gly Glu Lys Pro Tyr
    50                  55                  60

Lys Cys Pro Glu Cys Gly Lys Ser Phe Ser Arg Ala Asp Asn Leu Thr
65                  70                  75                  80

Glu His Gln Arg Thr His Thr Gly Lys Lys Thr Ser
                85                  90
```

<210> SEQ ID NO 195
<211> LENGTH: 3182
<212> TYPE: DNA
<213> ORGANISM: Hepatitus B virus

<400> SEQUENCE: 195

```
aattccacaa cctttcacca aactctgcaa gatcccagag tgagaggcct gtatttccct     60

gctggtggct ccagttcagg agcagtaaac cctgttccga ctactgcctc tcccttatcg    120

tcaatcttct cgaggattgg ggaccctgcg ctgaacatgg agaacatcac atcaggattc    180

ctaggacccc ttctcgtgtt acaggcgggg tttttcttgt tgacaagaat cctcacaata    240

ccgcagagtc tagactcgtg gtggacttct ctcaattttc tagggggaac taccgtgtgt    300

cttggccaaa attcgcagtc cccaacctcc aatcactcac caacctcctg tcctccaact    360

tgtcctggtt atcgctggat gtgtctgcgg cgttttatca tcttcctctt catcctgctg    420

ctatgcctca tcttcttgtt ggttcttctg gactatcaag gtatgttgcc cgtttgtcct    480

ctaattccag gatcctcaac caccagcacg ggaccatgcc gaacctgcat gactactgct    540

caaggaacct ctatgtatcc ctcctgttgc tgtaccaaac cttcggacgg aaattgcacc    600

tgtattccca tcccatcatc ctgggctttc ggaaaattcc tatgggagtg ggcctcagcc    660

cgtttctcct ggctcagttt actagtgcca tttgttcagt ggttcgtagg gctttccccc    720

actgtttggc tttcagttat atggatgatg tggtattggg ggccaagtct gtacagcatc    780
```

-continued

```
ttgagtccct ttttaccgct gttaccaatt ttcttttgtc tttgggtata catttaaacc    840
ctaacaaaac aaagagatgg ggttactctc tgaattttat gggttatgtc attggaagtt    900
atgggtcctt gccacaagaa cacatcatac aaaaaatcaa agaatgtttt agaaaacttc    960
ctattaacag gcctattgat tggaaagtat gtcaacgaat tgtgggtctt ttgggttttg   1020
ctgccccatt tacacaatgt ggttatcctg cgttaatgcc cttgtatgca tgtattcaat   1080
ctaagcaggc tttcactttc tcgccaactt acaaggcctt tctgtgtaaa caatacctga   1140
acctttaccc cgttgcccgg caacggccag gtctgtgcca agtgtttgct gacgcaaccc   1200
ccactggctg gggcttggtc atgggccatc agcgcgtgcg tggaaccttt tcggctcctc   1260
tgccgatcca tactgcggaa ctcctagccg cttgttttgc tcgcagcagg tctggagcaa   1320
acattatcgg gactgataac tctgttgtcc tctcccgcaa atatacatcg tatccatggc   1380
tgctaggctg tgctgccaac tggatcctgc gcgggacgtc ctttgtttac gtcccgtcgg   1440
cgctgaatcc tgcggacgac ccttctcggg gtcgcttggg actctctcgt ccccttctcc   1500
gtctgccgtt ccgaccgacc acggggcgca cctctcttta cgcggactcc ccgtctgtgc   1560
cttctcatct gccggaccgt gtgcacttcg cttcacctct gcacgtcgca tggagaccac   1620
cgtgaacgcc caccgaatgt tgcccaaggt cttacataag aggactcttg gactctctgc   1680
aatgtcaacg accgaccttg aggcatactt caaagactgt ttgtttaaag actgggagga   1740
gttgggggag gagattagat taaaggtctt tgtactagga ggctgtaggc ataaattggt   1800
ctgcgcacca gcaccatgca actttttcac ctctgcctaa tcatctcttg ttcatgtcct   1860
actgttcaag cctccaagct gtgccttggg tggctttggg gcatggacat cgacccttat   1920
aaagaatttg gagctactgt ggagttactc tcgtttttgc cttctgactt ctttccttca   1980
gtacgagatc ttctagatac cgcctcagct ctgtatcggg aagccttaga gtctcctgag   2040
cattgttcac ctcaccatac tgcactcagg caagcaattc tttgctgggg ggaactaatg   2100
actctagcta cctgggtggg tgttaatttg gaagatccag catctagaga cctagtagtc   2160
agttatgtca acactaatat gggcctaaag ttcaggcaac tcttgtggtt tcacatttct   2220
tgtctcactt ttggaagaga aaccgttata gagtatttgg tgtctttcgg agtgtggatt   2280
cgcactcctc cagcttatag accaccaaat gccccctatcc tatcaacact tccggaaact   2340
actgttgtta gacgacgagg caggtcccct agaagaagaa ctccctcgcc tcgcagacga   2400
aggtctcaat cgccgcgtcg cagaagatct caatctcggg aacctcaatg ttagtattcc   2460
ttggactcat aaggtgggga actttactgg tctttattct tctactgtac ctgtctttaa   2520
tcctcattgg aaaacaccat cttttcctaa tatacattta caccaagaca ttatcaaaaa   2580
atgtgaacag tttgtaggcc cacttacagt taatgagaaa agaagattgc aattgattat   2640
gcctgctagg ttttatccaa aggttaccaa atatttacca ttggataagg gtattaaacc   2700
ttattatcca gaacatctag ttaatcatta cttccaaact agacactatt tacacactct   2760
atggaaggcg ggtatattat ataagagaga aacaacacat agcgcctcat tttgtgggtc   2820
accatattct tgggaacaag atctacagca tggggcagaa tctttccacc agcaatcctc   2880
tgggattctt tcccgaccac cagttggatc cagccttcag agcaaacaca gcaaatccag   2940
attgggactt caatcccaac aaggacacct ggccagacgc caacaaggta ggagctggag   3000
cattcgggct gggtttcacc ccaccgcacg gaggcctttt ggggtggagc cctcaggctc   3060
agggcatact acaaactttg ccagcaaatc cgcctcctgc ctccaccaat cgccagacag   3120
gaaggcagcc taccccgctg tctccacctt tgagaaacac tcatcctcag gccatgcagt   3180
```

gg 3182

<210> SEQ ID NO 196
<211> LENGTH: 3021
<212> TYPE: DNA
<213> ORGANISM: Hepatitus B virus

<400> SEQUENCE: 196
catgctcatt tgaaagctta tgcaaaaatt aacgaggaat cactggatag ggctaggaga 60
ttgctttggt ggcattacaa ctgtttactg tggggagaag ctcaagttac taactatatt 120
tctcgcttgc gtacttggtt gtcaactcct gagaaatata gaggtagaga tgccccgacc 180
attgaagcaa tcactagacc aatccaggtg gctcagggag gcagaaaaac aactacgggt 240
actagaaaac ctcgtggact cgaacctaga agaagaaaag ttaaaaccac agttgtctat 300
gggagaagac gttcaaagtc ccgggaaagg agagcccta catcccaacg tgcgggctcc 360
cctctcccac gtagttcgag cagccaccat agatctccct cgcctaggaa ataaattacc 420
tgctaggcat cacttaggta aattgtcagg actatatcaa atgaagggct gtacttttaa 480
cccagaatgg aaagtaccag atatttcgga tactcatttt aatttagatg tagtgaatga 540
gtgcccttcc cgaaattgga aatatttgac tccagccaaa ttctggccca agagcatttc 600
ctactttcct gtccaggtag gggttaaacc aaagtatcct gacaatgtga tgcaacatga 660
atcaatagta ggtaaatatt taaccaggct ctatgaagca ggaatccttt ataagcggat 720
atctaaacat ttggtaacat ttaaaggtca gccttataat tgggaacagc aacaccttgt 780
caatcaacat cacatttatg atggggcaac atccagcaaa atcaatggac gtcagacgga 840
tagaaggagg agaaatactg ttaaaccaac ttgccggaag gatgatccca aaagggactt 900
tgacatggtc aggcaagttt ccaacgctag atcacgtgtt agaccatgtg caaacaatgg 960
aggagataaa caccctccag aatcagggag cttggcctgc tggggcggga aggagagtag 1020
gattatcaaa tccgactcct caagagattc ctcagcccca gtggactccc gaggaagacc 1080
aaaaagcacg cgaagctttt cgccgttatc aagaagaaag accaccggaa accaccacca 1140
ttcctccgtc ttcccctcct cagtggaagc tacaacccgg ggacgatcca ctcctgggaa 1200
atcagtctct cctcgagact catccgctat accagtcaga accagcggtg ccagtgataa 1260
aaactccccc cttgaagaag aaaatgtctg gtaccttcgg gggaatacta gctggcctaa 1320
tcggattact ggtaagcttt ttcttgttga taaaaattct agaaatactg aggaggctag 1380
attggtggtg gatttctctc agttctccaa agggaaaaat gcaatgcgct ttccaagata 1440
ctggagccca aatctctcca cattacgtag gatcctgccc gtggggatgc ccaggatttc 1500
tttggaccta tctcaggctt tttatcatct tcctcttaat cctgctagta gcagcaggct 1560
tgctgtatct gacggacaac gggtctacta ttttaggaaa gctccaatgg gcgtcggtct 1620
cagccctttt ctcctccatc tcttcactac tgccctcgga tccgaaatct ctcgtcgctt 1680
taacgtttgg actttcactt atatggatga cttcctcctc tgccacccaa acgctcgtca 1740
ccttaacgca attagccacg ctgtctgctc tttttacaa gagttaggaa taagaataaa 1800
ctttgacaaa accacgcctt ctccggtgaa tgaaataaga ttcctcggtt accagattga 1860
tgaaaatttc atgaagattg aagaaagcag atggaaagaa ttaaggactg taatcaagaa 1920
aataaaagta ggagaatggt atgactggaa atgtattcaa agatttgtgg ggcatttgaa 1980
ttttgtcttg ccttttacta aaggtaatat tgaaatgtta aaaccaatgt atgctgctat 2040
tactaaccaa gtaaacttta gcttctcttc atcctatagg actttgttat ataaactaac 2100

-continued

```
aatgggtgtg tgtaaattaa gaataaagcc aaagtcctct gtacctttgc cacgtgtagc   2160

tacagatgct accccaacac atggcgcaat atcccatatc accggcggga gcgcagtgtt   2220

tgctttttca aaggtcagag atatacatgt tcaggaacta ttgatgtctt gtttagccaa   2280

gataatgatt aaaccgcgct gtctcttatc tgattcaact tttgtttgcc ataagcgtta   2340

tcagacgtta ccatggcatt ttgctatgtt ggccaaacaa ttgctcaaac ctatacaatt   2400

gtactttgtc ccgagcaaat acaatcctgc tgacggccca tccaggcaca aacctcctga   2460

ttggacggct tttccataca cccctctctc gaaagcaata tatattccac ataggctatg   2520

tggaacttaa gaattacacc cctctccttc ggagctgctt gccaaggtat ctttacgtct   2580

acattgctgt tgtcgtgtgt gactgtacct ttggtatgta ccattgttta tgattcttgc   2640

ttatatatgg atatcaatgc ttctagagcc ttagccaatg tgtatgatct gccagatgat   2700

ttctttccaa aaatagatga tcttgttaga gatgctaaag acgctttaga gccttattgg   2760

aaatcagatt caataaagaa acatgttttg attgcaactc actttgtgga tcttattgaa   2820

gacttttggc agactacaca gggtatgcat gaaatagccg aatcattaag agctgttata   2880

cctcccacta ctactcctgt tccaccgggt tatcttattc agcacgaaga agctgaagag   2940

ataccttttgg gagatttatt taaacaccaa gaagaaagga tagtgagctt tcaacctgac   3000

tatccgatta cggctagaat t                                              3021
```

<210> SEQ ID NO 197
<211> LENGTH: 588
<212> TYPE: DNA
<213> ORGANISM: Flavobacterium okeanokoites

<400> SEQUENCE: 197

```
caactagtca aaagtgaact ggaggagaag aaatctgaac ttcgtcataa attgaaatat     60

gtgcctcatg aatatattga attaattgaa attgccagaa attccactca ggatagaatt    120

cttgaaatga aggtaatgga attttttatg aaagtttatg gatatagagg taaacatttg    180

ggtggatcaa ggaaaccgga cggagcaatt tatactgtcg gatctcctat tgattacggt    240

gtgatcgtgg atactaaagc ttatagcgga ggttataatc tgccaattgg ccaagcagat    300

gaaatgcaac gatatgtcga agaaaatcaa acacgaaaca aacatatcaa ccctaatgaa    360

tggtggaaag tctatccatc ttctgtaacg gaatttaagt tttatttgt gagtggtcac    420

tttaaaggaa actacaaagc tcagcttaca cgattaaatc atatcactaa ttgtaatgga    480

gctgttctta gtgtagaaga gcttttaatt ggtggagaaa tgattaaagc cggcacatta    540

accttagagg aagtgagacg gaaatttaat aacggcgaga taaacttt                588
```

<210> SEQ ID NO 198
<211> LENGTH: 196
<212> TYPE: PRT
<213> ORGANISM: Flavobacterium okeanokoites

<400> SEQUENCE: 198

```
Gln Leu Val Lys Ser Glu Leu Glu Glu Lys Lys Ser Glu Leu Arg His
1               5                   10                  15

Lys Leu Lys Tyr Val Pro His Glu Tyr Ile Glu Leu Ile Glu Ile Ala
            20                  25                  30

Arg Asn Ser Thr Gln Asp Arg Ile Leu Glu Met Lys Val Met Glu Phe
        35                  40                  45

Phe Met Lys Val Tyr Gly Tyr Arg Gly Lys His Leu Gly Gly Ser Arg
    50                  55                  60
```

```
Lys Pro Asp Gly Ala Ile Tyr Thr Val Gly Ser Pro Ile Asp Tyr Gly
65                  70                  75                  80

Val Ile Val Asp Thr Lys Ala Tyr Ser Gly Gly Tyr Asn Leu Pro Ile
                85                  90                  95

Gly Gln Ala Asp Glu Met Gln Arg Tyr Val Glu Glu Asn Gln Thr Arg
            100                 105                 110

Asn Lys His Ile Asn Pro Asn Glu Trp Trp Lys Val Tyr Pro Ser Ser
        115                 120                 125

Val Thr Glu Phe Lys Phe Leu Phe Val Ser Gly His Phe Lys Gly Asn
    130                 135                 140

Tyr Lys Ala Gln Leu Thr Arg Leu Asn His Ile Thr Asn Cys Asn Gly
145                 150                 155                 160

Ala Val Leu Ser Val Glu Glu Leu Leu Ile Gly Gly Glu Met Ile Lys
                165                 170                 175

Ala Gly Thr Leu Thr Leu Glu Glu Val Arg Arg Lys Phe Asn Asn Gly
            180                 185                 190

Glu Ile Asn Phe
        195
```

<210> SEQ ID NO 199
<211> LENGTH: 591
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 199

```
caactagtca aaagtgaact ggaggagaag aaatctgaac ttcgtcataa attgaaatat      60

gtgcctcatg aatatattga attaattgaa attgccagaa attccactca ggatagaatt     120

cttgaaatga aggtaatgga attttttatg aaagtttatg gatatagagg taaacatttg     180

ggtggatcaa ggaaaccgga cggagcaatt tatactgtcg gatctcctat tgattacggt     240

gtgatcgtgg atactaaagc ttatagcgga ggttataatc tgccaattgg ccaagcagat     300

gaaatgcaac gatatgtcga agaaaatcaa acacgaaaca aacatatcaa ccctaatgaa     360

tggtggaaag tctatccatc ttctgtaacg gaatttaagt ttttatttgt gagtggtcac     420

tttaaaggaa actacaaagc tcagcttaca cgattaaatc atatcactaa ttgtaatgga     480

gctgttctta gtgtagaaga gcttttaatt ggtggagaaa tgattaaagc cggcacatta     540

accttagagg aagtgagacg gaaatttaat aacggcgaga taaactttta a             591
```

<210> SEQ ID NO 200
<211> LENGTH: 196
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 200

```
Gln Leu Val Lys Ser Glu Leu Glu Glu Lys Lys Ser Glu Leu Arg His
1               5                   10                  15

Lys Leu Lys Tyr Val Pro His Glu Tyr Ile Glu Leu Ile Glu Ile Ala
            20                  25                  30

Arg Asn Ser Thr Gln Asp Arg Ile Leu Glu Met Lys Val Met Glu Phe
        35                  40                  45

Phe Met Lys Val Tyr Gly Tyr Arg Gly Lys His Leu Gly Gly Ser Arg
```

```
    50                  55                  60

Lys Pro Asp Gly Ala Ile Tyr Thr Val Gly Ser Pro Ile Asp Tyr Gly
65                  70                  75                  80

Val Ile Val Asp Thr Lys Ala Tyr Ser Gly Gly Tyr Asn Leu Pro Ile
                85                  90                  95

Gly Gln Ala Asp Glu Met Gln Arg Tyr Val Glu Glu Asn Gln Thr Arg
            100                 105                 110

Asn Lys His Ile Asn Pro Asn Glu Trp Trp Lys Val Tyr Pro Ser Ser
        115                 120                 125

Val Thr Glu Phe Lys Phe Leu Phe Val Ser Gly His Phe Lys Gly Asn
    130                 135                 140

Tyr Lys Ala Gln Leu Thr Arg Leu Asn His Ile Thr Asn Cys Asn Gly
145                 150                 155                 160

Ala Val Leu Ser Val Glu Glu Leu Leu Ile Gly Gly Glu Met Ile Lys
                165                 170                 175

Ala Gly Thr Leu Thr Leu Glu Glu Val Arg Arg Lys Phe Asn Asn Gly
            180                 185                 190

Glu Ile Asn Phe
        195


<210> SEQ ID NO 201
<211> LENGTH: 897
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 201

ctcgagggtg atatcttgga acccggtgaa aaaccataca aatgtccgga atgcggaaaa     60

tccttcagta ggaacgacac cctgactgaa catcagagaa cacacaccgg cgaaaagcca    120

tacaagtgtc ccgagtgtgg aaaatccttt tccacaaaaa attccctgac tgagcaccag    180

cggacgcata caggggagaa accatacaaa tgcccagagt gtgggaagtc attttccagg    240

tctgaccatc tgaccaacca tcaaaggacc cacaccggca aaaagacaag cgatatcggt    300

actagtcaac tagtcaaaag tgaactggag gagaagaaat ctgaacttcg tcataaattg    360

aaatatgtgc ctcatgaata tattgaatta attgaaattg ccagaaattc cactcaggat    420

agaattcttg aaatgaaggt aatggaattt tttatgaaag tttatggata tagaggtaaa    480

catttgggtg gatcaaggaa accggacgga gcaatttata ctgtcggatc tcctattgat    540

tacggtgtga tcgtggatac taaagcttat agcggaggtt ataatctgcc aattggccaa    600

gcagatgaaa tgcaacgata tgtcgaagaa aatcaaacac gaaacaaaca tatcaaccct    660

aatgaatggt ggaaagtcta tccatcttct gtaacggaat ttaagttttt atttgtgagt    720

ggtcacttta aaggaaacta caaagctcag cttacacgat taaatcatat cactaattgt    780

aatggagctg ttcttagtgt agaagagctt ttaattggtg gagaaatgat taaagccggc    840

acattaacct tagaggaagt gagacggaaa tttaataacg gcgagataaa cttttaa       897


<210> SEQ ID NO 202
<211> LENGTH: 288
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 202
```

```
Leu Glu Pro Gly Glu Lys Pro Tyr Lys Cys Pro Glu Cys Gly Lys Ser
1               5                   10                  15

Phe Ser Arg Asn Asp Thr Leu Thr Glu His Gln Arg Thr His Thr Gly
            20                  25                  30

Glu Lys Pro Tyr Lys Cys Pro Glu Cys Gly Lys Ser Phe Ser Thr Lys
        35                  40                  45

Asn Ser Leu Thr Glu His Gln Arg Thr His Thr Gly Glu Lys Pro Tyr
    50                  55                  60

Lys Cys Pro Glu Cys Gly Lys Ser Phe Ser Arg Ser Asp His Leu Thr
65                  70                  75                  80

Asn His Gln Arg Thr His Thr Gly Lys Lys Thr Ser Gln Leu Val Lys
                85                  90                  95

Ser Glu Leu Glu Glu Lys Lys Ser Glu Leu Arg His Lys Leu Lys Tyr
            100                 105                 110

Val Pro His Glu Tyr Ile Glu Leu Ile Glu Ile Ala Arg Asn Ser Thr
        115                 120                 125

Gln Asp Arg Ile Leu Glu Met Lys Val Met Glu Phe Phe Met Lys Val
    130                 135                 140

Tyr Gly Tyr Arg Gly Lys His Leu Gly Gly Ser Arg Lys Pro Asp Gly
145                 150                 155                 160

Ala Ile Tyr Thr Val Gly Ser Pro Ile Asp Tyr Gly Val Ile Val Asp
                165                 170                 175

Thr Lys Ala Tyr Ser Gly Gly Tyr Asn Leu Pro Ile Gly Gln Ala Asp
            180                 185                 190

Glu Met Gln Arg Tyr Val Glu Glu Asn Gln Thr Arg Asn Lys His Ile
        195                 200                 205

Asn Pro Asn Glu Trp Trp Lys Val Tyr Pro Ser Ser Val Thr Glu Phe
    210                 215                 220

Lys Phe Leu Phe Val Ser Gly His Phe Lys Gly Asn Tyr Lys Ala Gln
225                 230                 235                 240

Leu Thr Arg Leu Asn His Ile Thr Asn Cys Asn Gly Ala Val Leu Ser
                245                 250                 255

Val Glu Glu Leu Leu Ile Gly Gly Glu Met Ile Lys Ala Gly Thr Leu
            260                 265                 270

Thr Leu Glu Glu Val Arg Arg Lys Phe Asn Asn Gly Glu Ile Asn Phe
        275                 280                 285
```

<210> SEQ ID NO 203
<211> LENGTH: 1095
<212> TYPE: DNA
<213> ORGANISM: Saccharomyces cerevisiae

<400> SEQUENCE: 203

```
atgctttctg aaaacacgac tattctgatg gctaacggtg aaattaaaga catcgcaaac      60

gtcacggcta actcttacgt tatgtgcgca gatggctccg ctgcccgcgt cataaatgtc     120

acacagggct atcagaaaat ctataatata cagcaaaaaa ccaaacacag agcttttgaa     180

ggtgaacctg gtaggttaga tcccaggcgt agaacagttt atcagcgtct tgcattacaa     240

tgtactgcag gtcataaatt gtcagtcagg gtccctacca aaccactgtt ggaaaaaagt     300

ggtagaaatg ccaccaaata taaagtgaga tggagaaatc tgcagcaatg tcagacgctt     360

gatggtagga taataataat tccaaaaaac catcataaga cattcccaat gacagttgaa     420

ggtgagtttg ccgcaaaacg cttcatagaa gaaatggagc gctctaaagg agaatatttc     480

aactttgaca ttgaagttag agatttggat tatcttgatg ctcaattgag aatttctagc     540
```

```
tgcataagat ttggtccagt actcgcagga aatggtgttt tatctaaatt tctcactgga    600

cgtagtgacc ttgtaactcc tgctgtaaaa agtatggctt ggatgcttgg tctgtggtta    660

ggtgacagta caacaaaaga gccagaaatc tcagtagata gcttggatcc taagctaatg    720

gagagtttaa gagaaaatgc gaaaatctgg ggtctctacc ttacggtttg tgacgatcac    780

gttccgctac gtgccaaaca tgtaaggctt cattatggag atggtccaga tgaaaacagg    840

aagacaagga atttgaggaa aaataatcca ttctggaaag ctgtcacaat tttaaagttt    900

aaaagggatc ttgatggaga gaagcaaatc cctgaattta tgtacggcga gcatatagaa    960

gttcgtgaag cattcttagc cggcttgatc gactcagatg ggtacgttgt gaaaaagggc   1020

gaaggccctg aatcttataa aatagcaatt caaactgttt attcatccat tatggacgga   1080

attgtccata tttca                                                    1095


<210> SEQ ID NO 204
<211> LENGTH: 365
<212> TYPE: PRT
<213> ORGANISM: Saccharomyces cerevisiae

<400> SEQUENCE: 204

Met Leu Ser Glu Asn Thr Thr Ile Leu Met Ala Asn Gly Glu Ile Lys
1               5                   10                  15

Asp Ile Ala Asn Val Thr Ala Asn Ser Tyr Val Met Cys Ala Asp Gly
            20                  25                  30

Ser Ala Ala Arg Val Ile Asn Val Thr Gln Gly Tyr Gln Lys Ile Tyr
        35                  40                  45

Asn Ile Gln Gln Lys Thr Lys His Arg Ala Phe Glu Gly Glu Pro Gly
    50                  55                  60

Arg Leu Asp Pro Arg Arg Arg Thr Val Tyr Gln Arg Leu Ala Leu Gln
65                  70                  75                  80

Cys Thr Ala Gly His Lys Leu Ser Val Arg Val Pro Thr Lys Pro Leu
                85                  90                  95

Leu Glu Lys Ser Gly Arg Asn Ala Thr Lys Tyr Lys Val Arg Trp Arg
            100                 105                 110

Asn Leu Gln Gln Cys Gln Thr Leu Asp Gly Arg Ile Ile Ile Ile Pro
        115                 120                 125

Lys Asn His His Lys Thr Phe Pro Met Thr Val Glu Gly Glu Phe Ala
    130                 135                 140

Ala Lys Arg Phe Ile Glu Glu Met Glu Arg Ser Lys Gly Glu Tyr Phe
145                 150                 155                 160

Asn Phe Asp Ile Glu Val Arg Asp Leu Asp Tyr Leu Asp Ala Gln Leu
                165                 170                 175

Arg Ile Ser Ser Cys Ile Arg Phe Gly Pro Val Leu Ala Gly Asn Gly
            180                 185                 190

Val Leu Ser Lys Phe Leu Thr Gly Arg Ser Asp Leu Val Thr Pro Ala
        195                 200                 205

Val Lys Ser Met Ala Trp Met Leu Gly Leu Trp Leu Gly Asp Ser Thr
    210                 215                 220

Thr Lys Glu Pro Glu Ile Ser Val Asp Ser Leu Asp Pro Lys Leu Met
225                 230                 235                 240

Glu Ser Leu Arg Glu Asn Ala Lys Ile Trp Gly Leu Tyr Leu Thr Val
                245                 250                 255

Cys Asp Asp His Val Pro Leu Arg Ala Lys His Val Arg Leu His Tyr
            260                 265                 270
```

```
Gly Asp Gly Pro Asp Glu Asn Arg Lys Thr Arg Asn Leu Arg Lys Asn
        275                 280                 285

Asn Pro Phe Trp Lys Ala Val Thr Ile Leu Lys Phe Lys Arg Asp Leu
    290                 295                 300

Asp Gly Glu Lys Gln Ile Pro Glu Phe Met Tyr Gly Glu His Ile Glu
305                 310                 315                 320

Val Arg Glu Ala Phe Leu Ala Gly Leu Ile Asp Ser Asp Gly Tyr Val
                325                 330                 335

Val Lys Lys Gly Glu Gly Pro Glu Ser Tyr Lys Ile Ala Ile Gln Thr
            340                 345                 350

Val Tyr Ser Ser Ile Met Asp Gly Ile Val His Ile Ser
        355                 360                 365


<210> SEQ ID NO 205
<211> LENGTH: 1095
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 205

atgctttctg aaaacacgac tattctgatg gctaacggtg aaattaaaga catcgcaaac     60

gtcacggcta actcttacgt tatgtgcgca gatggctccg ctgcccgcgt cataaatgtc    120

acacagggct atcagaaaat ctataatata cagcaaaaaa ccaaacacag agcttttgaa    180

ggtgaacctg gtaggttaga tcccaggcgt agaacagttt atcagcgtct tgcattacaa    240

tgtactgcag gtcataaatt gtcagtcagg gtccctacca aaccactgtt ggaaaaaagt    300

ggtagaaatg ccaccaaata taaagtgaga tggagaaatc tgcagcaatg tcagacgctt    360

gatggtagga taataataat tccaaaaaac catcataaga cattcccaat gacagttgaa    420

ggtgagtttg ccgcaaaacg cttcatagaa gaaatggagc gctctaaagg agaatatttc    480

aactttgaca ttgaagttag agatttggat tatcttgatg ctcaattgag aatttctagc    540

tgcataagat ttggtccagt actcgcagga aatggtgttt tatctaaatt tctcactgga    600

cgtagtgacc ttgtaactcc tgctgtaaaa agtatggctt ggatgcttgg tctgtggtta    660

ggtgacagta caacaaaaga gccagaaatc tcagtagata gcttggatcc taagctaatg    720

gagagtttaa gagaaaatgc gaaaatctgg ggtctctacc ttacggtttg tgacgatcac    780

gttccgctac gtgccaaaca tgtaaggctt cattatggag atggtccaga tgaaaacagg    840

aagacaagga atttgaggaa aaataatcca ttctggaaag ctgtcacaat tttaaagttt    900

aaaagggatc ttgatggaga gaagcaaatc cctgaattta tgtacggcga gcatatagaa    960

gttcgtgaag cattcttagc cggcttgatc gactcagatg ggtacgttgt gaaaaagggc   1020

gaaggccctg aatcttataa aatagcaatt caaactgttt attcatccat tatggacgga   1080

attgtccata tttca                                                    1095


<210> SEQ ID NO 206
<211> LENGTH: 365
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 206

Met Leu Ser Glu Asn Thr Thr Ile Leu Met Ala Asn Gly Glu Ile Lys
1               5                   10                  15
```

```
Asp Ile Ala Asn Val Thr Ala Asn Ser Tyr Val Met Cys Ala Asp Gly
            20                  25                  30

Ser Ala Ala Arg Val Ile Asn Val Thr Gln Gly Tyr Gln Lys Ile Tyr
        35                  40                  45

Asn Ile Gln Gln Lys Thr Lys His Arg Ala Phe Glu Gly Glu Pro Gly
    50                  55                  60

Arg Leu Asp Pro Arg Arg Arg Thr Val Tyr Gln Arg Leu Ala Leu Gln
65                  70                  75                  80

Cys Thr Ala Gly His Lys Leu Ser Val Arg Val Pro Thr Lys Pro Leu
                85                  90                  95

Leu Glu Lys Ser Gly Arg Asn Ala Thr Lys Tyr Lys Val Arg Trp Arg
            100                 105                 110

Asn Leu Gln Gln Cys Gln Thr Leu Asp Gly Arg Ile Ile Ile Ile Pro
        115                 120                 125

Lys Asn His His Lys Thr Phe Pro Met Thr Val Glu Gly Glu Phe Ala
    130                 135                 140

Ala Lys Arg Phe Ile Glu Glu Met Glu Arg Ser Lys Gly Glu Tyr Phe
145                 150                 155                 160

Asn Phe Asp Ile Glu Val Arg Asp Leu Asp Tyr Leu Asp Ala Gln Leu
                165                 170                 175

Arg Ile Ser Ser Cys Ile Arg Phe Gly Pro Val Leu Ala Gly Asn Gly
            180                 185                 190

Val Leu Ser Lys Phe Leu Thr Gly Arg Ser Asp Leu Val Thr Pro Ala
        195                 200                 205

Val Lys Ser Met Ala Trp Met Leu Gly Leu Trp Leu Gly Asp Ser Thr
    210                 215                 220

Thr Lys Glu Pro Glu Ile Ser Val Asp Ser Leu Asp Pro Lys Leu Met
225                 230                 235                 240

Glu Ser Leu Arg Glu Asn Ala Lys Ile Trp Gly Leu Tyr Leu Thr Val
                245                 250                 255

Cys Asp Asp His Val Pro Leu Arg Ala Lys His Val Arg Leu His Tyr
            260                 265                 270

Gly Asp Gly Pro Asp Glu Asn Arg Lys Thr Arg Asn Leu Arg Lys Asn
        275                 280                 285

Asn Pro Phe Trp Lys Ala Val Thr Ile Leu Lys Phe Lys Arg Asp Leu
    290                 295                 300

Asp Gly Glu Lys Gln Ile Pro Glu Phe Met Tyr Gly Glu His Ile Glu
305                 310                 315                 320

Val Arg Glu Ala Phe Leu Ala Gly Leu Ile Asp Ser Asp Gly Tyr Val
                325                 330                 335

Val Lys Lys Gly Glu Gly Pro Glu Ser Tyr Lys Ile Ala Ile Gln Thr
            340                 345                 350

Val Tyr Ser Ser Ile Met Asp Gly Ile Val His Ile Ser
        355                 360                 365
```

<210> SEQ ID NO 207
<211> LENGTH: 1653
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 207

```
atgctttctg aaaacacgac tattctgatg gctaacggtg aaattaaaga catcgcaaac      60
```

gtcacggcta actcttacgt tatgtgcgca gatggctccg ctgcccgcgt cataaatgtc 120
acacagggct atcagaaaat ctataatata cagcaaaaaa ccaaacacag agcttttgaa 180
ggtgaacctg gtaggttaga tcccaggcgt agaacagttt atcagcgtct tgcattacaa 240
tgtactgcag gtcataaatt gtcagtcagg gtccctacca aaccactgtt ggaaaaaagt 300
ggtagaaatg ccaccaaata taaagtgaga tggagaaatc tgcagcaatg tcagacgctt 360
gatggtagga taataataat tccaaaaaac catcataaga cattcccaat gacagttgaa 420
ggtgagtttg ccgcaaaacg cttcatagaa gaaatggagc gctctaaagg agaatatttc 480
aactttgaca ttgaagttag agatttggat tatcttgatg ctcaattgag aatttctagc 540
tgcataagat ttggtccagt actcgcagga aatggtgttt tatctaaatt tctcactgga 600
cgtagtgacc ttgtaactcc tgctgtaaaa agtatggctt ggatgcttgg tctgtggtta 660
ggtgacagta caacaaaaga gccagaaatc tcagtagata gcttggatcc taagctaatg 720
gagagtttaa gagaaaatgc gaaaatctgg ggtctctacc ttacggtttg tgacgatcac 780
gttccgctac gtgccaaaca tgtaaggctt cattatggag atggtccaga tgaaaacagg 840
aagacaagga atttgaggaa aaataatcca ttctggaaag ctgtcacaat tttaaagttt 900
aaaagggatc ttgatggaga gaagcaaatc cctgaattta tgtacggcga gcatatagaa 960
gttcgtgaag cattcttagc cggcttgatc gactcagatg ggtacgttgt gaaaaagggc 1020
gaaggccctg aatcttataa aatagcaatt caaactgttt attcatccat tatggacgga 1080
attgtccata tttcactcga gggtgatatc ctggagcccg gcgagaaacc gtataaatgc 1140
cccgagtgcg gcaagtcctt tagccagagg gcgcacctgg aacggcacca aagaacacat 1200
actggggaaa agccatacaa gtgccctgag tgcggcaagt cattctcttc acccgccgac 1260
ctgacaaggc accagagaac tcacactggc gaaaagccat acaagtgccc tgaatgcggg 1320
aaatcctttt cccgggctga caatctgacc gagcatcagc gcacccacac aggcgagaag 1380
ccttacaagt gcccggagtg tggcaagagc ttttcacaca cggggcacct gttggaacat 1440
caaaggactc acactggcga aaagccctat aaatgtccgg agtgtgggaa gagttttagc 1500
accaccggga atctgaccgt acaccaacgg acacacacag gcgagaaacc ctacaagtgc 1560
cccgaatgtg gcaaatcttt cagcgataag aaagatttga caaggcatca gagaacacac 1620
actggtaaga agacgtctga tatcggtact agt 1653

<210> SEQ ID NO 208
<211> LENGTH: 541
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 208

Met Leu Ser Glu Asn Thr Thr Ile Leu Met Ala Asn Gly Glu Ile Lys
1 5 10 15

Asp Ile Ala Asn Val Thr Ala Asn Ser Tyr Val Met Cys Ala Asp Gly
20 25 30

Ser Ala Ala Arg Val Ile Asn Val Thr Gln Gly Tyr Gln Lys Ile Tyr
35 40 45

Asn Ile Gln Gln Lys Thr Lys His Arg Ala Phe Glu Gly Glu Pro Gly
50 55 60

Arg Leu Asp Pro Arg Arg Arg Thr Val Tyr Gln Arg Leu Ala Leu Gln
65 70 75 80

-continued

```
Cys Thr Ala Gly His Lys Leu Ser Val Arg Val Pro Thr Lys Pro Leu
                85                  90                  95

Leu Glu Lys Ser Gly Arg Asn Ala Thr Lys Tyr Lys Val Arg Trp Arg
            100                 105                 110

Asn Leu Gln Gln Cys Gln Thr Leu Asp Gly Arg Ile Ile Ile Ile Pro
        115                 120                 125

Lys Asn His His Lys Thr Phe Pro Met Thr Val Glu Gly Glu Phe Ala
    130                 135                 140

Ala Lys Arg Phe Ile Glu Glu Met Glu Arg Ser Lys Gly Glu Tyr Phe
145                 150                 155                 160

Asn Phe Asp Ile Glu Val Arg Asp Leu Asp Tyr Leu Asp Ala Gln Leu
                165                 170                 175

Arg Ile Ser Ser Cys Ile Arg Phe Gly Pro Val Leu Ala Gly Asn Gly
            180                 185                 190

Val Leu Ser Lys Phe Leu Thr Gly Arg Ser Asp Leu Val Thr Pro Ala
        195                 200                 205

Val Lys Ser Met Ala Trp Met Leu Gly Leu Trp Leu Gly Asp Ser Thr
    210                 215                 220

Thr Lys Glu Pro Glu Ile Ser Val Asp Ser Leu Asp Pro Lys Leu Met
225                 230                 235                 240

Glu Ser Leu Arg Glu Asn Ala Lys Ile Trp Gly Leu Tyr Leu Thr Val
                245                 250                 255

Cys Asp Asp His Val Pro Leu Arg Ala Lys His Val Arg Leu His Tyr
            260                 265                 270

Gly Asp Gly Pro Asp Glu Asn Arg Lys Thr Arg Asn Leu Arg Lys Asn
        275                 280                 285

Asn Pro Phe Trp Lys Ala Val Thr Ile Leu Lys Phe Lys Arg Asp Leu
    290                 295                 300

Asp Gly Glu Lys Gln Ile Pro Glu Phe Met Tyr Gly Glu His Ile Glu
305                 310                 315                 320

Val Arg Glu Ala Phe Leu Ala Gly Leu Ile Asp Ser Asp Gly Tyr Val
                325                 330                 335

Val Lys Lys Gly Glu Gly Pro Glu Ser Tyr Lys Ile Ala Ile Gln Thr
            340                 345                 350

Val Tyr Ser Ser Ile Met Asp Gly Ile Val His Ile Ser Leu Glu Pro
        355                 360                 365

Gly Glu Lys Pro Tyr Lys Cys Pro Glu Cys Gly Lys Ser Phe Ser Gln
    370                 375                 380

Arg Ala His Leu Glu Arg His Gln Arg Thr His Thr Gly Glu Lys Pro
385                 390                 395                 400

Tyr Lys Cys Pro Glu Cys Gly Lys Ser Phe Ser Ser Pro Ala Asp Leu
                405                 410                 415

Thr Arg His Gln Arg Thr His Thr Gly Glu Lys Pro Tyr Lys Cys Pro
            420                 425                 430

Glu Cys Gly Lys Ser Phe Ser Arg Ala Asp Asn Leu Thr Glu His Gln
        435                 440                 445

Arg Thr His Thr Gly Glu Lys Pro Tyr Lys Cys Pro Glu Cys Gly Lys
    450                 455                 460

Ser Phe Ser His Thr Gly His Leu Leu Glu His Gln Arg Thr His Thr
465                 470                 475                 480

Gly Glu Lys Pro Tyr Lys Cys Pro Glu Cys Gly Lys Ser Phe Ser Thr
                485                 490                 495

Thr Gly Asn Leu Thr Val His Gln Arg Thr His Thr Gly Glu Lys Pro
            500                 505                 510
```

Tyr Lys Cys Pro Glu Cys Gly Lys Ser Phe Ser Asp Lys Lys Asp Leu
        515                 520                 525

Thr Arg His Gln Arg Thr His Thr Gly Lys Lys Thr Ser
    530                 535                 540

<210> SEQ ID NO 209
<211> LENGTH: 3182
<212> TYPE: DNA
<213> ORGANISM: Hepatitus B virus

<400> SEQUENCE: 209
ttccacaacc tttcaccaaa ctctgcaaga tcccagagtg agaggcctgt atttccctgc 60
tggtggctcc agttcaggaa cagtaaaccc tgttccgact actgcctctc ccttatcgtc 120
aatcttctcg aggattgggg accctgcgct gaacatggag aacatcacat caggattcct 180
aggacccctt ctcgtgttac aggcggggtt tttcttgttg acaagaatcc tcacaatacc 240
gcagagtcta gactcgtggt ggacttctct caattttcta gggggaacta ccgtgtgtct 300
tggccaaaat tcgcagtccc caacctccaa tcactcacca acctcctgtc ctccaacttg 360
tcctggttat cgctggatgt gtctgcggcg ttttatcatc ttcctcttca tcctgctgct 420
atgcctcatc ttcttgttgg ttcttctgga ctatcaaggt atgttgcccg tttgtcctct 480
aattccagga tcctcaacca ccagcacggg accatgccga acctgcatga ctactgctca 540
aggaacctct atgtatccct cctgttgctg taccaaacct tcggacggaa attgcacctg 600
tattcccatc ccatcatcct gggctttcgg aaaattccta tgggagtggg cctcagcccg 660
tttctcctgg ctcagtttac tagtgccatt tgttcagtgg ttcgtagggc tttcccccac 720
tgtttggctt tcagttatat ggatgatgtg gtattggggg ccaagtctgt acagcatctt 780
gagtcccttt ttaccgctgt taccaatttt cttttgtctt tgggtataca tttaaaccct 840
aacaaaacaa agagatgggg ttactctctg aattttatgg gttatgtcat tggaagttat 900
gggtccttgc cacaagaaca catcatacaa aaaatcaaag aatgttttag aaaacttcct 960
attaacaggc ctattgattg gaaagtatgt caaagaattg tgggtctttt gggttttgct 1020 gccccccttta cacaatgtgg ttatcctgcg ttaatgccct tgtatgcatg tattcaatct 1080
aagcaggctt tcactttctc gccaacttac aaggcctttc tgtgtaaaca atacctgaac 1140
ctttaccccg ttgcccggca acggccaggt ctgtgccaag tgtttgctga cgcaaccccc 1200
actggctggg gcttggtcat gggccatcag cgcatgcgtg gaacctttc ggctcctctg 1260 ccgatccata ctgcggaact cctagccgct tgttttgctc gcagcaggtc tggagcaaac 1320
attatcggga ctgataactc tgttgtcctc tcccgcaaat atacatcgta tccatggctg 1380
ctaggctgtg ctgccaactg gatcctgcgc gggacgtcct ttgtttacgt cccgtcggcg 1440
ctgaatcctg cggacgaccc ttctcggggt cgcttgggac tctctcgtcc tcttctccgt 1500
ctgccgttcc gaccgaccac ggggcgcacc tctctttacg cggactcccc gtctgtgcct 1560
tctcatctgc cggaccgtgt gcacttcgct tcacctctgc acgtcgcatg gagaccaccg 1620
tgaacgccca ccggatgttg cccaaggtct tacataagag gactcttgga ctctctgcaa 1680
tgtcaacgac cgaccttgag gcatacttca aagactgttt gtttaaagac tgggaggagt 1740
tgggggagga gatgaggtta aaggtctttg tactaagagg ctgtatgcat aaattggtct 1800
gcgcaccagc accatgcaac tttttcacct ctgcctaatc atctcttgtt catgtcctac 1860
tgttcaagcc tccaagctgt gccttgggtg gctttggggc atggacatcg acccttataa 1920
agaatttgga gctactgtgg agttactctc gtttttgcct tctgacttct ttccttcagt 1980
acgagatctt ctagataccg cctcagctct gtatcgggaa gccttagagt ctcctgagca 2040
ttgttcacct caccatactg cactcaggca agcaattctt tgctgggggg aactaatgac 2100
tctagctacc tgggtgggtg ttaatttgga agatccagca tctagagacc tagtagtcag 2160
ttatgtcaac actaatatgg gcctaaagtt caggcaactc ttgtggtttc acatttcttg 2220
tctcactttt ggaagagaaa ccgttataga gtatttggtg tctttcggag tgtggattcg 2280
cactcctcca gcttatagac caccaaatgc ccctatccta tcaacacttc cggaaactac 2340
tgttgttaga cgacgaggca ggtcccctag aagaagaact ccctcgcctc gcagacgaag 2400
gtctcaatcg ccgcgtcgca gaagatctca atctcgggaa tctcaatgtt agtattcctt 2460
ggactcataa ggtggggaac tttactggtc tttattcttc tactgtacct gtctttaatc 2520
ctcattggaa aacaccatct tttcctaata tacatttaca tcaagacatc atcaaaaaat 2580
gtgaacagtt tgtaggccca cttacagtta atgagaaaag aagattgcaa ttgattatgc 2640
ctgctaggtt ttatccaaag gttaccaaat atttaccatt ggataagggt attaaacctt 2700
attatccaca acatctagtt aatcattact tcaaaactag acactattta cacactctat 2760
ggaaggcggg tatattatat aagagagaaa caacacatag cgcctcattt tgtgggtcac 2820
catattcttg ggaacaagat ctacagcatg gggcagaatc tttccaccag caatcctctg 2880
ggattctttc ccgaccacca gttggatcca gccttcagag caaacaccgc aaatccagat 2940
tgggacttca atcccaacaa ggacacctgg ccagacgcca acaaggtagg agctggagca 3000
ttcgggctgg gtttcacccc accgcacgga ggccttttgg ggtggagccc tcaggctcag 3060
ggcatactac aaactttgcc agcaaatccg cctcctgcct ccaccaatcg ccagacagga 3120
aggcagccta ccccgctgtc tccacctttg agaaacactc atcctcaggc catgcagtgg 3180
aa 3182

<210> SEQ ID NO 210
<211> LENGTH: 3215
<212> TYPE: DNA
<213> ORGANISM: Hepatitus B virus

<400> SEQUENCE: 210
ctccaccaca ttccaccaag ctctgctaga tcccagagtg aggggcctat attttcctgc 60
tggtggctcc agttccggaa cagtaaaccc tgttccgact actgcctcac ccatatcgtc 120
aatcttctcg aggactgggg accctgcaca gaacatggag aacacaacat caggattcct 180
aggacccctg ctcgtgttac aggcggggtt tttcttgttg acaaaaatcc tcacaatacc 240
acagagtcta gactcgtggt ggacttctct caattttcta gggggagcac ccacgtgtcc 300
tggccaaaat tcgcagtccc caacctccaa tcactcacca acctcttgtc ctccaatttg 360
tcctggctat cgctggatgt gtctgcggcg ttttatcata ttcctcttca tcctgctgct 420
atgcctcatc ttcttgttgg ttcttctgga ctaccaaggt atgttgcccg tttgtcctct 480
acttccagga acaacaacta ccagcacggg accatgcaag acctgcacga ttcctgctca 540
aggaacctct atgtttccct cttgttgctg tacaaaacct tcggacggaa actgcacttg 600
tattcccatc ccatcatcct gggctttcgc aagattccta tgggagtggg cctcagtccg 660
tttctcctgg ctcagtttac tagtgccatt tgttcagtgg ttcgtagggc tttcccccac 720
tgtttggctt tcagttatat ggatgatgtg gtattggggg ccaagtctgt acaacatctt 780
gagtcccttt ttacctctat taccaatttt cttttgtctt tgggtataca tttgaatcct 840
aataaaacca aacgttgggg ctactccctt aacttcatgg gatatgtaat tggaagttgg 900

-continued

```
ggtactttac cacaggaaca tattgtacgg aaactcaagc aatgttttcg aaaactgcct    960
gtaaatagac ctattgattg gaaagtatgt caaagaattg tgggtctttt gggctttgct   1020
gccccttta cacaatgtgg ctatcctgcc ttgatgcctt tatatgcatg tatacactct    1080
aagcaggctt tcactttctc gccaacttac aaggcctttc tgtgtaaaca atatctgcac   1140
ctttaccccg ttgcccggca acggtcaggt ctctgccaag tgtttgctga cgcaaccccc   1200
actggatggg gcttggccat aggccatcgg cgcatgcgcg gaacctttgt ggctcctctg   1260
ccgatccata ctgcggaact cctagcagct tgttttgctc gcagccggtc tggagcaaaa   1320
cttatcggga ctgacaactc tgttgtcctc tctcggaaat acacctcctt cccatggctg   1380
ctcgggtgtg ctgccaactg gatccttcgc gggacgtcct ttgtctacgt cccgtcggcg   1440
ctgaatcccg cggacgaccc gtctcggggc cgtttggggc tctatcgtcc ccttcttcat   1500
ctgccgttcc ggccgaccac ggggcgcacc tctctttacg cggtctcccc gtctgtgcct   1560
tctcatctgc cggaccgtgt gcacttcgct tcacctctgc acgtcgcatg gagaccaccg   1620
tgaacgccca ccaggtcttg cccaaggtct tacataagag gactcttgga ctctcatcaa   1680
tgtcaacgac cgaccttgag gcatacttca aagactgttt gtttaaggac tgggaggagt   1740
tgggggagga gattaggtta aaggtctttg tactaggagg ctgtaggcat aaattggtct   1800
gttcaccagc accatgcaac tttttcacct ctgcctaatc atctcatgtt catgtcctac   1860
tgttcaagcc tccaagctgt gccttgggtg gctttggggc atggacattg acccgtataa   1920
agaatttgga gcttctgtgg agttactctc tttttttgcct tctgacttct ttccttctat   1980
tcgagatctc ctcgacaccg cctctgctct gtatcgggag gccttagagt ctccggaaca   2040
ttgttcacct caccatacag cactcaggca agctattctg tgttggggtg agttgatgaa   2100
tctggccacc tgggtgggaa gtaatttgga agacccagca tccagggaat tagtagtcag   2160
ctatgtcaat gttaatatgg gcctaaaaat cagacaacta ttgtggtttc acatttcctg   2220
tcttactttt ggaagagaaa ctgttcttga gtatttggta tcttttggag tgtggattcg   2280
cactcctcca gcttacagac caccaaatgc ccctatctta tcaacacttc cggaaactac   2340
tgttgttaga cgacgaggca ggtcccctag aagaagaact ccctcgcctc gcagacgaag   2400
gtctcaatcg ccgcgtcgca gaagatctca atctcgggaa tctcaatgtt agtatccctt   2460
ggactcataa ggtgggaaac tttactgggc tttattcttc tactgtacct gtctttaatc   2520
ctgagtggca aactccctcc tttcctaaca ttcatttaca ggaggacatt attaatagat   2580
gtgaacaata tgtgggccct cttacaacta atgaaaaaag gagattaaaa ttaattatgc   2640
ctgctaggtt ttatcctaac cttaccaaat acttgccctt ggataaaggc attaaacctt   2700
attatcctga acatgcagtt aatcattact tcaaaactag gcattattta catactctgt   2760
ggaaggccgg cattctatat aagagagaaa ctacacgcag cgcttcattt tgtgggtcac   2820
catattcttg ggaacaagag ctacagcatg ggaggttggt cttccaaacc tcgacaaggc   2880
atggggacga atctttctgt tcccaatcct ctgggatttt ttcccgatca ccagttggac   2940
cctgcgttcg gagccaactc aaacaatcca gattgggact tcaaccccaa caaggatcac   3000
tggccagagg caaatcaggt aggagcggga gcattcgggc cagggttcac cccaccacac   3060
ggcggtcttt tggggtggag ccctcaggct cagggcatat tgaccacagt gccagcagcg   3120
cctcctcctg cctccaccaa tcggcagtca ggaagacagc ctactcccat ctctccacct   3180
ctaagagaca gtcatcctca ggccatgcag tggaa                              3215
```

<210> SEQ ID NO 211
<211> LENGTH: 3215
<212> TYPE: DNA
<213> ORGANISM: Hepatitus B virus

<400> SEQUENCE: 211
ctccaccacg ttccaccaaa ctcttcaaga tcccagagtc agggctctgt actttcctgc 60
tggtggctcc agttcaggaa cagtaaaccc tgttcagaac actgcctctt ccatatcgtc 120
aatcttatcg acgactgggg accctgtgcc gaacatggag aacatcgcat caggactcct 180
aggacccctg ctcgtgttac aggcggggtt tttctcgttg acaaaaatcc tcacaatacc 240
acagagtcta gactcgtggt ggacttctct caattttcta gggggaacac ccgtgtgtct 300
tggccaaaat tcgcagtccc aaatctccag tcactcacca acttgttgtc ctccgatttg 360
tcctggttat cgctggatgt gtctgcggcg ttttatcatc ttcctctgca tcctgctgct 420
atgcctcatc ttcttgttgg ttcttctgga ctatcaaggt atgttgcccg tttgtcctct 480
aattccagga tcatcaacca ccagcacagg accatgcaaa acctgcacga ctcctgctca 540
aggaacctct atgtttccct catgttgctg tataaaacct acggacggaa actgcacctg 600
tattcccatc ccatcatctt gggctttcgc aaaataccta tgggagtggg cctcagtccg 660
tttctcttgg ctcagtttac tagtgccatt tgttcagtgg ttcgtagggc tttcccccac 720
tgtctggctt tcagttatat ggatgatgtg gttttggggg ccaagtctgt acaacatctt 780
gagtcccttt atgccgctgt taccaatttt cttttgtctt tgggcataca tttaaaccct 840
cagaaaacaa aaagatgggg ctactccctt aacttcatgg ggtatgtaat tggaagttgg 900
gggaccttac cccaagaaca tattgtgttg aaaatcaaac aatgttttag gaaacttcct 960
gtaaacaggc ctattgattg gaaagtatgt caacgaattg tgggtctttt gggatttgct 1020
gctcctttca cacaatgtgg atatcctgct ttaatgcctt tatatgcatg tatacaagct 1080
aaacaggctt ttactttttc gccaacgtat aaggcctttc tccacaaaca atatctgaac 1140
ctttaccccg ttgctcggca acggccaggt ctgtgccaag tgtttgctga cgcaaccccc 1200
actggctggg gcttggccat aggccatcag cgcatgcgtg ggacctttgt gtctcctctg 1260
ccgatccata ctgcggaact cctagccgct tgttttgctc gcagcaggtc tggagcaaaa 1320
cttatcggga ctgacaattc tgtcgtcctt tcccgcaaat atacatcgtt tccatggctg 1380
ctaggctgtg ctgccaactg gatcctgcgc gggacgtcct ttgtctacgt cccgtcggcg 1440
ctgaatcccg cggacgaccc ctcccggggc cgcttggggc tctaccgccc gcttctccgc 1500
ctgccgtacc gtccgaccac ggggcgcacc tctctttacg cggactcccc gtctgtgcct 1560
tctcatctgc cggaccgtgt gcacttcgct tcacctctgc acgtcgcatg gagaccaccg 1620
tgaacgccca tcggaacctg cccaaggtct tgcataagag gactcttgga ctttcagcaa 1680
tgtcaacgac cgaccttgag gcatacttca aagactgtgt gtttactgag tgggaggagt 1740
tgggggagga gatcaggtta aaggtctttg tactaggagg ctgtaggcat aaattggtct 1800
gttcaccagc accatgcaac tttttcacct ctgcctaatc atctcatgtt catgtcctac 1860
tgttcaagcc tccaagctgt gccttgggtg gctttggggc atggacattg acacctataa 1920
agaatttgga gcttctgtgg agttactctc ttttttgcct tctgacttct ttccttctat 1980
tcgagatctt ctcgacaccg cctctgctct gtatcgggag gccttagagt ctccggaaca 2040
ttgttcacct caccatacgg cactcaggca agctattgtg tgttggggtg agttgatgaa 2100
tctagccacc tgggtgggaa gtaatttgga agacccagcc tcccgggaat tagtagtcag 2160
ttatgtcaat gttaatatgg gcctaaaaat cagacaacta ttgtggtttc acatttcctg 2220
tcttactttt ggaagagaaa ctgttcttga atatttggtg tcttttggag tgtggattcg 2280
cacacctcca gcatatagac caccaaatgc ccctatctta tcaacacttc cggaaactac 2340
tgttgttaga cgacgaggca ggtcccctag aagaagaact ccctcgcctc gcagacgaag 2400
gtctcaatcg ccgcgtcgca gaagatctca atctcgggaa tctaaatgtt agtattcctt 2460
ggactcataa ggtgggaaac tttacggggc tttattcttc tacggtacct agctttaatc 2520
ctcaatggca aactccttca tttcctgaca ttcatttgca ggaggacatc attgataagt 2580
gtaaacaatt tgtgggaccc cttacagtga atgaaaacag gagactaaaa ttgattatgc 2640
ctgctaggtt ctatcccaat gttactaaat atttgccctt agataaagga attaaacctt 2700
attatccaga gcatgtagtt aatcattact tccagacgag acattattta catactcttt 2760
ggaaggcggg tatcttatat aaaagagaga caacacgtag cgcctcattt tgcgggtcac 2820
catattcttg ggaacaagag ctacagcatg ggaggttggt cctccaaacc tcgaaaaggc 2880
atggggacaa atctttccgt ccccaatcct ctgggattct ttcccgatca ccagttggac 2940
cctgcattca aagccaactc cgacaatccc gattgggacc tcaacccaca caaggacaac 3000
tggccggact ccaacaaggt gggagtggga gcattcgggc cgggattcac tccaccccat 3060
gggggactgt tggggtggag ccctcaagct cagggcatac tcacaactgt gccaacagct 3120
cctcctcctg cctccaccaa tcggcagtta ggaaggaagc ctactcccct gtctccacct 3180
ctaagagaca ctcatcctca ggcaatgcag tggaa 3215

<210> SEQ ID NO 212
<211> LENGTH: 3212
<212> TYPE: DNA
<213> ORGANISM: Hepatitus B virus

<400> SEQUENCE: 212
ttccacaaca tttcaccaag ctctgcagga tcccagagta agaggcctgt attttcctgc 60
tggtggctcc agttccggaa cagtgaaccc tgttccgact actgcctcac tcatctcgtc 120
aatcttctcg aggattgggg accctgcacc gaacatggaa agcatcacat caggattcct 180
aggacccctg ctcgtattac aggcggggtt tttcttgttg acaaaaatcc tcacaatacc 240
gcagagtcta gactcgtggt ggacttctct caattttcta gggggagctc ccgtgtgtct 300
tggccaaaat tcgcagtccc caacctccaa tcactcacca acctcttgtc ctccaatttg 360
tcctggctat cgctggatgt gtctgcggcg ttttatcatc ttcctcttca tcctgctgct 420
atgcctcatc ttcttgttgg ttcttctgga ctatcaaggt atgttgcccg tttgtcctct 480
aattccagga tcatcaacca ccagtacggg accctgccga acctgcacga ctcttgctca 540
aggaacctct atgtttccct catgttgctg ttcaaaacct tcggacggaa attgcacttg 600
tattcccatc ccatcatcat gggctttcgg aaaattccta tgggagtggg cctcagcccg 660
tttctcctgg ctcagtttac tagtgccatt tgttcagtgg ttcgccgggc tttcccccac 720
tgtctggctt tcagttatat ggatgatgtg gtattggggg ccaagtctgt acaacatctt 780
gagtcccttt atacctctgt taccaatttt cttttgtctt tgggtataca tttaaatccc 840
aacaaaacaa aaagatgggg atattccctg aatttcatgg gttatgtaat tggaagttgg 900
ggatcattac cacaggaaca catcataatg aaaatcaaag actgttttag aaaactcccc 960
gttaaccggc ctattgattg gaaagtatgt caacgaattg tgggtctttt gggctttgct 1020 gccccttta cacaatgtgg gtatcctgct ttaatgcctc tgtatgcgtg tattcaatct 1080
aagcaggctt tcactttctc gccaacttac aaggcctttc tgtgtaaaca atacctgaac 1140
ctttaccccg ttgcccggca acggccaggt ctgtgccaag tgtttgctga tgcaaccccc 1200
actggctggg gcttggccat aggccatcag cgcatgcgcg gaacctttat ggctcctctg 1260
ccgatccata ctgcggaact cctagccgct tgttttgctc gcagcaggtc tggagcgaaa 1320
cttatcggga cagataattc tgtcgttctc tcccggaaat atacatcctt tccatggctg 1380
ctaggctgtg ctgccaactg gatcctgcga gggacgtcct ttgtctacgt cccgtcagcg 1440
ctgaatcctg cggacgaccc gtctcggggt cgcttgggga tctatcgtcc ccttctccgt 1500
ctgccgttcc agccgtccac ggggcgcacc tctctttacg cggtctcccc gtctgtgcct 1560
tctcatctgc cggaccgtgt gcacttcgct tcacctctgc acgtcgcatg gagaccaccg 1620
tgaacgccca ccaaatcttg cccaaggtct tacataagag gactcttgga ctctctgcaa 1680
tgtcaacgac cgaccttgag gcatacttca aagactgttt gtttaaagac tgggaggagt 1740
tgggggagga gattagatta aaggtctttg tactaggagg ctgtaggcat aaattggtct 1800
gcgcaccagc accatgcaac tttttcacct ctgcctaatc atctcttgtt catgtcctac 1860
tgttcaagcc tccaagctgt gccttgggtg gctttggggc atggacattg acccttataa 1920
agaatttgga gctactgtgg agttactctc gtttttgcct tctgacttct ttccttcagt 1980
aagagatctt ctagataccg cctcagcttt gtatcgggat gccttagaat ctcctgagca 2040
ttgttcaccg catcacactg cactcaggca agccattctt tgctgggggg aactaatgac 2100
tctagctacc tgggtgggtg taaatttgga agatccagca tccagggacc tagtagtcag 2160
ttatgtcaat actaatatgg gcctaaagtt caggcaatta ttgtggtttc acatttcttg 2220
tctcactttt ggaagagaaa ccgtcataga gtatttggtg tcttttggag tgtggattcg 2280
cactcctcca gcttatagac caccaaatgc ccctatctta tcaacacttc cggagaatac 2340
tgttgttaga cgaagaggca ggtcccctag aagaagaact ccctcgcctc gcagacgaag 2400
atctcaatcg ccgcgtcgca gaagatctca atctccagct tcccaatgtt agtattcctt 2460
ggactcacaa ggtgggaaat tttacggggc tttactcttc tactatacct gtctttaatc 2520
ctaactggaa aactccatct tttcctgata ttcatttgca ccaggacatt attaacaaat 2580
gtgaacaatt tgtaggtcct ctaacagtaa atgaaaaacg aagattaaac ttagtcatgc 2640
ctgctagatt ttttcccatc tctacgaaat atttgcccct agagaaaggt ataaaacctt 2700
attatccaga taatgtagtt aatcattact tccaaaccag acactattta cacaccctat 2760
ggaaggcggg catcttatat aaaagagaaa ctacacgtag cgcctcattt tgtgggtcac 2820
cttattcttg ggaacaagag ctacatcatg ggctttcttg gacggtcccg tctcgaatgg 2880
gggaagaatc attccaccac caatcctctg ggattttttc ccgaccacca gttggatcca 2940
gcattcagag caaacaccag aaatccagat tgggaccaca atcccaacaa agaccactgg 3000
acggaagcca acaaggtagg agtgggagca ttcgggccgg ggttcactcc cccacacgga 3060
ggccttttgg ggtggagccc tcaggctcaa ggcatgctaa aaacattgcc agcagatccg 3120
cctcctgcct ccaccaatcg gcagtcagga aggcagccta ccccaatcac tccacctttg 3180
agagacactc atcctcaggc catgcagtgg aa 3212

<210> SEQ ID NO 213
<211> LENGTH: 3215
<212> TYPE: DNA
<213> ORGANISM: Hepatitus B virus

<400> SEQUENCE: 213
ctcaacccag ttccaccagg ctctgttaga tccgagggta agggctctgt attttcctgc 60

-continued

```
tggtggctcc agttcaggga cacagaaccc tgttccgact attgcctctc tcacatcatc    120
aatcttctcg aagactgggg gccctgctat gaacatggag aacatcacat caggactcct    180
aggacccctg ctcgtgttac aggcggtgtg tttcttgttg acaaaaatcc tcacaatacc    240
acagagtcta gactcgtggt ggacttctct caattttcta gggggactac ccgggtgtcc    300
tggccaaaat tcgcagtccc caacctccaa tcacttacca acctcctgtc ctccaacttg    360
tcctggctat cgttggatgt gtctgcggcg ttttatcatc ttcctcttca tcctgctgct    420
atgcctcatc ttcttgttgg ttcttctgga ctatcaaggt atgttgcccg tttgtcctct    480
acttccagga tccacaacca ccagcacggg accatgcaaa acctgcacaa ctcttgctca    540
aggaacctct atgtttccct cctgttgctg ttccaaaccc tcggacggaa actgcacctg    600
tattcccatc ccatcatctt gggctttagg aaaataccta tgggagtggg cctcagcccg    660
tttctcctgg ctcagtttac tagtgcaatt tgttcagtgg tgcgtagggc tttcccccac    720
tgtctggctt ttagttatat ggatgatctg gtattggggg ccaaatctgt gcagcatctt    780
gagtcccttt ataccgctgt taccaatttt ttgttatctg tgggtatcca tttaaatact    840
tctaaaacaa aaagatgggg ttacaaccta catttcatgg gttatgttat tggtagttgg    900
ggaacgttac cccaagatca tattgtacac aaaatcaaag attgttttcg gaaacttcct    960
gtaaatcgtc caattgattg gaaagtttgt cagcgcattg tgggtctttt gggctttgcg   1020
gcccctttca cccaatgtgg ttatcctgct ctcatgcctt tatatacctg tattactgct   1080
aaacaggctt ttgtcttttc gccaacttac aaggcctttc tctgtaaaca atacatgaac   1140
ctttaccccg ttgctcggca acggccaggc ctgtgccaag tgtttgctga cgcaaccccc   1200
actggttggg gcttggccat tggccatcag cgcatgcgtg gaacctttgt ggctcctctg   1260
ccgatccata ctgcggaact ccttgcagcc tgtttcgctc gcagccggtc tggagcgaac   1320
attatcggca cagacaactc tgttgtcctc tctaggaagt acacctcctt tccatggctg   1380
ctcggttgtg ctgccaactg gatcctgcgc gggacgtcct ttgtttacgt cccgtcggcg   1440
ctgaatcccg cggacgaccc ttcccggggt cgcttggggc tgtaccgccc ccttcttcgt   1500
ctgccgttcc agccgacgac gggtcgcacc tctctttacg cggactcccc gtctgttcct   1560
tctcatctgc cggaccgtgt gcacttcgct tcacctctgc acgtcgcatg gagaccaccg   1620
tgaacgcccc ctggaatctg ccaacagtct tacataagag gactcttgga ctttcaggac   1680
ggtcaatgac ctggatcgaa gaatacatca aagactgtgt atttaaggac tgggaggagc   1740
tgggggagga gatcaggtta aaggtctttg tactaggagg ctgtaggcat aaattggtct   1800
gttcaccagc accatgcaac tttttcacct ctgcctaatc atcttttgtt catgtcccac   1860
tgttcaagcc tccaagctgt gccttgggtg gctttggggc atggacattg acccttataa   1920
agaatttgga gcttctgtgg aattgctctc ttttttgcct tctgatttct tcccgtctgt   1980
tcgggaccta ctcgacaccg cttcagccct ttaccgggat gctctagagt caccggaaca   2040
ttgcaccccc aatcataccg ctctcaggca agctattttg tgctggggtg agttaatgac   2100
tttggcttcc tgggtgggta ataatttgga agaccctgca gctagggatt tagtagttaa   2160
ttatgtcaac actaatatgg gcctgaaaat tagacaactg ttgtggtttc acatttcctg   2220
tcttactttt ggaagagaaa cagttcttga gtatttggtg tcctttggag tgtggattcg   2280
cactccacct gcttataggc caccaaatgc ccctatccta tccacacttc cggaaactac   2340
tgttgttaga cgaagaggca ggtcccctag aagaagaact ccctcgcctc gccgacgaag   2400
atctcaatcg ccgcgtcgca gaagatctca atctccagct tcccaatgtt agtattcctt   2460
```

-continued ggactcataa ggtgggaaat tttacggggc tctactcttc tactgtacct gctttcaatc 2520
ctaactggtt aactccttct tttcctgata ttcatttaca tcaagatctg atatctaaat 2580
gtgaacaatt tgtaggcccg ctcactaaaa atgaattgag aagattaaaa ttggtcatgc 2640
cagctagatt ttatcctaag gttaccaaat actttcctat ggagaaaggg attaaaccct 2700
attatcctga gcattcagtt aatcattatt ttaaaacaag acattatttg catactcttt 2760
ggaaggcggg aatcttatat aagagagaat ccacacgtag cgcctcattt tgtgggtcac 2820
catattcctg ggaacaagag ctacagcatg ggagcacctc tctcaacgac aagaaggggc 2880
atgggactga atctttctgt gcccaatcct ctgggcttcc tgccagacca tcagctggat 2940
ccgctattca gggcaaattc cagcagtccc gactgggact tcaacacaaa caaggacagt 3000
tggccaatgg caaacaaggt aggagtggga ggctacggcc cagggtttac acccccacac 3060
ggtggcctgc tggggtggag ccctcaggca cagggtgttt tracaacctt gccagcagat 3120
ccgcctcctg cttccaccaa tcggcggtcc gggagaaagc caaccccagt ctctccacct 3180
ctaagagaca cacatccaca ggccatgcag tggaa 3215

<210> SEQ ID NO 214
<211> LENGTH: 3221
<212> TYPE: DNA
<213> ORGANISM: Hepatitus B virus

<400> SEQUENCE: 214
ttccactgcc ttccaccaag cactgcagga tcccagagtc aggggtccgt attttcctgc 60
tggtggctcc agttcaggaa cagtaaaccc tgctccgaat attgcctctc acatctcgtc 120
aatctccgcg aggactgggg accctgtgac gaacatggag aacatcacat caggactcct 180
aggacccctg ctcgtgttac aggcggggtt tttcttgttg acaagaatcc tcacaatacc 240
gcagagtcta ggctcgtggt ggacttctct caattttcta gggggatcac ccgtgtgtct 300
tggccaaaat tcgcagtccc caacctccaa tcactcacca acctcctgtc ctccaatttg 360
tcctggttat cgttggatgt gtctgcggcg ttttatcata ttcctcttca tcctgctgct 420
atgcctcatc ttcttattgg ttcttctgga ttatcaaggt atgttgcccg tttgtcctct 480
aattccagga tcaacaacaa ccggtacggg accatgcaaa acctgcacga ctcctgctca 540
aggcaactct atgtttccct catgttgctg tacaaaacct acggacggaa attgcacctg 600
tattcccatc ccatcgtcct gggctttcgc aaaataccta tgggagtggg cctcagtccg 660
tttctcttgg ctcagtttac tagtgccatt tgttcagtgg ttcgtagggc tttcccccac 720
tgtttggctt tcagctatat ggatgatgtg gtattggggg ccaagactgt acagcatcgt 780
gagtcccttt ataccgctgt taccaatttt cttttgtctc tgggtataca tttaaaccct 840
aacaaaacaa aaagatgggg ttattcccta aacttcatgg gttacataat tggaagttgg 900
ggaactttgc cacaggatca tattgtacaa aagatcaaac actgttttag aaaacttcct 960
gttaacaggc ctattgattg gaaagtatgt caaagaattg tgggtctttt gggctttgct 1020
gctccattta cacaatgtgg atatcctgcc ttaatgcctt tgtatgcatg tatacaagct 1080
aaacaggctt tcactttctc gccaacttac aaggcctttc taagtaaaca gtacatgaac 1140
ctttaccccg ttgctcggca acggcctggt ctgtgccaag tgtttgctga cgcaaccccc 1200
actggctggg gcttggccat aggccatcag cgcatgcgtg gaacctttgt ggctcctctg 1260
ccgatccata ctgcggaact cctagccgct tgttttgctc gcagccggtc tggagcaaag 1320
ctcatcggaa ctgacaattc tgtcgtcctc tcgcggaaat atacatcgtt tccatggctg 1380

```
ctaggctgta ctgccaactg gatccttcgc gggacgtcct ttgtttacgt cccgtcggcg   1440

ctgaatcccg cggacgaccc ctctcggggc cgcttgggac tctatcgtcc ccttctccgt   1500

ctgccgttcc agccgaccac ggggcgcacc tctctttacg cggtctcccc gtctgtgcct   1560

tctcatctgc cggtccgtgt gcacttcgct tcacctctgc acgttgcatg gagaccaccg   1620

tgaacgccca tcagatcctg cccaaggtct tacataagag gactcttgga ctcccagcaa   1680

tgtcaacgac cgaccttgag gcctacttca aagactgtgt gtttaaggac tgggaggagc   1740

tgggggagga gagtaggtta atgatctttg tattaggagg ctgtaggcat aaattggtct   1800

gcgcaccagc accatgcaac tttttcacct ctgccaaatc atctcttgta catgtcccac   1860

tgttcaagcc tccaagctgt gccttgggtg gctttggggc atggacattg acccttataa   1920

agaatttgga gctactgttg agttactctc gtttttgcct tctgacttct ttccttccgt   1980

cagagatctt ctagacaccg cctcagctct gtatcgagaa gccttagagt ctcctgagca   2040

ctgctcacct caccatactg cactcaggca agccattctc tgctgggggg aattgatgac   2100

tctagctacc tgggtgggta ataatttgga tgatccagca tccagggatc tagtagtcaa   2160

ttatgttaat actaacatgg gtttaaagat caggcaacta ttgtggtttc atatatcttg   2220

ccttactttt ggaagagaga ctgtacttga atatttggtc tctttcggag tgtggattcg   2280

cactcctcca ccctatagac caccaaatgc ccctatctta tcaacacttc cggaaactac   2340

tgttattaga cgacgggacc gaggcaggtc ccctagaaga agaactccct cgcctcgcag   2400

acgcagatct caatcgccgc gtcgcagaag atctcaatct cgggaatctc aatgttagta   2460

ttccttggac tcataaggtg ggaaacttta cggggcttta ttcctctaca gtacctatct   2520

ttaatcctga atggcaaact ccttcctttc ctaagattca tttacaagag gacattatta   2580

ataggtgtca acaatttgtg ggccctctca ctgtaaatga aaagagaaga ttgaaattaa   2640

ttatgcctgc tagattctat cctacccaca ctaaatattt gcccttagac aaaggaatta   2700

aaccttatta tccagatcag gtagttaatc attacttcca aaccagacat tatttacata   2760

ctctttggaa ggcgggtatt ctatataaga gggaaaccac acgtagcgca tcattttgcg   2820

ggtcaccata ttcttgggaa caagagctac agcatgggag gttggtcatc aaaacctcgc   2880

aaaggcatgg ggacgaatct ttctgttccc aaccctctgg gattctttcc cgatcatcag   2940

ttggaccctg cattcggagc caactcaaac aatccagatt gggacttcaa ccccatcaag   3000

gaccactggc cagcagccaa ccaggtggga gtgggggcat tcgggccagg gctcacccct   3060

ccacacggcg gtatcttggg gtggagccct caggctcagg gcatattgac cacagtgtca   3120

acaattcctc ctcctgcctc caccaatcgg cagtcaggaa ggcagcctac tcccatctct   3180

ccacctctcc gagacagtca tcctcaggcc acgcagtgga a                       3221
```

```
<210> SEQ ID NO 215
<211> LENGTH: 175
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(2)
<223> OTHER INFORMATION: Variable amino acid; Region may encompass 0-2
      residues
<220> FEATURE:
<221> NAME/KEY: MOD_RES
<222> LOCATION: (4)..(7)
<223> OTHER INFORMATION: Variable amino acid; Region may encompass 2-4
```

```
      residues
<220> FEATURE:
<221> NAME/KEY: MOD_RES
<222> LOCATION: (9)..(11)
<223> OTHER INFORMATION: Variable amino acid
<220> FEATURE:
<221> NAME/KEY: MOD_RES
<222> LOCATION: (14)..(20)
<223> OTHER INFORMATION: Variable amino acid
<220> FEATURE:
<221> NAME/KEY: MOD_RES
<222> LOCATION: (22)..(24)
<223> OTHER INFORMATION: Variable amino acid
<220> FEATURE:
<221> NAME/KEY: MOD_RES
<222> LOCATION: (26)..(35)
<223> OTHER INFORMATION: Variable amino acid; Region may encompass 2-10
      residues
<220> FEATURE:
<221> NAME/KEY: MOD_RES
<222> LOCATION: (36)..(37)
<223> OTHER INFORMATION: Variable amino acid; Region may encompass 0-2
      residues
<220> FEATURE:
<221> NAME/KEY: MOD_RES
<222> LOCATION: (39)..(42)
<223> OTHER INFORMATION: Variable amino acid; Region may encompass 2-4
      residues
<220> FEATURE:
<221> NAME/KEY: MOD_RES
<222> LOCATION: (44)..(46)
<223> OTHER INFORMATION: Variable amino acid
<220> FEATURE:
<221> NAME/KEY: MOD_RES
<222> LOCATION: (49)..(55)
<223> OTHER INFORMATION: Variable amino acid
<220> FEATURE:
<221> NAME/KEY: MOD_RES
<222> LOCATION: (57)..(59)
<223> OTHER INFORMATION: Variable amino acid
<220> FEATURE:
<221> NAME/KEY: MOD_RES
<222> LOCATION: (61)..(70)
<223> OTHER INFORMATION: Variable amino acid; Region may encompass 2-10
      residues
<220> FEATURE:
<221> NAME/KEY: MOD_RES
<222> LOCATION: (71)..(72)
<223> OTHER INFORMATION: Variable amino acid; Region may encompass 0-2
      residues; May or may not be present
<220> FEATURE:
<221> NAME/KEY: MOD_RES
<222> LOCATION: (74)..(77)
<223> OTHER INFORMATION: Variable amino acid; Region may encompass 2-4
      residues; May or may not be present
<220> FEATURE:
<221> NAME/KEY: MOD_RES
<222> LOCATION: (79)..(81)
<223> OTHER INFORMATION: Variable amino acid; May or may not be present
<220> FEATURE:
<221> NAME/KEY: MOD_RES
<222> LOCATION: (84)..(90)
<223> OTHER INFORMATION: Variable amino acid; May or may not be present
<220> FEATURE:
<221> NAME/KEY: MOD_RES
<222> LOCATION: (92)..(94)
<223> OTHER INFORMATION: Variable amino acid; May or may not be present
<220> FEATURE:
<221> NAME/KEY: MOD_RES
<222> LOCATION: (96)..(105)
<223> OTHER INFORMATION: Variable amino acid; Region may encompass 2-10
      residues; May or may not be present
<220> FEATURE:
<221> NAME/KEY: MOD_RES
<222> LOCATION: (106)..(107)
<223> OTHER INFORMATION: Variable amino acid; Region may encompass 0-2
      residues; May or may not be present
<220> FEATURE:
<221> NAME/KEY: MOD_RES
<222> LOCATION: (109)..(112)
```

```
<223> OTHER INFORMATION: Variable amino acid; Region may encompass 2-4
      residues; May or may not be present
<220> FEATURE:
<221> NAME/KEY: MOD_RES
<222> LOCATION: (114)..(116)
<223> OTHER INFORMATION: Variable amino acid; May or may not be present
<220> FEATURE:
<221> NAME/KEY: MOD_RES
<222> LOCATION: (119)..(125)
<223> OTHER INFORMATION: Variable amino acid; May or may not be present
<220> FEATURE:
<221> NAME/KEY: MOD_RES
<222> LOCATION: (127)..(129)
<223> OTHER INFORMATION: Variable amino acid; May or may not be present
<220> FEATURE:
<221> NAME/KEY: MOD_RES
<222> LOCATION: (131)..(140)
<223> OTHER INFORMATION: Variable amino acid; Region may encompass 2-10
      residue; May or may not be present
<220> FEATURE:
<221> NAME/KEY: MOD_RES
<222> LOCATION: (141)..(142)
<223> OTHER INFORMATION: Variable amino acid; Region may encompass 0-2
      residues; May or may not be present
<220> FEATURE:
<221> NAME/KEY: MOD_RES
<222> LOCATION: (144)..(147)
<223> OTHER INFORMATION: Variable amino acid; Region may encompass 2-4
      residues; May or may not be present
<220> FEATURE:
<221> NAME/KEY: MOD_RES
<222> LOCATION: (149)..(151)
<223> OTHER INFORMATION: Variable amino acid; May or may not be present
<220> FEATURE:
<221> NAME/KEY: MOD_RES
<222> LOCATION: (154)..(160)
<223> OTHER INFORMATION: Variable amino acid; May or may not be present
<220> FEATURE:
<221> NAME/KEY: MOD_RES
<222> LOCATION: (162)..(164)
<223> OTHER INFORMATION: Variable amino acid; May or may not be present
<220> FEATURE:
<221> NAME/KEY: MOD_RES
<222> LOCATION: (166)..(175)
<223> OTHER INFORMATION: Variable amino acid; Region may encompass 2-10
      residues; May or may not be present

<400> SEQUENCE: 215

Xaa Xaa Cys Xaa Xaa Xaa Xaa Cys Xaa Xaa Xaa Phe Ser Xaa Xaa Xaa
1               5                   10                  15

Xaa Xaa Xaa Xaa His Xaa Xaa Xaa His Xaa Xaa Xaa Xaa Xaa Xaa Xaa
            20                  25                  30

Xaa Xaa Xaa Xaa Xaa Cys Xaa Xaa Xaa Xaa Cys Xaa Xaa Xaa Phe Ser
        35                  40                  45

Xaa Xaa Xaa Xaa Xaa Xaa Xaa His Xaa Xaa Xaa His Xaa Xaa Xaa Xaa
    50                  55                  60

Xaa Xaa Xaa Xaa Xaa Xaa Xaa Xaa Cys Xaa Xaa Xaa Xaa Cys Xaa Xaa
65                  70                  75                  80

Xaa Phe Ser Xaa Xaa Xaa Xaa Xaa Xaa Xaa His Xaa Xaa Xaa His Xaa
                85                  90                  95

Xaa Xaa Xaa Xaa Xaa Xaa Xaa Xaa Xaa Xaa Xaa Cys Xaa Xaa Xaa Xaa
            100                 105                 110

Cys Xaa Xaa Xaa Phe Ser Xaa Xaa Xaa Xaa Xaa Xaa Xaa His Xaa Xaa
        115                 120                 125

Xaa His Xaa Xaa Xaa Xaa Xaa Xaa Xaa Xaa Xaa Xaa Xaa Xaa Cys Xaa
    130                 135                 140

Xaa Xaa Xaa Cys Xaa Xaa Xaa Phe Ser Xaa Xaa Xaa Xaa Xaa Xaa Xaa
145                 150                 155                 160

His Xaa Xaa Xaa His Xaa Xaa Xaa Xaa Xaa Xaa Xaa Xaa Xaa Xaa
```

-continued

```
                165                 170                 175


<210> SEQ ID NO 216
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 216

His His His His His His
1               5


<210> SEQ ID NO 217
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 217

Asp Asp Asp Asp Lys
1               5


<210> SEQ ID NO 218
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

Leu Ala Gly Leu Ile Asp Ala Asp Gly
1               5
```

HEPATITIS B VIRUS-BINDING POLYPEPTIDES AND METHODS OF USE THEREOF

CROSS-REFERENCE

This application claims the benefit of U.S. Provisional Patent Application No. 60/972,644, filed Sep. 14, 2007, which application is incorporated herein by reference in its entirety.

BACKGROUND

Hepatitis B virus (HBV) causes a significant global health burden with an estimated 360 million people persistently infected and 500,000-700,000 deaths annually from HBV-associated liver disease. Five percent of adults and ninety-five percent of neonates exposed to the virus become persistently infected. Persistent infection with HBV leads to liver cirrhosis and hepatocellular carcinoma, which has a five-year survival rate of only 9%. Therapeutics such as nucleoside analogs are effective at clearing the infection in approximately 20-30% of treated patients; however, resistance to nucleoside analogs is an increasing problem, with 70% of patients becoming resistant to lamivudine and 18% becoming resistant to adefovir and tenofovir after four years of treatment.

HBV is a member of the Hepadnaviridae family and has a small double-stranded DNA genome of approximately 3,200 base pairs and a strict tropism for hepatocytes. A model virus for HBV is the duck hepatitis B virus (DHBV), which has a comparable tropism for avian hepatocytes, and a common viral structure, life cycle and genome. Upon infection, the viral genome is converted from a relaxed circular form to a covalently closed circular (cccDNA) form in the nucleus of hepatocytes. This cccDNA form associates with several proteins to form a 'mini-chromosome' structure. and is the reservoir from which transcription of viral genes and progeny genomes occur. It is highly stable with 3-50 copies per nucleus and a half-life of approximately fifty days. Thus, when treatment with nucleoside analogs is stopped in infected patients, the cccDNA reservoir can result in a resurgence of viral production. There are currently no therapeutics available which target the cccDNA of HBV.

There remains a need for treatment options for individuals persistently infected with HBV.

LITERATURE

Mino et al. (2006) *J. Virol.* 80(11): 5405-5412; Reynolds et al. (2003) *Proc. Natl. Acad. Sci.* 100(4): 1615-1620; Segal et al, 2004; Beerli et al. (1998) *Proc. Natl. Acad. Sci.* 95: 14628-14633; Lilienbaum et al. (1993) *J. Virol.* 67(10): 6192-6200; Liu et al. (1994) *J. Virol.* 68(4): 2286-2296.

SUMMARY OF THE INVENTION

The present invention provides non-naturally occurring polypeptides that specifically bind hepatitis B virus (HBV) DNA; and polynucleotides encoding the polypeptides. The present invention further provides methods of detecting HBV DNA; methods of detecting a covalently closed circular DNA (cccDNA) form of HBV; and methods for treating HBV infection.

BRIEF DESCRIPTION OF THE DRAWINGS

FIG. 1 shows a map of the DHBV cccDNA genome.

FIG. 2 shows the DNA sequence of the DHBV cccDNA enhancer region with the ZFP binding sites identified. SEQ ID NO:159 is the upper sequence; SEQ ID NO:160 is the complement of SEQ ID NO:159.

FIG. 16A shows a schematic of the HBV pre-S2/s promoter region and the target sites of the ZFPs; and FIG. 16B is a schematic depiction of the HBV genome, showing the location of the pre-S2/s promoter region.

FIG. 23*a-c* show the nucleotide sequence of ZFPa, the amino acid sequence of ZFPa, and the DNA target sequence of ZFPa, respectively.

FIG. 24*a-c* show the nucleotide sequence of ZFPb, the amino acid sequence of ZFPb, and the DNA target sequence of ZFPb, respectively.

FIG. 25*a-c* show the nucleotide sequence of ZFPc, the amino acid sequence of ZFPc, and the DNA target sequence of ZFPc, respectively.

FIG. 26*a-c* show the nucleotide sequence of ZFPd, the amino acid sequence of ZFPd, and the DNA target sequence of ZFPd, respectively.

FIG. 27*a-c* show the nucleotide sequence of ZFPe, the amino acid sequence of ZFPe, and the DNA target sequence of ZFPe, respectively.

FIG. 28*a-c* shows the nucleotide sequence of ZFPf, the amino acid sequence of ZFPf, and the DNA target sequence of ZFPf, respectively.

FIG. 29*a-c* show the nucleotide sequence of ZFPg, the amino acid sequence of ZFPg, and the target sequence of ZFPg, respectively.

FIG. 30*a-c* show the nucleotide sequence of ZFPk, the amino acid sequence of ZFPk, and the DNA target sequence of ZFPk, respectively.

FIG. 31*a-c* show the nucleotide sequence of ZFPm, the amino acid sequence of ZFPm, and the DNA target sequence of ZFPm, respectively.

FIG. 32*a-c* show the nucleotide sequence of ZFPn, the amino acid sequence of ZFPn, and the DNA target sequence of ZFPn, respectively.

FIG. 33*a-c* show the nucleotide sequence of ZFPp, the amino acid sequence of ZFPp, and the DNA target sequence of ZFPp, respectively FIG. 34*a-c* show the nucleotide sequence of ZFPq, the amino acid sequence of ZFPq, and the DNA target sequence of ZFPq, respectively.

FIG. 35*a-c* show the nucleotide sequence of ZFPr, the amino acid sequence of ZFPr, and the DNA target sequence of ZFPr, respectively.

FIG. 36*a-c* show the nucleotide sequence of ZFPt, the amino acid sequence of ZFPt, and the DNA target sequence of ZFPt, respectively.

FIG. 37*a-c* show the nucleotide sequence of ZFPu, the amino acid sequence of ZFPu, and the DNA target sequence of ZFPu, respectively.

FIG. 38*a-c* show the nucleotide sequence of ZFPv, the amino acid sequence of ZFPv, and the DNA target sequence of ZFPv, respectively.

FIG. 39*a-c* show the nucleotide sequence of ZFPw, the amino acid sequence of ZFPw, and the DNA target sequence of ZFPw, respectively.

FIG. 40 provides a nucleotide sequence of an HBV genome (subtype ayw).

FIG. 41 provides a nucleotide sequence of a duck HBV genome.

FIGS. 42A-F provide nucleotide and amino acid sequences of FokI endonuclease domain (FIGS. 42A and 42B, respectively), nucleotide and amino acid sequences of an HBV DNA-binding ZFP (FIGS. 42C and 42D, respectively), and nucleotide and amino acid sequences of exemplary FokI-HBV DNA-binding ZFP fusion proteins (FIGS. 42E and 42F, respectively). In FIG. 42E, upper case letters indicate the endonuclease-encoding nucleotide sequence; lower case letters indicate the HBV DNA-binding ZFP-encoding nucleotide sequences. In FIG. 42F, the amino acid sequence of the FokI endonuclease is in bold text.

FIGS. 43A-F provide nucleotide and amino acid sequences of homothallism (HO) endonuclease domain (FIGS. 43A and 43B, respectively), nucleotide and amino acid sequences of an HBV DNA-binding ZFP (FIGS. 43C and 43D, respectively), and nucleotide and amino acid sequences of exemplary HO-HBV DNA-binding ZFP fusion proteins (FIGS. 43E and 43F, respectively). In FIG. 43E, HBV DNA-binding ZFP-encoding nucleotides are in lower case; HO endonuclease-encoding nucleotides are in upper case. In FIG. 43F, the amino acid sequence of the HO endonuclease is in bold.

FIG. 44 provides a nucleotide sequence of an HBV genotype D genome.

FIG. 45 provides a nucleotide sequence of an HBV genotype C genome.

FIG. 46 provides a nucleotide sequence of an HBV genotype B genome.

FIG. 47 provides a nucleotide sequence of an HBV genotype E genome.

FIG. 48 provides a nucleotide sequence of an HBV genotype F genome.

FIG. 49 provides a nucleotide sequence of an HBV serotype A genome.

DEFINITIONS

Figure 3:
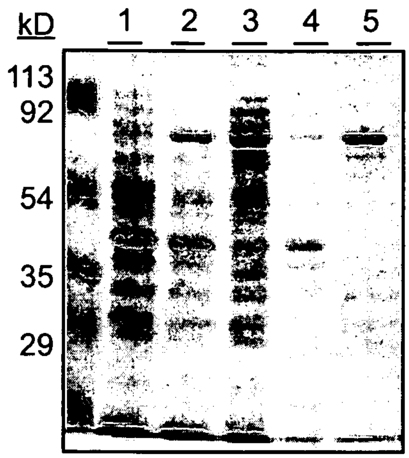
FIG. 3 shows a Coomassie blue stain of purified ZFPa.

As used herein, "hepatitis B virus" or "HBV" refers to a member of the Hepadnaviridae family having a small double-stranded DNA genome of approximately 3,200 base pairs and a tropism for liver cells. "HBV" includes HBV that infects any of a variety of mammalian (e.g., human, non-human primate, etc.) and avian (duck, etc.) hosts. "HBV" includes any known HBV genotype, e.g., serotype A, B, C, D, E, F, and G; any HBV serotype or HBV subtype; any HBV isolate; HBV variants, e.g., HBeAg-negative variants, drug-resistant HBV variants (e.g., lamivudine-resistant variants; adefovir-resistant mutants; tenofovir-resistant mutants; entecavir-resistant mutants; etc.); and the like.

By "nucleic acid" herein is meant either DNA or RNA, or molecules which contain both deoxy- and ribonucleotides. The nucleic acids include genomic DNA, cDNA and oligonucleotides. The nucleic acid may be double stranded, single stranded, or contain portions of both double stranded or single stranded sequence. As will be appreciated by those in the art, the depiction of a single strand ("Watson") also defines the sequence of the other strand ("Crick"). By the term "recombinant nucleic acid" herein is meant nucleic acid, originally formed in vitro, in general, by the manipulation of nucleic acid by endonucleases, in a form not normally found in nature. Thus an isolated nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell or organism, it will replicate non-recombinantly, i.e. using the in vivo cellular machinery of the host cell rather than in vitro manipulations; however, such nucleic acids, once produced recombinantly, although subsequently replicated non-recombinantly, are still considered recombinant for the purposes of the invention.

Nucleic acid sequence identity (as well as amino acid sequence identity) is calculated based on a reference sequence, which may be a subset of a larger sequence, such as a conserved motif, coding region, flanking region, etc. A reference sequence will usually be at least about 18 residues long, more usually at least about 30 residues long, and may extend to the complete sequence that is being compared. Algorithms for sequence analysis are known in the art, such as BLAST, described in Altschul et al. (1990), *J. Mol. Biol.* 215:403-10 (using default settings, i.e. parameters w=4 and T=17).

Where a nucleic acid is said to hybridize to a recited nucleic acid sequence, hybridization is under stringent conditions. An example of stringent hybridization conditions is hybridization at 50° C. or higher and 0.1×SSC (15 mM sodium chloride/1.5 mM sodium citrate). Another example of stringent hybridization conditions is overnight incubation at 42° C. in a solution: 50% formamide, 5×SSC (150 mM NaCl, 15 mM trisodium citrate), 50 mM sodium phosphate (pH7.6), 5×Denhardt's solution, 10% dextran sulfate, and 20 μg/ml denatured, sheared salmon sperm DNA, followed by washing the filters in 0.1×SSC at about 65° C. Stringent hybridization conditions are hybridization conditions that are at least as stringent as the above representative conditions, where conditions are considered to be at least as stringent if they are at least about 80% as stringent, typically at least about 90% as stringent as the above specific stringent conditions. Other stringent hybridization conditions are known in the art and may also be employed to identify nucleic acids of this particular embodiment of the invention.

Similarly, "polypeptide" and "protein" as used interchangeably herein, and can encompass peptides and oligopeptides. Where "polypeptide" is recited herein to refer to an amino acid sequence of a naturally-occurring protein molecule, "polypeptide" and like terms are not necessarily limited to the amino acid sequence to the complete, native amino acid sequence associated with the recited protein molecule, but instead can encompass biologically active variants or fragments, including polypeptides having substantial sequence similarity or sequence identify relative to the amino acid sequences provided herein. In general, fragments or variants retain a biological activity of the parent polypeptide from which their sequence is derived.

A "variant" of a polypeptide is defined as an amino acid sequence that is altered by one or more amino acids (e.g., by deletion, addition, insertion and/or substitution). The variant can have "conservative" changes, wherein a substituted amino acid has similar structural or chemical properties, e.g., replacement of leucine with isoleucine. More rarely, a variant can have "nonconservative" changes, e.g., replacement of a glycine with a tryptophan. Similar minor variations can also include amino acid deletions or insertions, or both. Guidance in determining which and how many amino acid residues may be substituted, added, inserted or deleted without abolishing biological or immunological activity can be found using computer programs well known in the art, for example, DNAStar software.

The term "isolated" indicates that the recited material (e.g, polypeptide, nucleic acid, etc.) is substantially separated from, or enriched relative to, other materials with which it occurs, e.g., during production of the material. A material (e.g., polypeptide, nucleic acid, etc.) that is isolated constitutes at least about 0.1%, at least about 0.5%, at least about 1% or at least about 5% by weight of the total material of the same type (e.g., total protein, total nucleic acid) in a given sample.

By "purified" is meant a compound of interest (e.g., a polypeptide) has been separated from components that may be present during its production. For example, "purified" can refer to a compound of interest (e.g., a polypeptide) separated from components that can accompany it during manufacture (e.g., in chemical synthesis). In some embodiments, a compound is substantially pure when it is at least 50% to 60%, by weight, free from organic molecules with which it is naturally associated or with which it is associated during manufacture. In some embodiments, the preparation is at least 75%, at least 90%, at least 95%, or at least 99%, by weight, of the compound of interest. A substantially pure polypeptide can be obtained, for example, by recombinant production of the polypeptide, by chemically synthesizing the polypeptide, by one or more purification steps, by a combination of recombinant synthesis and purification, or by a combination of recombinant production (e.g., production in a cell) and purification. Purification steps can include, e.g., size exclusion chromatography, precipitation with salt, immunoprecipitation, affinity chromatography, high performance liquid chromatography, and the like. Purity can be measured by any appropriate method, e.g., chromatography, mass spectroscopy, high performance liquid chromatography analysis, etc.

"Treating" or "treatment" of a condition or disease includes: (1) preventing at least one symptom of the conditions, i.e., causing a clinical symptom to not significantly develop in an avian species or a mammalian species that may be exposed to a disease-causing agent (e.g., HBV) or predisposed to the disease but does not yet experience or display symptoms of the disease, (2) inhibiting the disease, e.g., arresting or reducing the development of the disease or its symptoms, or (3) relieving the disease, i.e., causing regression of the disease or its clinical symptoms.

A "therapeutically effective amount" or "efficacious amount" means the amount of a compound that, when administered to a mammal or other subject for treating a disease, is sufficient to effect such treatment for the disease. The "therapeutically effective amount" will vary depending on the compound, the disease and its severity and the age, weight, etc., of the subject to be treated.

The terms "subject," "host," "individual," and "patient" are used interchangeably herein to refer to a member or members of any mammalian or non-mammalian species that may have a need for the pharmaceutical methods, compositions and treatments described herein. Subjects and patients thus include, without limitation, primate (including humans), canine, feline, ungulate (e.g., equine, bovine, swine (e.g., pig)), avian, and other subjects. Humans and non-human animals having commercial importance (e.g., livestock and domesticated animals) are of particular interest.

"Mammal" means a member or members of any mammalian species, and includes, by way of example, canines; felines; equines; bovines; ovines; rodentia, etc. and primates, e.g., humans and non-human primates. Non-human animal models, including avian species; and mammals, e.g. non-human primates, murines, lagomorpha, etc., may be used for experimental investigations.

The term "unit dosage form," as used herein, refers to physically discrete units suitable as unitary dosages for human and animal subjects, each unit containing a predetermined quantity of compounds calculated in an amount sufficient to produce the desired effect in association with a pharmaceutically acceptable diluent, carrier or vehicle.

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents; washed; or enrichment for certain cell populations, such as liver cells, peripheral blood mononuclear cells (PBMC), and the like. The term "biological sample" encompasses a clinical sample, and also includes cells in culture, cell supernatants, tissue samples, organs, bone marrow, blood, plasma, serum, and the like. In some embodiments, a biological sample comprises nucleated cells, e.g., nucleated blood cells, liver cells, etc.

"Gene delivery vehicle" refers to a construct which is capable of delivering, and, within some embodiments expressing, one or more gene(s) or nucleotide sequence(s) of interest in a host cell. Representative examples of such vehicles include viral vectors, nucleic acid expression vectors, naked DNA, and certain eukaryotic cells (e.g., producer cells).

"Operably linked" refers to an arrangement of elements wherein the components so described are configured so as to perform their usual function. Thus, control elements operably linked to a coding sequence are capable of effecting the expression of the coding sequence. The control elements need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "an HBV genome" includes a plurality of such genomes and reference to "the HBV-binding polypeptide" includes reference to one or more HBV-binding polypeptides and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present invention provides non-naturally occurring polypeptides that specifically bind hepatitis B virus (HBV) DNA; and polynucleotides encoding the polypeptides. The present invention further provides methods of detecting HBV DNA; methods of detecting a covalently closed circular DNA (cccDNA) form of HBV; and methods for treating HBV infection.

HBV-Binding Polypeptides

The present invention provides non-naturally occurring, HBV DNA-binding, polypeptides. A subject polypeptide comprises a "zinc finger" structure, and specifically binds a nucleotide sequence present in HBV DNA.

In some embodiments, the polypeptide binds specifically to a covalently closed circular DNA (cccDNA) form of HBV DNA. In some embodiments, in addition to binding an HBV nucleotide sequence, a subject HBV-binding polypeptide exhibits one or more of the following activities when present in an HBV-infected cell: 1) reduces production of HBV RNA in the infected cell; 2) reduces production of a core HBV antigen in the infected cell; 3) reduces production of an HBV surface antigen in the infected cell; and 4) reduces production of HBV intracellular virus particles in the infected cell.

In some embodiments, a subject non-naturally occurring, HBV DNA-binding polypeptide, when contacted with a eukaryotic cell that comprises HBV DNA, reduces the production of HBV RNA in the cell by at least about 5%, at least about 10%, at least about 15%, at least about 20%, at least about 25%, at least about 30%, at least about 35%, at least about 40%, at least about 50%, at least about 60%, at least about 70%, at least about 80%, or at least about 90%, or more, compared to the level of HBV RNA produced by the cell in the absence of the subject non-naturally occurring, HBV DNA-binding polypeptide.

In some embodiments, a subject non-naturally occurring, HBV DNA-binding polypeptide, when contacted with a eukaryotic cell that comprises HBV DNA, reduces the production of an HBV core antigen encoded by the HBV DNA by at least about 5%, at least about 10%, at least about 15%, at least about 20%, at least about 25%, at least about 30%, at least about 35%, at least about 40%, at least about 50%, at least about 60%, at least about 70%, at least about 80%, or at least about 90%, or more, compared to the level of the HBV core antigen produced by the cell in the absence of the subject non-naturally occurring, HBV DNA-binding polypeptide.

In some embodiments, a subject non-naturally occurring, HBV DNA-binding polypeptide, when contacted with a eukaryotic cell that comprises HBV DNA, reduces the production of an HBV surface antigen encoded by the HBV DNA by at least about 5%, at least about 10%, at least about 15%, at least about 20%, at least about 25%, at least about 30%, at least about 35%, at least about 40%, at least about 50%, at least about 60%, at least about 70%, at least about 80%, or at least about 90%, or more, compared to the level of the HBV surface antigen produced by the cell in the absence of the subject non-naturally occurring, HBV DNA-binding polypeptide.

In some embodiments, a subject non-naturally occurring, HBV DNA-binding polypeptide, when contacted with a eukaryotic cell that comprises HBV DNA, reduces the level of cccDNA form of HBV by at least about 5%, at least about 10%, at least about 15%, at least about 20%, at least about 25%, at least about 30%, at least about 35%, at least about 40%, at least about 50%, at least about 60%, at least about 70%, at least about 80%, or at least about 90%, or more, compared to the level of cccDNA form of HBV in the cell in the absence of the subject non-naturally occurring, HBV DNA-binding polypeptide.

In some embodiments, a subject non-naturally occurring, HBV DNA-binding polypeptide, when contacted with a eukaryotic cell that comprises HBV DNA, reduces production of infectious HBV particles by at least about 5%, at least about 10%, at least about 15%, at least about 20%, at least about 25%, at least about 30%, at least about 35%, at least about 40%, at least about 50%, at least about 60%, at least about 70%, at least about 80%, or at least about 90%, or more, compared to the level of infectious HBV particles produced the cell in the absence of the subject non-naturally occurring, HBV DNA-binding polypeptide.

In some embodiments, a subject non-naturally occurring, HBV DNA-binding polypeptide, when administered to an individual in need thereof (e.g., an HBV-infected individual; an individual with a cccDNA HBV reservoir; etc.), reduces the likelihood of relapse. In the following formulas, a subscript immediately adjacent an amino acid or a moiety indicates a designation of the amino acid or the moiety; and a subscript following a parenthesis indicates the number of the amino acid or moiety. For example, "$(J_1)$" refers to a first flanking sequence; "$(J_2)$" refers to a second flanking sequence; "$X_1$" refers to a first amino acid; "$X_2$" refers to a second amino acid sequence; "$B_1$" refers to a first DNA-binding moiety; "$B_2$" refers to a second DNA-binding moiety; etc. In contrast, "$(X)_{2-4}$" indicates a contiguous stretch of two to four amino acids, e.g., XX, XXX, or XXXX; "$(X)_3$" indicates a contiguous stretch of three amino acids; and "$(X_1X_2Cys(X)_{2-4}Cys(X)_3PheSer(B_{0+n})His(X)_3His(Z))_n$" (SEQ ID NO:215) indicates that "$(X_1X_2Cys(X)_{2-4}Cys(X)_3PheSer(B_{0+n})His(X)_3His(Z))$" (SEQ ID NO:1) is present n times (e.g., 2 to 5 times) in tandem.

Formula 1

In some embodiments, a subject non-naturally occurring, HBV DNA-binding polypeptide comprises an amino acid sequence represented by Formula 1: $(J_1)(X_1X_2Cys(X)_{2-4}Cys(X)_3PheSer(B_{0+n})His(X)_3His(Z))_nX_1X_2Cys(X)_{2-4}Cys(X)_3PheSer(B_{0+n})His(X)_3His(J_2)$ (SEQ ID NO:2), wherein each of $J_1$ and $J_2$, if present, is independently flanking sequences of 1 amino acid to about 100 amino acids; $X_1$ and $X_2$, if present, are any amino acid; X is any amino acid; Z is a linker of from 2 amino acids to 10 amino acids in length; n is 2 to 5; each of $B_{0+n}$ and $B_{n+1}$ is seven amino acids in length; wherein each B individually binds DNA; and wherein $B_{0+n}$ and $B_{n+1}$ collectively provide for binding to an HBV nucleotide sequence.

For example, in some of these embodiments, a subject non-naturally occurring, HBV DNA-binding polypeptide comprises the amino acid sequence:

$(J_1)X_1X_2Cys(X)_{2-4}Cys(X)_3PheSer(B_1)His(X)_3His(Z)$ $X_1X_2Cys(X)_{2-4}Cys(X)_3PheSer(B_2)His(X)_3His(Z)X_1X_2Cys(X)_{2-4}Cys(X)_3PheSer(B_3)His(X)_3His(J_2)$ (SEQ ID NO:3), wherein each of $J_1$ and $J_2$, if present, is independently flanking sequences of 1 amino acid to about 100 amino acids; $X_1$ and $X_2$, if present, are any amino acid; X is any amino acid; Z is a linker of from 2 amino acids to 10 amino acids in length; each of $B_1$, $B_2$ and $B_3$ is seven amino acids in length; wherein each B individually binds DNA; and wherein $B_1$, $B_2$ and $B_3$ collectively provide for binding to an HBV nucleotide sequence.

As another example, in some embodiments, a subject non-naturally occurring, HBV DNA-binding polypeptide comprises the amino acid sequence:

$(J_1)X_1X_2Cys(X)_{2-4}Cys(X)_3PheSer(B_1)His(X)_3His(Z)$ $X_1X_2Cys(X)_{2-4}Cys(X)_3PheSer(B_2)His(X)_3His(Z)$ $X_1X_2Cys(X)_{2-4}Cys(X)_3PheSer(B_3)His(X)_3His(Z)$ $X_1X_2Cys(X)_{2-4}Cys(X)_3PheSer(B_4)His(X)_3His(Z)$ $X_1X_2Cys(X)_{2-4}Cys(X)_3PheSer(B_5)His(X)_3His(Z)$ $X_1X_2Cys(X)_{2-4}Cys(X)_3PheSer(B_6)His(X)_3His(J_2)$ (SEQ ID NO:4), wherein each of $J_1$ and $J_2$, if present, is independently flanking sequences of 1 amino acid to about 100 amino acids; $X_1$ and $X_2$, if present, are any amino acid; X is any amino acid; Z is a linker of from 2 amino acids to 10 amino acids in length; each of $B_1$, $B_2$, $B_3$, $B_4$, $B_5$, and $B_6$ is seven amino acids in length; wherein each B individually binds DNA; and wherein $B_1$, $B_2$, $B_3$, $B_4$, $B_5$, and $B_6$ collectively provide for binding to an HBV nucleotide sequence.

Formula 2

In some embodiments, $X_1$ is Tyr and $X_2$ Lys. Thus, in some embodiments, a subject non-naturally occurring, HBV DNA-binding polypeptide comprises an amino acid sequence represented by Formula 2: $(J_1)(TyrLysCys(X)_{2-4}Cys(X)_3PheSer(B_{0+n})His(X)_3His(Z))_nTyrLysCys(X)_{2-4}Cys(X)_3PheSer(B_{0+n})His(X)_3His(J_2)$ (SEQ ID NO:5), wherein each of $J_1$ and $J_2$, if present, is independently flanking sequences of 1 amino acid to about 100 amino acids; X is any amino acid; Z is a linker of from 2 amino acids to 10 amino acids in length; n is 2 to 5; each of $B_{0+n}$ and $B_{n+1}$ is seven amino acids in length; wherein each B individually binds DNA; and wherein $B_{0+n}$ and $B_{n+1}$ collectively provide for binding to an HBV nucleotide sequence.

For example, in some of these embodiments, a subject non-naturally occurring, HBV DNA-binding polypeptide comprises the amino acid sequence:

$(J_1)TyrLysCys(X)_{2-4}Cys(X)_3PheSer(B_1)His(X)_3His(Z)$ $TyrLysCys(X)_{2-4}Cys(X)_3PheSer(B_2)His(X)_3His(Z)$ $TyrLysCys(X)_{2-4}Cys(X)_3PheSer(B_3)His(X)_3His(J_2)$ (SEQ ID NO:6), wherein each of $J_1$ and $J_2$, if present, is independently flanking sequences of 1 amino acid to about 100 amino acids; X is any amino acid; Z is a linker of from 2 amino acids to 10 amino acids in length; each of $B_1$, $B_2$ and $B_3$ is seven amino acids in length; wherein each B individually binds DNA; and wherein $B_1$, $B_2$ and $B_3$ collectively provide for binding to an HBV nucleotide sequence.

As another example, in some embodiments, a subject non-naturally occurring, HBV DNA-binding polypeptide comprises the amino acid sequence:

$(J_1)TyrLysCys(X)_{2-4}Cys(X)_3PheSer(B_1)His(X)_3His(Z)$ $TyrLysCys(X)_{2-4}Cys(X)_3PheSer(B_2)His(X)_3His(Z)$ $TyrLysCys(X)_{2-4}Cys(X)_3PheSer(B_3)His(X)_3His(Z)$ $TyrLys_2Cys(X)_{2-4}Cys(X)_3PheSer(B_4)His(X)_3His(Z)$ $TyrLysCys(X)_{2-4}Cys(X)_3PheSer(B_5)His(X)_3His(Z)$ $TyrLysCys(X)_{2-4}Cys(X)_3PheSer(B_6)His(X)_3His(J_2)$ (SEQ ID NO:7), wherein each of $J_1$ and $J_2$, if present, is independently flanking sequences of 1 amino acid to about 100 amino acids; X is any amino acid; Z is a linker of from 2 amino acids to 10 amino acids in length; each of $B_1$, $B_2$, $B_3$, $B_4$, $B_5$, and $B_6$ is seven amino acids in length; wherein each B individually binds DNA; and wherein $B_1$, $B_2$, $B_3$, $B_4$, $B_5$, and $B_6$ collectively provide for binding to an HBV nucleotide sequence.

Formula 3

In some embodiments, a subject non-naturally occurring, HBV DNA-binding polypeptide comprises an amino acid sequence represented by Formula 3: $(J_1)(YKCPECGKSFS(B_{0+n})HQRTHTGEKP)_nYKCPECGKSFS(B_{n+1})$ HQRTH $(J_2)$ (SEQ ID NO:8), wherein each of $J_1$ and $J_2$, if present, is independently 1-100 amino acids; n is 2 to 5; each of $B_{0+n}$ and $B_{n+1}$ is 5 amino acids in length; and wherein $B_{0+n}$ and $B_{n+1}$ collectively provide for binding to an HBV nucleotide sequence. The underlined sequence "TGEKP" (SEQ ID NO:119) is a linker sequence.

For example, in some of these embodiments, a subject non-naturally occurring, HBV DNA-binding polypeptide comprises the amino acid sequence: $(J_1)$ $YKCPECGKSFS(B_1)HQRTHTGEKPYKCPECGKSFS(B_2)$ HQRTHTGEKPYKCPECGKS FS$(B_3)$HQRTH$(J_2)$ (SEQ ID NO:9), wherein each of $J_1$ and $J_2$, if present, is independently 1-100 amino acids; each of $B_1$, $B_2$ and $B_3$ is seven amino acids in length; wherein each B individually binds DNA; and wherein $B_1$, $B_2$ and $B_3$ collectively provide for binding to an HBV nucleotide sequence.

As another example, in some of these embodiments, a subject non-naturally occurring, HBV DNA-binding polypeptide comprises the amino acid sequence: $(J_1)$ $YKCPECGKSFS(B_1)HQRTHTGEKPYKCPECGKSFS(B_2)HQRTHTGEKPYKCPECGKS$ FS$(B_3)$HQRTH TGEKPYKCPECGKSFS$(B_4)$HQRTHTGEKPYKCPEC GKSFS$(B_5)$HQRTHTGEKPYKCPECGKSFS $(B_6)$ HQRTH ($J_2$) (SEQ ID NO:10), wherein each of $J_1$ and $J_2$, if present, is independently 1-100 amino acids; each of $B_1$, $B_2$, $B_3$, $B_4$, $B_5$, and $B_6$ is seven amino acids in length; wherein each B individually binds DNA; and wherein $B_1$, $B_2$, $B_3$, $B_4$, $B_5$, and $B_6$ collectively provide for binding to an HBV nucleotide sequence.

DNA-Binding Moieties

As noted above, each of $B_{0+n}$ and $B_{n+1}$ is seven amino acids in length; each B individually binds DNA; and $B_{0+n}$ and $B_{n+1}$ collectively provide for binding to an HBV nucleotide sequence. Thus, each B is a DNA-binding moiety. In some embodiments, each B binds a sequence of 3 nucleotides. In some embodiments, n is 2, i.e., a subject polypeptide comprises three DNA-binding moieties: $B_1$, $B_2$, and $B_3$. Where n is 2, and where a subject polypeptide comprises three DNA-binding moieties, $B_1$, $B_2$, and $B_3$ collectively provide for binding to a 9-nucleotide sequence of HBV DNA. In other embodiments, n is 5, i.e., a subject polypeptide comprises six DNA-binding moieties: $B_1$, $B_2$, $B_3$, $B_4$, $B_5$, and $B_6$. Where n is 2, and where a subject polypeptide comprises six DNA-binding moieties, $B_1$, $B_2$, $B_3$, $B_4$, $B_5$, and $B_6$ collectively provide for binding to an 18-nucleotide sequence of HBV DNA. Exemplary target HBV nucleotide sequences are provided below.

As noted above, each B moiety is seven amino acids in length. The fifth amino acid is Leu, such that each B moiety has the formula, in the amino to carboxyl direction, XXXX-LXX, where X is any amino acid.

Exemplary, non-limiting DNA-binding moieties include the following:

1) QRANLRA (SEQ ID NO:11), which can bind AAA;
2) QKSSLIA (SEQ ID NO:12), which can bind ATA;
3) QLAHLRA (SEQ ID NO:13), which can bind AGA;
4) ERSHLRE (SEQ ID NO:14), which can bind AGC;
5) RRDELNV (SEQ ID NO:15), which can bind ATG;
6) DKKDLTR (SEQ ID NO:16), which can bind ACC;
7) RSDHLTN (SEQ ID NO:17), which can bind AGG;
8) TTGNLTV (SEQ ID NO:18), which can bind AAT;
9) DSGNLRV (SEQ ID NO:19), which can bind AAC;
10) RKDNLKN (SEQ ID NO:20), which can bind AAG;
11) HKNALQN (SEQ ID NO:21), which can bind ATT;
12) SPADLTR (SEQ ID NO:22), which can bind ACA;
13) THLDLIR (SEQ ID NO:23), which can bind ACT;
14) RTDTLRD (SEQ ID NO:24), which can bind ACG;
15) HRTTLTN (SEQ ID NO:25), which can bind AGT;
16) RADNLTE (SEQ ID NO:26), which can bind CAG;
17) QNSTLTE (SEQ ID NO:27), which can bind CTA;
18) QSGNLTE (SEQ ID NO:28), which can bind CAA;
19) TKNSLTE (SEQ ID NO:29), which can bind CCT;
20) TSGNLTE (SEQ ID NO:30), which can bind CAT;
21) SKKALTE (SEQ ID NO:31), which can bind CAC;
22) TTGALTE (SEQ ID NO:32), which can bind CTT;
23) RNDALTE (SEQ ID NO:33), which can bind CTG;
24) TSHSLTE (SEQ ID NO:34), which can bind CCA;
25) SKKHLAE (SEQ ID NO:35), which can bind CCC;
26) RNDTLTE (SEQ ID NO:36), which can bind CCG;
27) QSGHLTE (SEQ ID NO:37), which can bind CGA;
28) SRRTLRA (SEQ ID NO:38), which can bind CGT;
29) HTGHLLE (SEQ ID NO:39), which can bind CGC;
30) RSDKLTE (SEQ ID NO:40), which can bind CGG;
31) QSGDLRR (SEQ ID NO:41), which can bind GCA;
32) QRAHLER (SEQ ID NO:42), which can bind GGA;
33) TSGELVR (SEQ ID NO:43), which can bind GCT;
34) TSGHLVR (SEQ ID NO:44), which can bind GGT;
35) TSGNLVR (SEQ ID NO:45), which can bind GAT;
36) DPGHLVR (SEQ ID NO:46), which can bind GGC;
37) RSDNLVR (SEQ ID NO:47), which can bind GAG;
38) DCRDLAR (SEQ ID NO:48), which can bind GCC;
39) QSSNLVR (SEQ ID NO:49), which can bind GAA;
40) DPGNLVR (SEQ ID NO:50), which can bind GAC;
41) QSSSLVR (SEQ ID NO:51), which can bind GTA;
42) TSGSLVR (SEQ ID NO:52), which can bind GTT;
43) DPGALVR (SEQ ID NO:53), which can bind GTC;
44) RSDELVR (SEQ ID NO:54), which can bind GTG;
45) RSDDLVR (SEQ ID NO:55), which can bind GCG;
46) RSDKLVR (SEQ ID NO:56), which can bind GGG;
47) RSDHLTT (SEQ ID NO:57), which can bind TGG;
48) REDNLHT (SEQ ID NO:58), which can bind TAG; and
49) QAGHLAS (SEQ ID NO:59), which can bind TGA.

Thus, for example, each B (e.g., each of $B_1$, $B_2$, and $B_3$, or each of $B_1$, $B_2$, $B_3$, $B_4$, $B_5$, and $B_6$) can be selected from one of amino acid sequences 1-49, as shown above, to form a DNA-binding moiety set, such that a stretch of 9 or 18 contiguous nucleotides will be collectively bound by a subject polypeptide comprising the DNA-binding moiety set. Exemplary, non-limiting DNA-binding moiety sets, which provide for binding a target nucleotide sequence, are provided below.

Target Nucleotide Sequences

A subject polypeptide can bind to a nucleotide sequence in an HBV enhancer and/or an HBV promoter region. HBV promoter and enhancer sequences are known in the art. For example, a duck HBV (e.g., an HBV that infects duck liver cells) nucleotide sequence is found under GenBank Accession No. AF047045 (DHBV Canada isolate; see FIG. 41); and a human HBV (e.g., an HBV that infects human liver cells) nucleotide sequence is found under GenBank Accession No. U95551 (HBV subtype ayw; see FIG. 40); a nucleotide sequence of HBV genotype C is found under GenBank Accession No. AB033550, and is presented in FIG. 45; a nucleotide sequence of HBV genotype D is found under GenBank Accession No. AJ344117, and is presented in FIG. 44; a nucleotide sequence of HBV genotype B is found under GenBank Accession No. AB033554, and is presented in FIG. 46; a nucleotide sequence of HBV genotype E is found under GenBank Accession No. AB032431, and is presented in FIG. 47; a nucleotide sequence of HBV genotype F is found under GenBank Accession No. AB036905, and is presented in FIG. 48; a nucleotide sequence of HBV genotype A is found under GenBank Accession No. AJ309369, and is presented in FIG. 49. Suitable target nucleotides include promoter and/or enhancer regions present in HBV genotype A, B, C, D, E, F, and G. Suitable target nucleotides include promoter and/or enhancer regions present in HBV serotypes ayw, adr, and adw (e.g., adw1, adw2).

In some embodiments, a subject polypeptide binds to a sequence of from about 9 contiguous nucleotides to about contiguous 18 nucleotides of an HBV nucleotide sequence having at least about 80%, at least about 85%, at least about 90%, at least about 95%, at least about 98%, at least about 99%, or 100% nucleotide sequence identity to nucleotides 2171-2361 of the nucleotide sequence depicted in FIG. 41, or the complement thereof.

For example, in some embodiments, a subject polypeptide binds to a sequence of from about 9 contiguous nucleotides to about contiguous 18 nucleotides of an HBV nucleotide sequence having at least about 80%, at least about 85%, at least about 90%, at least about 95%, at least about 98%, at least about 99%, or 100% nucleotide sequence identity to Target Sequence 1 or the complement thereof:

Target Sequence 1

5'-accccaacac atggcgcaat atcccatatc accggcggga gcgcagt-gtt tgctttttca aaggtcagag atatacatgt tcaggaacta ttgatgtctt gtt-tagccaa gataatgatt aaaccgcgct gtctcttatc tgattcaact tttgtttgcc ataagcgtta tcagacgtta ccatggcatt t-3' (SEQ ID NO:60), or the complement thereof.

The following are non-limiting examples of target sequences within Target Sequence 1 to which a subject polypeptide can bind:

Target Sequence 1a:

5'-GCCAAGATAATGATTAA-3' (SEQ ID NO:61), corresponding to nucleotides 2276-2293 (forward strand) of the nucleotide sequence depicted in FIG. 41. Target Sequence 1a is bound by the exemplary polypeptide ZFPa.

Target Sequence 1b:

5'-ATGGCAAACAAAAGTTGA-3' (SEQ ID NO:62), nucleotides 690-707 on the reverse strand, corresponding to forward strand nucleotides 2315-2332 of the nucleotide sequence depicted in FIG. 41. Target Sequence 1a is bound by the exemplary polypeptide ZFPb.

Target Sequence 1c:

5'-AGAGATATA-3', corresponding to nucleotides 2237-2245 (forward strand) of the nucleotide sequence depicted in FIG. 41. Target Sequence 1a is bound by the exemplary polypeptide ZFPc.

Target Sequence 1d:

5'-AAAAGCAAA-3', nucleotides 794-782 of the reverse strand, corresponding to forward strand nucleotides 2219-2227 of the nucleotide sequence depicted in FIG. 41. Target Sequence 1a is bound by the exemplary polypeptide ZFPd.

Target Sequence 1e:

5'-ATAATGATT-3', nucleotides 2292-2290 (forward strand) of the nucleotide sequence depicted in FIG. 41. Target Sequence 1a is bound by the exemplary polypeptide ZFPe.

Target Sequence 1f:

5'-AACAAGACA-3', nucleotides 749-757 of the reverse strand, corresponding to forward strand nucleotides 2265-2273 of the nucleotide sequence depicted in FIG. 41. Target Sequence 1a is bound by the exemplary polypeptide ZFPf.

Target Sequence 1g:

5'-ATAAGAGACAGCGCGGTT-3' (SEQ ID NO:63), nucleotides 713-730 of the reverse strand, corresponding to forward strand nucleotides 2292-2309 of the nucleotide sequence depicted in FIG. 41. Target Sequence 1a is bound by the exemplary polypeptide ZFPg.

In other embodiments, a subject polypeptide binds to a sequence of from about 9 contiguous nucleotides to about 18 contiguous nucleotides of an HBV nucleotide sequence having at least about 80%, at least about 85%, at least about 90%, at least about 95%, at least about 98%, at least about 99%, or 100% nucleotide sequence identity to nucleotides 3007-3150 of the nucleotide sequence depicted in FIG. 40, or the complement thereof.

For example, in some embodiments, a subject polypeptide binds to a sequence of from about 9 contiguous nucleotides to about contiguous 18 nucleotides of an HBV nucleotide sequence having at least about 80%, at least about 85%, at least about 90%, at least about 95%, at least about 98%, at least about 99%, or 100% nucleotide sequence identity to Target Sequence 2, or the complement thereof:

Target Sequence 2:

5'-ggct gggtttcacc ccaccgcacg gaggcctttt ggggtggagc cct-caggctc agggcatact acaaactttg ccagcaaatc cgcctcctgc ctccac-caat cgccagacag gaaggcagcc taccccgctg tctccacctt-3' (SEQ ID NO:64).

The following are non-limiting examples of target sequences within Target Sequence 2 to which a subject polypeptide can bind:

Target Sequence 2a:

5'-ACCAATCGCCAGACAGGA-3' (SEQ ID NO:65), nucleotides 3105-3121 (forward strand) of the nucleotide sequence depicted in FIG. 40. Target Sequence 2a is bound by the exemplary polypeptide ZFPk.

Target Sequence 2b:

5'-GCTCAGGGCATACTACAA-3' (SEQ ID NO:66), nucleotides 3056-3074 (forward strand) of the nucleotide sequence depicted in FIG. 40. Target Sequence 2b is bound by the exemplary polypeptide ZFPm.

Target Sequence 2c:

5'-TGGTGGAGGCAGGAGGCG-3' (SEQ ID NO:67), reverse strand, corresponding to nucleotides 3091-3108 of the nucleotide sequence depicted in FIG. 40. Target Sequence 2c is bound by the exemplary polypeptide ZFPn.

Target Sequence 2d:

5'-CAGCGGGGTAGGCTGCCT-3' (SEQ ID NO:68), reverse strand, corresponding to nucleotides 3123-3140 of the nucleotide sequence depicted in FIG. 40. Target Sequence 2d is bound by the exemplary polypeptide ZFPp.

Target Sequence 2e:

5'-AGGCCTCCG-3', reverse strand, corresponding to nucleotides 3029-3037 of the nucleotide sequence depicted in FIG. 40. Target Sequence 2e is bound by the exemplary polypeptide ZFPq.

Target Sequence 2f:

5'-AGCCCTCAG-3', forward strand, corresponding to nucleotides 3048-3056 of the nucleotide sequence depicted in FIG. 40. Target Sequence 2f is bound by the exemplary polypeptide ZFPr.

Target Sequence 2g:

5'-AGTATGCCC-3', reverse strand, corresponding to nucleotides 3062-3070 of the nucleotide sequence depicted in FIG. 40. Target Sequence 2g is bound by the exemplary polypeptide ZFPt.

Target Sequence 2h:

5'-CCAGCAAAT-3', forward strand, corresponding to nucleotides 3081-3089 of the nucleotide sequence depicted in FIG. 40. Target Sequence 2h is bound by the exemplary polypeptide ZFPu.

Target Sequence 2i:

5'-GGCGATTGG-3', reverse strand, corresponding to nucleotides 3106-3114 of the nucleotide sequence depicted in FIG. 40. Target Sequence 2i is bound by the exemplary polypeptide ZFPv.

Target Sequence 2j:

5'-CAGCCTACC-3', forward strand, corresponding to nucleotides 3126-3134 of the nucleotide sequence depicted in FIG. 40. Target Sequence 2j is bound by the exemplary polypeptide ZFPw.

Exemplary DNA Binding Moiety Sets

The following are exemplary DNA binding moiety set suitable for inclusion in a subject HBV DNA-binding polypeptide.

Exemplary DNA Binding Moiety Set 1

As one non-limiting example, $B_1$, $B_2$, $B_3$, $B_4$, $B_5$, and $B_6$ can have the amino acid sequences:

$B_1$: QRANLRA (SEQ ID NO:11), binding AAA;

$B_2$: HKNALQN (SEQ ID NO:21), binding ATT;

$B_3$: RRDELNV (SEQ ID NO:15), binding ATG;

$B_4$: QKSSLIA (SEQ ID NO:12), binding ATA;

$B_5$: RKDNLKN (SEQ ID NO:20), binding AAG; and $B_6$: DCRDLAR (SEQ ID NO:48) binding GCC, where $B_1$, $B_2$, $B_3$, $B_4$, $B_5$, and $B_6$, when present in a subject HBV DNA-binding polypeptide, collectively provide for binding to 5'-GCCAAGATAATGATTAAA-3' (SEQ ID NO:69), as depicted in FIG. 23C. For example, DNA-binding moiety set 1 is present in ZFPa.

Exemplary DNA Binding Moiety Set 2

As another non-limiting example, $B_1$, $B_2$, $B_3$, $B_4$, $B_5$, and $B_6$ can have the amino acid sequences:

$B_1$: QAGHLAS (SEQ ID NO:59), binding TGA;

$B_2$: HRTTLTN (SEQ ID NO:25), binding AGT;

$B_3$: QRANLRA (SEQ ID NO:11), binding AAA;

$B_4$: DSGNLRV (SEQ ID NO:19), binding AC;

$B_5$: QSGDLRR (SEQ ID NO:41), binding GCA; and $B_6$: RRDELNV (SEQ ID NO:15), binding ATG, where $B_1$, $B_2$, $B_3$, $B_4$, $B_5$, and $B_6$, when present in a subject HBV DNA-binding polypeptide, collectively provide for binding to 5'-ATGGCAAACAAAAGTTGA-3' (SEQ ID NO:62), as depicted in FIG. 24C. For example, DNA-binding moiety set 2 is present in ZFPb.

Exemplary DNA-Binding Moiety Set 3

As another non-limiting example, $B_1$, $B_2$, and $B_3$ can have the amino acid sequences:

$B_1$: QKSSLIA (SEQ ID NO:12), binding ATA;

$B_2$: TSGNLVR (SEQ ID NO:45), binding GAT; and $B_3$: QLAHLRA (SEQ ID NO:13), binding AGA, where $B_1$, $B_2$, and $B_3$, when present in a subject HBV DNA-binding polypeptide, collectively provide for binding to 5'-AGAGATATA-3', as depicted in FIG. 25C. For example, DNA-binding moiety set 3 is present in ZFPc.

Exemplary DNA-Binding Moiety Set 4

As another non-limiting example, $B_1$, $B_2$, and $B_3$ can have the amino acid sequences:

$B_1$: QRANLRA (SEQ ID NO:11), binding AAA;

$B_2$: ERSHLRE (SEQ ID NO:14), binding AGC; and $B_3$: QRANLRA (SEQ ID NO:11), binding AAA, where $B_1$, $B_2$, and $B_3$, when present in a subject HBV DNA-binding polypeptide, collectively provide for binding to 5'-AAAAGCAAA-3', as depicted in FIG. 26C. For example, DNA-binding moiety set 4 is present in ZFPd.

Exemplary DNA-Binding Moiety Set 5

As another non-limiting example, $B_1$, $B_2$, and $B_3$ can have the amino acid sequences:

$B_1$: HKNALQN (SEQ ID NO:21), binding ATT;

$B_2$: RRDELNV (SEQ ID NO:15), binding ATG; and $B_3$: QKSSLIA (SEQ ID NO:12), binding ATA, where $B_1$, $B_2$, and $B_3$, when present in a subject HBV DNA-binding polypeptide, collectively provide for binding to 5'-ATAATGATT-3', as depicted in FIG. 27C. For example, DNA-binding moiety set 5 is present in ZFPe.

Exemplary DNA-Binding Moiety Set 6

As another non-limiting example, $B_1$, $B_2$, and $B_3$ can have the amino acid sequences:

$B_1$: SPADLTR (SEQ ID NO:22), binding ACA;

$B_2$: RKDNLKN (SEQ ID NO:20) binding AAG; and $B_3$: DSGNLRV (SEQ ID NO:19), binding AAC, where $B_1$, $B_2$, and $B_3$, when present in a subject HBV DNA-binding polypeptide, collectively provide for binding to 5'-AACAAGACA-3', as depicted in FIG. 28C. For example, DNA-binding moiety set 6 is present in ZFPf.

Exemplary DNA-Binding Moiety 7

As another non-limiting example, $B_1$, $B_2$, $B_3$, $B_4$, $B_5$, and $B_6$ can have the amino acid sequences:

$B_1$: TSGSLVR (SEQ ID NO:52), binding GTT;

$B_2$: RSDDLVR (SEQ ID NO:55), binding GCG;

$B_3$: ERSHLRE (SEQ ID NO:14), binding AGC;

$B_4$: DPGNLVR (SEQ ID NO:50), binding GAC;

$B_5$: QLAHLRA (SEQ ID NO:13), binding AGA; and $B_6$: QKSSLIA (SEQ ID NO:12), binding ATA, where $B_1$, $B_2$, $B_3$, $B_4$, $B_5$, and $B_6$, when present in a subject HBV DNA-binding polypeptide, collectively provide for binding to 5'-ATAAGAGACAGCGCGGTT-3' (SEQ ID NO:63), as depicted in FIG. 29C. For example, DNA-binding moiety set 7 is present in ZFPg.

Exemplary DNA-Binding Moiety Set 8

As another non-limiting example, $B_1$, $B_2$, $B_3$, $B_4$, $B_5$, and $B_6$ can have the amino acid sequences:

$B_1$: QRAHLER (SEQ ID NO:42), binding GGA;

$B_2$: SPADLTR (SEQ ID NO:22), binding ACA;

$B_3$: RADNLTE (SEQ ID NO:26), binding CAG;

$B_4$: HTGHLLE (SEQ ID NO:39), binding CGC;

$B_5$: TTGNLTV (SEQ ID NO:18), binding AAT; and $B_6$: DKKDLTR (SEQ ID NO:16), binding ACC, where $B_1$, $B_2$, $B_3$, $B_4$, $B_5$, and $B_6$, when present in a subject HBV DNA-binding polypeptide, collectively provide for binding to 5'-ACCAATCGCCAGACAGGA-3' (SEQ ID NO:65), as depicted in FIG. 30C. For example, DNA-binding moiety set 8 is present in ZFPk.

Exemplary DNA-Binding Moiety Set 9

As another non-limiting example, $B_1$, $B_2$, $B_3$, $B_4$, $B_5$, and $B_6$ can have the amino acid sequences:

$B_1$: QSGNLTE (SEQ ID NO:28), binding CAA;

$B_2$: QNSTLTE (SEQ ID NO:27), binding CTA;

$B_3$: QKSSLIA (SEQ ID NO:12), binding ATA;

$B_4$: DPGHLVR (SEQ ID NO:46), binding GGC;

$B_5$: RADNLTE (SEQ ID NO:26), binding CAG; and $B_6$: TSGELVR (SEQ ID NO:43), binding GCT, where $B_1$, $B_2$, $B_3$, $B_4$, $B_5$, and $B_6$, when present in a subject HBV DNA-binding polypeptide, collectively provide for binding to 5'-GCTCAGGGCATACTACAA-3' (SEQ ID NO:66), depicted in FIG. 31C. For example, DNA-binding moiety set 9 is present in ZFPm.

Exemplary DNA-Binding Moiety Set 10

As another non-limiting example, $B_1$, $B_2$, $B_3$, $B_4$, $B_5$, and $B_6$ can have the amino acid sequences:

$B_1$: RSDDLVR (SEQ ID NO:55), binding GCG;

$B_2$: RSDNLVR (SEQ ID NO:47), binding GAG;

$B_3$: RADNLTE (SEQ ID NO:26), binding CAG;

$B_4$: RSDHLTN (SEQ ID NO:17), binding AGG;

$B_5$: RSDHLTT (SEQ ID NO:57), binding TGG; and $B_6$: RSDHLTT (SEQ ID NO:57), binding TGG, where $B_1$, $B_2$, $B_3$, $B_4$, $B_5$, and $B_6$, when present in a subject HBV DNA-binding polypeptide, collectively provide for binding to 5'-TGGTGGAGGCAGGAGGCG-3' (SEQ ID NO:67), depicted in FIG. 32C. For example, DNA-binding moiety set 10 is present in ZFPn.

Exemplary DNA-Binding Moiety Set 11

As another non-limiting example, $B_1$, $B_2$, $B_3$, $B_4$, $B_5$, and $B_6$ can have the amino acid sequences:

$B_1$: TKNSLTE (SEQ ID NO:29), binding CCT;

$B_2$: RNDALTE (SEQ ID NO:33), binding CTG;

$B_3$: RSDHLTN (SEQ ID NO:17), binding AGG;

$B_4$: TSGHLVR (SEQ ID NO:44), binding GGT; and $B_5$: RSDKLTE (SEQ ID NO:40), binding CGG;

$B_6$: RADNLTE (SEQ ID NO:26), binding CAG, where $B_1$, $B_2$, $B_3$, $B_4$, $B_5$, and $B_6$, when present in a subject HBV DNA-binding polypeptide, collectively provide for binding to 5'-CAGCGGGGTAGGCTGCCT-3' (SEQ ID NO:68), depicted in FIG. 33C. For example, DNA-binding moiety set 11 is present in ZFPp.

Exemplary DNA-Binding Moiety Set 12

As another non-limiting example, $B_1$, $B_2$, and $B_3$ can have the amino acid sequences:

$B_1$: RNDTLTE (SEQ ID NO:36), binding CCG;

$B_2$: TKNSLTE (SEQ ID NO:29), binding CCT; and $B_3$RSDHLTN (SEQ ID NO:17), binding AGG, where $B_1$, $B_2$, and $B_3$, when present in a subject HBV DNA-binding polypeptide, collectively provide for binding to 5'-AGGCCTCCG-3', as depicted in FIG. 34C. For example, DNA-binding moiety set 12 is present in ZFPq.

Exemplary DNA-Binding Moiety Set 13

As another non-limiting example, $B_1$, $B_2$, and $B_3$ can have the amino acid sequences:

$B_1$: RADNLTE (SEQ ID NO:26), binding CAG;

$B_2$: TKNSLTE (SEQ ID NO:29), binding CCT; and $B_3$: ERSHLRE (SEQ ID NO:14), binding AGC, where $B_1$, $B_2$, and $B_3$, when present in a subject HBV DNA-binding polypeptide, collectively provide for binding to 5'-AGCCCTCAG-3', as depicted in FIG. 35C. For example, DNA-binding moiety set 13 is present in ZFPr.

Exemplary DNA-Binding Moiety Set 14

As another non-limiting example, $B_1$, $B_2$, and $B_3$ can have the amino acid sequences:

$B_1$: SKKHLAE (SEQ ID NO:35), binding CCC;

$B_2$: RRDELNV (SEQ ID NO:15), binding ATG; and $B_3$: HRTTLTN (SEQ ID NO:25), binding AGT, where $B_1$, $B_2$, and $B_3$, when present in a subject HBV DNA-binding polypeptide, collectively provide for binding to 5'-AGTATGCCC-3', as depicted in FIG. 36C. For example, DNA-binding moiety set 14 is present in ZFPt.

Exemplary DNA-Binding Moiety Set 15

As another non-limiting example, $B_1$, $B_2$, and $B_3$ can have the amino acid sequences:

$B_1$: TTGNLTV (SEQ ID NO:18), binding AAT;

$B_2$: QSGDLRR (SEQ ID NO:41), binding GCA; and $B_3$: TSHSLTE (SEQ ID NO:34), binding CCA, where $B_1$, $B_2$, and $B_3$, when present in a subject HBV DNA-binding polypeptide, collectively provide for binding to 5'-CCAGCAAAT-3', as depicted in FIG. 37C. For example, DNA-binding moiety set 15 is present in ZFPu.

Exemplary DNA-Binding Moiety Set 16

As another non-limiting example, $B_1$, $B_2$, and $B_3$ can have the amino acid sequences:

$B_1$: RSDHLTT (SEQ ID NO:57), binding TGG;

$B_2$: TSGNLVR (SEQ ID NO:45), binding GAT; and $B_3$: DPGHLVR (SEQ ID NO:46), binding GGC, where $B_1$, $B_2$, and $B_3$, when present in a subject HBV DNA-binding polypeptide, collectively provide for binding to 5'-GGCGATTGG-3', as depicted in FIG. 38C. For example, DNA-binding moiety set 16 is present in ZFPv.

Exemplary DNA-Binding Moiety Set 17

As another non-limiting example, $B_1$, $B_2$, and $B_3$ can have the amino acid sequences:

$B_1$: DKKDLTR (SEQ ID NO:16), binding ACC;

$B_2$: TKNSLTE (SEQ ID NO:29), binding CCT; and $B_3$: RADNLTE (SEQ ID NO:26), binding CAG, where $B_1$, $B_2$, and $B_3$, when present in a subject HBV DNA-binding polypeptide, collectively provide for binding to 5'-CAGCCTACC-3', as depicted in FIG. 39C. For example, DNA-binding moiety set 17 is present in ZFPw.

Exemplary HBV DNA-Binding Polypeptides

Exemplary HBV DNA-binding polypeptides are described in the Examples; amino acid sequences of exemplary HBV DNA-binding polypeptides are presented in FIGS. 23-39. In some embodiments, a subject HBV DNA-binding polypeptide has at least about 80%, at least about 85%, at least about 90%, at least about 95%, at least about 98%, at least about 99%, or 100% amino acid sequence identity to the amino acid sequence set forth in one of FIGS. 23B, 24B, 25B, 26B, 27B, 28B, 29B, 30B, 31B, 32B, 33B, 34B, 35B, 36B, 37B, 38B, and 39B.

In some embodiments, a subject HBV DNA-binding polypeptide comprises an amino acid sequence that differs from a "parent" amino acid sequence set forth in one of FIGS. 23B, 24B, 25B, 26B, 27B, 28B, 29B, 30B, 31B, 32B, 33B, 34B, 35B, 36B, 37B, 38B, and 39B, by one amino acid, two amino acids, three amino acids, four amino acids, five amino acids, six amino acids, seven amino acids, eight amino acids, nine amino acids, ten amino acids, or from ten amino acids to fifteen amino acids. In some embodiments, the amino acid differences are present only within one or more DNA-binding moieties. In other embodiments, the amino acid differences are present only within the "scaffolding" or non-DNA-binding moiety portion of the polypeptide. In other embodiments, the amino acid differences are present in both a DNA-binding moiety and the scaffolding portion of the polypeptide. In some embodiments, the one or more amino acid differences are present only in one or more DNA-binding moieties, and the one or more amino acid differences provide for a binding to a target DNA having a nucleotide sequence that differs by at least one nucleotide from the nucleotide sequence of the target DNA bound by the "parent" or unmodified polypeptide.

Flanking Sequences

If present, $J_1$ and $J_2$ are each independently flanking peptides of from about 1 amino acid to about 100 amino acids in length, e.g., if present, $J_1$ and $J_2$ are each independently from about 1 amino acid to about 5 amino acids, from about 5 amino acids to about 10 amino acids, from about 10 amino acids to about 15 amino acids, from about 15 amino acids to about 20 amino acids, from about 20 amino acids to about 25 amino acids, from about 25 amino acids to about 30 amino acids, from about 30 amino acids to about 35 amino acids, from about 35 amino acids to about 40 amino acids, from about 40 amino acids to about 45 amino acids, from about 45 amino acids to about 50 amino acids, from about 50 amino acids to about 60 amino acids, from about 60 amino acids to about 70 amino acids, from about 70 amino acids to about 80 amino acids, from about 80 amino acids to about 90 amino acids, or from about 90 amino acids to about 100 amino acids in length. In some embodiments, a subject polypeptide comprises $J_1$ and not $J_2$ (i.e., $J_2$ is absent). In other embodiments, a subject polypeptide comprises $J_2$ and not $J_1$ (i.e., $J_1$ is absent). In other embodiments, a subject polypeptide comprises both $J_1$ and $J_2$.

$J_1$ and $J_2$ can each independently be a nuclear localization signal; an epitope tag (e.g., glutathione-S-transferase, hemagglutinin (HA; e.g., CYPYDVPDYA; SEQ ID NO:70), FLAG (e.g., DYKDDDDK; SEQ ID NO:71), c-myc (e.g., CEQKLISEEDL; SEQ ID NO:72), and the like); a polypeptide that provides a detectable signal (e.g., an enzyme that converts a substrate into a product that can be detected colorimetrically, fluorimetrically, etc., where suitable enzymes include, but are not limited to luciferase, alkaline phosphatase, peroxidase, and the like; a fluorescent protein (e.g., a green fluorescent protein, a red fluorescent protein, a yellow fluorescent protein, etc.); a luminescent protein; etc.); a polypeptide that provides for ease of purification of the polypeptide (e.g., a metal ion affinity peptide e.g., $(His)_n$, e.g., 6His (SEQ ID NO:216), and the like); glutathione-S-transferase; and the like); a polypeptide that provides for insertion into a eukaryotic cell membrane; a polypeptide that provides for solubility; a polypeptide that provides for attachment to another moiety, to a solid support, etc.; polypeptides that are members of a specific binding pair (e.g., a peptide ligand for a receptor; a peptide antigen specifically bound by an antibody binding site; an antibody binding site, such as a single-chain antibody; a sugar-binding polypeptide, such as a maltose-binding protein; etc.); and the like.

In some embodiments, a protease cleavage site ("proteolytic cleavage site") is positioned between $J_1$ and the remainder of the polypeptide and/or between $J_2$ and the remainder of the polypeptide. For example, in some embodiments, a subject polypeptide comprises an amino acid sequence of the formula:

$(J_1)(O_1)(X_1X_2Cys(X)_{2\text{-}4}Cys(X)_3PheSer(B_{0+n})His(X)_3His(Z))_nX_1X_2Cys(X)_{2\text{-}4}Cys(X)_3PheSer(B_{0+n})His(X)_3His(O_2)(J_2)$ (SEQ ID NO:73), where $O_1$ and $O_2$, if present, is each independently a protease cleavage site, where the other elements of the formula are as described above.

Proteolytic cleavage sites are known to those skilled in the art; a wide variety are known and have been described amply in the literature, including, e.g., *Handbook of Proteolytic Enzymes* (1998) A J Barrett, N D Rawlings, and J F Woessner, eds., Academic Press. Proteolytic cleavage sites include, but are not limited to, an enterokinase cleavage site: $(Asp)_4Lys$ (SEQ ID NO:217); a factor Xa cleavage site: Ile-Glu-Gly-Arg (SEQ ID NO:74); a thrombin cleavage site, e.g., Leu-Val-Pro-Arg-Gly-Ser (SEQ ID NO:75); a renin cleavage site, e.g., His-Pro-Phe-His-Leu-Val-Ile-His (SEQ ID NO:76); a collagenase cleavage site, e.g., X-Gly-Pro (where X is any amino acid); a trypsin cleavage site, e.g., Arg-Lys; a viral protease cleavage site, such as a viral 2A or 3C protease cleavage site, including, but not limited to, a protease 2A cleavage site from a picornavirus (see, e.g., Sommergruber et al. (1994) *Virol.* 198:741-745), a Hepatitis A virus 3C cleavage site (see, e.g., Schultheiss et al. (1995) *J. Virol.* 69:1727-1733), human rhinovirus 2A protease cleavage site (see, e.g., Wang et al. (1997) *Biochem. Biophys. Res. Comm.* 235:562-566), and a picornavirus 3 protease cleavage site (see, e.g., Walker et al. (1994) *Biotechnol.* 12:601-605.

Nuclear Localization Signals

In some embodiments, a subject HBV DNA-binding polypeptide comprises a nuclear localization signal (NLS).

Suitable NLS are 6 to 15 amino acids in length, and facilitate transport of the associated polypeptide into the nucleus of a eukaryotic cell. Suitable NLS include, e.g., a Simian Virus 40 (SV40) large T antigen nuclear localization signal sequence, a polyoma large T antigen nuclear localization signal sequence, an adenovirus E1a nuclear localization signal sequence, and an adenovirus E1b nuclear localization signal sequence.

Suitable NLS include, but are not limited to:

```
1)   KIPIK;                  (SEQ ID NO: 77)
2)   VRILESWFAKNI;           (SEQ ID NO: 78)
3)   PKKKRKV;                (SEQ ID NO: 79)
4)   AAFEDLRVRS;             (SEQ ID NO: 80)
5)   PRKR;                   (SEQ ID NO: 81)
6)   VSRKRPRPA;              (SEQ ID NO: 82)
7)   APTKRK;                 (SEQ ID NO: 83)
8)   KRPRP;                  (SEQ ID NO: 84)
9)   PNKKKRK;                (SEQ ID NO: 85)
10)  RPAATKKAGQAKKKKLD;      (SEQ ID NO: 86)
```

-continued

```
11)  KKKIK;                  (SEQ ID NO: 87)
12)  RVTIRTVRVRRPPKGKHRK;    (SEQ ID NO: 88)
13)  DGKKWS;                 (SEQ ID NO: 89)
14)  KAKRQR;                 (SEQ ID NO: 90)
15)  DRLRR;                  (SEQ ID NO: 91)
16)  PKQKRK;                 (SEQ ID NO: 92)
17)  VRKKRKT;                (SEQ ID NO: 93)
18)  AKKSKQE;                (SEQ ID NO: 94)
19)  PAAKRVKLD;              (SEQ ID NO: 95)
20)  RQRRNELKRSF;            (SEQ ID NO: 96)
21)  TKKRKLE;                (SEQ ID NO: 97)
22)  PKTRRRP;                (SEQ ID NO: 98)
23)  SQRKRPP;                (SEQ ID NO: 99)
24)  RLPVRRRRRVP;            (SEQ ID NO: 100)
25)  GRKKR;                  (SEQ ID NO: 101)
26)  VWTTKGKRKRIDV;          (SEQ ID NO: 102)
27)  RKFKK;                  (SEQ ID NO: 103)
28)  RRNRRRRW;               (SEQ ID NO: 104)
29)  PRESGKKRKRKRLKPT;       (SEQ ID NO: 105)
30)  SALIKKKKMAP;            (SEQ ID NO: 106)
31)  PPKKR;                  (SEQ ID NO: 107)
32)  PKKKKK;                 (SEQ ID NO: 108)
33)  SKRVAKRKL;              (SEQ ID NO: 109)
34)  PLLKKIKQ;               (SEQ ID NO: 110)
35)  PPQKKIKS;               (SEQ ID NO: 111)
36)  PQPKKKP;                (SEQ ID NO: 112)
37)  FKRKHKKDISQNKRAVRR;     (SEQ ID NO: 113)
38)  SKCLGWLWG;              (SEQ ID NO: 114)
39)  GKRKNKPK;               (SEQ ID NO: 115)
40)  KTRKHRG;                (SEQ ID NO: 116)
41)  KHRKHPG;                (SEQ ID NO: 117)
and
42)  MCPKKRKV.               (SEQ ID NO: 118)
```

Endonucleases

In some embodiments, one or both of $J_1$ and $J_2$ are endonucleases that specifically cleave HBV cccDNA. Suitable endonucleases include, but are not limited to, a FokI endonuclease, a yeast homothallism endonuclease, and the like.

For example, in some embodiments, a suitable endonuclease comprises an amino acid sequence having at least about 75%, at least about 80%, at least about 85%, at least about 90%, at least about 95%, at least about 98%, at least about 99%, or 100%, amino acid sequence identity to the amino acid sequence depicted in FIG. 42B, which depicts a FokI endonuclease domain amino acid sequence. Suitable nucleotide sequences encoding an endonuclease include nucleotide sequences encoding an amino acid sequence having at least about 75%, at least about 80%, at least about 85%, at least about 90%, at least about 95%, at least about 98%, at least about 99%, or 100%, amino acid sequence identity to the amino acid sequence depicted in FIG. 42B. For example, a suitable nucleotide sequence encoding an endonuclease can have at least about 75%, at least about 80%, at least about 85%, at least about 90%, at least about 95%, at least about 98%, at least about 99%, or 100%, nucleotide sequence identity to the nucleotide sequence depicted in FIG. 42A.

As another example, in some embodiments, a suitable endonuclease comprises an amino acid sequence having at least about 75%, at least about 80%, at least about 85%, at least about 90%, at least about 95%, at least about 98%, at least about 99%, or 100%, amino acid sequence identity to the amino acid sequence depicted in FIG. 43B, which depicts a yeast homothallism (HO) endonuclease domain amino acid sequence. Suitable nucleotide sequences encoding an endonuclease include nucleotide sequences encoding an amino acid sequence having at least about 75%, at least about 80%, at least about 85%, at least about 90%, at least about 95%, at least about 98%, at least about 99%, or 100%, amino acid sequence identity to the amino acid sequence depicted in FIG. 43B. For example, a suitable nucleotide sequence encoding an endonuclease can have at least about 75%, at least about 80%, at least about 85%, at least about 90%, at least about 95%, at least about 98%, at least about 99%, or 100%, nucleotide sequence identity to the nucleotide sequence depicted in FIG. 43A.

Additional Components

A subject HBV DNA-binding polypeptide can comprise, in addition to above-described features, one or more additional components. For example, in some embodiments, a subject HBV DNA-binding polypeptide comprises one or more of: a radiolabel; a biotin moiety; a poly(ethyleneglycol) (PEG) or other polymer moiety; a targeting moiety (e.g., a moiety that provides for targeting to a specific cell type, e.g., a liver cell; a fluorophore (e.g., fluorescein, rhodamine, tetramethylrhodamine, eosin, erythrosin, coumarin, methyl-coumarins, pyrene, Malacite green, stilbene, Lucifer Yellow, Cascade Blue™, Texas Red, IAEDANS, EDANS, BODIPY FL, LC Red 640, Cy 5, Cy 5.5, LC Red 705 and Oregon green); etc.

Preparation of a Subject Polypeptide

A subject HBV DNA-binding polypeptide may be synthesized chemically or enzymatically, may be produced recombinantly, or a combination of the foregoing. A subject HBV DNA-binding polypeptide may be isolated from a sample (e.g., a recombinant cell expressing the HBV DNA-binding polypeptide; or other sample comprising the synthesized HBV DNA-binding polypeptide) using standard methods of protein purification known in the art, including, but not limited to, high performance liquid chromatography, exclusion chromatography, gel electrophoresis, affinity chromatography, or other purification technique. One may employ solid phase peptide synthesis techniques, where such techniques are known to those of skill in the art. See Jones, *The Chemical Synthesis of Peptides* (Clarendon Press, Oxford)(1994). Generally, in such methods a peptide is produced through the sequential additional of activated monomeric units to a solid phase bound growing peptide chain. Peptides can be synthesized in solution or on a solid support in accordance with conventional techniques. Various automatic synthesizers are commercially available and can be used in accordance with known protocols. See, for example, Stewart and Young, Solid Phase Peptide Synthesis, 2d. ed., Pierce Chemical Co. (1984); Tam et al., J. Am. Chem. Soc. 105:6442 (1983); Merrifield, Science 232:341-347 (1986); and Barmy and Merrifield, The Peptides, Gross and Meienhofer, eds., Academic Press, New York, pp. 1-284 (1979), each of which is incorporated herein by reference. Well-established recombinant DNA techniques can be employed for production of a subject polypeptide.

For production of a subject HBV DNA-binding polypeptide by recombinant means, a subject polynucleotide (described in more detail below) comprising a nucleotide sequence encoding the HBV DNA-binding polypeptide is expressed in any convenient expression system, including, for example, bacterial, yeast, insect, amphibian and mammalian systems. Suitable vectors and host cells are described in U.S. Pat. No. 5,654,173. In the expression vector, a subject polynucleotide is linked to a regulatory sequence as appropriate to obtain the desired expression properties. These regulatory sequences can include promoters (attached either at the 5' end of the sense strand or at the 3' end of the antisense strand), enhancers, terminators, operators, repressors, and inducers. The promoters can be regulated or constitutive. In some situations it may be desirable to use conditionally active promoters, such as tissue-specific (e.g., liver-specific) promoters. These are linked to the desired nucleotide sequence using the techniques described above for linkage to vectors. Any techniques known in the art can be used. In other words, the expression vector will provide a transcriptional and translational initiation region, which may be inducible or constitutive, where the coding region is operably linked under the transcriptional control of the transcriptional initiation region, and a transcriptional and translational termination region. These control regions may be native to the subject species from which the subject nucleic acid is obtained, or may be derived from exogenous sources.

Expression vectors generally have convenient restriction sites located near the promoter sequence to provide for the insertion of nucleic acid sequences encoding heterologous proteins. A selectable marker operative in the expression host may be present.

Expression cassettes may be prepared comprising a transcription initiation region, the gene or fragment thereof, and a transcriptional termination region. After introduction of the expression cassette containing a subject polynucleotide, the cells containing the construct may be selected by means of a selectable marker, the cells expanded and then used for expression.

The above described expression systems may be employed with prokaryotes or eukaryotes in accordance with conventional ways, depending upon the purpose for expression. For large scale production of the protein, a unicellular organism, such as *Escherichia coli, Bacillus subtilis, Saccharomyces cerevisiae*, insect cells in combination with baculovirus vectors, or cells of a higher organism such as vertebrates, e.g. COS 7 cells, HEK 293, CHO, *Xenopus* oocytes, etc., may be used as the expression host cells. In some situations, it is desirable to express the polynucleotide in eukaryotic cells, where the expressed protein will benefit from native folding and post-translational modifications. Specific expression systems of interest include bacterial, yeast, insect cell and mammalian cell derived expression systems, which expression systems are well known in the art.

Compositions Comprising a Subject HBV DNA-Binding Polypeptide

The present invention provides compositions comprising a subject HBV DNA-binding polypeptide. Compositions comprising a subject HBV DNA-binding polypeptide can include one or more of: a salt, e.g., NaCl, MgCl, KCl, $MgSO_4$, etc.; a buffering agent, e.g., a Tris buffer, N-(2-Hydroxyethyl)piperazine-N'-(2-ethanesulfonic acid) (HEPES), 2-(N-Morpholino)ethanesulfonic acid (MES), 2-(N-Morpholino)

ethanesulfonic acid sodium salt (MES), 3-(N-Morpholino) propanesulfonic acid (MOPS), N-tris[Hydroxymethyl] methyl-3-aminopropanesulfonic acid (TAPS), etc.; a solubilizing agent; a detergent, e.g., a non-ionic detergent such as Tween-20, etc.; a protease inhibitor; and the like.

In some instances, a subject HBV DNA-binding polypeptide composition can comprise a pharmaceutically acceptable excipient, a variety of which are known in the art and need not be discussed in detail herein. Pharmaceutically acceptable excipients have been amply described in a variety of publications, including, for example, "Remington: The Science and Practice of Pharmacy", 19th Ed. (1995), or latest edition, Mack Publishing Co; A. Gennaro (2000) "Remington: The Science and Practice of Pharmacy", 20th edition, Lippincott, Williams, & Wilkins; Pharmaceutical Dosage Forms and Drug Delivery Systems (1999) H. C. Ansel et al., eds $7^{th}$ ed., Lippincott, Williams, & Wilkins; and Handbook of Pharmaceutical Excipients (2000) A. H. Kibbe et al., eds., $3^{rd}$ ed. Amer. Pharmaceutical Assoc.

Nucleic Acids, Vectors, Host Cells

The present invention provides nucleic acids encoding a subject HBV DNA-binding polypeptide, as well as recombinant vectors and recombinant host cells comprising the nucleic acids or recombinant vectors. In many embodiments, a subject nucleic acid is isolated, and can be synthetic. In some embodiments, a subject nucleic acid is pure, e.g., at least about 50% pure, at least about 60% pure, at least about 70% pure, at least about 80% pure, at least about 90%, or at least about 95% or more pure. In many embodiments, a subject host cell is isolated. In some embodiments, a subject host cell is in vitro and is cultured as a unicellular entity.

A subject nucleic acid comprises a nucleotide sequence encoding a subject HBV DNA-binding polypeptide. A subject recombinant vector comprises a subject nucleic acid. In many embodiments, a subject recombinant vector comprises a subject nucleic acid operably linked to one or more control elements, such as a promoter, a transcription terminator, and the like. A subject recombinant vector in some embodiments provides for amplification of the copy number of a subject nucleic acid. A subject recombinant vector is in some embodiments an expression vector that provides for synthesis of a subject HBV DNA-binding polypeptide in a host cell, e.g., a prokaryotic host cell or a eukaryotic host cell.

In some embodiments, a subject nucleic acid comprises a nucleotide sequence encoding a subject HBV DNA-binding polypeptide, where the HBV DNA-binding polypeptide comprises an amino acid sequence having at least about 80%, at least about 85%, at least about 90%, at least about 95%, at least about 98%, at least about 99%, or 100% amino acid sequence identity to the amino acid sequence set forth in one of FIGS. 23B, 24B, 25B, 26B, 27B, 28B, 29B, 30B, 31B, 32B, 33B, 34B, 35B, 36B, 37B, 38B, and 39B.

In some embodiments, a subject nucleic acid comprises a nucleotide sequence encoding a subject HBV DNA-binding polypeptide that comprises an amino acid sequence that differs from a "parent" amino acid sequence set forth in one of FIGS. 23B, 24B, 25B, 26B, 27B, 28B, 29B, 30B, 31B, 32B, 33B, 34B, 35B, 36B, 37B, 38B, and 39B, by one amino acid, two amino acids, three amino acids, four amino acids, five amino acids, six amino acids, seven amino acids, eight amino acids, nine amino acids, ten amino acids, or from ten amino acids to fifteen amino acids, as described above.

In some embodiments, a subject nucleic acid comprises a nucleotide sequence encoding a subject HBV DNA-binding polypeptide, where the nucleotide sequence has at least about 75%, at least about 80%, at least about 85%, at least about 90%, at least about 95%, at least about 98%, at least about 99%, or 100%, nucleotide sequence identity to the nucleotide sequence set forth in one of FIG. 23A, 24A, 25A, 26A, 27A, 28A, 29A, 30A, 31A, 32A, 33A, 34A, 35A, 36A, 37A, 38A, or 39A.

A subject nucleic acid will in some embodiments be an expression construct, e.g., a nucleic acid comprising a nucleotide sequence encoding a subject HBV DNA-binding polypeptide; and including elements that provide for expression of the HBV DNA-binding polypeptide-encoding nucleic acid in a eukaryotic cell (e.g., a liver cell) and production of the HBV DNA-binding polypeptide in the cell. The expression vector will provide a transcriptional and translational initiation region, which may be inducible or constitutive, where the HBV DNA-binding polypeptide coding region is operably linked to and under the transcriptional control of the transcriptional initiation region, and a transcriptional and translational termination region.

Any expression vector known in the art can be used to express an HBV DNA-binding polypeptide-encoding nucleic acid. An expression vector will generally include a promoter and/or other transcription control elements which are active in the cell, and appropriate termination and polyadenylation signals. Expression vectors generally have convenient restriction sites located near the promoter sequence to provide for the insertion of nucleic acid sequences encoding a subject HBV DNA-binding polypeptide. A selectable marker operative in the expression host may be present.

Suitable expression vectors include, but are not limited to, viral vectors (e.g. viral vectors based on vaccinia virus; poliovirus; adenovirus (see, e.g., Li et al., Invest Opthalmol Vis Sci 35:2543 2549, 1994; Borras et al., Gene Ther 6:515 524, 1999; Li and Davidson, PNAS 92:7700 7704, 1995; Sakamoto et al., H Gene Ther 5:1088 1097, 1999; WO 94/12649, WO 93/03769; WO 93/19191; WO 94/28938; WO 95/11984 and WO 95/00655); adeno-associated virus (see, e.g., Ali et al., Hum Gene Ther 9:8186, 1998, Flannery et al., PNAS 94:6916 6921, 1997; Bennett et al., Invest Opthalmol Vis Sci 38:2857 2863, 1997; Jomary et al., Gene Ther 4:683 690, 1997, Rolling et al., Hum Gene Ther 10:641648, 1999; Ali et al., Hum Mol Genet. 5:591594, 1996; Srivastava in WO 93/09239, Samulski et al., J. Vir. (1989) 63:3822-3828; Mendelson et al., Virol. (1988) 166:154-165; and Flotte et al., PNAS (1993) 90:10613-10617); SV40; herpes simplex virus; human immunodeficiency virus (see, e.g., Miyoshi et al., PNAS 94:10319 23, 1997; Takahashi et al., J Virol 73:7812 7816, 1999); a retroviral vector (e.g., Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus); and the like.

Numerous suitable expression vectors are known to those of skill in the art, and many are commercially available. The following vectors are provided by way of example; for eukaryotic host cells: pCMV, pcDNA3, pXT1, pSG5 (Stratagene), pSVK3, pBPV, pMSG, and pSVLSV40 (Pharmacia). However, any other vector may be used so long as it is compatible with the host cell.

Depending on the host/vector system utilized, any of a number of suitable transcription and translation control elements, including constitutive and inducible promoters, transcription enhancer elements, transcription terminators, etc. may be used in the expression vector (see e.g., Bitter et al. (1987) *Methods in Enzymology,* 153:516-544).

In some embodiments, the HBV DNA-binding polypeptide-encoding nucleotide sequence is operably linked to a promoter, e.g., a eukaryotic promoter. Non-limiting examples of suitable eukaryotic promoters include CMV immediate early, HSV thymidine kinase, early and late SV40, long terminal repeats (LTRs) from retrovirus, and mouse metallothionein-I. Selection of the appropriate vector and promoter is well within the level of ordinary skill in the art. The expression vector may also contain a ribosome binding site for translation initiation and a transcription terminator. The expression vector may also include appropriate sequences for amplifying expression.

In some embodiments, the HBV DNA-binding polypeptide-encoding nucleotide sequence is operably linked to a cell type-specific control element (e.g., a promoter, an enhancer). For example, in some embodiments, a liver cell-specific control element is included.

In some embodiments, cells containing a subject nucleic acid are identified by including a marker in the expression vector; and detecting the marker or selecting for expression of the marker. Such markers would confer an identifiable change to the cell permitting easy identification of cells containing the expression vector. A selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

The inclusion of a drug selection marker aids in identification of transformants; for example, genes that confer resistance to neomycin, puromycin, hygromycin, DHFR, GPT, zeocin and histidinol are useful selectable markers. Also suitable for inclusion in an E1A expression vector are screenable markers such as a green fluorescent protein (GFP), which provides a fluorescent signal, are also contemplated. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with FACS analysis.

Any of a variety of methods can be used to deliver a subject expression vector into a target cell (e.g., into liver cells, e.g., HBV-infected liver cells, etc.). Suitable methods include various mechanical methods, including the use of fusogenic lipid vesicles (liposomes incorporating cationic lipids such as lipofection); pneumatic delivery of DNA-coated gold particles with a device referred to as the gene gun; and administration of any of a variety of viral vectors (e.g., non-replicative mutants/variants of adenovirus, adeno-associated virus-based vectors, herpes simplex virus (HSV) vectors, cytomegalovirus (CMV) vectors, vaccinia virus vectors, retroviral vectors, lentiviral vectors, and poliovirus vectors). Suitable delivery vehicles and methods for introducing a subject nucleic acid into a target host cell are those discussed above for delivering a subject nucleic acid into a target cell.

The present invention further provides compositions comprising a subject nucleic acid. Compositions comprising a subject nucleic acid will in many embodiments include one or more of: a salt, e.g., NaCl, MgCl, KCl, $MgSO_4$, etc.; a buffering agent, e.g., a Tris buffer, N-(2-Hydroxyethyl)piperazine-N'-(2-ethanesulfonic acid) (HEPES), 2-(N-Morpholino) ethanesulfonic acid (MES), 2-(N-Morpholino) ethanesulfonic acid sodium salt (MES), 3-(N-Morpholino) propanesulfonic acid (MOPS), N-tris[Hydroxymethyl] methyl-3-aminopropanesulfonic acid (TAPS), etc.; a solubilizing agent; a detergent, e.g., a non-ionic detergent such as Tween-20, etc.; a nuclease inhibitor; and the like.

The present invention provides genetically modified host cells, including in vitro host cells that are cultured as unicellular entities, comprising a subject nucleic acid. In some embodiments, a subject genetically modified host cell is a prokaryotic cell. A prokaryotic host cell that is genetically modified to contain a subject nucleic acid (including a subject recombinant vector) can be used to propagate the nucleic acid. In other embodiments, a subject genetically modified host cell is a eukaryotic cell. A eukaryotic host cell that is genetically modified to contain a subject nucleic acid (including a subject recombinant vector) can be used to produce a subject HBV DNA-binding polypeptide.

To generate a genetically modified host cell, a subject nucleic acid or a subject recombinant vector is introduced stably or transiently into a host cell, using established techniques, including, but not limited to, electroporation, calcium phosphate precipitation, DEAE-dextran mediated transfection, liposome-mediated transfection, and the like. For stable transformation, a nucleic acid will generally further include a selectable marker, e.g., any of several well-known selectable markers such as neomycin resistance, ampicillin resistance, tetracycline resistance, chloramphenicol resistance, kanamycin resistance, and the like.

Suitable host cells for cloning or expressing a subject nucleic acid (including a subject recombinant vector) include prokaryote, yeast, or higher eukaryote cells. Suitable prokaryotes for this purpose include eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. These examples are illustrative rather than limiting.

In addition to prokaryotes, eukaryotic microbes such as filamentous fungi or yeast are suitable cloning or expression hosts. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe; Kluyveromyces* hosts such as, e.g., *K. lactis, K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus; yarrowia* (EP 402,226); *Pichia pastoris* (EP 183,070); *Candida; Trichoderma reesia* (EP 244,234); *Neurospora crassa; Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger.*

In some embodiments, a subject genetically modified host cell is a mammalian cell. Suitable mammalian cells include primary cells and immortalized cell lines. Suitable mammalian cell lines include human cell lines, non-human primate cell lines, rodent (e.g., mouse, rat) cell lines, and the like. Suitable mammalian cell lines include, but are not limited to, HeLa cells (e.g., American Type Culture Collection (ATCC) No. CCL-2), CHO cells (e.g., ATCC Nos. CRL9618, CCL61, CRL9096), 293 cells (e.g., ATCC No. CRL-1573), Vero cells, NIH 3T3 cells (e.g., ATCC No. CRL-1658), Huh-7 cells, BHK cells (e.g., ATCC No. CCL10), PC12 cells (ATCC No. CRL1721), COS cells, COS-7 cells (ATCC No. CRL1651), RAT1 cells, mouse L cells (ATCC No. CCLI.3), human embryonic kidney (HEK) cells (ATCC No. CRL1573), HLHepG2 cells, and the like. Also suitable are avian cells and cell lines.

The present invention further provides compositions comprising a subject genetically modified host cell. A subject composition comprises a subject genetically modified host cell; and will in some embodiments comprise one or more further components, which components are selected based in part on the intended use of the genetically modified host cell. Suitable components include, but are not limited to, salts; buffers; stabilizers; protease-inhibiting agents; cell membrane- and/or cell wall-preserving compounds, e.g., glycerol, dimethylsulfoxide, etc.; nutritional media appropriate to the cell; and the like.

Utility

A subject polypeptide is useful for various in vitro and in vivo applications. In vitro applications include detection methods. In vivo applications include therapeutic methods.

Detection Methods

A subject polypeptide is useful in various in vitro detection methods. For example, a subject polypeptide can be used to detect the presence of HBV DNA, e.g., HBV cccDNA, in a biological sample. A subject detection method is useful in diagnostic assays. For example, a subject detection method can provide for detection of cccDNA form of HBV in a liver cell in an individual, thereby providing an indication that the individual has a reservoir of HBV DNA and may experience a relapse. Where cccDNA is detected, treatment of the individual to reduce the level of or eradicate the cccDNA form of HBV may be recommended.

In some embodiments, a subject detection method comprises contacting a biological sample with a subject HBV DNA-binding polypeptide; and detecting binding, if any, of the HBV DNA-binding polypeptide with molecules in the sample, e.g., detecting formation of a complex between the HBV DNA-binding polypeptide and an HBV DNA which may be present in the sample. In some of these embodiments, the HBV DNA-binding polypeptide detects cccDNA form of HBV DNA.

In some embodiments, the HBV DNA-binding polypeptide that it used in the assay is detectably labeled, e.g., is directly detectably labeled. Suitable detectable labels include, e.g., radiolabels; enzymes that act on a substrate to yield a colored, luminescent, or fluorescent product; fluorescent proteins (a green fluorescent protein, a yellow fluorescent protein, a red fluorescent protein, etc.); a fluorophore (e.g., fluorescein, rhodamine, tetramethylrhodamine, eosin, erythrosin, coumarin, methyl-coumarins, pyrene, Malacite green, stilbene, Lucifer Yellow, Cascade Blue™, Texas Red, IAEDANS, EDANS, BODIPY FL, LC Red 640, Cy 5, Cy 5.5, LC Red 705 and Oregon green); and the like. In other embodiments, the HBV DNA-binding polypeptide is indirectly labeled. Indirect labels include, e.g., detectably labeled antibodies that are specific for the HBV DNA-binding polypeptide; detectably-labeled avidin, e.g., where the HBV DNA-binding polypeptide is biotinylated; and the like.

In some embodiments, the detection method comprises an immunological-based assay, e.g., an enzyme-linked immunosorbent assay (ELISA); a radioimmunoassay (RIA); and the like, wherein an antibody specific for a subject HBV DNA-binding polypeptide is used to detect any complexes formed between the HBV DNA-binding polypeptide and HBV DNA. In other embodiments, the detection method comprises use of an electrophoretic mobility shift assay. In other embodiments, the detection method comprises formation of insoluble complexes between a subject HBV DNA-binding polypeptide and HBV DNA.

In some embodiments, the biological sample includes liver cells obtained from an individual. The biological sample is in some embodiments a liver biopsy.

Therapeutic Methods

The present invention further provides methods of treating an HBV infection; methods of reducing the level of cccDNA form of HBV in an individual; and methods of reducing the likelihood that an individual will suffer a relapse of an HBV infection. The methods generally involve administering to an individual in need thereof an effective amount of a subject HBV DNA-binding polypeptide and/or a subject nucleic acid.

Treating an HBV infection can provide for treating sequelae of an HBV infection, e.g., treating one or more of chronic liver inflammation caused by HBV, cirrhosis, acute hepatitis, fulminant hepatitis, chronic persistent hepatitis, and fatigue.

In some embodiments, an effective amount of a subject HBV DNA-binding polypeptide, or an effective amount of a subject nucleic acid, is an amount that, when administered to an individual in need thereof in one or more doses, reduces the level of cccDNA form of HBV in the individual by at least about 10%, at least about 15%, at least about 20%, at least about 25%, at least about 30%, at least about 35%, at least about 40%, at least about 45%, at least about 50%, at least about 60%, at least about 70%, at least about 80%, or at least about 90%, compared to the level of cccDNA form of HBV in the individual not treated with the polypeptide or the nucleic acid.

In some embodiments, an effective amount of a subject HBV DNA-binding polypeptide, or an effective amount of a subject nucleic acid, is an amount that, when administered to an individual in need thereof in one or more doses, reduces the HBV viral load in the individual by at least about 10%, at least about 15%, at least about 20%, at least about 25%, at least about 30%, at least about 35%, at least about 40%, at least about 45%, at least about 50%, at least about 60%, at least about 70%, at least about 80%, or at least about 90%, compared to the viral load in the individual not treated with the polypeptide or the nucleic acid.

In some embodiments, an effective amount of a subject HBV DNA-binding polypeptide, or an effective amount of a subject nucleic acid, is an amount that, when administered to an individual in need thereof in one or more doses, increases liver function in the individual.

Administration and Formulation of Polypeptide Agents

Formulation of a subject HBV DNA-binding polypeptide to a subject, as well as method of delivery of polypeptide agents, are available in the art. A subject HBV DNA-binding polypeptide can be administered together with a suitable pharmaceutically acceptable carrier or excipient. Pharmaceutically acceptable excipients have been amply described in a variety of publications, including, for example, A. Gennaro (2000) "Remington: The Science and Practice of Pharmacy," 20th edition, Lippincott, Williams, & Wilkins; Pharmaceutical Dosage Forms and Drug Delivery Systems (1999) H. C. Ansel et al., eds., $7^{th}$ ed., Lippincott, Williams, & Wilkins; and Handbook of Pharmaceutical Excipients (2000) A. H. Kibbe et al., eds., $3^{rd}$ ed. Amer. Pharmaceutical Assoc. The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Suitable pharmaceutically acceptable carriers include essentially chemically inert and nontoxic pharmaceutical compositions that do not interfere with the effectiveness of the biological activity of the pharmaceutical composition. Examples of suitable pharmaceutical carriers include, but are not limited to, saline solutions, glycerol solutions, ethanol, N-(1(2,3-dioleyloxy)propyl)-N,N,N-trimethylammonium chloride (DOTMA), diolesylphosphotidylethanolamine (DOPE), and liposomes. Such pharmaceutical compositions should contain a therapeutically effective amount of the compound, together with a suitable amount of carrier so as to provide the form for proper administration to the subject. The formulation should suit the mode of administration. For example, a formulation suitable for oral administration can include an enteric coating to protect a subject HBV DNA-binding polypeptide from degradation within the gastrointestinal tract. In another example, a subject HBV DNA-binding polypeptide may be administered in a liposomal formulation, to shield the polypeptide from degradative enzymes, facilitate transport in circulatory system, and effect delivery across cell membranes to intracellular sites.

In another embodiment, a pharmaceutical composition comprises a subject HBV DNA-binding polypeptide, and/or one or more additional therapeutic agents; and a pharmaceutically acceptable carrier. In one embodiment, a pharmaceutical composition, comprising a subject HBV DNA-binding polypeptide, with or without other therapeutic agents; and a pharmaceutically acceptable carrier, is at an effective dose.

A subject HBV DNA-binding polypeptide can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

In some embodiments, a subject HBV DNA-binding polypeptide composition is formulated in accordance with routine procedures as a pharmaceutical composition adapted for subcutaneous injection or intravenous administration to humans. Typically, pharmaceutical compositions for subcutaneous injection or intravenous administration are solutions in sterile isotonic aqueous buffer. Where necessary, the composition may also include a solubilizing agent and a local anesthetic such as lidocaine to ease pain at the site of the injection. Generally, the ingredients are supplied either separately or mixed together in unit dosage form, for example, as a dry lyophilized powder or water-free concentrate in a hermetically sealed container such as an ampule or sachette indicating the quantity of active agent. Where the composition is to be administered by infusion, it can be dispensed with an infusion bottle, bag, or other acceptable container, containing sterile pharmaceutical grade water, saline, or other acceptable diluents. Where the composition is administered by injection, an ampule of sterile water for injection or saline can be provided so that the ingredients may be mixed prior to administration.

Pharmaceutical compositions adapted for oral administration may be provided, for example, as capsules or tablets; as powders or granules; as solutions, syrups or suspensions (in aqueous or non-aqueous liquids); as edible foams or whips; or as emulsions. Tablets or hard gelatine capsules may comprise, for example, lactose, starch or derivatives thereof, magnesium stearate, sodium saccharine, cellulose, magnesium carbonate, stearic acid or salts thereof. Soft gelatine capsules may comprise, for example, vegetable oils, waxes, fats, semi-solid, or liquid polyols, etc. Solutions and syrups may comprise, for example, water, polyols and sugars.

A subject HBV DNA-binding polypeptide intended for oral administration may be coated with or admixed with a material (e.g., glyceryl monostearate or glyceryl distearate) that delays disintegration or affects absorption of the polypeptide in the gastrointestinal tract. Thus, for example, the sustained release of a subject HBV DNA-binding polypeptide may be achieved over many hours and, if necessary, the polypeptide can be protected from being degraded within the gastrointestinal tract. Taking advantage of the various pH and enzymatic conditions along the gastrointestinal tract, pharmaceutical compositions for oral administration may be formulated to facilitate release of subject HBV DNA-binding polypeptide at a particular gastrointestinal location.

Pharmaceutical compositions adapted for parenteral administration include, but are not limited to, aqueous and non-aqueous sterile injectable solutions or suspensions, which may contain antioxidants, buffers, bacteriostats and solutes that render the pharmaceutical compositions substantially isotonic with the blood of an intended recipient. Other components that may be present in such pharmaceutical compositions include water, alcohols, polyols, glycerine and vegetable oils, for example. Compositions adapted for parenteral administration may be presented in unit-dose or multi-dose containers, for example, sealed ampules and vials, and may be stored in a freeze-dried (lyophilized) condition requiring the addition of a sterile liquid carrier, e.g., sterile saline solution for injections, immediately prior to use. Extemporaneous injection solutions and suspensions may be prepared from sterile powders, granules and tablets. Such pharmaceutical compositions should contain a therapeutically or cosmetically effective amount of an active agent, together with a suitable amount of carrier so as to provide the form for proper administration to the subject. The formulation should suit the mode of administration.

Pharmaceutical compositions adapted for transdermal administration may be provided as discrete patches intended to remain in intimate contact with the epidermis for a prolonged period of time. Pharmaceutical compositions adapted for topical administration may be provided as, for example, ointments, creams, suspensions, lotions, powders, solutions, pastes, gels, sprays, aerosols or oils. A topical ointment or cream is used for topical administration to the skin, mouth, eye or other external tissues. When formulated in an ointment, the active ingredient may be employed with either a paraffinic or a water-miscible ointment base. Alternatively, the active ingredient may be formulated in a cream with an oil-in-water base or a water-in-oil base.

Pharmaceutical compositions adapted for topical administration to the eye include, for example, eye drops or injectable pharmaceutical compositions. In these pharmaceutical compositions, the active ingredient can be dissolved or suspended in a suitable carrier, which includes, for example, an aqueous solvent with or without carboxymethylcellulose. Pharmaceutical compositions adapted for topical administration in the mouth include, for example, lozenges, pastilles and mouthwashes.

Pharmaceutical compositions adapted for nasal administration may comprise solid carriers such as powders (e.g., having a particle size in the range of 20 to 500 microns). Powders can be administered in the manner in which snuff is taken, i.e., by rapid inhalation through the nose from a container of powder held close to the nose. Alternatively, pharmaceutical compositions adopted for nasal administration may comprise liquid carriers such as, for example, nasal sprays or nasal drops. These pharmaceutical compositions may comprise aqueous or oil solutions of the active ingredient. Compositions for administration by inhalation may be supplied in specially adapted devices including, but not limited to, pressurized aerosols, nebulizers or insufflators, which can be constructed so as to provide predetermined dosages of the active ingredient. In yet another embodiment, a subject HBV DNA-binding polypeptide may be administered using long-acting HBV DNA-binding polypeptide formulations that either delay the clearance of the HBV DNA-binding polypeptide from the site or cause a slow release of the HBV DNA-binding polypeptide from, e.g., an injection or administration site. The long-acting formulation that prolongs clearance of sa ubject HBV DNA-binding polypeptide may be in the form of a subject HBV DNA-binding polypeptide complexed, or covalently conjugated (by reversible or irreversible bonding) to a macromolecule such as a water-soluble polymer selected from poly(ethylene glycol) (PEG) and polypropylene glycol homopolymers and polyoxyethylene polyols, i.e., those that are soluble in water at room temperature. See, e.g., U.S. Pat. No. 5,824,642, hereby expressly incorporated by reference in its entirety. Alternatively, a subject HBV DNA-binding polypeptide may be complexed or bound to a polymer to increase its circulatory half-life. Examples of polyethylene polyols and polyoxyethylene polyols useful for this purpose include polyoxyethylene glycerol, polyethylene glycol, polyoxyethylene sorbitol, polyoxyethylene glucose, or the like. The glycerol backbone of polyoxyethylene glycerol is the same backbone occurring in, for example, animals and humans in mono-, di-, and triglycerides. The polymer need not have any particular molecular weight. In some embodiments, the molecular weight is between about 3500 and 100,000, or between 5000 and 40,000. In some embodiments, the PEG homopolymer is unsubstituted, but it may also be substituted at one end with an alkyl group. In some embodiments, the alkyl group is a C1-C4 alkyl group, and most preferably a methyl group. In some embodiments, the polymer is an unsubstituted homopolymer of PEG, a monomethyl-substituted homopolymer of PEG (mPEG), or polyoxyethylene glycerol (POG) and has a molecular weight of about 5000 to 40,000.

Suitable routes and modes of administration of a subject HBV DNA-binding polypeptide include, but are not limited to, oral, intravenous infusion, subcutaneous injection, intramuscular, topical, depot injection, implantation, time-release mode, intracavitary, intranasal, inhalation, intraocular, and controlled release. A subject HBV DNA-binding polypeptide polypeptide also may be introduced parenterally, transmucosally (e.g., orally), nasally, rectally, intravaginally, sublingually, submucosally, intracranially, or transdermally. In some embodiments, administration is parenteral, i.e., not through the alimentary canal but rather through some other route via, for example, intravenous, subcutaneous, intramuscular, intraperitoneal, intraorbital, intracapsular, intraspinal, intrasternal, intra-arterial, or intradermal administration. The skilled artisan can appreciate the specific advantages and disadvantages to be considered in choosing a route and mode of administration.

In one embodiment, a subject HBV DNA-binding polypeptide is delivered by a controlled-release or sustained release system. For example, a subject HBV DNA-binding polypeptide may be administered using intravenous infusion, an implantable osmotic pump, a transdermal patch, liposomes, or other modes of administration. In one embodiment, a pump may be used (See, e.g., Langer, 1990, Science 249: 1527-33; Sefton, 1987, CRC Crit. Ref. Biomed. Eng. 14:201; Buchwald et al., 1980, Surgery 88:507; Saudek et al., 1989, N. Engl. J. Med. 321:574). In another embodiment, a subject HBV DNA-binding polypeptide can be delivered in a vesicle, e.g., a liposome (See, e.g., Langer, Science 249:1527-33 (1990); Treat et al., 1989, in *Liposomes in the Therapy of Infectious Disease and Cancer*, Lopez-Berestein and Fidler (eds.), Liss, New York, pp. 353-65; Lopez-Berestein, ibid., pp. 317-27 International Patent Publication No. WO 91/04014; U.S. Pat. No. 4,704,355). In another embodiment, polymeric materials can be used (See, e.g., *Medical Applications of Controlled Release*, Langer and Wise (eds.), CRC Press: Boca Raton, Fla., 1974; *Controlled Drug Bioavailability, Drug Product Design and Performance*, Smolen and Ball (eds.), Wiley: New York (1984); Ranger and Peppas, 1953, J. Macromol. Sci. Rev. Macromol. Chem. 23:61; Levy et al., 1985, Science 228:190; During et al., 1989, Ann. Neurol. 25:351; Howard et al., 1989, J. Neurosurg. 71:105). Suitable examples of sustained-release compositions include semi-permeable polymer matrices in the form of shaped articles, e.g., films, or microcapsules. Sustained-release matrices include polylactides (U.S. Pat. No. 3,773,919, EP 58,481), copolymers of L-glutamic acid and gamma-ethyl-L-glutamate (see Sidman et al., 1983, Biopolymers, 22:547-556), poly(2-hydroxyethyl methacrylate) (Langer et al., 1981, J. Biomed Mater Res, 15:167-277), and Langer, 1982, Chem Tech, 12:98-105), ethylene vinyl acetate (Langer et al., supra) or poly-D-(−)-3-hydroxybutyric acid (EP 133,988). Sustained-release HBV DNA-binding polypeptide compositions also include liposomally entrapped HBV DNA-binding polypeptide. Liposomes containing a subject HBV DNA-binding polypeptide are prepared by methods known per se: DE 3,218,121; Epstein et al., 1985, Proc Natl Acad Sci USA, 82:3688-3692; Hwang et al, 1980, Proc Natl Acad Sci USA, 77: 4030-4034; EP 52,322; EP 36,676; EP 88,046; EP 143,949; EP 142,641; Japanese Pat. Appln. 83-118008; U.S. Pat. Nos. 4,485,045 and 4,544,545; and EP 102,324. The liposomes can be of the small (from or about 200 to 800 Angstroms) unilamellar type in which the lipid content is greater than about 30 mol percent cholesterol, the selected proportion being adjusted for the optimal therapy.

In yet another embodiment, a controlled release system can be placed in proximity of the target. For example, a micropump may deliver controlled doses directly into the liver, thereby requiring only a fraction of the systemic dose (See, e.g., Goodson, 1984, in *Medical Applications of Controlled Release*, vol. 2, pp. 115-138).

In one embodiment, it may be desirable to administer the agent locally to the area in need of treatment; this may be achieved, for example, and not by way of limitation, by local infusion during surgery, topical application, injection, by means of a catheter, by means of a suppository, or by means of an implant. An implant can be of a porous, non-porous, or gelatinous material, including membranes, such as sialastic membranes, or fibers.

Administration and Formulation of Nucleic Acid Agents

Formulation of a subject nucleic acid for delivery to a subject, as well as method of delivery of nucleic acid agents, are available in the art. These include formulations and delivery methods to effect systemic delivery of a nucleic acid agent, as well as formulation and delivery methods to effect local delivery of a nucleic acid agent (e.g., to effect to a particular organ or compartment (e.g., to effect delivery to liver tissue, etc.). Nucleic acid agents can be formulated to include a delivery vehicle for administration to a subject, carriers and diluents and their salts, and/or can be present in pharmaceutically acceptable formulations.

Suitable formulations at least in part depend upon the use or the route of entry, for example parenteral, oral, or transdermal. The term "parenteral" as used herein includes percutaneous, subcutaneous, intravascular (e.g., intravenous), intratumoral, peritumoral, intramuscular, or intrathecal injection or infusion techniques, and the like. Formulations include pharmaceutically acceptable salts of an agent of interest, e.g., acid addition salts.

In one embodiment, a nucleic acid agent is administered to a subject by systemic administration in a pharmaceutically acceptable composition or formulation. By "systemic administration" is meant in vivo systemic absorption or accumulation of drugs in the blood stream to facilitate distribution through the body. Systemic administration routes include, e.g., intravenous, subcutaneous, portal vein, intraperitoneal, inhalation, oral, intrapulmonary and intramuscular.

Formulations of a nucleic acid agent can also be administered orally, topically, parenterally, by inhalation or spray, or rectally in dosage unit formulations containing pharmaceutically acceptable carriers, adjuvants and/or vehicles. Pharmaceutically acceptable carriers or diluents for therapeutic use are well known in the pharmaceutical art, and are described, for example, in Remington's Pharmaceutical Sciences, Mack Publishing Co. (A. R. Gennaro edit. 1985), hereby incorporated herein by reference. For example, preservatives, stabilizers, dyes and flavoring agents can be provided. These include sodium benzoate, sorbic acid and esters of p-hydroxybenzoic acid. In addition, antioxidants and suspending agents can be used.

A pharmaceutically effective dose is that dose required to prevent, inhibit the occurrence, or treat (alleviate a symptom at least to some extent) of a disease state. The pharmaceutically effective dose depends on the type of disease, the composition used, the route of administration, the type of subject being treated, subject-dependent characteristics under consideration, concurrent medication, and other factors that those skilled in the medical arts will recognize. Generally, an amount between 0.1 mg/kg and 100 mg/kg body weight/day of active ingredients (e.g., a nucleic acid agent) is administered.

Formulations and methods of delivery of agents (including nucleic acid molecules) to the liver are known in the art, see, e.g., Wen et al., 2004, World J. Gastroenterol., 10, 244-9; Murao et al., 2002, Pharm Res., 19, 1808-14; Liu et al., 2003, Gene Ther., 10, 180-7; Hong et al., 2003, J Pharm Pharmacol., 54, 51-8; Herrmann et al., 2004, Arch Virol., 149, 1611-7; and Matsuno et al., 2003, Gene Ther., 10, 1559-66.

Where pulmonary delivery is desired, a nucleic acid agent can be administered by, e.g., inhalation of an aerosol or spray dried formulation administered by an inhalation device (e.g., nebulizer, insufflator, metered dose inhaler, and the like), providing uptake of the agent into pulmonary tissues. Solid particulate compositions containing respirable dry particles of micronized compositions containing a compound of interest (e.g., nucleic acid) can be prepared by standard techniques. A solid particulate composition can optionally contain a dispersant which serves to facilitate the formation of an aerosol. A suitable dispersant is lactose, which can be blended with the agent in any suitable ratio, such as a 1 to 1 ratio by weight. The active ingredient typically in about 0.1 to 100 w/w of the formulation. The agent can be delivered as a suspension or solution formulation, and may involve use of a liquified propellant, e.g., a chlorofluorocarbon compound such as dichlorodifluoromethane, trichlorofluoromethane, dichlorotetrafluoroethane and mixtures thereof. Aerosol formulation can additionally contain one or more co-solvents, for example, ethanol, emulsifiers and other formulation surfactants, such as oleic acid or sorbitan trioleate, anti-oxidants and suitable flavoring agents. Other methods for pulmonary delivery are described in, for example US 2004/0037780, and U.S. Pat. No. 6,592,904; U.S. Pat. No. 6,582,728; U.S. Pat. No. 6,565,885, each of which are incorporated herein by reference.

Formulations and methods of delivery of a nucleic acid agent to hematopoietic cells, including monocytes and lymphocytes, are known in the art, see, e.g., Hartmann et al., 1998, J. Phamacol. Exp. Ther., 285(2), 920-928; Kronenwett et al., 1998, Blood, 91(3), 852-862; Filion and Phillips, 1997, Biochim. Biophys. Acta., 1329(2), 345-356; Ma and Wei, 1996, Leuk. Res., 20(11/12), 925-930; and Bongartz et al., 1994, Nucleic Acids Research, 22(22), 4681-8. Such methods, as described above, include the use of free compound (e.g., oligonucleotide), cationic lipid formulations, liposome formulations including pH sensitive liposomes and immunoliposomes, and bioconjugates including oligonucleotides conjugated to fusogenic peptides, for delivery of compounds into hematopoietic cells.

Formulations and methods of delivery of a nucleic acid agent to the skin or mucosa are known in the art. Such delivery systems include, e.g., aqueous and nonaqueous gels, creams, multiple emulsions, microemulsions, liposomes, ointments, aqueous and nonaqueous solutions, lotions, patches, suppositories, and tablets, and can contain excipients such as solubilizers, permeation enhancers (e.g., fatty acids, fatty acid esters, fatty alcohols and amino acids), and hydrophilic polymers (e.g., polycarbophil and polyvinylpyrolidone).

Delivery to the central nervous system (CNS) and/or peripheral nervous system can be accomplished by, for example, local administration of a nucleic acid agent to nerve cells. Conventional approaches to CNS delivery that can be used include, but are not limited to, intrathecal and intracerebroventricular administration, implantation of catheters and pumps, direct injection or perfusion at the site of injury or lesion, injection into the brain arterial system, or by chemical or osmotic opening of the blood-brain barrier. Other approaches can include the use of various transport and carrier systems, for example though the use of conjugates and biodegradable polymers. See also, U.S. Pat. No. 6,180,613; WO 04/013280, describing delivery of nucleic acid molecules to the CNS, which are incorporated herein by reference.

Oral administration can be accomplished using pharmaceutical compositions containing a nucleic acid agent formulated as tablets, lozenges, aqueous or oily suspensions, dispersible powders or granules, emulsion, hard or soft capsules, or syrups or elixirs. Such oral compositions can contain one or more such sweetening agents, flavoring agents, coloring agents or preservative agents in order to provide pharmaceutically elegant and palatable preparations. Tablets, which can be coated or uncoated, can be formulated to contain the active ingredient in admixture with non-toxic pharmaceutically acceptable excipients, e.g., inert diluents; such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example magnesium stearate, stearic acid or talc. Where a coating is used, the coating delay disintegration and absorption in the gastrointestinal tract and thereby provide a sustained action over a longer period.

Where the formulation is an aqueous suspension, such can contain the active agent in a mixture with a suitable excipient(s). Such excipients can be, as appropriate, suspending agents (e.g., sodium carboxymethylcellulose, methylcellulose, hydropropyl-methylcellulose, sodium alginate, polyvinylpyrrolidone, gum tragacanth and gum acacia); dispersing or wetting agents; preservatives; coloring agents; and/or flavoring agents.

Suppositories, e.g., for rectal administration of agents, can be prepared by mixing the agent with a suitable non-irritating excipient that is solid at ordinary temperatures but liquid at the rectal temperature and will therefore melt in the rectum to release the drug. Such materials include cocoa butter and polyethylene glycols.

Dosage levels can be readily determined by the ordinarily skilled clinician, and can be modified as required, e.g., as required to modify a subject's response to therapy. Dosage levels can be on the order of from about 0.1 mg to about 100 mg per kilogram of body weight per day. The amount of active ingredient that can be combined with the carrier materials to produce a single dosage form varies depending upon the host treated and the particular mode of administration. Dosage unit forms can contain between from about 1 mg to about 500 mg of an active ingredient.

A nucleic acid agent can be administered to a subject in combination with other therapeutic compounds, e.g., so as to increase the overall therapeutic effect. For example, as described in more detail below, a subject nucleic acid can be administered to an individual in need thereof in conjunction with administration of at least a second agent suitable for the treatment of an HBV infection.

Exemplary formulations and methods for the delivery of nucleic acid molecules are known in the art. For example, nucleic acid molecules can be administered to cells by a variety of methods known to those of skill in the art, including, but not restricted to, encapsulation in liposomes, by iontophoresis, or by incorporation into other vehicles, such as biodegradable polymers, hydrogels, cyclodextrins (see for example Gonzalez et al., 1999, Bioconjugate Chem., 10, 1068-1074; Wang et al., International PCT publication Nos. WO 03/47518 and WO 03/46185), poly(lactic-co-glycolic) acid (PLGA) and PLCA microspheres (see for example U.S. Pat. No. 6,447,796 and US Patent Application Publication No. U.S. 2002130430), biodegradable nanocapsules, and bioadhesive microspheres, or by proteinaceous vectors (O'Hare and Normand, International PCT Publication No. WO 00/53722). In another embodiment, nucleic acids can also be formulated or complexed with polyethyleneimine and derivatives thereof, such as polyethyleneimine-polyethyleneglycol-N-acetylgalactosamine (PEI-PEG-GAL) or polyethyleneimine-polyethyleneglycol-tri-N-acetylgalactosamine (PEI-PEG-triGAL) derivatives. In one embodiment, the nucleic acid is formulated as described in U.S. Patent Application Publication No. 20030077829, incorporated by reference herein in its entirety.

In one embodiment, a nucleic acid agent is complexed with membrane disruptive agents such as those described in US 2001/0007666, incorporated by reference herein in its entirety. In another embodiment, the membrane disruptive agent or agents and a nucleic acid agent are also complexed with a cationic lipid or helper lipid molecule, such as those lipids described in U.S. Pat. No. 6,235,310, incorporated by reference herein in its entirety. In one embodiment, a nucleic acid agent is complexed with delivery systems as described in US 2003/077829, WO 00/03683 and WO 02/087541, each incorporated herein by reference.

Alternatively, a nucleic acid agent can be expressed within cells from eukaryotic promoters (e.g., promoters that are functional in a eukaryotic cell) (e.g., Izant and Weintraub, 1985, Science, 229, 345; McGarry and Lindquist, 1986, Proc. Natl. Acad. Sci., USA 83, 399; Scanlon et al., 1991, Proc. Natl. Acad. Sci. USA, 88, 10591-5; Kashani-Sabet et al., 1992, Antisense Res. Dev., 2, 3-15; Dropulic et al., 1992, J. Virol., 66, 1432-41; Weerasinghe et al., 1991, J. Virol., 65, 5531-4; Ojwang et al., 1992, Proc. Natl. Acad. Sci. USA, 89, 10802-6; Chen et al., 1992, Nucleic Acids Res., 20, 4581-9; Sarver et al., 1990 Science, 247, 1222-1225; Thompson et al., 1995, Nucleic Acids Res., 23, 2259; Good et al., 1997, Gene Therapy, 4, 45. Those skilled in the art realize that any nucleic acid can be expressed in eukaryotic cells from the appropriate DNA/RNA vector.

A nucleic acid agent can be expressed from transcription units inserted into a vector. The recombinant vectors can be DNA plasmids, non-viral vectors or viral vectors. An HBV DNA-binding polypeptide-expressing viral vectors can be constructed based on, but not limited to, adeno-associated virus, retrovirus, adenovirus, a lentivirus, or alphavirus. The recombinant vectors capable of expressing a nucleic acid agent can be delivered as described above, and provide for transient or stable expression.

Combination Therapy

In some embodiments, a subject HBV DNA-binding polypeptide, or a subject nucleic acid, is administered in conjunction with at least a second anti-HBV therapeutic agent. Suitable second anti-HBV therapeutic agents include, but are not limited to, nucleotide and nucleoside analogs, e.g., Epivir-HBV (lamivudine; 3TC); Hepsera (Adefovir Dipivoxi); Coviracil (emtricitabine; FTC); Entecavir; Clevudine (L-FMAU); ACH 126, 443 (L-Fd4C); AM 365; Amdoxovir; LdT (telbivudine); MCC 478; ValLdC (valtorcitabine); ICN 2001; Fluoro L and D nucleosides; Racivir; and Robustaflavone. Suitable second anti-HBV therapeutic agents also include inteferons, e.g., Intron A (interferon α2b); monoclonal antibodies, e.g., XTL 001 (XTL Biopharm); immunostimulatory compounds, e.g., Theradigm, Zadaxin (thymosin), and the like; etc.

A subject HBV DNA-binding polypeptide, or a subject nucleic acid, can be administered within 15 minutes, within one hour, within 24 hours, within one week, or within one month, of the time at which the second anti-HBV therapeutic agent is administered.

Subjects Suitable for Treatment

Subjects suitable for ("in need of") treatment using a subject treatment method include: 1) individuals who have been infected with HBV of any genotype or serotype; 2) individuals who are at risk of being infected with HBV; 3) individuals who are considered "treatment failure" patients, including "non-responder" individuals who were treated with an anti-HBV agent and who failed to respond to such treatment, and "relapsers," e.g., individuals who were treated with an anti-HBV agent, who initially responded to such treatment, and in whom the infection re-emerged (e.g., viral load increased, e.g., to pre-treatment levels); 4) individuals infected with a drug-resistant strain of HBV, e.g., individuals who were treated with lamivudine, and in whom lamivudine-resistant HBV have emerged; 5) individuals infected with an HBV surface antigen-negative strain of HBV; 6) individuals having a chronic HBV infection; 7) individuals having an acute HBV infection. Also suitable for treatment with a subject method are individuals having a disease caused by HBV infection, including, e.g., chronic liver inflammation caused by HBV, cirrhosis caused by HBV infection, acute hepatitis caused by HBV infection, fulminant hepatitis caused by HBV infection, and chronic persistent hepatitis caused by HBV infection. Also suitable for treatment with a subject method are HBV-infected individuals in which the HBV is resistant to, e.g., lamivudine, adefovir, tenofovir, or entecavir.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Example 1

Designing ZFPs to Target DHBV cccDNA and HBV cccDNA

Materials and Methods

The Zinc Finger Tools site, which can be located on the world wide web at the following address (www.scripps.edu/mb/barbas/zfdesign/zfdesignhome.php) (Mandell and Barbas, *Nucleic Acids Res.* 2006 Jul. 1; 34 (Web Server issue): W516-23), provides several tools for selecting zinc finger protein (ZFP) target sites and for designing the proteins that will target them. The first tool, "Search DNA Sequence for Contiguous or Separated Target Sites", was used to scan a given DNA sequence for consecutive DNA triplets that can be targeted with the zinc finger domains published (Dreier B et al, 2000 *J Mol Biol.* 303(4): 489-502; Dreier B et al, 2001 *J Biol Chem.* 276(31): 29466-78; Dreier et al, 2005 J Biol Chem. 280(42): 35588-97; Segal D J et al, 1999 *J Biol Chem.* 279(15): 14509-14519). Specifically, the entire DHBV genome (Canada isolate, AF047045) was scanned and the entire HBV genome (subtype ayw U95551) to find DNA sites that can be targeted by zinc finger domains. After selecting target sites within the enhancer region of DHBV or the preS/S2 promoter region of HBV, the second tool, "Design a Zinc Finger Protein," was used to input the valid zinc finger target site. This tool then outputs the amino acid sequence required in the zinc finger, in order to bind that target site.

Design of DHBV-Specific Zinc Finger Proteins.

Zinc finger proteins (ZFPs) were designed to target DHBV Canada isolate (AF047045) using the program "Zinc Finger Tools" (Mandell and Barbas, *Nucleic Acids Res.* 2006 Jul. 1; 34 (Web Server issue):W516-23). ZFPs were designed with flanking XhoI and SpeI restriction endonuclease sites, and each zinc finger was linked in tandem to the next by the canonical TGEKP (SEQ ID NO:19) linker. All ZFPs were designed to bind to target sites within the enhancer region of DHBV (2170-2361) as shown in FIGS. 1 and 2.

Design of HBV-Specific Zinc Finger Proteins.

Zinc finger proteins (ZFPs) were designed to target HBV subtype ayw (U95551) using the program "Zinc Finger Tools" (Mandell and Barbas, 2006). ZFPs were designed with flanking XhoI and SpeI restriction endonuclease sites, and each zinc finger was linked in tandem to the next by the canonical TGEKP (SEQ ID NO:119) linker. All ZFPs were designed to bind to target sites within the preS/S2 promoter region of HBV (3007-3150) as shown in FIG. 16.

Expression and Purification of DHBV-Specific ZFPs.

ZFPs sequences were codon optimized for *Anas platyrhyncos* (Peking duck) and synthesized by Blue Heron Biotechnology (Bothell, Wash.) before being cloned into pUC19 vectors lacking the multiple cloning site. ZFPs were transferred to pMAL (NEB E8000S) using the flanking XhoI and SpeI sites, creating maltose-binding protein (MBP) fusion proteins. These constructs were expressed in BL21(DE3) *Escherichia coli* and purified on amylose resin (NEB E8021 L) according to manufacturer's specifications, with the addition of 15% glycerol to the elution buffer. Proteins were stored at −80° C. Proteins were approximately 95% pure, as assessed by SDS-PAGE and Coomassie blue staining.

Expression and Purification of HBV-Specific ZFPs.

ZFPs sequences were codon optimized for *Homo sapiens* and synthesized by Blue Heron Biotechnology (Bothell, Wash.) before being cloned into pUC19 vectors lacking the multiple cloning site. ZFPs were transferred to pMAL (NEB E8000S) using the flanking XhoI and SpeI sites, creating maltose-binding protein (MBP) fusion proteins. These constructs were expressed in BL21(DE3) *Escherichia coli* and purified on amylose resin (NEB E8021 L) according to manufacturer's specifications, with the addition of 15% glycerol to the elution buffer. Proteins were stored at −80° C. Proteins were approximately 95% pure, as assessed by SDS-PAGE and Coomassie blue staining.

Electrophoretic Mobility Shift (EMSA) for DHBV-Specific ZFPs.

ZFPs were incubated with dsDNA oligonucleotides at 2.5 uM (ZFPa and ZFPb) or 1 uM (ZFPc) in gel-shift buffer (25 mM Tris-HCl pH 8, 100 mM NaCl, 2 mM DTT, 100 uM $ZnCl_2$, 10% glycerol, 50 μg/mL BSA, 4 μg/mL polyI:C and 0.01% bromophenol blue) for 1 hour at room temperature with ½ serial dilutions of ZFP from 150 nM down to 9.5 nM, in duplicate (Smith et al. 1999 *Nucleic Acids Res.* 27(2): 674-681; Moore et al. 2001 *PNAS* 98:1432-1436). The oligonucleotides were as follows: ZFPa: 5'-AGTACTGCCAAGATAATGAITAAAAGTACT-3' (SEQ ID NO:120) and its complement. ZFPb: 5'-AGTACTATGGCAAACAAAAGTTGAAGTACT-3' (SEQ ID NO:121) and its complement. ZFPc: 5'-AGTACTAGAGATATAAGTACT-3' (SEQ ID NO:122) and its complement. ZFPd: 5'-AGTACTAAAAGCAAAAGTACT-3' (SEQ ID NO:123) and its complement ZFPe: 5'-AGTACTATAATGATTAGTACT-3' (SEQ ID NO:124) and its complement. ZFPf: 5'AGTACTAACAAGACAAGTACT-3' (SEQ ID NO:125) and its complement. Reactions were run on 7% non-denaturing polyacrylamide gels at 100V for 1 hour, and then stained with SYBR-Green using the Molecular Probes EMSA kit (catalog #E33075) according to manufacturer's specifications and scanned using the Fujifilm FLA-5100 phosphoimager. EMSAs were quantified using Fujifilm ImageGauge v4.22 (2003) software. Non-linear regression plots were produced from this data using the program Enzyme Kinetics v1.11 (Trinity Software).

Radioactive [$^{32}$P]-dsDNA probes for competition EMSAs were made using T4 polynucleotide kinase (Invitrogen 18004-010) according to manufacturer's specifications, and unincorporated [γ-$^{32}$P]ATP was removed using the Qiagen QIAquick Nucleotide Removal Kit (28304) (Smith et al. 1999 *Nucleic Acids Res.* 27(2): 674-681). 150 nM of each ZFP was incubated with 10,000 cpm of radioactive dsDNA probe in gel-shift buffer for 1 hour at room temperature. Cold competitor oligonucleotides were added at concentrations of 5, 10 and 50 uM. Reactions were run on 7% non-denaturing polyacrylamide gels at 100V for 1 hour, then the gels were sealed in a plastic bag and exposed to an image plate overnight at room temperature. Image plates were scanned using the Fujifilm FLA-5100 phosphoimager.

Electrophoretic Mobility Shift (EMSA) for HBV-Specific ZFPs.

ZFPs were incubated with dsDNA oligonucleotides at 1 uM in gel-shift buffer (25 mM Tris-HCl pH 8, 100 mM NaCl, 2 mM DTT, 100 uM $ZnCl_2$, 10% glycerol, 50 ug/mL BSA, 4 ug/mL polyI:C and 0.01% bromophenol blue) for 1 hour at room temperature with ½ serial dilutions of ZFP from 150 nM down to 9.5 nM, in duplicate (Smith et al, 1999; Moore et al, 2001). The oligonucleotides were as follows:

ZFPk: 5'-AGTACTACCAATCGCCAGACAGGAAGTACT-3' (SEQ ID NO:126) and its complement. ZFPm: 5'-AGTACTGCTCAGGGCATACTACAAAGTACT-3' (SEQ ID NO:127) and its complement. ZFPn: 5'-AGTACTTGGTGGAGGCAGGAGGCGAGTACT-3' (SEQ ID NO:128) and its complement. ZFPq: 5'-AGTACTAGGCCTCCGAGTACT-3' (SEQ ID NO:129) and its complement. ZFPr: 5 AGTACTAGCCCTCAGAGTACT-3' (SEQ ID NO:130) and its complement.

ZFPt: 5'-AGTACTAGTATGCCCAGTACT-3' (SEQ ID NO:131) and its complement.

ZFPu: 5'-AGTACTCCAGCAAATAGTACT-3' (SEQ ID NO:132) and its complement.

ZFPv: 5'-AGTACTGGCGATTGGAGTACT-3' (SEQ ID NO:133) and its complement.

ZFPw: 5'-AGTACTCAGCCTACCAGTACT-3' (SEQ ID NO:134) and its complement.

Reactions were run on 7% non-denaturing polyacrylamide gels at 100V for 1 hour, then stained with SYBR-Green using the Molecular Probes EMSA kit (catalog #E33075) according to manufacturer's specifications and scanned using the Fujifilm FLA-5100 phosphoimager. EMSAs were quantified using Fujifilm ImageGauge v4.22 (2003) software. Non-linear regression plots were produced from this data using the program Enzyme Kinetics v1.11 (Trinity Software).

Radioactive [$^{32}$P]-dsDNA probes for competition EMSAs were made using T4 polynucleotide kinase (Invitrogen 18004-010) according to manufacturer's specifications, and unincorporated [γ-$^{32}$P]ATP was removed using the Qiagen QIAquick Nucleotide Removal Kit (28304) (Smith et al, 1999). 150 nM of each ZFP was incubated with 10,000 cpm of radioactive dsDNA probe in gel-shift buffer for 1 hour at room temperature. Cold competitor oligonucleotides were added at concentrations of 5, 10 and 50 uM. Reactions were run on a 7% non-denaturing polyacrylamide gels at 100V for 1 hour, then gels were sealed in a plastic bag and exposed to an image plate overnight at room temperature. Image plates were scanned using the Fujifilm FLA-5100 phosphoimager.

Surface Plasmon Resonance for DHBV-Specific ZFPs.

Surface plasmon resonance (SPR) was performed using BIAcore technology, which measures real-time interactions between a ligand anchored to a detection surface and an analyte that flows over the detection surface. ZFPs were dialyzed into 1×HBS-EP (BIAcore BR-1001-88), which was used as running and sample buffers. All solutions were filtered and degassed before use, and protein samples were centrifuged at 14,000 rpm for 5 minutes to remove any precipitate. Oligonucleotides were produced by Operon Biotechnologies (Huntsville, Ala.) and were biotinylated at the 5' end of the sense strand only. Sequences were as shown above for EMSA. Biotinylated oligonucleotides were annealed to the bottom oligonucleotide strands and then coupled to the Sensor Chip SA (BIAcore BR-1003-98) on the BIAcore 3000 using manual inject mode. 50 nM solutions of biotinylated oligonucleotides were injected onto one flow cell at 5 uL/min until the calculated $R_L$ was reached ($R_L$=105RU for ZFPa and ZFPb and $R_L$=182RU for ZFPc, ZFPd, ZFPe and ZFPf). $R_L=R_{MAX}(1/Sm)(MW_L/MW_A)$ where $R_{MAX}$=100RU for kinetic analysis, Sm=stoichiometry of binding (1:1) and $MW_L$ and $MW_A$=molecular weight of ligand and analyte (20 kDa for biotin-DNA and 19 kDa for ZFPa and ZFPb or 11 kDa for ZFPc, ZFPd, ZFPe and ZFPf), respectively. Actual amounts of immobilized oligonucleotides was 139 RU for ZFPa, 183 RU for ZFPb, 181 RU for ZFPc, 80 RU for ZFPd, 257 RU for ZFPe and 156 RU for ZFPf. Free streptavidin sites were blocked on the flow cell and an empty reference flow cell by injecting 30 uL of 1 uM biotin at 30 uL/min. After coupling, 3-5 rounds of surface regeneration tests were carried out using ZFP concentrations around the Kd for ZFPa, ZFPb and ZFPc (see Table 2), or at 128 nM for ZFPd, ZFPe and ZFPf. 30 uL of ZFP was injected at 30 uL/min, followed by 1 minute of buffer and 30 uL of 0.5% SDS at 30 uL/min to remove the bound ZFP. Once baseline remained constant after regeneration tests, kinetic analysis with direct binding was carried out using ZFP concentrations ranging from 0.1× to 10× Kd in doubling dilutions for ZFPa, ZFPb and ZFPc or 1 nM to 256 nM, 512 nM or 940 nM in doubling dilutions for ZFPd, ZFPe and ZFPf, respectively. Samples were measured from low to high concentrations with a flow rate of 30 μL/min, 3 minute injection time and 15 minute dissociation time. Regeneration between concentrations were completed with a single 30 μL injection of 0.5% SDS at a flow rate of 30 μL/min, followed by 5 minute stabilization time between runs. Bulk shift was accounted for by subtracting the signal from the reference flow cell. Kinetic analysis was done on the BIAeval software program and curves were fit to a 1:1 binding with drifting baseline model, except for ZFPf, which fit a 1:1 Langmuir binding model because the baseline did not drift.

Surface Plasmon Resonance for Human HBV-Specific ZFPs.

Surface plasmon resonance (SPR) was performed using BIAcore technology, which measures real-time interactions between a ligand anchored to a detection surface and an analyte that flows over the detection surface. ZFPs were dialyzed into 1×HBS-EP (BIAcore BR-1001-88), which was used as running and sample buffers. All solutions were filtered and degassed before use, and protein samples were centrifuged at 14,000 rpm for 5 minutes to remove any precipitate. Oligonucleotides were produced by Operon Biotechnologies (Huntsville, Ala.) and were biotinylated at the 5' end of the sense strand only. Sequences were as shown above for EMSA. Biotinylated oligonucleotides were annealed to the bottom oligonucleotide strands and then coupled to the Sensor Chip SA (BIAcore BR-1003-98) on the BIAcore 3000 using manual inject mode. 50 nM solutions of biotinylated oligonucleotides were injected onto one flow cell at 5 uL/min until the calculated $R_L$ was reached ($R_L$=95RU for ZFPk, ZFPm and ZFPn and $R_L$=182RU for ZFPq, ZFPr, ZFPt, ZFPu and ZFPv). $R_L=R_{MAX}(1/Sm)(MW_L/MW_A)$ where $R_{MAX}$=100RU for kinetic analysis, Sm=stoichiometry of binding (1:1) and $MW_L$ and $MW_A$=molecular weight of ligand and analyte (20 kDa for biotin-DNA and 21 kDa for ZFPk, ZFPm and ZFPn or 11 kDa for ZFPq, ZFPr, ZFPt, ZFPu and ZFPv), respectively. Actual amount of immobilized oligonucleotides was 110 RU for ZFPk, 87 RU for ZFPm, 95 RU for ZFPn, 194 RU for ZFPq, 180 RU for ZFPr, 185 RU for ZFPt, 167 RU for ZFPu and 193 RU for ZFPv. Free streptavidin sites were blocked on the flow cell and an empty reference flow cell by injecting 30 uL of 1 uM biotin at 30 uL/min. After coupling, 3-5 rounds of surface regeneration tests were carried out using ZFP concentrations around the Kd for ZFPk, ZFPm and ZFPn (see Table 2) or at 128 nM for ZFPd, ZFPe and ZFPf. 30 uL of ZFP was injected at 30 uL/min, followed by 1 minute of buffer and 30 uL of 0.5% SDS at 30 uL/min to remove the bound ZFP. Once baseline remained constant after regeneration tests, kinetic analysis with direct binding was carried out using ZFP concentrations ranging from 0.1× to 10× Kd in doubling dilutions for ZFPk, ZFPm and ZFPn or 1 nM to 256 nM in doubling dilutions for ZFPq, ZFPr, ZFPt, ZFPu and ZFPv. Samples were measured from low to high concentrations with a flow rate was 30 uL/min, 3 minute injection time and 15 minute dissociation time. Regeneration between concentrations were completed with a single 30 uL injection of 0.5% SDS at a flow rate of 30 uL/min, followed by 5 minute stabilization time between runs. Bulk shift was accounted for by subtracting the signal from the reference flow cell. Kinetic analysis was done on the BIAeval software program and curves were fit to a 1:1 binding with drifting baseline model.

CccDNA Pulldown Assay for DHBV-Specific ZFPs.

In a 1.7 mL microfuge tube, 30 μL of amylose resin was washed three times with wash buffer (10 mM Tris-HCl pH 7.5, 200 mM NaCl, 1 mM EDTA, 1 mM sodium azide and 10 mM β-mercaptoethanol). 150 nM of purified ZFP-MBP fusion proteins was added to the amylose resin and incubated on ice for 30 minutes, then washed three times with wash buffer. 50 μL (12.5 μg) of DHBV cccDNA was added, or wash buffer as control, or pUC18 non-specific DNA for 30 minutes at room temperature. Samples were centrifuged for 30 seconds at 14,000 rpm and supernatants collected as 'input'. Samples were washed three times with wash buffer and then 100 μL of elution buffer (wash buffer plus 15% glycerol and 10 mM maltose) was added and incubated for 5 minutes at room temperature. Samples were centrifuged again as above and supernatant was collected as 'output'. Samples were dot-blotted onto Hybond-XL membranes (Amersham Bioscience RPN303S), and membranes were denatured by laying face up on filter paper soaked with denaturation solution (0.5M NaOH, 1.5M NaCl). Next, membranes were neutralized on filter paper with neutralization solution (0.5M Tris HCl pH 8, 1.5M NaCl), followed by 3 minutes of exposure to UV light to cross-link the DNA to the membrane. Membranes were prehybridized with 5×SSC, 2% SDS, 1×Denhardt's solution and 50 μg/ml herring sperm DNA for 4 hours at 65° C. Radioactive probe was produced from EcoRI-digested fragments of pDHBV1.3 using the random primer labeling kit (Invitrogen 18187-013) and $^{32}$P[dCTP], and incubated with the membranes overnight at 65° C. Membranes were washed twice with 1×SSC, 0.1% SDS and twice with 0.1×SSC, 0.1% SDS, each for 10 minutes. Image plates were exposed to the membranes overnight and then scanned by the Fujifilm FLA-5100 phosphoimager.

CccDNA Pulldown Assay for Human HBV-Specific ZFPs.

In a 1.7 mL microfuge tube, 30 uL of amylose resin was washed three times with wash buffer (10 mM Tris-HCl pH 7.5, 200 mM NaCl, 1 mM EDTA, 1 mM sodium azide and 10 mM β-mercaptoethanol). 150 nM of purified ZFP-MBP fusion proteins was added to the amylose resin and incubated on ice for 30 minutes, then washed three times with wash buffer. 50 μL (0.75 ug) of HBV cccDNA was added, or wash buffer as control, or pUC18 non-specific DNA for 30 minutes at room temperature. Samples were centrifuged for 30 seconds at 14,000 rpm and supernatants collected as 'input'. Samples were washed three times with wash buffer and then 100 μL of elution buffer (wash buffer plus 15% glycerol and 10 mM maltose) was added and incubated for 5 minutes at room temperature. Samples were centrifuged again as above and supernatant was collected as 'output'. Samples were dot-blotted onto Hybond-XL membranes (Amersham Bioscience RPN303S), and membranes were denatured by laying face up on filter paper soaked with denaturation solution (0.5M NaOH, 1.5M NaCl). Next, membranes were neutralized on filter paper with neutralization solution (0.5M Tris HCl pH 8, 1.5M NaCl), followed by 3 minutes of exposure to UV light to cross-link the DNA to the membrane. Membranes were prehybridized with 5×SSC, 2% SDS, 1×Denhardt's solution and 50 μg/ml herring sperm DNA for 4 hours at 65° C. Radioactive probe was produced from EcoRI-digested fragments of pDHBV1.3 using the random primer labeling kit (Invitrogen 18187-013) and $^{32}$P[dCTP], and incubated with the membranes overnight at 65° C. Membranes were washed twice with 1×SSC, 0.1% SDS and twice with 0.1×SSC, 0.1% SDS, each for 10 minutes. Image plates were exposed to the membranes overnight and then scanned by the Fujifilm FLA-5100 phosphoimager.

Isolation of cccDNA from Primary Duck Hepatocytes.

CccDNA was isolated from primary duck hepatocytes (PDH) by taking a portion of liver and slicing it into small pieces. Liver pieces were incubated in PBS supplemented with 0.21 g/L $CaCl_2$, 0.1 g/L $MgCl_2.6H_2O$ and 0.1 g/L $MgSO_4.7H_2O$ and 1 mg/mL collagenase at 37° C. for 1 hour with stirring, then the slurry was transferred into 50 mL tubes. Larger pieces were allowed to settle out and the single cell suspension was decanted into a new tube. Cells were centrifuged for 5 minutes at 1000 rpm and washed twice with PBS. A modified miniprep protocol was performed using the QIAprep Spin Miniprep kit (Qiagen 27106) (Zeigler et al, 2004). Briefly, cells were aliquoted into 1.7 mL microfuge tubes and then 250 uL of buffers P1 and P2 were added and incubated for 5 minutes at room temperature. Cell lysates were then incubated with 800 μg/mL of proteinase K (Invitrogen 25530-015) for 55° C. for 2 hours. Next, 350 uL of Buffer N3 was added and mixed by gentle agitation, followed by incubation on ice for 5 minutes. Lysates were spun at 14,000 rpm for 10 minutes and then supernatant was loaded onto a spin column. Columns were spun at 14,000 rpm for 1 minute. Columns were washed once each with 750 μL of buffers PB and PE, then spun an additional minute to remove residual wash buffer. Columns were left open in a sterile hood for 5 minutes and then eluted with 80 μL of elution buffer (10 mM Tris-HCl, pH8.5) incubated at 37° C. for 5 minutes. Columns were spun at 14,000 rpm for 1 minute, and then the elution step was repeated with another 80 μL of elution buffer.

Isolation of cccDNA from HepAD38 Cells.

CccDNA was isolated from HepaD38 cells grown in the absence of tetracycline for two weeks. A modified miniprep protocol was performed using the QIAprep Spin Miniprep kit (Qiagen 27106) (Zeigler et al, 2004). Briefly, cells were trypsinized and washed with PBS, then aliquoted into 1.7 mL microfuge tubes. 250 μL of buffers P1 and P2 were added and incubated for 5 minutes at room temperature. Cell lysates were then incubated with 800 ug/mL of proteinase K (Invitrogen 25530-015) for 55° C. for 2 hours. Next, 350 uL of Buffer N3 was added and mixed by gentle agitation, followed by incubation on ice for 5 minutes. Lysates were spun at 14,000 rpm for 10 minutes and then supernatant was loaded onto a spin column. Columns were spun at 14,000 rpm for 1 minute. Columns were washed once each with 750 μL of buffers PB and PE, then spun an additional minute to remove residual wash buffer. Columns were left open in a sterile hood for 5 minutes and then eluted with 80 uL of elution buffer (10 mM Tris-HCl, pH8.5) incubated at 37° C. for 5 minutes. Columns were spun at 14,000 rpm for 1 minute, and then the elution step was repeated with another 80 uL of elution buffer.

Cloning of ZFPs into Mammalian Expression Vector.

Primers encoding an SV40 nuclear localization signal and a 6× histidine (SEQ ID NO:216) tag at the 5' end were used to amplify each ZFP by PCR. PCR products were cloned into pCR4 using the TOPO TA cloning kit and then transferred into the mammalian expression vector pcDNA3.1(+) (Invitrogen V790-20) using BamHI and EcoRI restriction endonuclease sites.

Cell Lines and Culture Conditions.

LMH cells were maintained in 1:1 MEM/F-12 medium (MEM: Gibco 11700-077; F-12: Gibco 21700-026) supplemented with 10% fetal calf serum (Gibco 12483-020), 50 IU/mL penicillin, 10 ug/mL streptomycin and 1 mM glutamine. LMH cells ($2\times10^5$ cells/9.5 $cm^2$ well) were cotransfected with 1 ug of pDHBV1.3 and 3 ug of pcDNA3.1 (+) or pcDNA3.1(+)-ZFPa, -ZFPb, -ZFPc, -ZFPd, -ZFPe or -ZFPf using Lipofectamine 2000 (LF2000: Invitrogen 11668-027) according to the manufacturer's specifications, with a DNA:LF2000 ratio of 2:1. After 24 hours, cells were harvested for RNA, DNA and whole cell lysates as described below.

Isolation of Intracellular Viral DNA.

LMH cells were lysed in 10 mM Tris-HCl pH 7.5, 50 mM NaCl, 1 mM EDTA, 0.3% Triton X 100 and 8% sucrose. Nuclei and cellular debris were pelleted by centrifugation at 14,000 rpm for 4 minutes, then supernatants were incubated at 37° C. for 30 minutes with 6 mM MgCl2, 100 ug/mL DNase and 10 ug/mL RNase A to digest cellular nucleic acids. Samples were centrifuged again as above and virus was precipitated from the supernatants with 0.3 volumes of 26% polyethylene glycol 8000, 1.4M NaCl, 10 mM EDTA overnight at 4° C. Virus was pelleted by centrifugation as above and resuspended in 100 ul of 50 mM Tris-HCl pH8, 150 mM NaCl, and 10 mM EDTA. Samples were incubated overnight at 42° C. with 800 ug/mL Proteinase K and 0.1% SDS to digest capsid and polymerase, then phenol:chloroform extracted. DNA was precipitated with 10 ug yeast tRNA as carrier, 0.1 volume 3M sodium acetate and 2× volume 95% ethanol. Virus was resuspended in 15 μL DNA loading buffer and the entire sample was used for Southern analysis.

RNA Isolation and Quantitative PCR.

RNA was isolated from LMH cells using Trizol reagent (Invitrogen 15596-018) according to the manufacturer's specifications. cDNA was produced from 1 μg of total RNA using oligo$(dT)_{20}$ (Invitrogen 18418-020) and SuperScript II Reverse Transcriptase (Invitrogen 18064-022) according to the manufacturer's specifications. Quantitative PCR was performed on the Roche LightCycler using the LightCycler FastStart DNA Master$^{PLUS}$ SYBR Green I kit (Roche 3515885001) and the following primer pairs:

```
DHBV.Pol.462.fw
5'-TGAAGGGCTGTACTTTTAACCCAG-3'     (SEQ ID NO: 135)
and

DHBV.Pol.641.rv
5'-CAGGATACTTTGGTTTAACCCC-3'.      (SEQ ID NO: 136)

DHBV.S.1480.fw
5'-CGTGGGGATGCCCAGGATTTCTTT-3'     (SEQ ID NO: 137)
and

DHBV.S.1670.rv
5'-AGATTTCGGATCCGAGGGCAGT-3'.      (SEQ ID NO: 138)

DHBV.core.2553.fw
5'-AGCTGCTTGCCAAGGTATCTTT-3'       (SEQ ID NO: 139)
and

DHBV.core.2752.rv
5'-GCTCTAAAGCGTCTTTAGCATCTC-3'.    (SEQ ID NO: 140)

DHBV.Pol.2324.fw
5'-GTTTGCCATAAGCGTTATCAGACG-3'     (SEQ ID NO: 141)
and

DHBV.Pol.2485.rv
5'-AGGGGTGTATGGAAAAGCCGTC-3'.      (SEQ ID NO: 142)
```

Western Blot.

Whole cell extracts were produced by lysing LMH cells in 10 mM Tris-HCl pH 7.5, 50 mM NaCl, 1 mM EDTA, 0.3% Triton X and 8% sucrose. Protein concentrations of lysates were measured using the BCA Protein Assay kit (Pierce 23235). SDS-PAGE was performed on 20 ug total protein on 10% polyacrylamide gels, then transferred to Hybond-ECL nitrocellulose membranes (Amersham Biosciences RPN303D) using semi-dry transfer. Membranes were blocked for 1 hour at room temperature with 2.5% skim milk powder in TBS-T (TBS plus 1% Tween 20). Primary antibodies to DHBV core (J112) and DHBV preS (1H1) were produced in house and used at dilutions of 1/10,000 and 1/500, respectively. 1/4000 goat anti-rabbit HRP (BioRad 1706515) and 1/5000 goat anti-mouse HRP (Jackson ImmunoResearch 115-035-174) were used as secondary antibodies, respectively. Anti-actin (Chemicon MAB1501) was used at 1/10,000 dilution with goat anti-mouse HRP as secondary, as above. SuperSignal West Dura Extended Substrate (Pierce 34076) was used to visualize on film.

MTT Assay.

Cells were plated at $2\times10^4$ cells/well in 96 well plates and transfected 24 hours later with LF2000 at a ratio of 2:1 DNA to LF2000. Twenty-four hours after transfection, 10 μL of 5 mg/mL MTT in PBS was added to the cells for 2 hours and incubated at 37° C. in 5% $CO_2$. Cells were washed once with PBS and then 100 uL of acidic isopropanol (0.1N HCl) was added to each well for 5 minutes before measuring at 570 nm on a Spectramax PLUS plate reader (Molecular Devices).

Statistical Analysis.

Results from the MIT assay were analyzed in Microsoft Excel 2004 for Mac (v11.3.6) using the ANOVA statistical package. Results from quantitative Lightcycler PCR were analyzed in Excel also, using two-tailed paired t-tests for two sample for means.

Confocal Microscopy.

LMH cells were transfected with 4 μg of pcDNA3.1(+)-ZFPa-EGFP or pcDNA3.1(+)-ZFPb-EGFP in 32 mm dishes with glass coverslips affixed. After 24 hours, 10 u/mL of 0.1 mg/mL Hoechst 33342 (14533 Biochemika) was added to the media and cells were incubated at 37° C./5% $CO_2$ for 15 minutes. The media was replaced and live cells were visualized using the Zeiss NLO510 multi-photon microscope. The emission/excitation was 488 nm/509 nm for EGFP and 355 nm/465 nm for Hoechst 33342.

Results

Design of DHBV-Specific Zinc Forger Proteins.

The program "Zinc Finger Tools" (Mandell and Barbas, *Nucleic Acids Res.* 2006 Jul. 1; 34 (Web Server issue):W516-23) was used to select ZFP binding sites within the DHBV Canada isolate (Addison et al. 2000 *Antiviral Res.* 48(1): 27-37) enhancer region where other cis-acting transcription factors (TF), such as hepatocyte nuclear factor 1 (HNF1), HNF3 and CCAAT/enhancer binding protein beta (C/EBPβ), are known to bind (Liu et al. 1994 *J. Virol.* 68(4): 2286-2296; Lilienbaum et al. 1993*J. Virol.* 67(10): 6192-6200). The sequence of the duck genome is not available, however, BLAST searches of the selected DNA sequences against the chicken genome were performed and zero matches were found, indicating these sequences were unique to DHBV. This is relevant because the LMH (chicken hepatoma) cell line was used for in vitro analysis.

FIG. 1 shows a map of the DHBV cccDNA genome. The grey circle represents the cccDNA of DHBV. The open arrows represent the open reading frames for core (C) and pre-Core (preC), Pol (P) and surface (preS and S). The square approximates the location of the enhancer region of DHBV, in which the ZFP binding sites can be found.

FIG. 2 is a schematic of the DHBV enhancer region and the target sites of all six DHBV-specific ZFPs. The enhancer is in light grey and the binding sites for other transcription factors, such as C/EBPβ, HNF1 and HNF3, are outlined.

Table 1 provides a summary of the DNA binding sites and corresponding amino acid sequences of the zinc fingers of ZFPs a-f. The entire DNA binding site sequence is shown from 5'-3'. Each subsite is shown with its corresponding zinc finger amino acid sequence displayed, with amino acid positions from −1 up to +6 representing the amino acids of the alpha helix that make site specific contacts with the DNA. The 3' base pair of the DNA subsite (small case) makes minor interactions with the alpha helix of the zinc finger.

TABLE 1

Figure 5A:
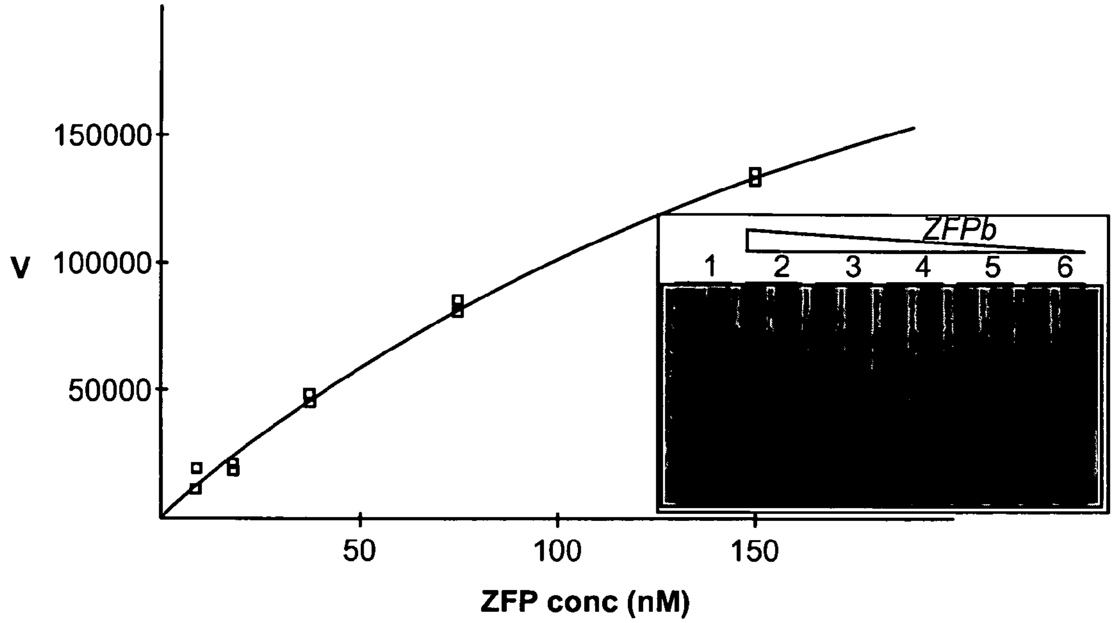
FIGS. 5A and 5B show non-linear regression plots and EMSAs for ZFPb and ZFPc respectively.
Figure 5B:
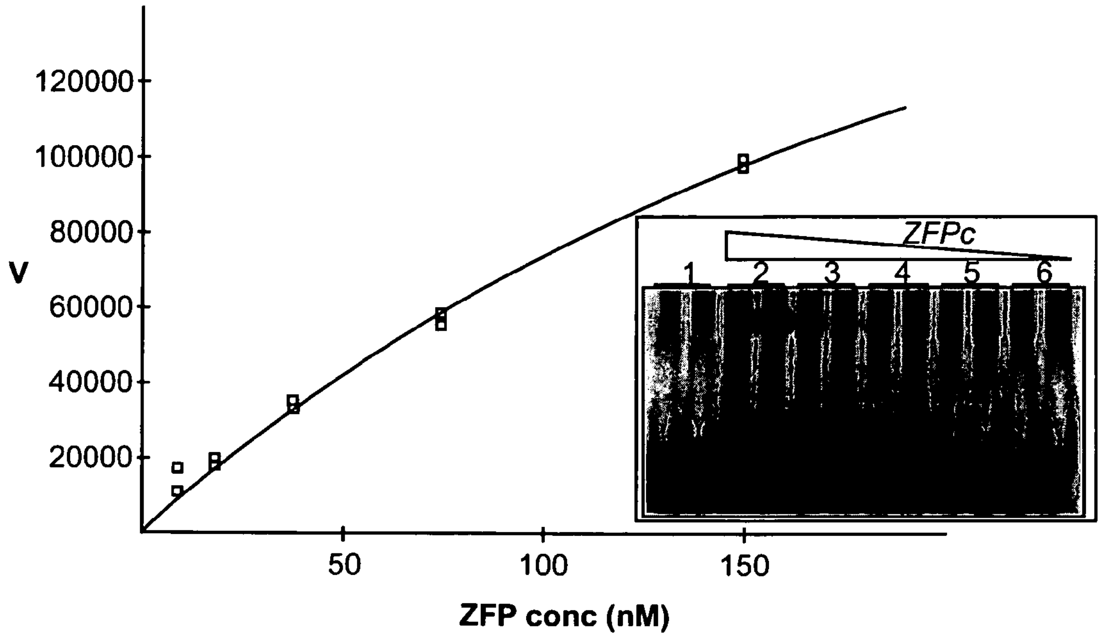

| ZFP Name | Target Sequence 5'-3' | Target Subsites 5'-3' | Finger Designs -1 1 2 3 4 5 6 | |
|---|---|---|---|---|
| ZFPa | GCCAAGATAATGATTAAAc | GCCa | DCRDLAR | (SEQ ID NO: 48) |
| | (SEQ ID NO: 143) | AAGa | RKDNLKN | (SEQ ID NO: 20) |
| | | ATAa | QKSSLIA | (SEQ ID NO: 12) |
| | | ATGa | RRDELNV | (SEQ ID NO: 15) |
| | | ATTa | HKNALQN | (SEQ ID NO: 21) |
| | | AAAc | QRANLRA | (SEQ ID NO: 11) |
| ZFPb | ATGGCAAACAAAAGTTGAt | ATGg | RRDELNV | (SEQ ID NO: 15) |
| | (SEQ ID NO: 144) | GCAa | QSGDLRR | (SEQ ID NO: 41) |
| | | AACa | DSGNLRV | (SEQ ID NO: 19) |
| | | AAAa | QRANLRA | (SEQ ID NO: 11) |
| | | | HRTTLTN | (SEQ ID NO: 25) |
| | | AGTt | QAGHLAS | (SEQ ID NO: 59) |
| | | TGAt | | |
| ZFPC | AGAGATATAc | AGAg | QLAHLRA | (SEQ ID NO: 13) |
| | (SEQ ID NO: 145) | GATa | TSGNLVR | (SEQ ID NO: 45) |
| | | ATAc | QKSSLIA | (SEQ ID NO: 12) |
| ZFPd | AAAAGCAAAg | AAAa | QRANLRA | (SEQ ID NO: 11) |
| | (SEQ ID NO: 146) | AGCa | ERSHLRE | (SEQ ID NO: 14) |
| | | AAAg | QRANLRA | (SEQ ID NO: 11) |
| ZFPe | ATAATGATTa | ATAa | QKSSLIA | (SEQ ID NO: 12) |
| | (SEQ ID NO: 147) | ATGa | RRDELNV | (SEQ ID NO: 15) |
| | | ATTa | HKNALQN | (SEQ ID NO: 21) |
| ZFPf | AACAAGACAa | AACa | DSGNLRV | (SEQ ID NO: 19) |
| | (SEQ ID NO: 148) | AAGa | RKDNLKN | (SEQ ID NO: 20) |
| | | ACAa | SPADLTR | (SEQ ID NO: 22) |

shows a Non-linear regression plot and EMSA for ZFPa. The non-linear regression plot of ZFPa is derived from quantifying the EMSA (inset) using the program Enzyme Kinetics v1.11. The inset EMSA shows the unbound probe in the absence of ZFPa (lane 1) and the mobility shift in the presence of ZFPa at 150 nM (lane 2), serial diluted 1 in 2 (lanes 3-5) down to 9.5 nM (lane 6). FIGS. 5A and 5B show Non-linear regression plots and EMSAs for ZFPb and ZFPc respectively. The non-linear regression plots of ZFPb and ZFPC were derived by quantifying the EMSA (inset) using the program Enzyme Kinetics v1.11. The inset EMSA shows the unbound probe in the absence of ZFP (lane 1) and the mobility shift in the presence of ZFP at 150 nM (lane 2), serial diluted 1 in 2 (lanes 3-5) down to 9.5 nM (lane 6). The dissociation constants ($K_d$), calculated by non-linear regression, were 36.9 nM (ZFPa), 179.4 nM (ZFPb) and 115.1 nM (ZFPc), respectively (Table 2).

The specificity of the designed ZFPs to their target sequence was assessed using competition EMSAs (Smith et al. 1999 *Nucleic Acids Res.* 27(2): 674-681; Reidling and Said 2007 *Am J Physiol Cell Physiol.* 292: 1305-1312). In preliminary experiments, 50-100 fold excess unlabeled oligonucleotides specific for each ZFP were added and no reduction in the intensity of the ZFP/DNA complex was visible. By adding 1000-10,000 fold excess unlabeled oligonucleotides, competition off by specific unlabeled oligonucleotides (FIG. 6, lanes 3-5) but not by non-specific unlabeled oligonucleotides (FIG. 6, lane 6) was visible, indicating the ZFPs had high affinities and specific binding to their target oligonucleotides.

Figure 6:
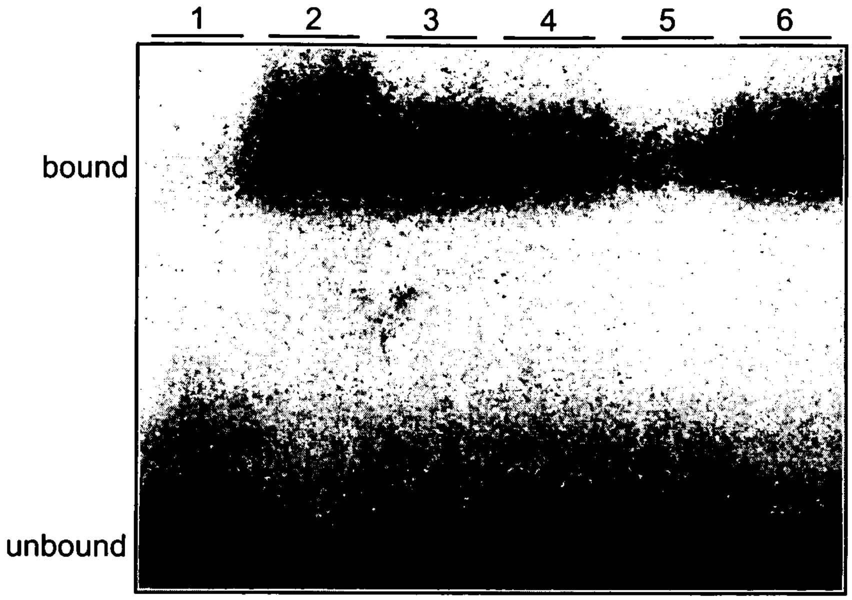
FIG. 6 shows a competition EMSA of ZFPa.
Figure 9A:
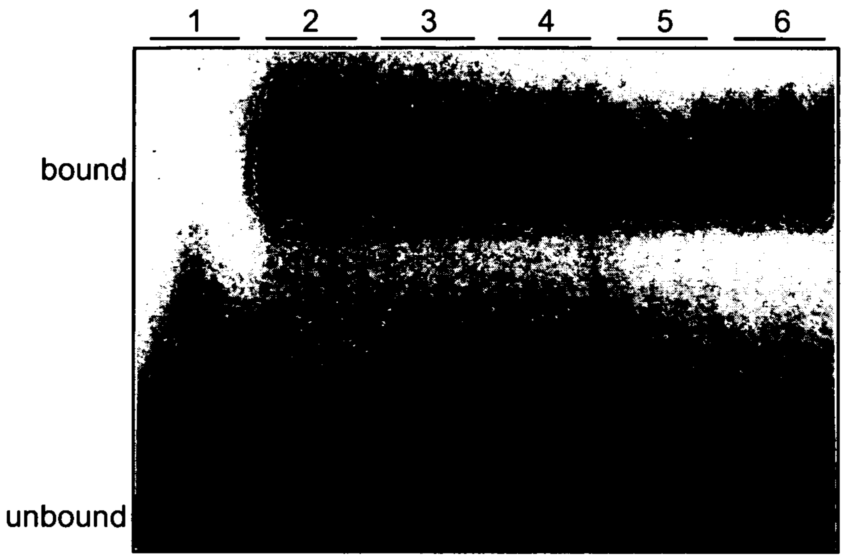
FIGS. 9A and 9B show competition EMSAs of ZFPb and ZFPc respectively.
Figure 9B:
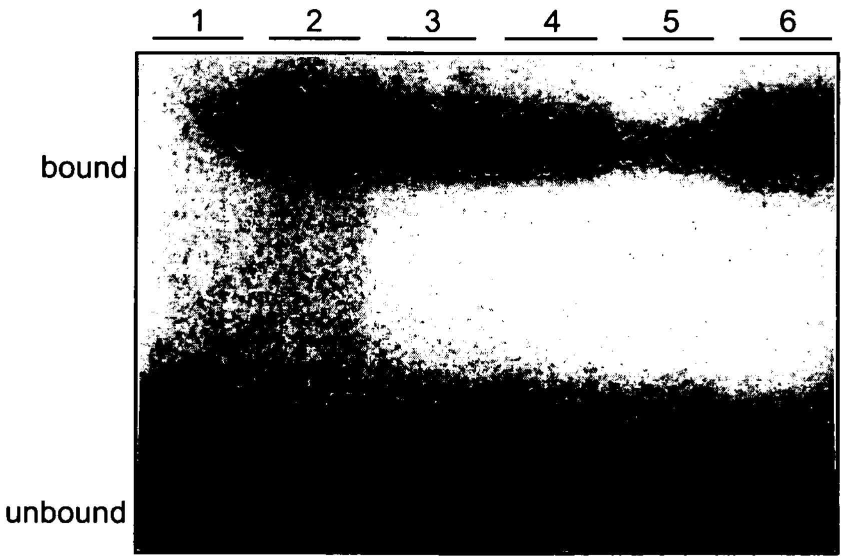
Figure 10A:
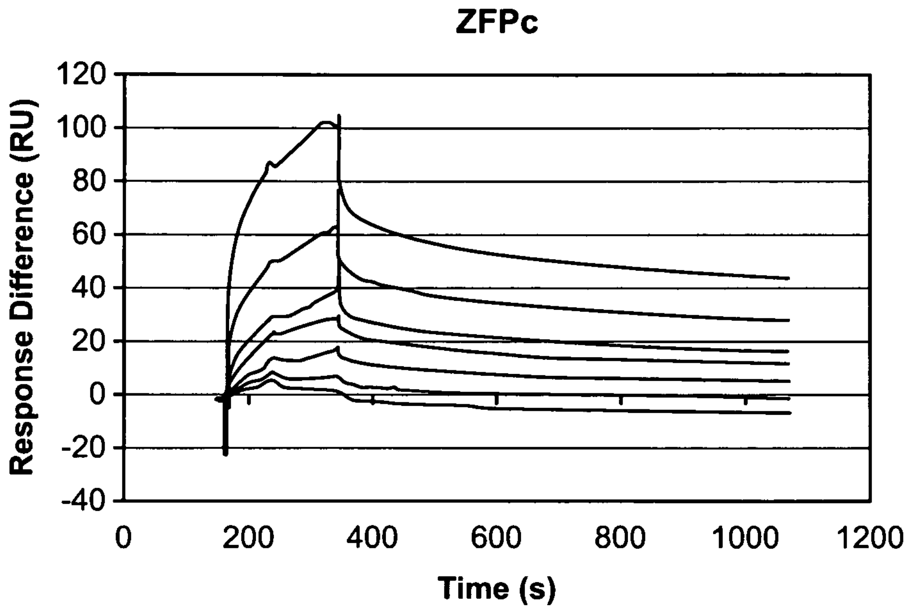
FIGS. 10A, 10B, 10C and 10D show BIAcore kinetic analysis of ZFPc, ZFPd, ZFPe and ZFPf respectively.
Figure 10B:
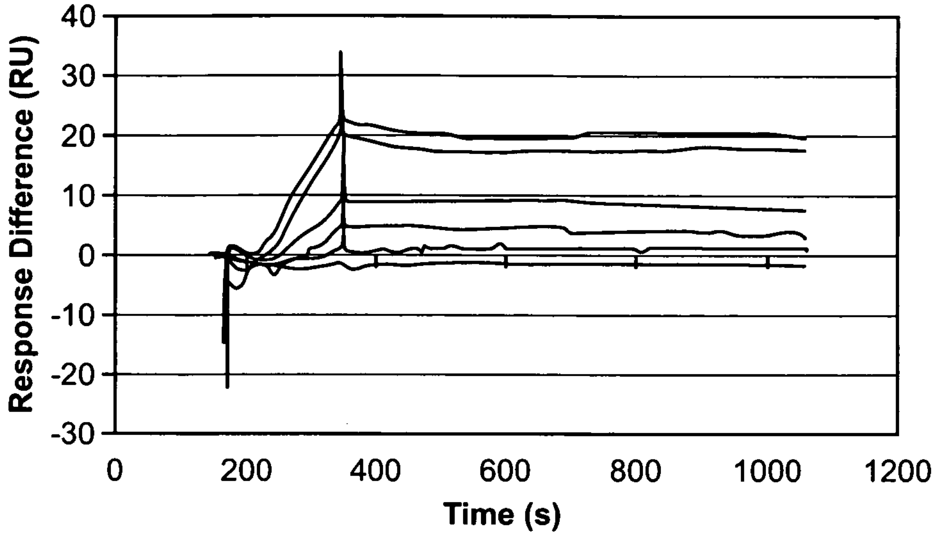
Figure 10C:
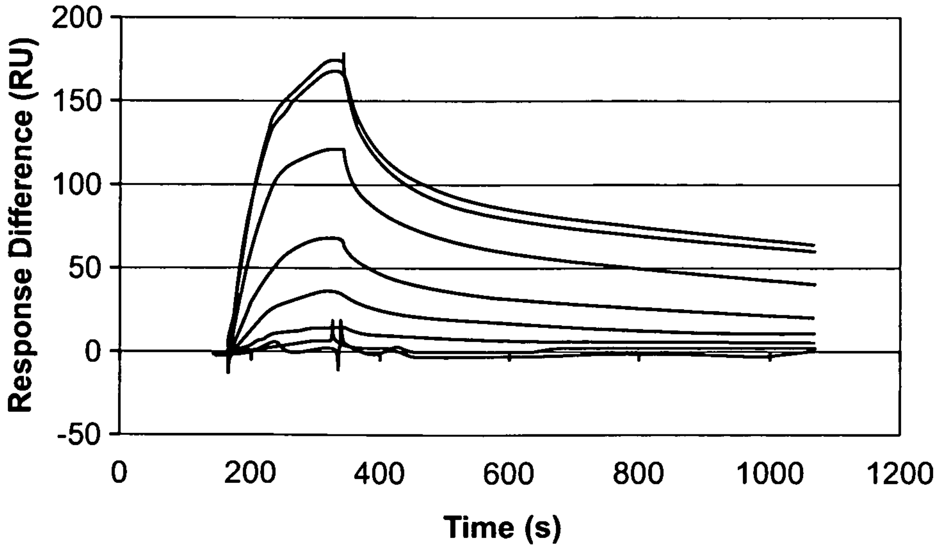
Figure 10D:
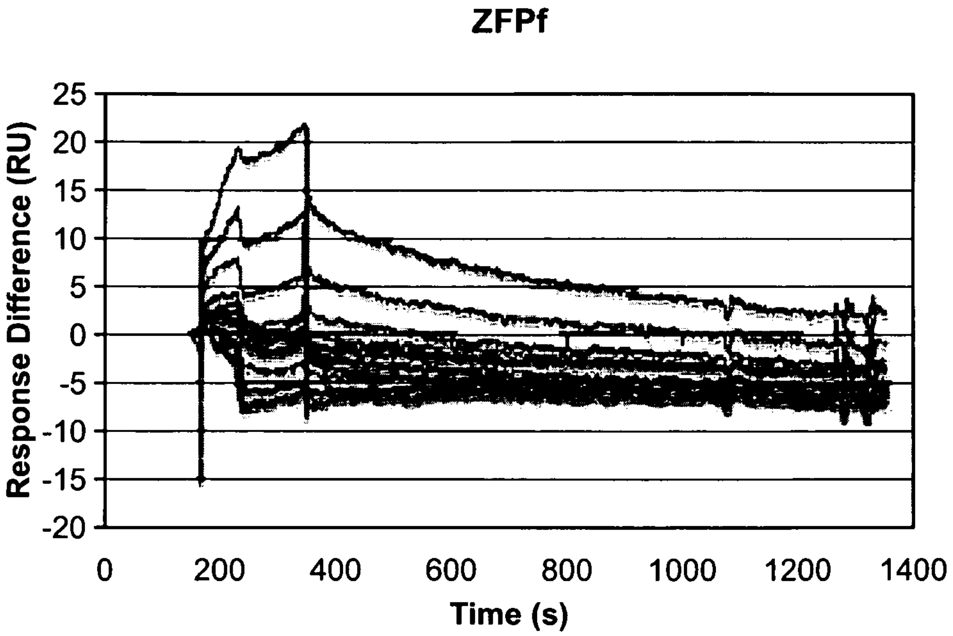

FIGS. 6, 9A and 9B show the results of competition EMSA for ZFPa, ZFPb and ZFPc respectively. Lane 1: [$^{32}$P]-labeled specific oligonucleotides alone without ZFP. Lane 2: 150 nM ZFP with labeled specific oligonucleotides. Lane 3-5: 150 nM ZFP with labeled specific oligonucleotides and 5, 10 or 50 uM

Example 2

Assessment of Dissociation Constants and Binding Affinities for ZFPs a-f Using Electrophoretic Mobility Shift Assays (EMSA)

ZFPs a-f were expressed and purified in *Escherichia coli* as fusions to maltose binding protein (MBP). ZFP-MBP fusion proteins were isolated on amylose columns and found to be approximately 95% pure by SDS-PAGE and Coomassie blue stain. FIG. 3 shows the results of a Coomassie blue stain of purified ZFPa. BL21(DE3) cells were transformed with the pMAL-ZFPa vector and induced using IPTG for 2 hours. Cells were lysed and ZFPa was isolated on an amylose resin column, then eluted using 10 mM maltose. Lane 1: Whole cell lysates. Lane 2: Whole cell lysates induced by IPTG. Lane 3: Soluble fraction. Lane 4. Insoluble fraction. Lane 5: Amylose column eluate.

Figure 4:
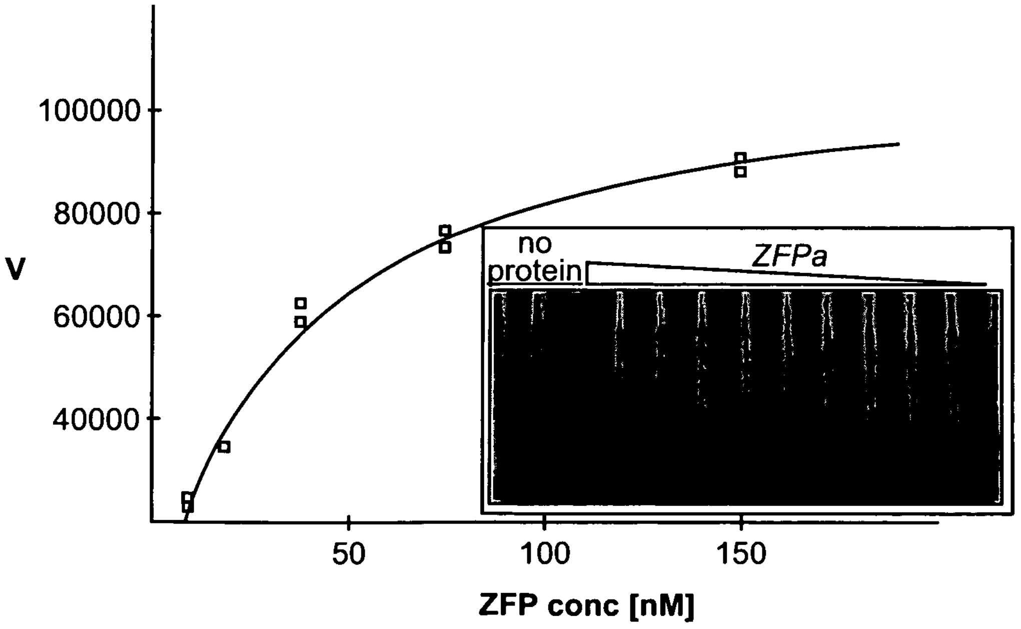
FIG. 4 shows a non-linear regression plot and EMSA of ZFPa.

Electrophoretic mobility shift assays (EMSA) were performed to assess the binding capacities of each ZFP. Three of the six ZFPs, caused a shift in the mobility of their cognate double-stranded (ds) DNA oligo, indicating binding by the ZFP to the target DNA (FIG. 4 and FIGS. 5*a* and 5*b*). FIG. 4

(respectively) of unlabeled specific oligonucleotides. Lane 6: 150 nM ZFP with labeled specific oligonucleotides and 50 uM of unlabeled non-specific oligonucleotides.

Example 3

Assessment of Dissociation Constants for ZFPs a-f Using SPR

Figure 22:
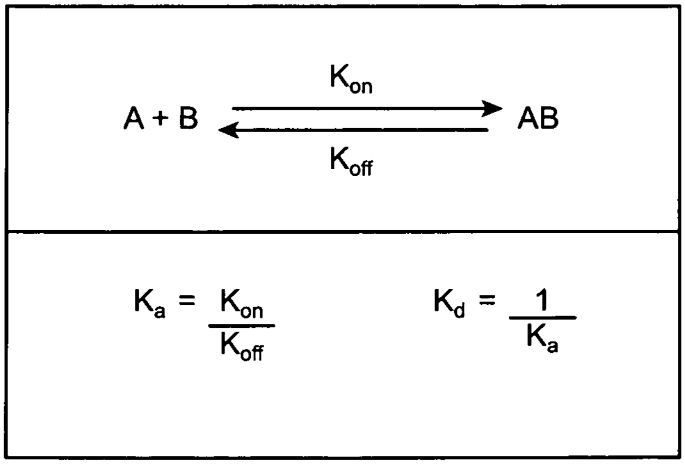
FIG. 22 shows the general kinetic equation, which describes the kinetic relationship between a ZFP (A) and its target DNA (B).

Surface plasmon resonance (SPR) is a more sensitive technique than EMSA and was able to detect binding by all six ZFPs to their target oligonucleotides. FIG. 22 shows the general kinetic equation, which describes the kinetic relationship between a ZFP (A) and its target DNA (B). The association constant (Ka) is the ratio of the $K_{on}$ over the $K_{off}$ rates, while the dissociation constant (Kd) is the inverse of the Ka.

Figure 7:
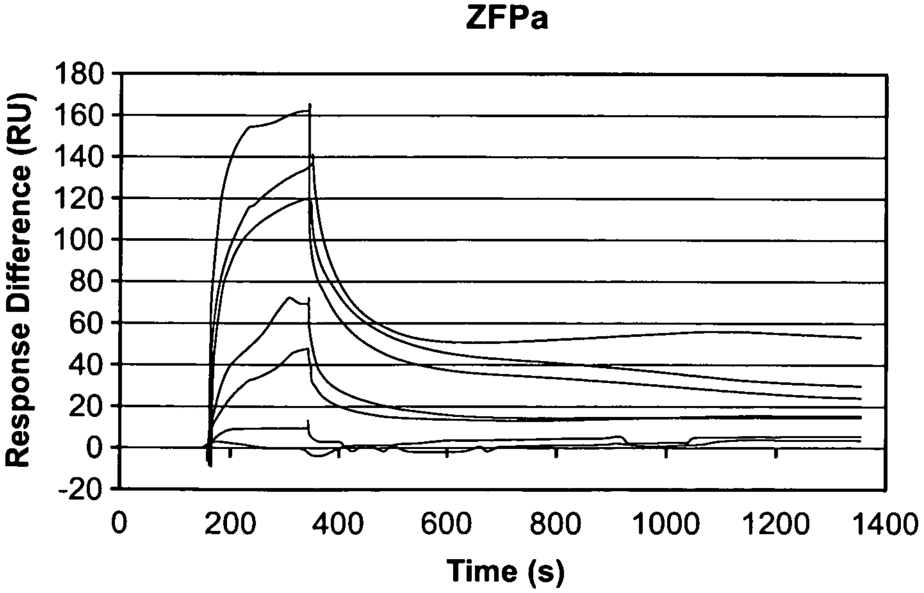
FIG. 7 shows a BIAcore kinetic analysis of ZFPa.
Figure 8:
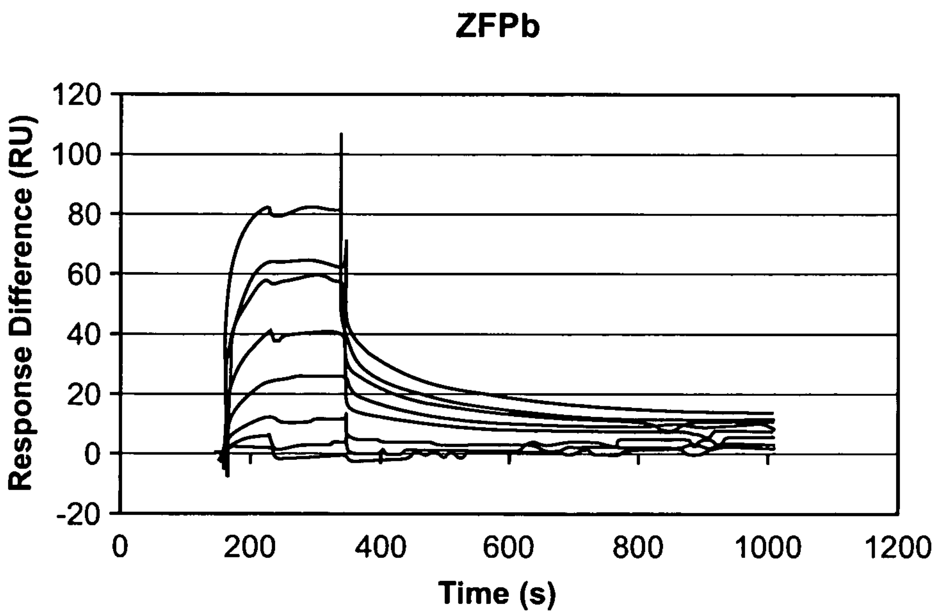
FIG. 8 shows a BIAcore kinetic analysis of ZFPb.

Kinetic graphs such as seen in FIGS. 7, 8 and 10A-10D were produced using BIA-evaluation software. FIGS. 7 and 8 show BIAcore kinetic analysis of ZFPa and ZFPb respectively. Each line represents duplicate analysis of different concentrations of ZFP, ranging from 4 nM to 128 nM (ZFPa) or 1.7 nM to 220 nM (ZFPb). Three blanks in duplicate were also performed. Response difference is measured in resonance units (RU) and represents the binding of the ZFP to the anchored oligonucleotides. FIGS. 10A, 10B, 10C and 10D show BIAcore kinetic analysis of ZFPc, ZFPd, ZFPe and ZFPf respectively. Each line represents duplicate analysis of different concentrations of ZFP, ranging from 12 nM-384 nM (ZFPc), 1 nM-256 nM (ZFPd), 1 nM-512 nM (ZFPe), and 1 nM-940 nM (ZFPf). Three blanks in duplicate were also performed. Response difference is measured in resonance units (RU) and represents the binding of the ZFP to the anchored oligonucleotides.

Dissociation constants ($K_d$) were calculated for each ZFP by fitting the data to a model of 1:1 Langmuir binding with drifting baseline, except for ZFPf, which was fit to a 1:1 Langmuir binding. As shown in Table 2, ZFPf had a $K_d$ in the micromolar range at 185 μM. Four ZFPs had $K_d$'s in the nanomolar range, with ZFPa at 12.3 nM, ZFPb at 40.2 nM, ZFPc at 99 nM and ZFPe at 67.1 nM. Lastly, ZFPd had a $K_d$ in the picomolar range at 471 pM. The dissociation constants derived from EMSA and SPR are comparable for ZFPs which were analyzed under both methods. All three Kd's from both protocols are within the same scale of magnitude of each other. In addition, the highly sensitive SPR method was able to detect binding for ZFPd, ZFPe and ZFPf, whose binding could not be demonstrated using EMSA. It is surprising that the BIAcore protocol detected a dissociation constant in the picomolar range for ZFPe, while the EMSA did not detect binding; however the curves fit the model well with a Chi squared value of 3.9. The lower the Chi squared value, the better the fit to the model. SPR is a much more sensitive method of determining kinetic interactions, thus the more sensitive method may have detected interactions that were not detected by the less sensitive EMSA method.

The size of the ZFP target sequence does not appear to directly affect the affinity of the designed ZFPs. ZFPa and ZFPb both recognize 18 base pairs of DNA and have dissociation constants in the nanomolar range. ZFPc-f each recognize 9 base pairs, however their dissociation constants have a larger range from the micromolar down to the nanomolar range. Thus, the size of the sequence does not affect the affinity of a ZFP for its target oligonucleotide. This relates to the design approach used for the subject ZFPs. Rather than using phage display or bacterial two-hybrid approaches (Jamieson et al. 2003 *Nature Rev Drug Discovery.* 2: 361-368; Wu et al. 1995 *Proc Nat Acad. Sci.* 92, 344-348; Joung et al. 2000 *Proc Nat Acad. Sci.* 97, 7382-7387), the design library in the "Zinc Finger Tools" program was used to design the subject ZFPs (Mandell and Barbas, *Nucleic Acids Res.* 2006 Jul. 1; 34 (Web Server issue): W516-23). There are some amino acid sequences of zinc fingers that have inherently higher affinities to their target DNA sequence, while others have lower affinities. It is not possible to tell this ahead of time using the program, thus the actual DNA sequence chosen may favor selection of a zinc finger that strongly binds its target.

Table 2 provides a summary of the dissociation constants ($K_d$) of ZFPs a-f derived from EMSA or BIAcore surface plasmon resonance. na=not available.

TABLE 2

| | Kd | |
|---|---|---|
| ZFP | EMSA | BIAcore |
| ZFPa | 37 nM | 12.3 nM |
| ZFPb | 179 nM | 40.2 nM |
| ZFPc | 115 nM | 99.0 nM |
| ZFPd | na | 471 pM |
| ZFPe | na | 67.1 nM |
| ZFPf | na | 185 μM |

Example 4

Assessment of Binding to cccDNA by ZFPs a-f

In order to demonstrate that the ZFPs could bind directly to cccDNA, as well as their specific oligonucleotides, a modified pulldown assay was performed. Purified ZFP-MBP fusion proteins were incubated with amylose resin, to which the ZFPs will bind due to the presence of the MBP. cccDNA was then incubated with the resin-bound ZFPs. After extensive washing, the ZFP was eluted from the resin and the resulting eluate was assessed for the presence of cccDNA, indicating ZFP was bound to cccDNA. It was demonstrated that ZFPa, ZFPb, ZFPd and ZFPf were able to bind cccDNA (FIG. 11), but not the control DNA, pUC18. ZFPc and ZFPe bound much less cccDNA—in fact, ZFPc does not appear to bind cccDNA. Importantly, however, it has been shown directly herein that ZFPs can bind cccDNA, in addition to the oligonucleotides designed for EMSA and SPR.

Figure 11:
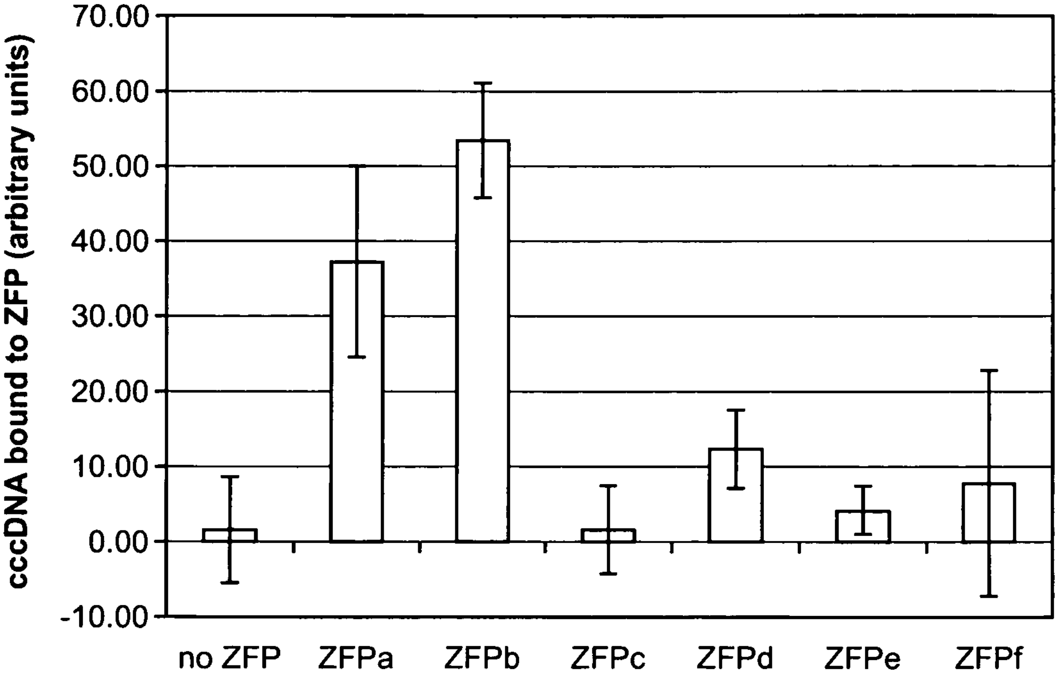
FIG. 11 shows the results of cccDNA pull-down assays for ZFPa, ZFPb, ZFPc, ZFPd, ZFPe and ZFPf.

FIG. 11 shows the results of the CccDNA pulldown assay for ZFPs a-f. ZFP-MBP fusion proteins were incubated with amylose resin, followed by incubation with DHBV cccDNA. Amylose resin was washed and then ZFPs were eluted from the resin with elution buffer. The bound cccDNA was measured by blotting the eluate onto Hybond XL and hybridizing a radioactive probe, followed by quantitation on the Fujifilm FLA-5100 phosphoimager. The chart is the quantification by the phosphoimager of triplicates. (a) $p<0.05$.

Example 5

Effects of ZFPs a-f on Viral Protein Expression in LMH Cells

The effect of ZFP expression on the DHBV life cycle was investigated in tissue culture cells. The DHBV live cycle is replicated when LMH cells are transfected with pDHBV1.3. Since these cells cannot be re-infected with progeny viruses, the only source for viral mRNA, protein and progeny production is the transfected pDHBV1.3. Once in the nucleus, pDHBV1.3 produces subgenomic RNA and pregenomic RNA. Subgenomic RNA is translated into viral core and surface proteins, while pregenomic RNA is translated into the polymerase protein or is packaged into the capsids of progeny viruses.

Figure 12:
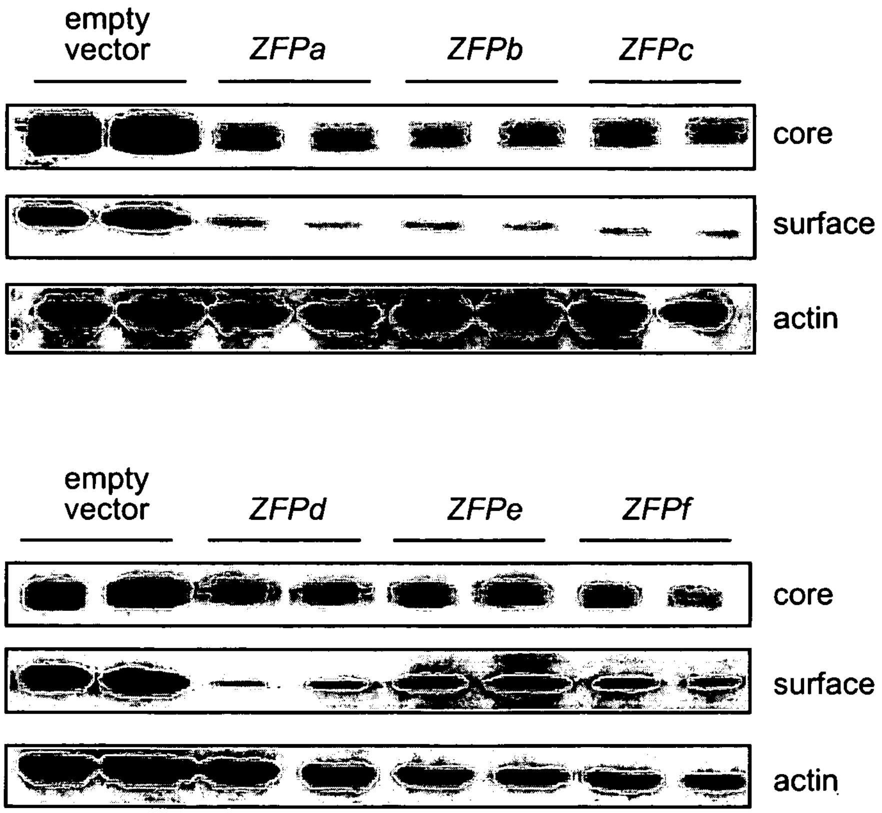
FIG. 12 shows Western Blot analysis of LMH cell lysates co-transfected with pDHBV1.3 and pcDNA3.1(+)-ZFPa, -ZFPb, -ZFPc, -ZFPd, -ZFPe and -ZFPf.
Figure 15:
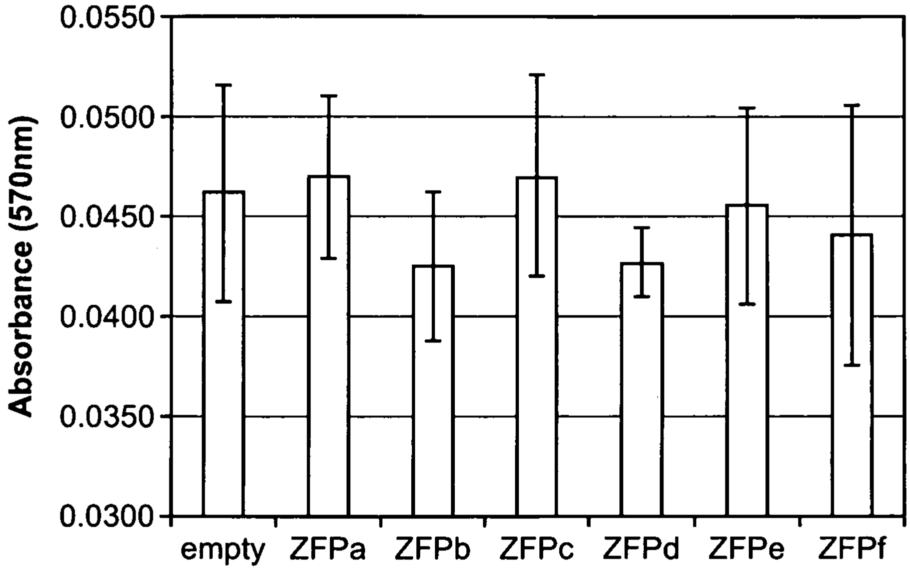
FIG. 15 shows an MIT assessment of cell death for transfected LMH (chicken hepatoma) cells.
Figure 17A:
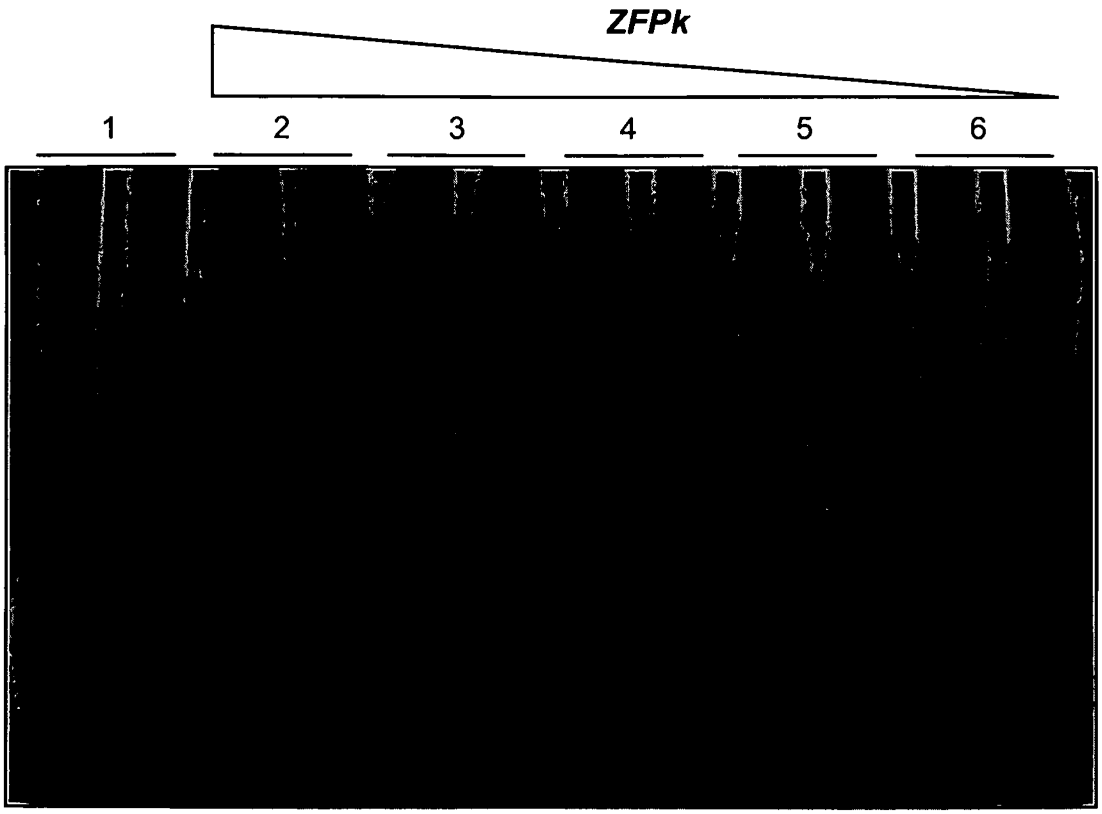
FIGS. 17A-17D show electrophoretic mobility shift assays (EMSA) of ZFPk, ZFPm, ZFPn and ZFPv respectively.
Figure 17B:
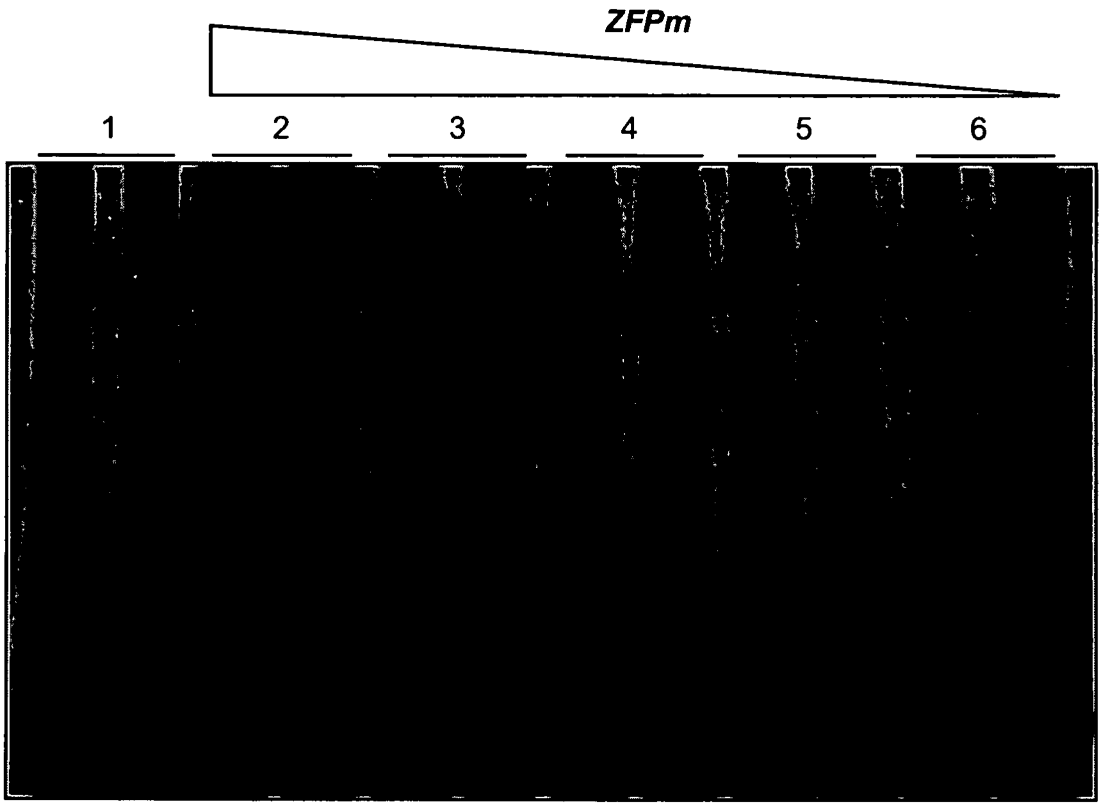
Figure 17C:
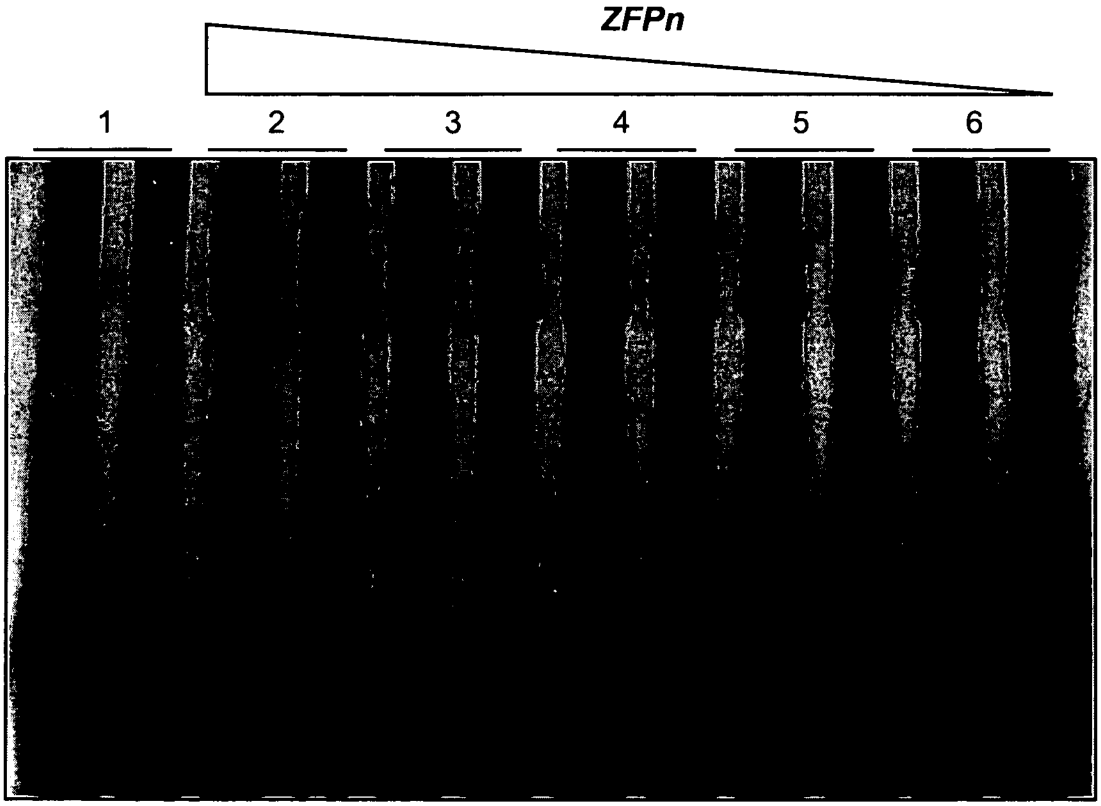
Figure 17D:
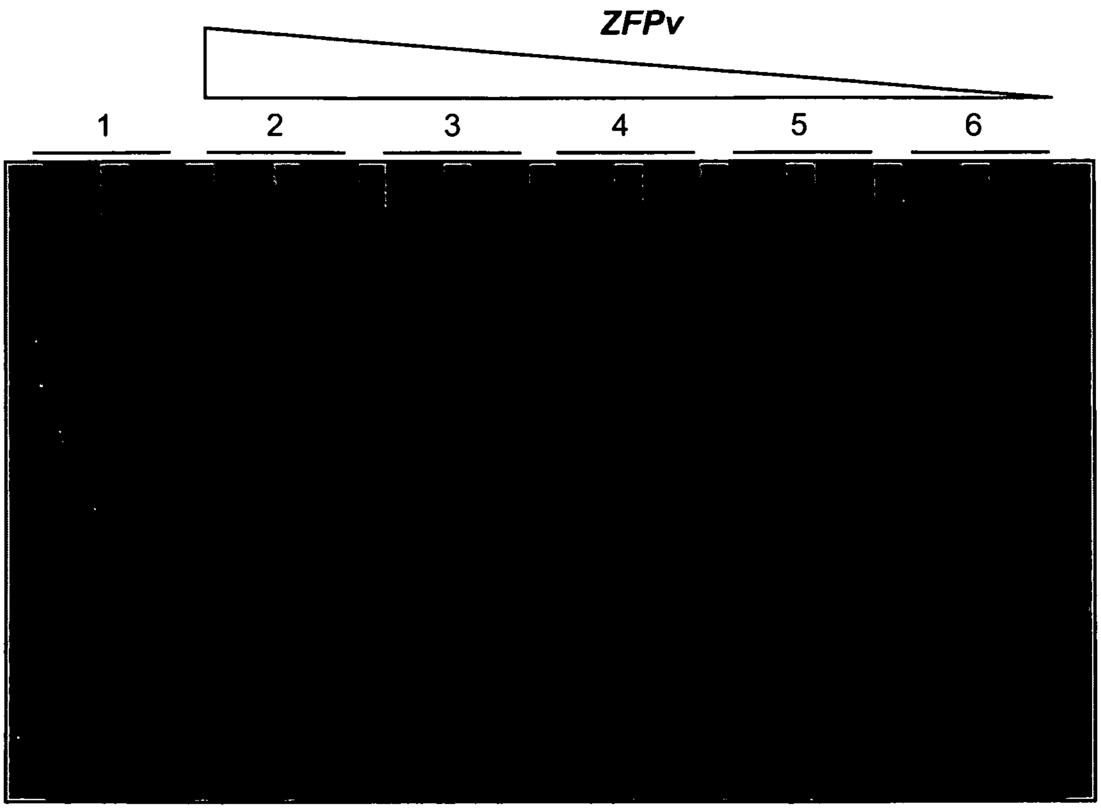
Figure 18A:
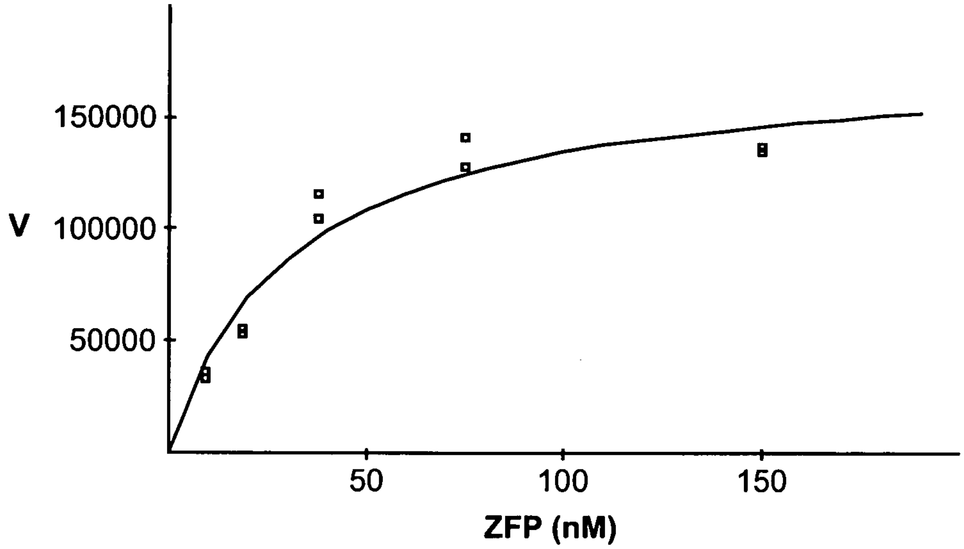
FIGS. 18A-18D show non-linear regression plots of ZFPk, ZFPm, ZFPn and ZFPv respectively.
Figure 18B:
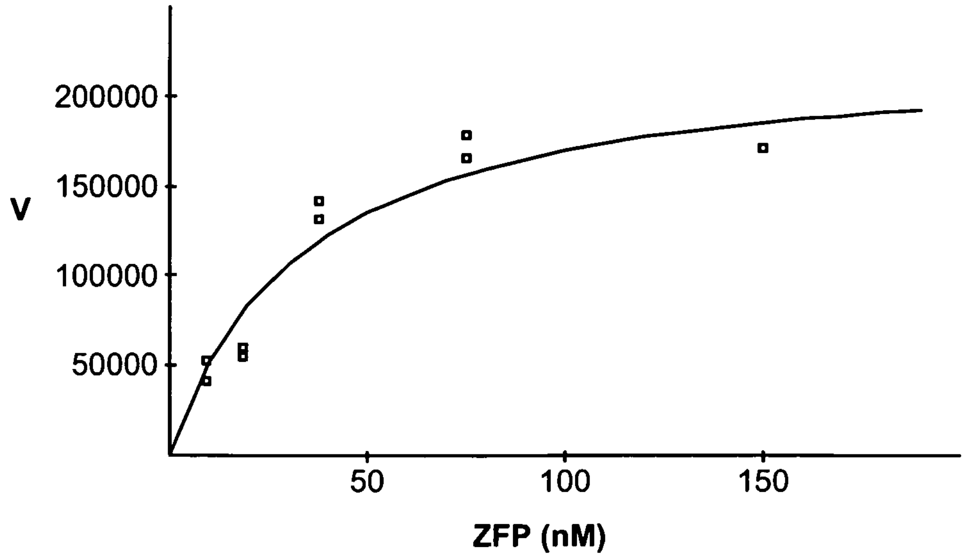
Figure 18C:
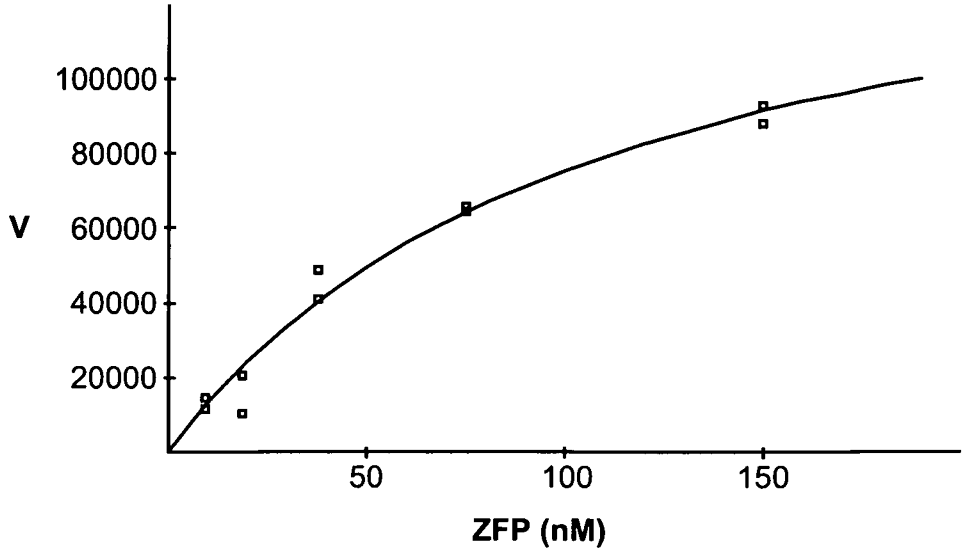
Figure 18D:
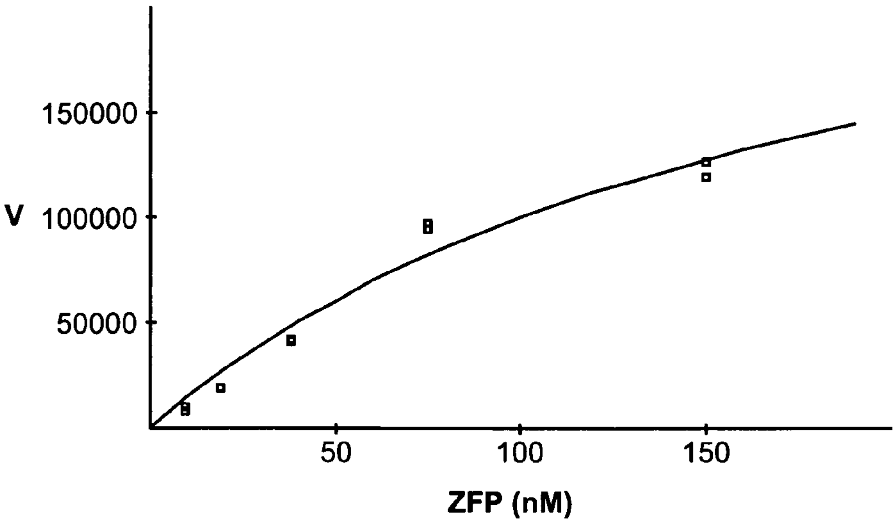

LMH cells were co-transfected with pDHBV1.3 and an excess of pcDNA3.1(+)-ZFPa, -ZFPb, -ZFPc, -ZFPd, -ZFPe or -ZFPf. Since, each ZFP had an SV40 nuclear localization signal, they were targeted to the nucleus where they could interact with pDHBV1.3. After 24 hours, lysates were collected and protein expression was analyzed by SDS-PAGE followed by Western blot. As seen in FIG. 12, there is a significant reduction in the amount of viral core and preS surface protein being produced in cells co-transfected with any of the six ZFPs, as compared to empty vector control. Actin controls were equivalent in all samples and these results were repeated five times. In addition, an MTT assay was performed on transfected LMH cells to determine whether there was greater cell death due to ZFP expression (FIG. 15). LMH cells were transfected in a 96-well plate and then assayed after 24 hours for cell death by incubating with 5 mg/mL of MTT for 2 hours at 37° C., 5% $CO_2$, followed by the addition of acidic isopropanol and measurement on a plate reader at 570 nm. There was no significant difference between any of the groups as analyzed by ANOVA, i.e., there was no significant difference in cell death in ZFP-transfected LMH compared to cells transfected with the empty vector control.

Example 6

Effects of ZFPs a-f on Viral RNA Production

Figure 13:
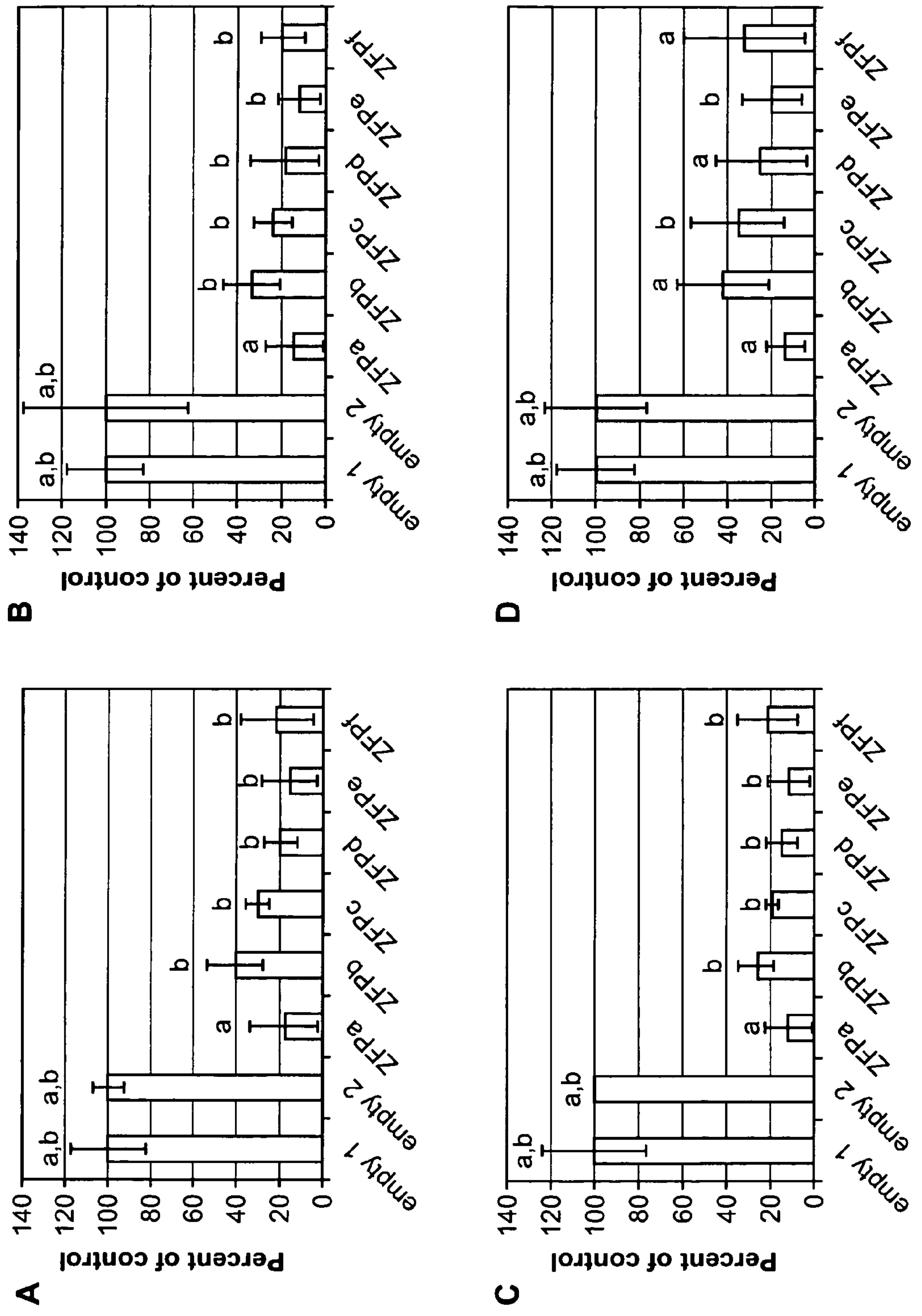
FIGS. 13A-D show Quantitative Lightcycler PCR data for viral RNA.

The effect of expressed ZFPs on viral RNA production was assessed using quantitative PCR. Since the designed ZFPs are specific for dsDNA, it was expected that the decrease in protein expression seen in FIG. 12 was due to their effect on pDHBV1.3 transcription and not viral RNA translation. If this were so, viral RNA expression should also be decreased similar to that seen with protein expression. Using primers specific for DHBV core, surface or polymerase RNAs, it was demonstrated this was the case. As seen in FIG. 13, panels B-E, there was a significant reduction in the amount of all three viral RNAs during co-transfection with any of the six ZFPs.

The average reduction of RNAs ranged from 82.04-88.09% for ZFPa, 57.83-73.50% for ZFPb, 64.92-80.64% for ZFPc, 75.02-85.15% for ZFPd, 80.44-87.98% for ZFPe and 67.60-80.21% for ZFPf. The results from two independent experiments were pooled together by normalizing each experiment as a percent of the control. Each control had a different standard deviation, thus there are two empty vector control columns in FIG. 13, panels B-E.

FIGS. 13A-D. Quantitative Lightcyler PCR for viral RNA. FIG. 13A. Surface antigen primers. FIG. 13B. Core primers. FIG. 13C. Polymerase 462 primers. FIG. 13D. Polymerase 2324 primers. Total RNA was collected and reverse transcribed into cDNA, upon which quantitative PCR was performed with various primers. (a) $p<0.05$, (b) $p<0.01$ using two-tailed paired t-tests for two sample for means.

There does not appear to be a direct correlation in the ability of an individual ZFP to reduce expression of viral protein and mRNA compared to its dissociation constant, however this may be due to the competition for the DHBV enhancer between endogenously expressed transcription factors and ZFPs. ZFPa, ZFPb and ZFPc, each with a Kd in the nanomolar range, reduce the expression of viral core and surface proteins to an equal extent. ZFPe, which has a Kd in the picomolar range, causes a smaller reduction in the expression of viral core and surface protein expression than might be expected for its high affinity. The binding site for ZFPe, however, is completely buried within the binding site for HNF1, thus there may be competition between these two proteins, resulting in decreased ZFPe binding and decreased inhibition by the ZFP. In addition, ZFPf, which has a dissociation constant in the micromolar range, was just as capable of decreasing viral protein and RNA levels as ZFPs with dissociation constants in the nanomolar range, such as ZFPb or ZFPc. This suggests the effects of ZFP expression are more complicated than simply the strength of binding, and likely includes other factors such as competition for binding sites with endogenous proteins and associated chromatin structure.

Example 7

Effects of ZFPs a-f on Intracellular Virus Production in LMH Cells

Figure 14A:
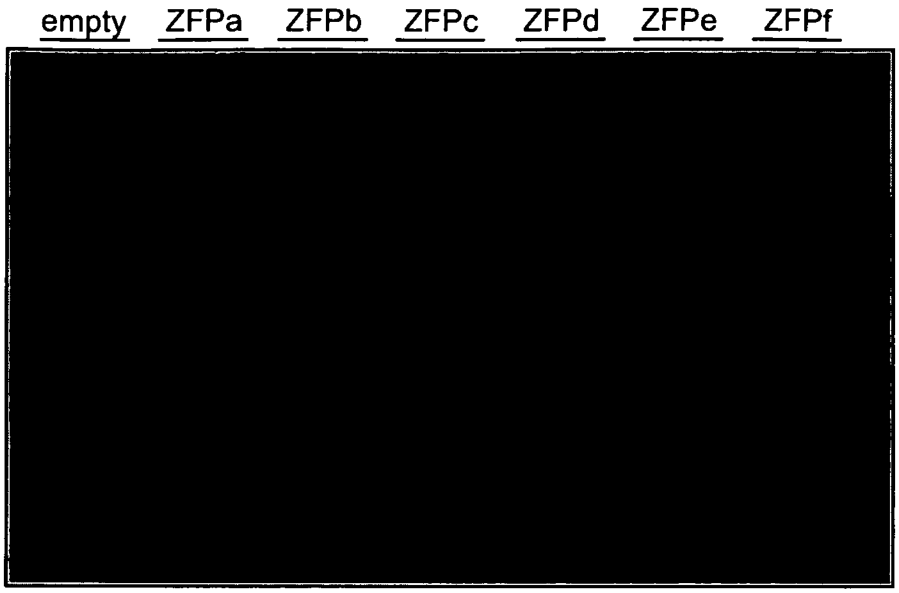
FIGS. 14A and 14B show a Southern blot of intracellular virus particles (ICV) and quantification of the Southern blot respectively.
Figure 14B:
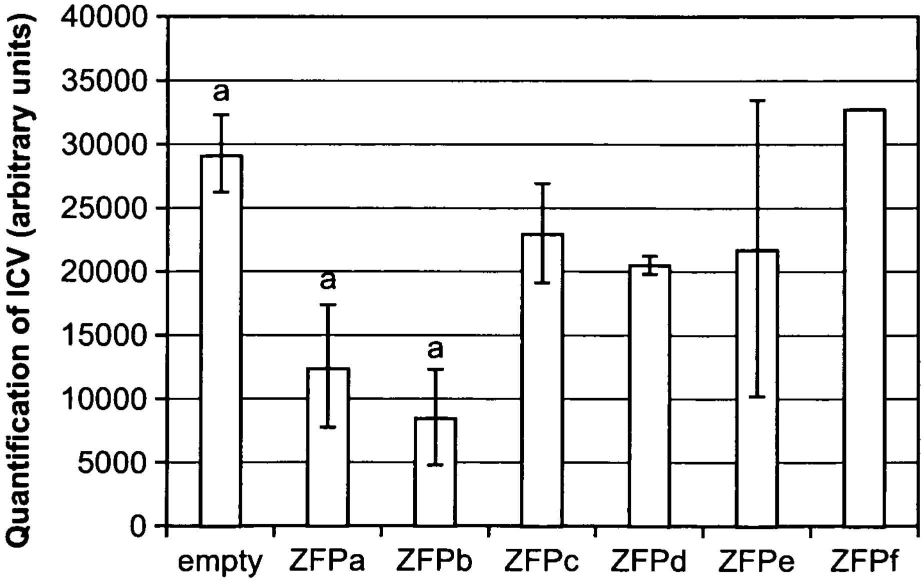

Viral RNA is encapsidated in the cytoplasm along with the polymerase protein. The polymerase reverse transcribes the viral RNA into relaxed circular DNA, which is partially double stranded. Intracellular virus (ICV) includes the capsid and polymerase proteins, and the viral DNA, and gives an indication of the amount of viral progeny being produced. ICV DNA was isolated from LMH cells co-transfected as above and analyzed by Southern blot analysis. FIG. 14A shows a Southern blot of intracellular virus particles (ICV) and FIG. 14B shows the quantification of the Southern blot. LMH cells were co-transfected with pDHBV1.3 and pcDNA3.1(+)-ZFPa, -ZFPb, -ZFPc, -ZFPd, -ZFPe or -ZFPf, or with an empty vector. After 24 hours, cells were harvested for ICV, which was used for Southern blot. There is a significant reduction in the amount of ICV being produced in the presence of ZFPa and ZFPb, and some reduction, albeit to a lesser extent, by ZFPc, ZFPd and ZFPe. ZFPf appears to have equivalent ICV as empty vector control.

Example 8

Designing ZFPs to Target Human HBV Pre-S2/S Promoter Region

Zinc finger proteins (ZFPs) were designed to target HBV subtype ayw (U95551) using the program 'Zinc Finger Tools' (Mandell and Barbas, 2006). ZFPs were designed with flanking XhoI and SpeI restriction endonuclease sites, and each zinc finger was linked in tandem to the next by the canonical TGEKP (SEQ ID NO:119) linker. All ZFPs were designed to bind to target sites within the preS/S2 promoter region of HBV (3007-3150) as shown in FIG. 16.

Tables 3 (below) provides a summary of the DNA binding sites and corresponding amino acid sequences of the zinc fingers of each ZFP. The entire DNA binding site sequence is shown from 5'-3'. Each subsite is shown with its corresponding zinc finger amino acid sequence displayed, with amino acid positions from −1 up to +6 representing the amino acids of the alpha helix that make site specific contacts with the DNA. The 3' base pair of the DNA subsite (lower case) makes minor interactions with the alpha helix of the zinc finger.

Example 9

Expression and Localization of ZFPs

To confirm the expression of the designed ZFPs, LMH cells were transfected with ZFPs fused to EGFP; the ZFPs were visualized using confocal microscopy. Cells were co-stained with DAPI to visualize the nucleus. Both ZFPa and ZFPb are found predominantly in the nucleus of cells, although the distribution within the nucleus differed between the two ZFPs. ZFPb was distributed homogeneously throughout the nucleus, while ZFPa appeared to collect into focused regions in the nucleus. Expression of the ZFPs was also confirmed by Western blot on total cell lysates using an anti-EGFP antibody.

TABLE 3

| | Target | | Finger | |
|---|---|---|---|---|
| ZFP Name | Sequence 5'-3' | Subsites 5'-3' | Designs -1 1 2 3 4 5 6 | |
| ZFPk | ACCAATCGCCAGACAGGAa | ACCa | DKKDLTR (SEQ ID NO: 16) | F1 |
| | (SEQ ID NO: 149) | AATc | TTGNLTV (SEQ ID NO: 18) | F2 |
| | HBV subtype ayw (U95551) at 3105-3121 | CGCc | HTGHLLE (SEQ ID NO: 39) | F3 |
| | in the forward direction | CAGa | RADNLTE (SEQ ID NO: 26) | F4 |
| | | ACAg | SPADLTR (SEQ ID NO: 22) | F5 |
| | | GGAa | QRAHLER (SEQ ID NO: 42) | F6 |
| ZFPm | GCTCAGGGCATACTACAAa | GCTc | TSGELVR (SEQ ID NO: 43) | F1 |
| | (SEQ ID NO: 150) | CAGg | DPGHLVR (SEQ ID NO: 46) | F2 |
| | HBV subtype ayw (U95551) at 3056-3074 | GGCa | QKSSLIA (SEQ ID NO: 12) | F3 |
| | in the forward direction | ATAc | QNSTLTE (SEQ ID NO: 27) | F4 |
| | | CTAc | QSGNLTE (SEQ ID NO: 28) | F5 |
| | | CAAa | | F6 |
| ZFPn | TGGTGGAGGCAGGAGGCGg | TGGt | RSDHLTT (SEQ ID NO: 57) | F1 |
| | (SEQ ID NO: 151) | TGGa | RSDHLTT (SEQ ID NO: 57) | F2 |
| | HBV subtype ayw (U95551) at 3091-3108 | AGGc | RSDHLTN (SEQ ID NO: 17) | F3 |
| | in the reverse direction | CAGg | RADNLTE (SEQ ID NO: 26) | F4 |
| | | GAGg | RSDNLVR (SEQ ID NO: 47) | F5 |
| | | GCCg | RSDDLVR (SEQ ID NO: 55) | F6 |
| ZFPp | CAGCGGGGTAGGCTGCCTt | CAGc | RADNLTE (SEQ ID NO: 26) | F1 |
| | (SEQ ID NO: 152) | CGGg | RSDKLTE (SEQ ID NO: 40) | F2 |
| | HBV subtype ayw (U95551) at 3123-3140 | GGTa | TSGHLVR (SEQ ID NO: 44) | F3 |
| | in the reverse direction | AGGc | RSDHLTN (SEQ ID NO: 17) | F4 |
| | | CTGc | RNDALTE (SEQ ID NO: 33) | F5 |
| | | CCTt | TKNSLTE (SEQ ID NO: 29) | F6 |
| ZFPq | AGGCCTCCGt | AGGc | RSDHLTN (SEQ ID NO: 17) | F1 |
| | (SEQ ID NO: 153) | CCTc | TKNSLTE (SEQ ID NO: 29) | F2 |
| | HBV subtype ayw (U95551) at 3029-3037 | CCGt | RNDTLTE (SEQ ID NO: 36) | F3 |
| | in the reverse direction | | | |
| ZFPr | AGCCCTCAGt | AGCc | ERSHLRE (SEQ ID NO: 14) | F1 |
| | (SEQ ID NO: 154) | CCTc | TKNSLTE (SEQ ID NO: 29) | F2 |
| | HBV subtype ayw (U95551) at 3048-3056 | CAGt | RADNLTE (SEQ ID NO: 26) | F3 |
| | in the forward direction | | | |
| ZFPt | AGTATGCCCt | AGTa | HRTTLTN (SEQ ID NO: 25) | F1 |
| | (SEQ ID NO: 155) | ATGc | RRDELNV (SEQ ID NO: 15) | F2 |
| | HBV subtype ayw (U95551) at 3062-3070 | CCCt | SKKHLAE (SEQ ID NO: 35) | F3 |
| | in the reverse direction | | | |
| ZFPu | CCAGCAAATc | CCAg | TSHSLTE (SEQ ID NO: 34) | F1 |
| | (SEQ ID NO: 156) | GCAa | QSGDLRR (SEQ ID NO: 41) | F2 |
| | HBV subtype ayw (U95551) at 3081-3089 | AATc | TTGNLTV (SEQ ID NO: 18) | F3 |
| | in the forward direction | | | |
| ZFPv | GGCGATTGGt | GGCg | DPGHLVR (SEQ ID NO: 46) | F1 |
| | (SEQ ID NO: 157) | GATt | TSGNLVR (SEQ ID NO: 45) | F2 |
| | HBV subtype ayw (U95551) at 3106-3114 | TTGt | RSDHLTT (SEQ ID NO: 57) | F3 |
| | in the reverse direction | | | |
| ZFPw | CAGCCTACCc | CAGc | RADNLTE (SEQ ID NO: 26) | F1 |
| | (SEQ ID NO: 158) | CCTa | TKNSLTE (SEQ ID NO: 29) | F2 |
| | HBV subtype ayw (U95551) at 3126-3134 | ACCc | DKKDLTR (SEQ ID NO: 16) | F3 |
| | in the forward direction | | | |

Example 9

Assessment of Dissociation Constants and Binding Affinities for Human HBV-Specific ZFPs Using EMSA Electrophoretic mobility shift assays (EMSA) were performed to assess the binding capacities of ZFPs k, m, n, q, r, t, u and v. The results of these assays are shown in FIGS.

17A-17D and 18A-18D. Each EMSA (FIGS. 17A-17D) shows the unbound probe in the absence of ZFP (lane 1) and the mobility shift in the presence of ZFP at 150 nM (lane 2), serial diluted 1 in 2 (lanes 3-5) down to 9.5 nM (lane 6). FIGS. 18A-18D show non-linear regression plots derived from quantifying the EMSA data of FIGS. 17A-17D using the program Enzyme Kinetics v1.11. Analysis of these results indicated that each of ZFPk, ZFPm and ZFPn has a dissociation constant in the nano-molar range, and that ZFPv has a dissociation constant in the μM range (see Table 4).

Figure 19A:
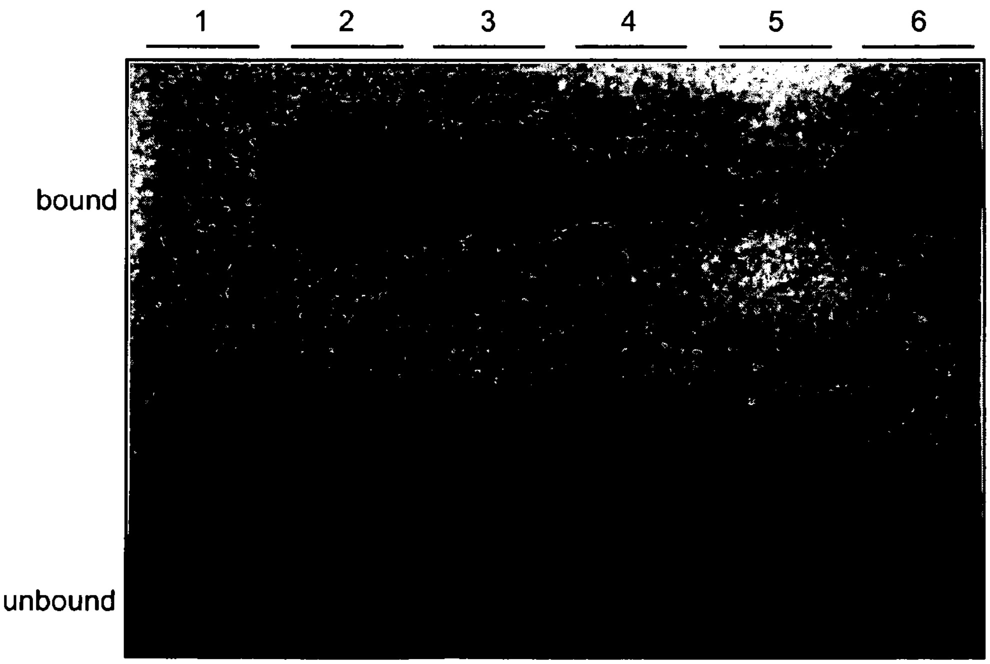
FIGS. 19A-19C show competition EMSA of ZFPk, ZFPm and ZFPn respectively.
Figure 19B:
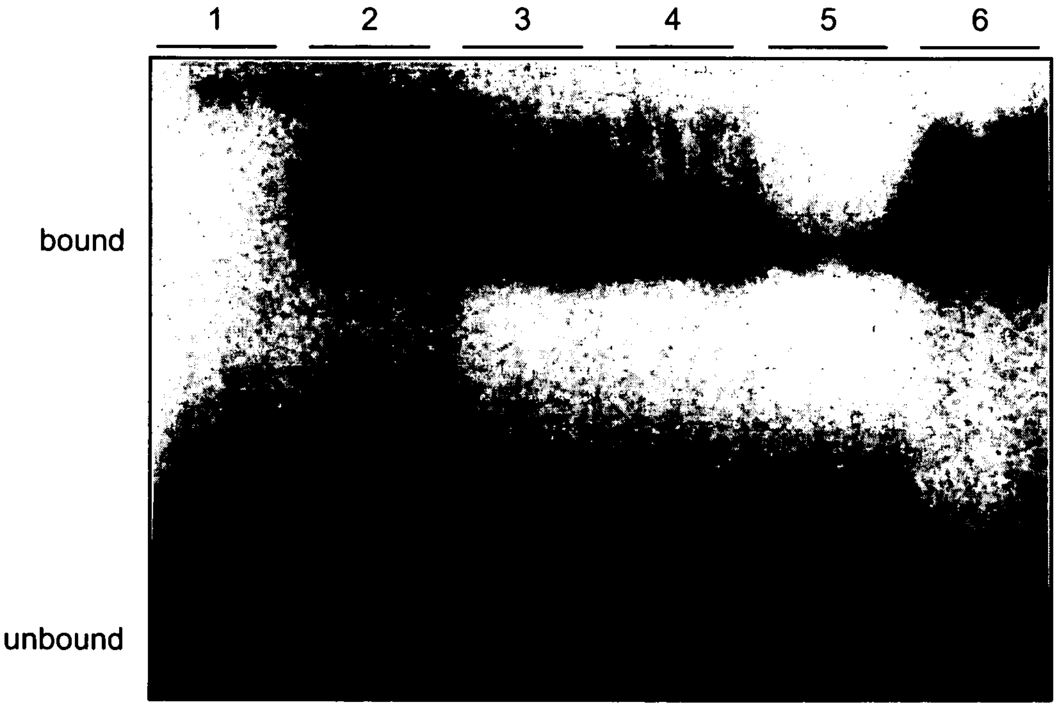
Figure 19C:
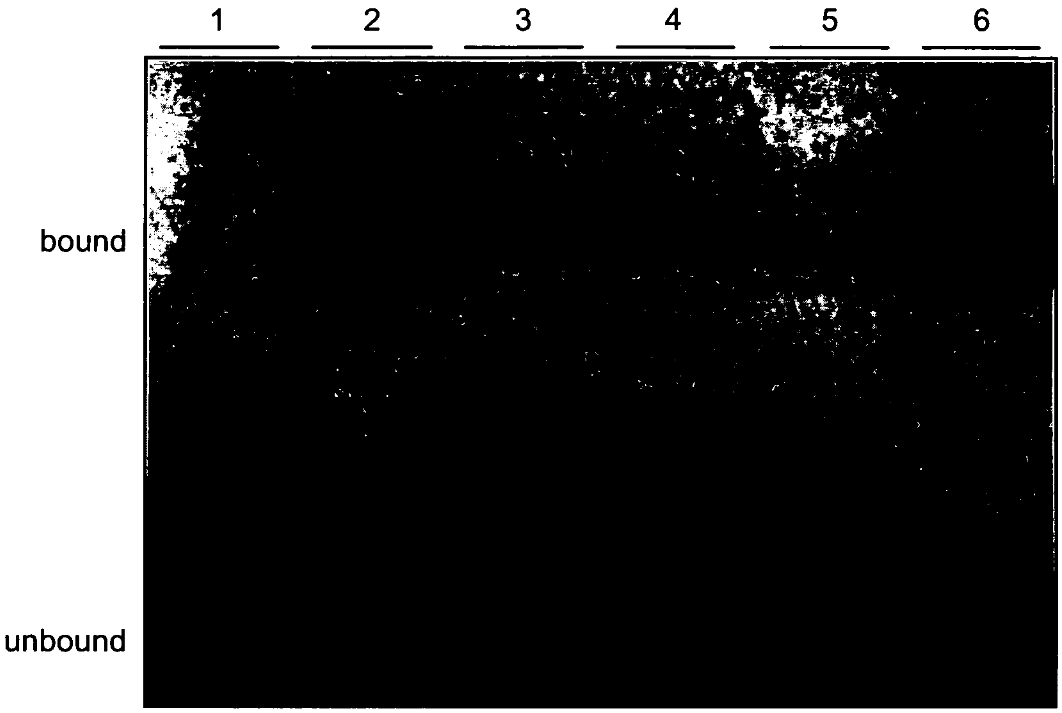
Figure 20A:
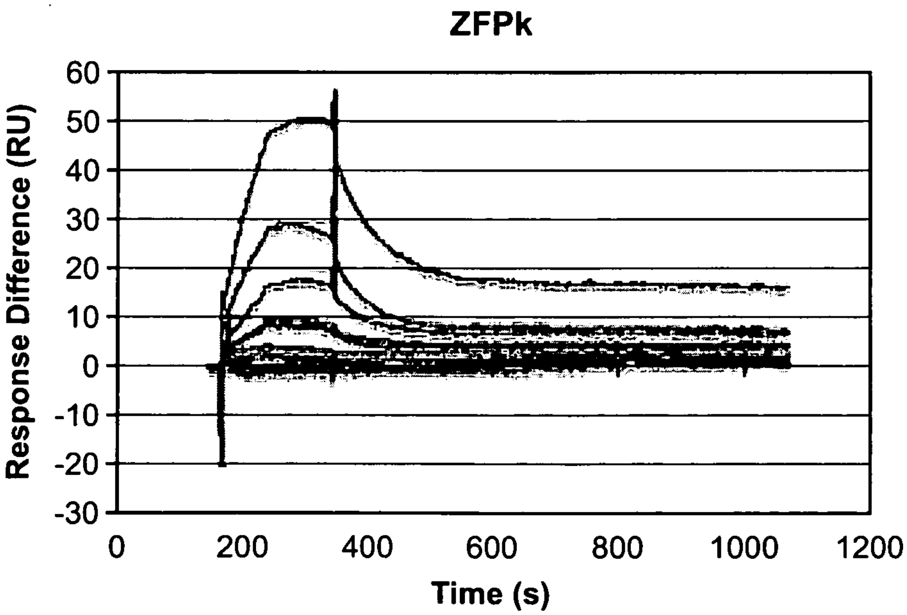
FIGS. 20A-20G show BIAcore kinetic analysis of ZFPk, ZFPm, ZFPn, ZFPq, ZFPr, ZFPt and ZFPu respectively.
Figure 20B:
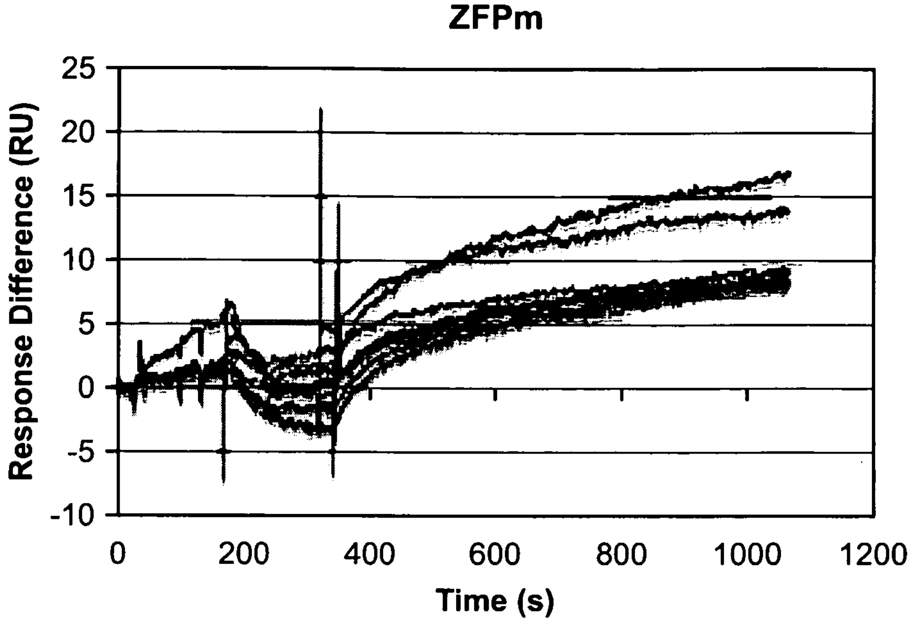
Figure 20C:
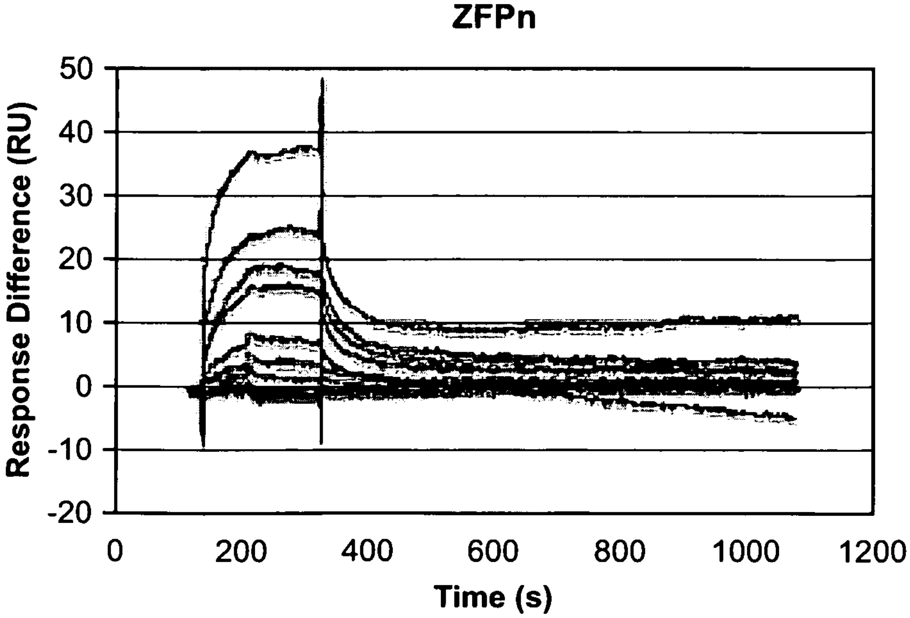
Figure 20D:
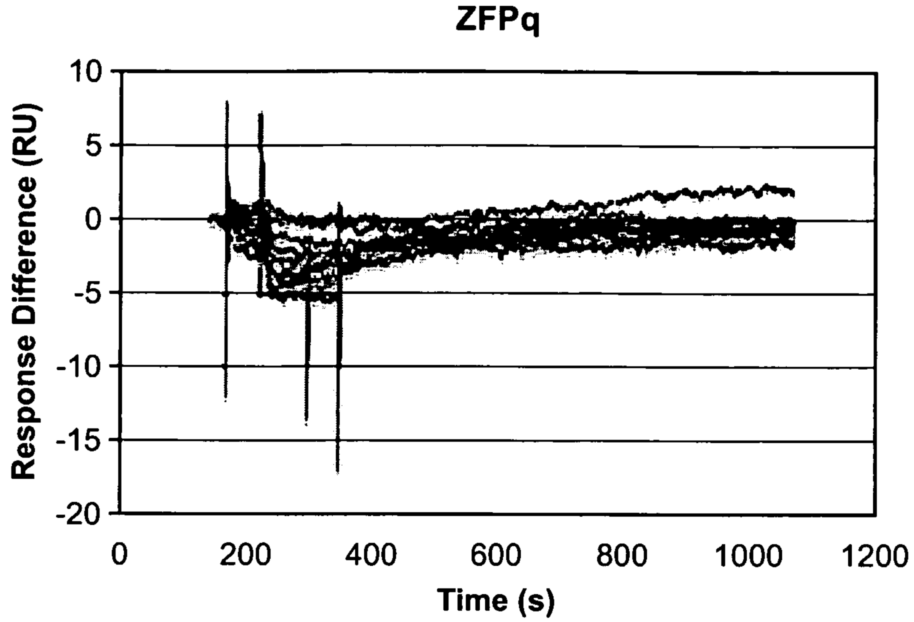
Figure 20E:
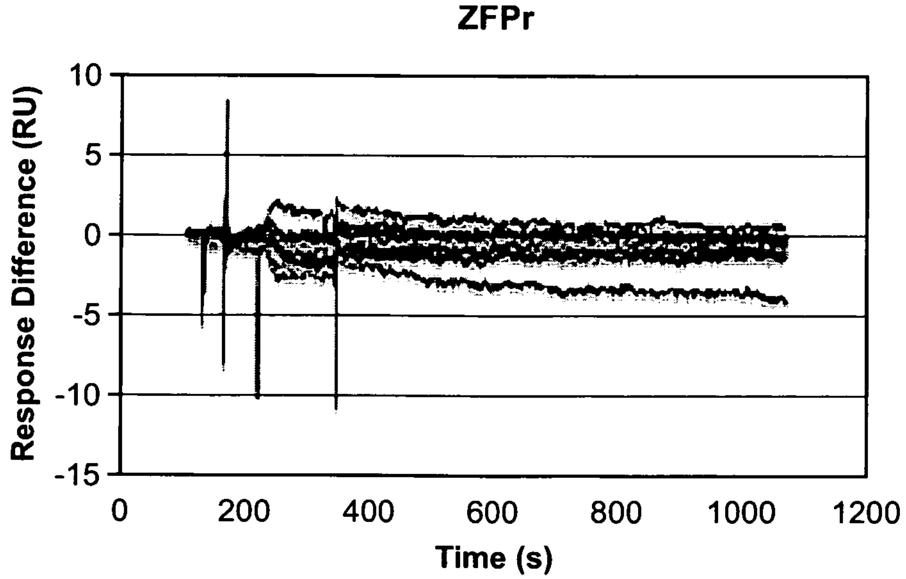
Figure 20F:
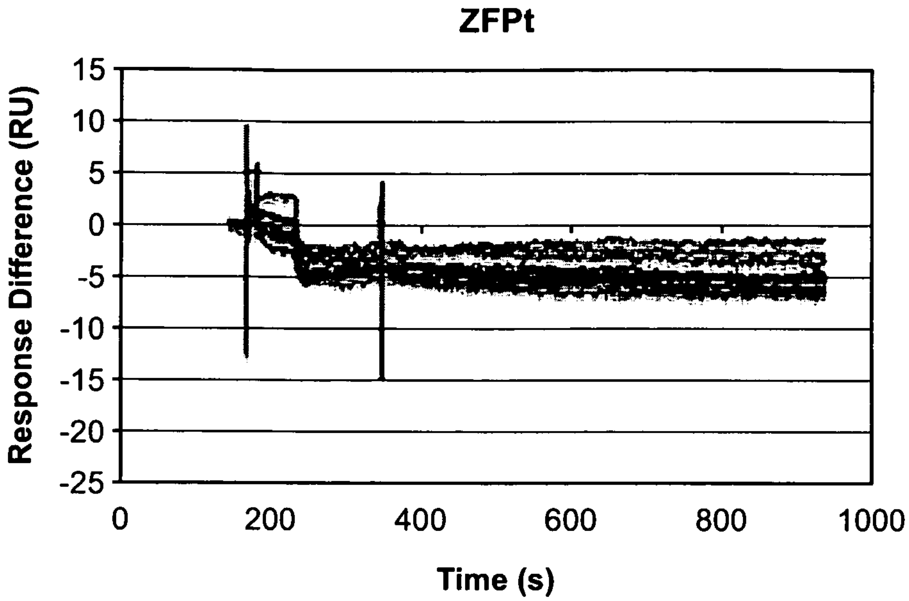
Figure 20G:
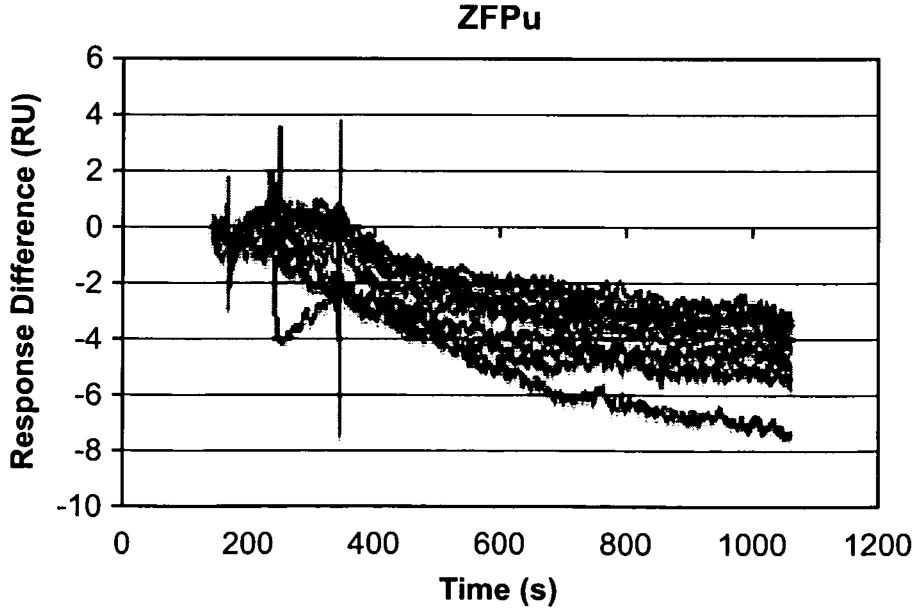

The specificity of the designed ZFPs to their target sequence was assessed using competition EMSAs (Smith et al. 1999 *Nucleic Acids Res.* 27(2): 674-681; Reidling and Said 2007 *Am J Physiol Cell Physiol.* 292: 1305-1312). FIGS. 19A-19C show the results of competition EMSAs for ZFPk, ZFPm and ZFPn respectively. Lane 1 represents [$^{32}$P]-labeled specific oligonucleotides alone without ZFP. Lane 2 represents 150 nM ZFPa with labeled specific oligonucleotides. Lanes 3-5 represent 150 nM ZFPa with labeled specific oligonucleotides and 5, 10 or 50 μM (respectively) of unlabeled specific oligonucleotides. Lane 6 represents 150 nM ZFPa with labeled specific oligonucleotides and 50 μM of unlabeled non-specific oligonucleotides.

By adding 1000-10,000 fold excess unlabeled oligonucleotides, competition off by specific unlabeled oligonucleotides (FIG. 19A, lanes 3-5) but not by non-specific unlabeled oligonucleotides (FIG. 19A, lane 6) was visible, indicating the ZFPs had high affinities and specific binding to their target oligonucleotides. Competition EMSAs for ZFPm and ZFPn (FIGS. 19B and 19C respectively) showed similar results.

Example 10

Assessment of Dissociation Constants for Human HBV-Specific ZFPs Using SPR

Binding of the human HBV-specific ZFPs: ZFPk, ZFPm, ZFPn, ZFPq, ZFPr, ZFPt, ZFPu and ZFPv to their respective target nucleic acids was assayed using surface plasmon resonance (SPR). Kinetic graphs (FIGS. 20A-20G) were produced using BIAcore kinetic analysis software. Each line represents duplicate analysis of different concentrations of ZFP, ranging from 3.7 nM to 230 nM (ZFPk), 2.6 nM to 280 nM (ZFPm), 2.6 nM to 338 nM (ZFPn), 1 nM to 256 nM (ZFPq, ZFPr, ZFPt, ZFPu) and 1 nM to 240 nM (ZFPv). Three blanks in duplicate were also performed. Response difference is measured in resonance units (RU) and represents the binding of the ZFP to the anchored oligonucleotides.

Dissociation constants ($K_d$) were calculated for the ZFPs. As shown in Table 4, ZFPk had a $K_d$ in the nanomolar range at 5.14 nM, ZFPm had a $K_d$ in the nanomolar range at 2.76 nM, ZFPn had a $K_d$ in the nanomolar range at 69.4 nM, ZFPq had a $K_d$ in the micromolar range at 1.29 μM, ZFPr had a $K_d$ in the micromolar range at 0.5 μM, ZFPt had a $K_d$ in the micromolar range at 1.07 μM and ZFPu had a $K_d$ in the micromolar range at 2.47 μM Table 4 provides a summary of the dissociation constants ($K_d$) of the ZFPs derived from EMSA or BIAcore surface plasmon resonance. Summary of the dissociation constants ($K_d$) of all ZFPs derived from EMSA or BIAcore surface plasmon resonance. na=not available. nd=no data.

TABLE 4

| | Kd | |
|---|---|---|
| ZFP | EMSA | BIAcore |
| ZFPk | 43.6 nM | 5.14 nM |
| ZFPm | 41.4 nM | 2.76 nM |
| ZFPn | 116.3 nM | 69.4 nM |
| ZFPq | na | 1.29 μM |
| ZFPr | na | .502 μM |
| ZFPt | na | 1.07 μM |
| ZFPu | na | 2.47 μM |
| ZFPv | 1.19 μM | na |
| ZFPw | nd | nd |

Example 11

Assessment of Binding to cccDNA by a Human HBV-Specific ZFP

Figure 21:
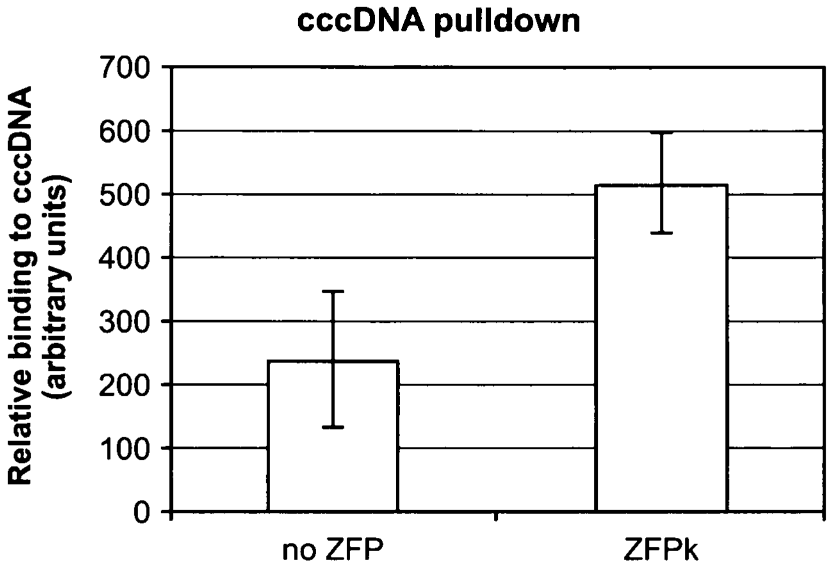
FIG. 21 shows the results of a cccDNA pull-down assay for ZFPk.

In order to demonstrate that a ZFP specific for a human HBV could bind directly to cccDNA, as well as its specific oligonucleotide, a modified pulldown assay was performed. A ZFPk-MBP fusion protein was incubated with amylose resin, to which the ZFP will bind due to the presence of the MBP. cccDNA was then incubated with the resin-bound ZFP. After extensive washing, the ZFP was eluted from the resin and the resulting eluate was assessed for the presence of cccDNA, indicating ZFP was bound to cccDNA. The bound cccDNA was measured by blotting the eluate onto Hybond XL and hybridizing a radioactive probe, followed by quantitation on the Fujifilm FLA-5100 phosphoimager. The chart is the quantification by the phosphoimager of triplicates. ZFPk was able to bind the HBV cccDNA directly as shown in FIG. 21.

Example 12

Testing of Human HBV-Specific ZFPs in Tissue Culture

The activity of the HBV-specific ZFPs in reducing viral RNA levels, viral protein levels, and viral particle levels is tested in the HepAD38 cell line, which has an integrated form of the HBV genome under tetracycline control. In the presence of tetracycline, viral transcription is repressed, and vice versa. When viral transcription occurs in the absence of tetracycline, it results in the formation of virus particles and an accumulation of cccDNA in the nucleus. Another benefit of this cell lines is that HBV E antigen (HBeAg) is secreted only when cccDNA is present, providing an easy diagnostic marker for the presence of cccDNA. Cells are transfected with 3 μg of pcDNA3.1(+) or pcDNA3.1(+)-ZFPk, -ZFPm, -ZFPn, -ZFPp, -ZFPq, ZFPr, ZFPt, ZFPu, ZFPv or -ZFPw using Lipofectamine 2000 (LF2000: Invitrogen 11668-027) according to the manufacturer's specifications, with a DNA: LF2000 ratio of 2:1. After 24 hours, cells are harvested for RNA, DNA and whole cell lysates as described above.

Example 13

Testing of Human HBV-Specific and DHBV-Specific ZFPs In Vivo

The SCID/Alb-UPa mouse model is used as an in vivo model for testing the HBV-specific ZFPs. In this mouse, the albumin promoter controls a tandem array of four murine urokinase genes. This establishes liver-specific urokinase over-production and accelerated hepatocyte death. The mice are transplanted at a young age with freshly isolated human hepatocytes, which repopulate the mouse liver due to their survival advantage over murine hepatocytes. These human cells are permissive to infection by human hepatotropic pathogens, such as HBV. In addition, adenovirus vectors can be used to deliver a subject ZFP to the infected liver.

The Peking duck (*Anas platyhrynchos*) model is used as an in vivo model for testing the DHBV-specific ZFPs. These animals can be either congenitally infected or postnatally infected with DHBV without serious side effects to the animal. Adenoviruses can also be used to deliver ZFPs to the duck liver.

Example 14

Chimeric HBV DNA-Binding ZFP/Endonuclease Polypeptides

The FokI endonuclease is a type II restriction endonuclease from *Flavobacterium okeanokoites*. It has an N-terminal DNA-binding domain and a C-terminal domain with nonspecific DNA-cleavage activity. Native FokI binds its target DNA as a monomer but requires dimerization of its endonuclease for cleavage. Thus, a chimeric endonuclease is generated that includes an HBV DNA-binding ZFPs and a FokI endonuclease domain. An example of a nucleotide sequence encoding a fusion protein comprising an HBV DNA-binding ZFP and a FokI endonuclease domain is presented in FIG. 42. A nucleotide sequence encoding a FokI endonuclease domain is presented in FIG. 42A; and the encoded amino acid sequence is presented in FIG. 42B. An example of a nucleotide sequence encoding a fusion protein comprising an HBV DNA-binding ZFP (ZFPq) and a FokI endonuclease domain is presented in FIG. 42E. The amino acid sequence of the encoded protein is presented in FIG. 42F.

Another example of a fusion protein comprising an HBV DNA-binding ZFP and an endonuclease is a fusion protein comprising an HBV DNA-binding ZFP and a yeast homothallism (HO) endonuclease. The HO endonuclease makes double stranded DNA breaks in a sequence specific manner. HO is the only member of the LAGLIDADG (SEQ ID NO:218) family with a C-terminal zinc finger domain through which DNA recognition occurs, and is thus an ideal endonuclease to use in generating a subject HBV DNA-binding ZFP/endonuclease polypeptide. The zinc finger domain of HO is replaced with a subject HBV DNA-binding ZFP, thereby generating a fusion protein comprising an HBV DNA-binding ZFP and a homothallism endonuclease domain. A nucleotide sequence encoding an HO endonuclease domain is presented in FIG. 43A; and the encoded amino acid sequence is presented in FIG. 43B. An example of a nucleotide sequence encoding a fusion protein comprising an HBV DNA-binding ZFP (ZFPk) and a homothallism endonuclease domain is presented in FIG. 43E. The amino acid sequence of the encoded protein is presented in FIG. 43F.

As shown in the Examples above, a number of ZFPs were designed, which target the enhancer or promoter regions of the HBV genome, an accessible region of the cccDNA minichromosome, as determined by DNA footprinting assays. Using electrophoretic mobility shift assays and surface plasmon resonance, it was shown that one ZFP binds with dissociation constants in the micromolar range, four in the nanomolar range and one in the picomolar range. It was demonstrated that several of our designed ZFPs can also directly bind cccDNA using an in vitro co-immunoprecipitation method. The ZFPs were cloned into the mammalian expression vector pcDNA3.1(+); and the ZFP-encoding expression vectors were co-transfected into LMH (chicken hepatoma) cells with the plasmid pDHBV1.3, which replicates the DHBV life cycle in these cells. It was found that production of viral mRNA, protein and virus progeny was decreased in the presence of each ZFP, indicating ZFPs binding the DHBV enhancer are capable of inhibiting the viral replicative process at the DNA level.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A non-naturally occurring polypeptide comprising an amino acid sequence selected from:

a) an amino acid sequence having at least 95% amino acid sequence identity to SEQ ID NO:176;

b) an amino acid sequence having at least 95% amino acid sequence identity to SEQ ID NO:162; and c) an amino acid sequence having at least 95% amino acid sequence identity to SEQ ID NO:164, wherein the polypeptide comprises a set of DNA binding moieties that collectively provide for binding to a hepatitis B virus (HBV) nucleotide sequence.

2. The polypeptide of claim 1, wherein the polypeptide binds specifically to covalently closed circular HBV DNA.

3. The polypeptide of claim 1, wherein the polypeptide binds to a contiguous stretch of 9 nucleotides of HBV DNA.

4. The polypeptide of claim 3, wherein the contiguous stretch of 9 nucleotides is present in an HBV enhancer or an HBV promoter region.

5. The polypeptide of claim 1, wherein the polypeptide binds to a contiguous stretch of 18 nucleotides of HBV DNA.

6. The polypeptide of claim 5, wherein the contiguous stretch of 18 nucleotides is present in an HBV enhancer or an HBV promoter region.

7. The polypeptide of claim 1, wherein the HBV nucleotide sequence has at least about 80% nucleotide sequence identity to nucleotides 3007-3150 of the nucleotide sequence set forth in FIG. 40.

8. The polypeptide of claim 7, wherein the HBV nucleotide sequence is selected from:

a) 5'-ACCAATCGCCAGACAGGA-3' (SEQ ID NO:65);

b) 5'-GCCAAGATAATGATTAAA-3' (SEQ ID NO:69); and c) 5'-ATGGCAAACAAAAGTTGA-3' (SEQ ID NO:62).

9. The polypeptide of claim 1, wherein the polypeptide includes a nuclear localization signal.

10. The polypeptide of claim 1, wherein the set of DNA binding moieties are:

a) QRAHLER (SEQ ID NO:42);

b) SPADLTR (SEQ ID NO:22);

c) RADNLTE (SEQ ID NO:26);

d) HTGHLLE (SEQ ID NO:39);

e) TTGNLTV (SEQ ID NO:18); and f) DKKDLTR (SEQ ID NO:16).

11. A method of reducing the level of covalently closed circular form of hepatitis B virus (HBV) DNA in an individual, the method comprising administering to an individual in need thereof an effective amount of the polypeptide of claim 1.

12. The method of claim 11, further comprising administering to the individual an effective amount of a least a second anti-HBV therapeutic agent.

13. The polypeptide of claim 1, wherein the set of DNA binding moieties are:

QRANLRA (SEQ ID NO:11);

HKNALQN (SEQ ID NO:21);

RRDELNV (SEQ ID NO:15);
QKSSLIA (SEQ ID NO:12);
RKDNLKN (SEQ ID NO:20); and
DCRDLAR (SEQ ID NO:48).

14. The polypeptide of claim 1, wherein the set of DNA binding moieties are:

QAGHLAS (SEQ ID NO:59);
HRTTLTN (SEQ ID NO:25);
QRANLRA (SEQ ID NO:11);
DSGNLRV (SEQ ID NO:19);
QSGDLRR (SEQ ID NO:41); and
RRDELNV (SEQ ID NO:15).

* * * * *